US012319671B2

(12) United States Patent
Zhou et al.

(10) Patent No.: US 12,319,671 B2
(45) **Date of Patent: *Jun. 3, 2025**

(54) 1-PYRAZOLYL, 5-, 6-DISUBSTITUTED INDAZOLE DERIVATIVES AS LRRK2 INHIBITORS, PHARMACEUTICAL COMPOSITIONS, AND USES THEREOF

(71) Applicant: Merck Sharp & Dohme LLC, Rahway, NJ (US)

(72) Inventors: Hua Zhou, Acton, MA (US); John J. Acton, III, Cranford, NJ (US); Michael J. Ardolino, Arlington, MA (US); Yi-Heng Chen, Whippany, NJ (US); Peter H. Fuller, Ashland, MA (US); Anmol Gulati, Watertown, MA (US); Rebecca Elizabeth Johnson, Oakland, CA (US); William P. Kaplan, Boston, MA (US); Solomon D. Kattar, Wakefield, MA (US); Mitchell H. Keylor, Malden, MA (US); Derun Li, West Roxbury, MA (US); Kaitlyn Marie Logan, Boston, MA (US); Min Lu, Brookline, MA (US); Gregori J. Morriello, Randolph, NJ (US); Santhosh F. Neelamkavil, Edison, NJ (US); Barbara Pio, West Orange, NJ (US); Nunzio Sciammetta, Sudbury, MA (US); Vladimir Simov, South Boston, MA (US); Jing Su, Scotch Plains, NJ (US); Luis Torres, Norwood, MA (US); Xin Yan, Newton, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 819 days.

This patent is subject to a terminal disclaimer.

(21) Appl. No.: 17/614,732

(22) PCT Filed: Jun. 1, 2020

(86) PCT No.: PCT/US2020/035505

§ 371 (c)(1),
(2) Date: Nov. 29, 2021

(87) PCT Pub. No.: WO2020/247298

PCT Pub. Date: Dec. 10, 2020

(65) Prior Publication Data

US 2022/0259188 A1 Aug. 18, 2022

Related U.S. Application Data

(60) Provisional application No. 62/858,137, filed on Jun. 6, 2019.

(51) Int. Cl.
*C07D 405/14* (2006.01)
*A61P 25/16* (2006.01)
(Continued)

(52) U.S. Cl.
CPC ............ *C07D 405/14* (2013.01); *A61P 25/16* (2018.01); *C07D 401/14* (2013.01);
(Continued)

(58) Field of Classification Search
CPC .. C07D 405/14; C07D 403/04; C07D 403/14; C07D 409/14; C07D 471/04; C07D 471/10; C07D 487/04; C07D 487/08; C07D 487/10; C07D 491/107; C07D 498/04; C07D 498/08; C07D 401/14; A61P 25/16
See application file for complete search history.

(56) References Cited

U.S. PATENT DOCUMENTS 4,166,452 A 9/1979 Generales, Jr.
4,256,108 A 3/1981 Theeuwes
(Continued)

FOREIGN PATENT DOCUMENTS

WO 2007149798 A2 12/2007
WO 2016036586 A1 3/2016
(Continued)

OTHER PUBLICATIONS

Ding, X. and Ren, F. Expert Opin. Ther. Pat. 2020, 30, 275-286 (Year: 2020).*
(Continued)

*Primary Examiner* — Clinton A Brooks
*Assistant Examiner* — Kendall Nicole Heitmeier
(74) *Attorney, Agent, or Firm* — Sylvia A. Ayler; Catherine Fitch

(57) ABSTRACT

The present invention is directed to substituted certain 1-pyrazolyl, 5-, 6-disubstituted indazole derivatives of Formula (I) and pharmaceutically acceptable salts thereof, wherein R1, R2, and ring A are as defined herein, which are potent inhibitors of LRRK2 kinase and may be useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of diseases, such as Parkinson's disease, in which LRRK-2 kinase is involved.

16 Claims, No Drawings

(51) Int. Cl.

| | |
|---|---|
| ***C07D 401/14*** | (2006.01) |
| ***C07D 403/04*** | (2006.01) |
| ***C07D 403/14*** | (2006.01) |
| ***C07D 409/14*** | (2006.01) |
| ***C07D 471/04*** | (2006.01) |
| ***C07D 471/10*** | (2006.01) |
| ***C07D 487/04*** | (2006.01) |
| ***C07D 487/08*** | (2006.01) |
| ***C07D 487/10*** | (2006.01) |
| ***C07D 491/107*** | (2006.01) |
| ***C07D 498/04*** | (2006.01) |
| ***C07D 498/08*** | (2006.01) |

(52) U.S. Cl.

CPC ......... *C07D 403/04* (2013.01); *C07D 403/14* (2013.01); *C07D 409/14* (2013.01); *C07D 471/04* (2013.01); *C07D 471/10* (2013.01); *C07D 487/04* (2013.01); *C07D 487/08* (2013.01); *C07D 487/10* (2013.01); *C07D 491/107* (2013.01); *C07D 498/04* (2013.01); *C07D 498/08* (2013.01)

(56) References Cited

U.S. PATENT DOCUMENTS

| | | | | |
|---|---|---|---|---|
| 4,265,874 | A | 5/1981 | Bonsen et al. | |
| 9,212,173 | B2 * | 12/2015 | Baker-Glenn | A61P 25/16 |
| 12,030,872 | B2 * | 7/2024 | Simov | A61P 25/16 |
| 2010/0197678 | A1 | 8/2010 | Kuzmich et al. | |

FOREIGN PATENT DOCUMENTS

| | | | | |
|---|---|---|---|---|
| WO | WO-2017012576 A1 * | 1/2017 | | A61K 31/4545 |
| WO | 2018137573 A1 | 8/2018 | | |
| WO | 2018137607 A1 | 8/2018 | | |
| WO | 2018137618 A1 | 8/2018 | | |
| WO | 2018137619 A1 | 8/2018 | | |
| WO | WO-2018137593 A1 * | 8/2018 | | A61P 25/16 |

OTHER PUBLICATIONS

Galatsis, P. et. al. Bioorg. Med. Chem. Lett. 2014, 24, 4132-4140 (Year: 2014).*

Aasly, J.O. et al., Clinical Features of LRRK2-Associated Parkinson's Disease in Central Norway, American Neurological Association, 2005, 762-765, 57(5).

Adams, J.R. et al., PET in LRRK2 mutations: comparison to sporadic Parkinson's disease and evidence for presymptomatic compensation, Brain, 2005, 2777-2785, 128.

Agalliu, I. et al., Higher Frequency of Certain Cancers in LRRK2 G2019S Mutation Carriers With Parkinson Disease, JAMA Neurology, 2015, 58-65, 72(1).

Bailey, R.M. et al., LRRK2 phosphorylates novel tau epitopes and promotes tauopathy, Acta Neuropathol, 2013, 809-827, 126.

Daher, J.P. et al., Leucine-rich Repeat Kinase 2 (LRRK2) Pharmacological Inhibition Abates alpha-Synuclein Gene-induced Neurodegeneration, The Journal of Biological Chemistry, 2015, 19433-19444, 290(32).

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Danoy, P. et al., Association of Variants at 1q32 and STAT3 with Ankylosing Spondylitis Suggests Genetic Overlap with Crohn's Disease, PLoS Genetics, 2010, 1-5, 6(12):e1001195.

Engel, P. et al., Therapeutic Targeting of B Cells for Rheumatic Autoimmune Diseases, Pharmacological Reviews, 2011, 127-156, 63(1).

Estrada, Anthony A. et al., Discovery of Highly Potent, Selective, and Brain-Penetrant Aminopyrazole Leucine-Rich Repeat Kinase 2 (LRRK2) Small Molecule Inhibitors, Journal of Medicinal Chemistry, 2014, 921-936, 57.

Gilks, W.P. et al., A common LRRK2 mutation in idiopathic Parkinson's disease, Lancet, 2005, 415-416, 365.

Goedert, M. et al., Mutations causing neurodegenerative tauopathies, Biochimica et Biophysica Acta, 2005, 240-250, 1739.

Guo, L. et al., The Parkinson's disease-associated protein, leucine-rich repeat kinase 2 (LRRK2), is an authentic GTPase that stimulates kinase activity, Experimental Cell Research, 2007, 3658-3670, 313.

Kawakami, F. et al., LRRK2 Phosphorylates Tubulin-Associated Tau but Not the Free Molecule: LRRK2-Mediated Regulation of the Tau-Tubulin Association and Neurite Outgrowth, PLoS ONE, 2012, 1-9, 7(1):e30834.

Kumari, U. et al., LRRK2 in Parkinson's disease: genetic and clinical studies from patients, The FEBS Journal, 2009, 6455-6463, 276.

Lee, B.D. et al., Inhibitors of leucine-rich repeat kinase-2 protect against models of Parkinson's disease, Nature Medicine, 2010, 998-1000, 16.

Li, Y. et al., Mutant LRRK2R1441G BAC transgenic mice recapitulate cardinal features of Parkinson's disease, Nature Neuroscience, 2009, 826-828, 12(7).

Looyenda, B.D. et al., Chromosomal amplification of leucine-rich repeat kinase-2 (LRRK2) is required for oncogenic MET signaling in papillary renal and thyroid carcinomas, Proc Natl Acad Sci USA, 2011, 1439-1444, 108(4).

Moehle, M.S. et al., LRRK2 Inhibition Attenuates Microglial Inflammatory Responses, The Journal of Neuroscience, 2012, 1602-1611, 32(5).

Nichols, W. C. et al., Genetic screening for a single common LRRK2 mutation in familial Parkinson's disease, Lancet, 2005, 410-412, 365.

Saunders-Pullman, R. et al., LRRK2 G2019S Mutations are Associated with an Increased Cancer Risk in Parkinson Disease, Movement Disorders, 2010, 2536-22541, 25(15).

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Shtilbans, A. et al., Differential gene expression in patients with amyotrophic lateral sclerosis, Amyotrophic Lateral Sclerosis, 2011, 250-256, 12(4).

Umeno, J. et al., Meta-analysis of Published Studies Identified Eight Additional Common Susceptibility Loci for Crohn's Disease and Ulcerative Colitis, Inflammatory Bowel Disease, 2011, 2407-2415, 17(12).

Volpicelli-Daley, L.A. et al., G2019S-LRRK2 Expression Augments alpha-Synuclein Sequestration into Inclusions in Neurons, The Journal of Neuroscience, 2016, 7415-7427, 36(28).

Zhang, Fu-Ren et al., Genomewide Association Study of Leprosy, The New England Journal of Medicine, 2009, 2609-2618, 361.

Zhao, Yi et al., LRRK2 variant associated with Alzheimer's disease, Neurobiology of Aging, 2011, 1990-1993, 32.

Zhu, X. et al., LRRK2 in Parkinson's disease and dementia with Lewy bodies, Molecular Neurodegeneration, 2006, 1-9, 1:17.

Zimprich, A. et al., Mutations in LRRK2 Cause Autosomal-Dominant Parkinsonism with Pleomorphic Pathology, Neuron, 2004, 601-607, 44(4).

* cited by examiner

1-PYRAZOLYL, 5-, 6-DISUBSTITUTED INDAZOLE DERIVATIVES AS LRRK2 INHIBITORS, PHARMACEUTICAL COMPOSITIONS, AND USES THEREOF

CROSS REFERENCE TO RELATED APPLICATIONS

This application is a U.S. National Phase application under 35 U.S.C. § 371 of PCT Application No. PCT/US2020/035505 filed Jun. 1, 2020, which claims priority from U.S. Ser. No. 62/858,137 filed Jun. 6, 2019.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al., Molecular Neurodegeneration, Vol 30, 2006, pp. 1-17). Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32):19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11):1990-3). Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7(1):e30834; Bailey et al., Acta Neuropathol. 2013 December; 126(6):809-27). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and Parkinson's linked to chromosome 17 (Goedert and Jakes Biochim Biophys Acta. 2005 Jan. 3).

A growing body of evidence suggests a role for LRRK2 in immune cell function in the brain with LRRK2 inhibitors demonstrated to attenuate microglial inflammatory responses (Moehle et al., J Neurosci. 2012 Feb. 1; 32(5):1602-11). As neuroinflammation is a hallmark of a number of neurodegenerative diseases such PD, AD, MS, HIV-induced dementia, ALS, ischemic stroke, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6).

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies (Engel at al., Pharmacol Rev. 2011 March; 63(1):127-56; Homam et al., Homam et al., Clin Neuromuscular disease, 2010) and ankylosing spondylitis (Danoy et al., PLoS Genet. 2010 Dec. 2; 6(12)). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4):1439-44).

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain 1-pyrazolyl, 5-, 6-disubstituted indazole derivatives, which are collectively or individually referred to herein as "compound(s) of the invention" or "compounds of Formula (I)", as described herein. LRRK2 inhibitors have been disclosed in the art, e.g., WO2016036586. Applicant has found, surprisingly and advantageously, that the compounds of Formula (I), exhibit excellent LRRK2 inhibitory activity. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I):

(I)

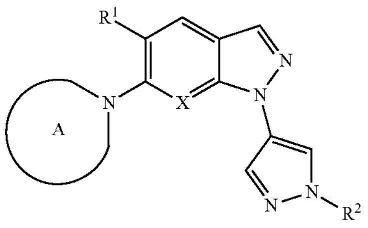

or a pharmaceutically acceptable salt thereof, wherein:

X is CH or N;

$R^1$ is selected from Cl, Br, F, $CH_3$, CN, and $CHF_2$;

$R^2$ is selected from:

$-(C_1\text{-}C_3)$alkyl, $-(C_1\text{-}C_3)$haloalkyl, optionally substituted cycloalkyl, optionally mono, di, or tri-substituted heteroaryl, optionally mono, di, or tri-substituted heterocycloalkyl, wherein each said optional substituent is independently selected from halogen, oxo, CN, $-(O)_{0\text{-}1}(C_1\text{-}C_3)$alkyl, $-(C_3\text{-}C_6)$cycloalkyl, $-(O)_{0\text{-}1}(C_1\text{-}C_3)$haloalkyl, $NR^{2A}R^{2B}$, $CH_2NHC(O)(C_1\text{-}C_3)$alkyl, $-C(O)OH$, $-C(O)O(C_1\text{-}C_3)$alkyl, wherein the alkyl in $-(O)_{0\text{-}1}(C_1\text{-}C_3)$alkyl is optionally substituted with 1, 2, or 3 substituents independently selected from halogen, OH, $(CH_2)_nO(C_1\text{-}C_3)$alkyl, $-(O)_{0\text{-}1}(C_1\text{-}C_3)$haloalkyl, $NR^{2A}R^{2B}$, and heterocycloalkyl, wherein n is 0-2, and $C(O)NR^{2A}R^{2B}$, $R^{2A}$ is selected from H and $-(C_1\text{-}C_3)$alkyl, $R^{2B}$ is selected from H and $-(C_1\text{-}C_3)$alkyl;

the moiety

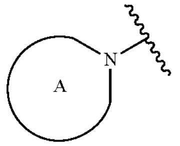

is selected from:

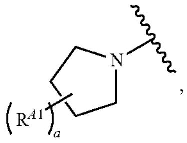, 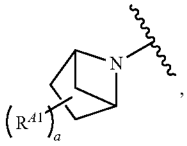, and

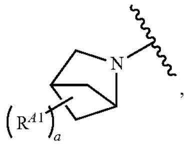, or, alternatively, the moiety

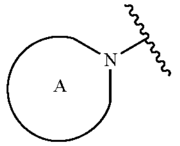

is selected from:

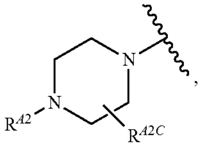, 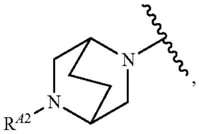,

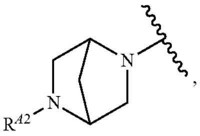, 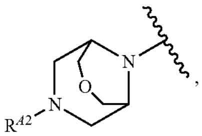,

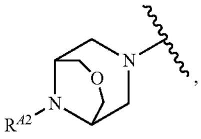, and 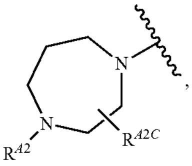, or, alternatively, the moiety
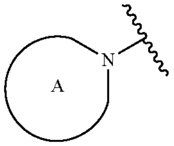
is selected from:
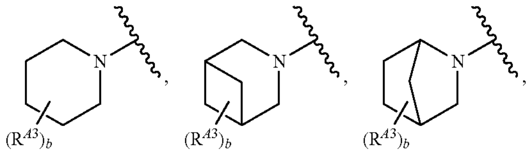
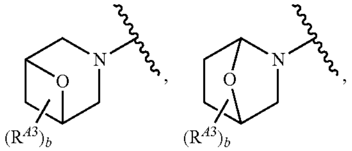
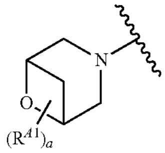
and
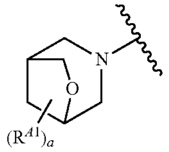
or, alternatively, the moiety
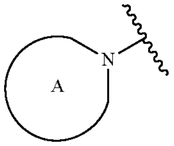
is a fused bicyclic moiety selected from:
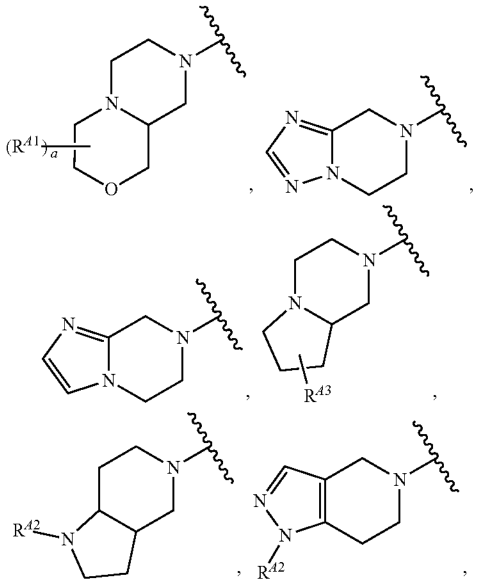
-continued
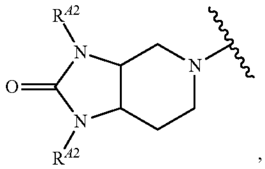
, and
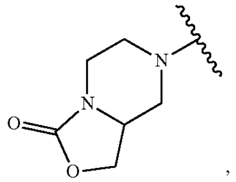
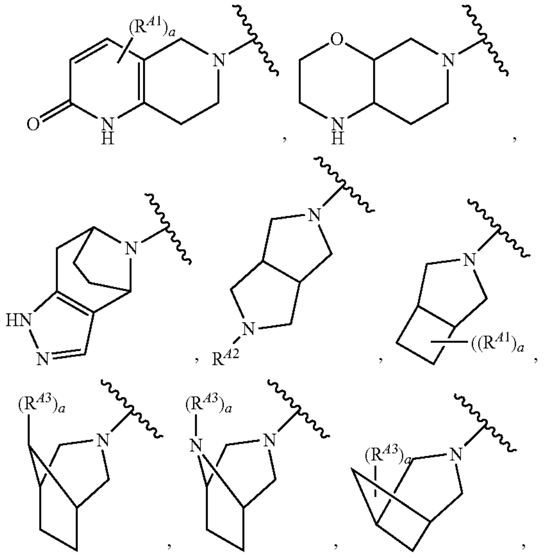
or, alternatively, the moiety
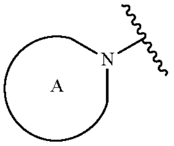
is a moiety selected from:
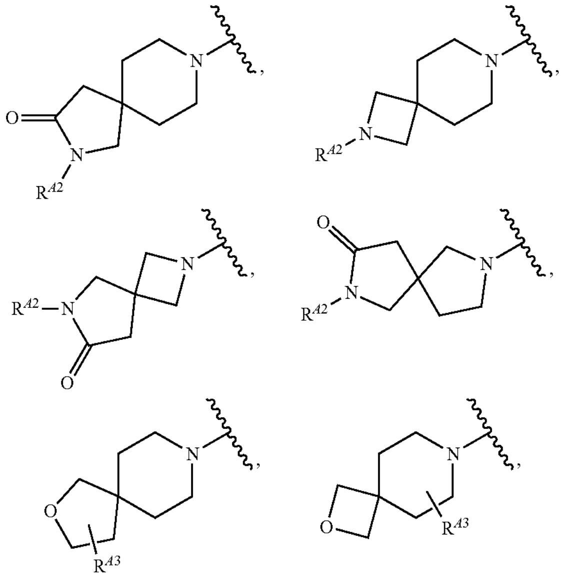

-continued

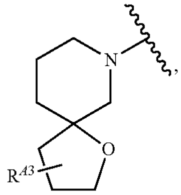,
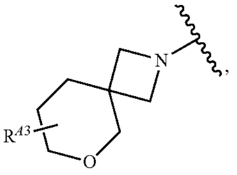,
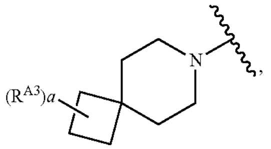,
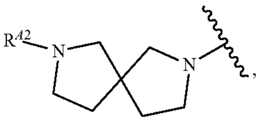,
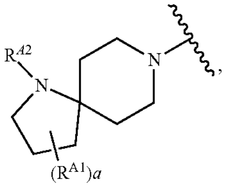, and
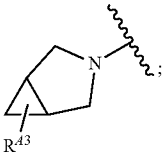;

a is 0, 1, or 2;

each $R^{A1}$ is independently selected from halogen, OH, —$(C_1$-$C_6)$alkyl, —$(C_1$-$C_6)$alkyl-OH, and —$(C_1$-$C_6)$alkyl-CN;

$R^{A2}$ is selected from H, —$(C_1$-$C_6)$alkyl, —$(C_1$-$C_6)$alkyl-OH, —$(C_1$-$C_6)$alkyl-CN, $S(O)_2(C_1$-$C_3)$alkyl, optionally mono-, di- or tri-substituted cyclopropyl, optionally mono-, di- or tri-substituted cyclobutyl, optionally mono-, di- or ti-substituted cyclopentyl, optionally mono-, di- or tri-substituted oxetanyl, optionally mono-, di- or tri-substituted tetrahydrofuranyl, optionally mono-, di- or tri-substituted thietanyl dioxide, optionally mono-, di- or tri-substituted tetrahydrothiophenyl dioxide, wherein each said optional substituent is independently selected from halogen, oxo, CN, OH, —$O(C_1$-$C_3)$alkyl, —$(C_1$-$C_3)$alkyl, and —$(C_1$-$C_3)$haloalkyl;

$R^{A2C}$ is selected from H and, —$(C_1$-$C_6)$alkyl;

b is 0, 1, 2, or 3; and each $R^{A3}$ is independently selected from H, halogen, CN, $NH_2$, OH, oxo, —$(C_1$-$C_3)$alkyl, —$(C_1$-$C_3)$alkyl-OH, —$(C_1$-$C_3)$alkyl-CN, —$(C_1$-$C_3)$haloalkyl, $O(C_1$-$C_3)$alkyl, —$(C_1$-$C_3)$alkylNHS$(O)_2(C_1$-$C_3)$alkyl, $S(O)_2(C_1$-$C_3)$alkyl, $S(O)_2(C_1$-$C_3)$cyclopropyl, said cyclopropyl optionally mono-, di- or ti-substituted, optionally mono-, di- or tri-substituted cyclopropyl, optionally mono-, di- or tri-substituted cyclobutyl, optionally mono-, di- or tri-substituted cyclopentyl, optionally mono-, di- or tri-substituted azetidinyl, optionally mono-, di- or tri-substituted oxetanyl, optionally mono-, di- or tri-substituted tetrahydrofuranyl, optionally mono-, di- or tri-substituted thietanyl dioxide, optionally mono-, di- or tri-substituted tetrahydrothiophenyl dioxide, and optionally mono-, di- or tri-substituted heteroaryl, wherein each said optional substituent independently selected from halogen, oxo, OH, —$(C_1$-$C_3)$alkyl, and —$(C_1$-$C_3)$haloalkyl.

In another embodiment, the compounds of the invention of structural Formula (I) are represented by structural Formula (Ia):

(I)

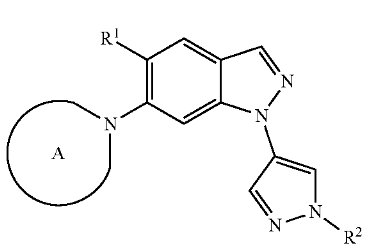

or a pharmaceutically acceptable salt thereof, wherein:

$R^1$ is selected from Cl, Br, and $CH_3$;

$R^2$ is selected from:

—$(C_1$-$C_3)$alkyl, —$(C_1$-$C_3)$haloalkyl, optionally substituted cycloalkyl, optionally substituted heteroaryl, optionally substituted heterocycloalkyl, wherein each said optional substituent is 1, 2, or 3 substituents independently selected from halogen, oxo, —$(C_1$-$C_3)$alkyl, —$(C_1$-$C_3)$haloalkyl, and —C(O)OH, —$C(O)O(C_1$-$C_3)$alkyl, and $C(O)NR^{2A}R^{2B}$, wherein $R^{2A}$ is selected from H and —$(C_1$-$C_3)$alkyl, and $R^{2B}$ is selected from H and —$(C_1$-$C_3)$alkyl; and the moiety

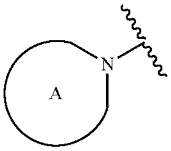

is selected from:

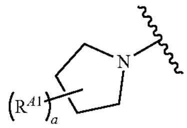,
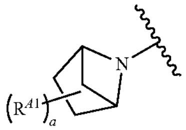, and
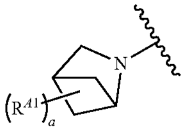, or, alternatively, the moiety

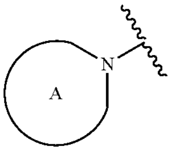

is selected from:
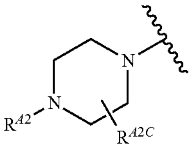
,
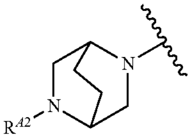
,
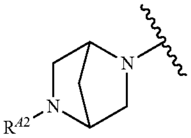
,
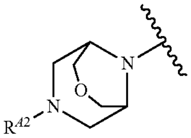
,
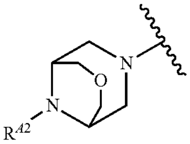
, and
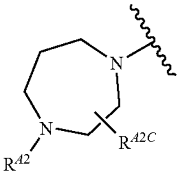
,
or, alternatively, the moiety
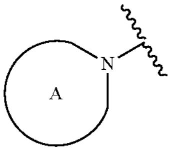
is selected from:
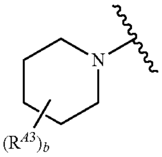
,
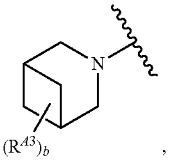
,
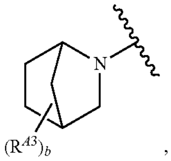
,
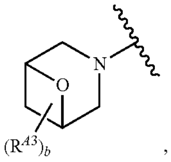
, and
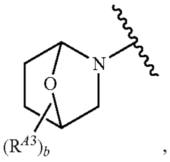
,
or, alternatively, the moiety
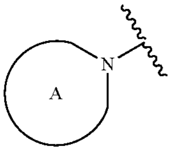
is a fused bicyclic moiety selected from:
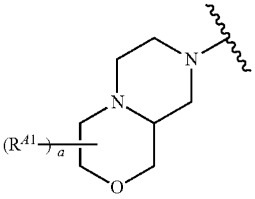
,
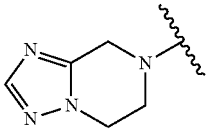
,
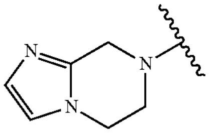
,
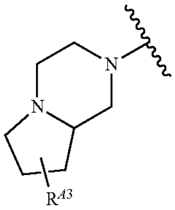
,
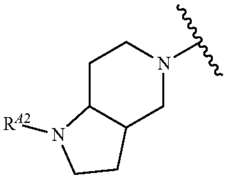
,
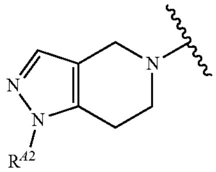
,
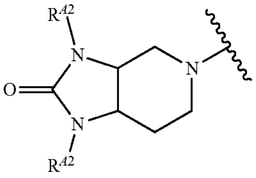
, and
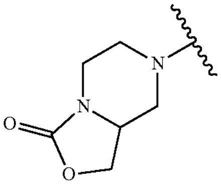
,
or, alternatively, the moiety
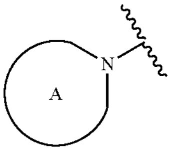
is a moiety selected from:
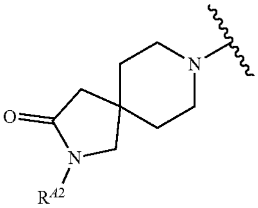
,
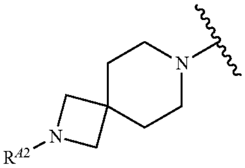
,
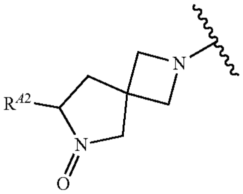
,
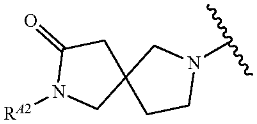
, -continued

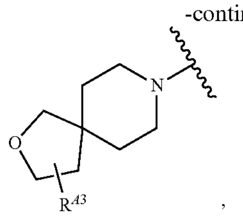
,
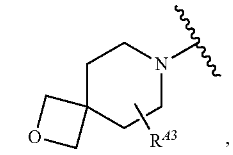
,
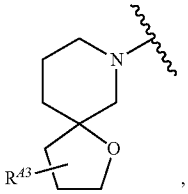
,
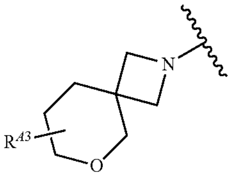
, and
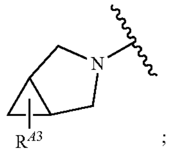
;

a is 0, 1, or 2;

each $R^{A1}$ is independently selected from halogen, OH, —$(C_1$-$C_6)$alkyl, —$(C_1$-$C_6)$alkyl-OH, and —$(C_1$-$C_6)$alkyl-CN;

$R^{A2}$ is selected from H, —$(C_1$-$C_6)$alkyl, —$(C_1$-$C_6)$alkyl-OH, —$(C_1$-$C_6)$alkyl-CN, $S(O)_2(C_1$-$C_3)$alkyl, optionally substituted cyclopropyl, optionally substituted cyclobutyl, optionally substituted cyclopentyl, optionally substituted oxetanyl, optionally substituted tetrahydrofuranyl, optionally substituted thietanyl dioxide, optionally substituted tetrahydrothiophenyl dioxide, wherein each said optional substituent is 1, 2, or 3 substituents independently selected from halogen, oxo, —$(C_1$-$C_3)$alkyl, and —$(C_1$-$C_3)$haloalkyl;

$R^{A2C}$ is selected from H and, —$(C_1$-$C_6)$alkyl;

b is 0, 1, 2, or 3; and each $R^{A3}$ is independently selected from H, halogen, $NH_2$, OH, oxo, —$(C_1$-$C_3)$alkyl, —$(C_1$-$C_3)$alkyl-OH, —$(C_1$-$C_3)$alkyl-CN, —$(C_1$-$C_3)$haloalkyl, $O(C_1$-$C_3)$alkyl, $S(O)_2(C_1$-$C_3)$alkyl, optionally substituted cyclopropyl, optionally substituted cyclobutyl, optionally substituted cyclopentyl, optionally substituted azetidinyl, optionally substituted oxetanyl, optionally substituted tetrahydrofuranyl, optionally substituted thietanyl dioxide, optionally substituted tetrahydrothiophenyl dioxide, and optionally substituted heteroaryl, wherein each said optional substituent is 1, 2, or 3 substituents independently selected from halogen, oxo, OH, —$(C_1$-$C_3)$alkyl, and —$(C_1$-$C_3)$haloalkyl.

In another embodiment, in Formula (I): X is CH.

In another embodiment, in Formula (I): X is N.

In another embodiment, in Formula (I): a is 1.

In another embodiment, in Formula (I): a is 2.

In another embodiment, in Formula (I) b is 0.

In another embodiment, in Formula (I) b is 1.

In another embodiment, in Formula (I) b is 2.

In another embodiment, in Formula (I) b is 3.

In another embodiment, in Formula (I):

$R^1$ is F.

In another embodiment, in Formula (I):

$R^1$ is $C_1$.

In another embodiment, in Formula (I):

$R^1$ is Br.

In another embodiment, in Formula (I):

$R^1$ is $CH_3$.

In another embodiment, in Formula (I):

$R^1$ is CN.

In another embodiment, in Formula (I):

$R^1$ is $CHF_2$.

In an alternative of each of the preceding embodiments, in Formula (I):

$R^2$ is: $(C_1$-$C_3)$alkyl.

In another alternative of each of the preceding embodiments, in Formula (I):

$R^2$ is: $CH_3$.

In another alternative of each of the preceding embodiments, in Formula (I):

$R^2$ is $(C_1$-$C_3)$haloalkyl.

In another alternative of each of the preceding embodiments, in Formula (I):

$R^2$ is selected from $CF_3$, $CHF_2$, $CH_2F$, $CHFCH_3$, $CF_2CH_3$, $CH_2CHF_2$, $CH_2CH_2F$, and $CH_2CF_3$.

In another alternative of each of the preceding embodiments, in Formula (I):

$R^2$ is cycloalkyl. A subembodiment of this aspect of the invention is realized when the cycloalkyl, including bicyclic cycloalkyls, is selected from unsubstituted or substituted cyclopropyl, cyclobutyl, bicyclopentanyl, bicyclohexanyl, bicycloheptanyl, and bicyclooctanyl.

In another alternative of each of the preceding embodiments, in Formula (I):

$R^2$ is cyclopropyl.

In another alternative of each of the preceding embodiments, in Formula (I):

$R^2$ is cyclobutyl.

In another alternative of each of the preceding embodiments, in Formula (I):

$R^2$ is bicyclopentanyl.

In another alternative of each of the preceding embodiments, in Formula (I):

$R^2$ is bicyclohexanyl.

In another alternative of each of the preceding embodiments, in Formula (I):

$R^2$ is bicycloheptanyl.

In another alternative of each of the preceding embodiments, in Formula (I):

$R^2$ is bicyclooctanyl.

In another alternative of each of the preceding embodiments, in Formula (I):

$R^2$ is selected from cyclopropyl, mono-, di- or tri-substituted cyclopropyl, cyclobutyl, mono-, di- or tri-substituted cyclobutyl, bicyclopentanyl, and mono-, di- or tri-substituted bicyclopentanyl, wherein each said substituent is independently selected from halogen, —$(C_1$-$C_3)$alkyl, —$(C_1$-$C_3)$haloalkyl, and —$C(O)O(C_1$-$C_3)$alkyl, wherein the alkyl in —$(C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

In another alternative of each of the preceding embodiments, in Formula (I):

$R^2$ is selected from cyclopropyl and mono-, di- or tri-substituted cyclopropyl, wherein each said substituent is independently selected from halogen, —$(C_1$-$C_3)$alkyl, —$(C_1$-$C_3)$haloalkyl, and —$C(O)O(C_1$-$C_3)$alkyl, wherein the alkyl in —$(C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl wherein n is 0-2.

In another alternative of each of the preceding embodiments, in Formula (I):

$R^2$ is selected from cyclopropyl and mono-, di- or ti-substituted cyclopropyl, wherein each said substituent is independently selected from halogen, —$(C_1$-$C_3)$alkyl, and —$(C_1$-$C_3)$haloalkyl wherein the alkyl in —$(C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

In another alternative of each of the preceding embodiments, in Formula (I):

$R^2$ is selected from cyclobutyl and mono-, di- or tri-substituted cyclobutyl, wherein each said substituent is independently selected from halogen, —$(C_1$-$C_3)$alkyl, —$(C_1$-$C_3)$haloalkyl, and —$C(O)O(C_1$-$C_3)$alkyl, wherein the alkyl in —$(C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

In another alternative of each of the preceding embodiments, in Formula (I):

$R^2$ is selected from cyclobutyl and mono-, di- or tri-substituted cyclobutyl, wherein each said substituent is independently selected from halogen, —$(C_1$-$C_3)$alkyl, and —$(C_1$-$C_3)$haloalkyl wherein the alkyl in —$(C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

In another alternative of each of the preceding embodiments, in Formula (I):

$R^2$ is selected from bicyclopentanyl and mono-, di- or tri-substituted bicyclopentanyl, wherein each said substituent is independently selected from halogen, —$(C_1$-$C_3)$alkyl, —$(C_1$-$C_3)$haloalkyl, and —$C(O)O(C_1$-$C_3)$alkyl wherein the alkyl in $C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

Non-limiting examples of $R^2$ when $R^2$ is selected from bicyclopentanyl and substituted bicyclopentanyl include

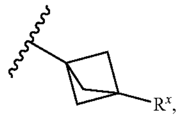, 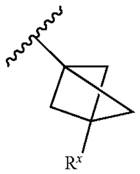 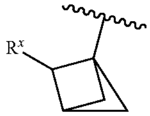, wherein $R^x$ is selected from H, $C(O)OCH_3$, $CH_2F$, I, F, CN, $OCH_3$, $(CH_2)_nOCH_3$, $CH(CH_3)OCH_3$, $(CH_2)_nOC(D)_3$, $(CH_2)_nOCHF_2$, $(CH_2)_nN(CH_3)_2$, and other such groups as are depicted in the examples below, wherein n is 0-2.

Non-limiting examples of $R^2$ when $R^2$ is selected from unsubstituted and substituted bicyclopentanyl include

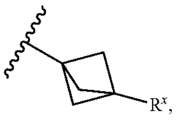, wherein $R^x$ is selected from H, $C(O)OCH_3$, $CH_2F$, I, F, CN, $OCH_3$, $(CH_2)_nOCH_3$, $CH(CH_3)OCH_3$, $(CH_2)_nOC(D)_3$, $(CH_2)_nOCHF_2$, $(CH_2)_nN(CH_3)_2$, and other such groups as are depicted in the examples below, wherein n is 0-2.

In another alternative of each of the preceding embodiments, in Formula (I):

$R^2$ is selected from optionally mono-, di- or tri-substituted heteroaryl and optionally mono-, di- or tri-substituted heterocycloalkyl, wherein each said optional substituent on said heteroaryl is independently selected from halogen, —$(C_1$-$C_3)$alkyl, and —$(C_1$-$C_3)$haloalkyl, and wherein each said optional substituent on said heterocycloalkyl independently selected from halogen, oxo, —$(C_1$-$C_3)$alkyl, and —$(C_1$-$C_3)$haloalkyl, and wherein the alkyl in —$(C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

In another alternative of each of the preceding embodiments, in Formula (I):

$R^2$ is heteroaryl or mono-, di- or tri-substituted heteroaryl, wherein said heteroaryl is selected from pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, pyridyl, pyrazinyl, furanyl, thienyl, pyrimidinyl, pyridazinyl, pyridonyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof, wherein each said optional substituent on said heteroaryl is independently selected from halogen, —$(C_1$-$C_3)$alkyl, and —$(C_1$-$C_3)$haloalkyl wherein the alkyl in —$(C_1$-$C_3)$alkyl is optionally substituted with 1, 2, or 3 substituents independently selected from halogen, OH, $(CH_2)_nO(C_1$-$C_3)$alkyl, and $(O)_{0-1}(C_1$-$C_3)$ haloalkyl, wherein n is 0-2.

In another alternative of each of the preceding embodiments, in Formula (I):

$R^2$ is selected from pyrimidinyl and mono-, di- or tri-substituted pyrimidinyl, wherein each said substituent is independently selected from halogen, —$(C_1$-$C_3)$ alkyl, and —$(C_1$-$C_3)$haloalkyl wherein the alkyl in —$(C_1$-$C_3)$alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

In another alternative of each of the preceding embodiments, in Formula (I):

$R^2$ is selected from pyrimidinyl and mono-, di- or tri-substituted pyrimidinyl, wherein each said substituent is independently selected from —$(C_1$-$C_3)$alkyl wherein alkyl is optionally substituted with 1, 2, or 3 substituents independently selected from halogen, OH, $(CH_2)_nO(C_1$-$C_3)$alkyl, —$(O)_{0-1}(C_1$-$C_3)$haloalkyl, wherein n is 0-2.

In another alternative of each of the preceding embodiments, in Formula (I):

$R^2$ is selected from heterocycloalkyl and mono-, di- or tri-substituted heterocycloalkyl, wherein each said substituent is independently selected from halogen, oxo, —$(C_1$-$C_3)$alkyl, and —$(C_1$-$C_3)$haloalkyl wherein the alkyl in ($C_1$-$C_3$)alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2

In another alternative of each of the preceding embodiments, in Formula (I):

$R^2$ is selected from heterocycloalkyl and mono-, di- or tri-substituted heterocycloalkyl, wherein said heterocycloalkyl is selected from piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, lactam, and pyrrolidinone, and oxides thereof, and wherein each said optional substituent on said heterocycloalkyl is independently selected from halogen, oxo, —($C_1$-$C_3$)alkyl, and —($C_1$-$C_3$)haloalkyl wherein the alkyl in —($C_1$-$C_3$)alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2

In another alternative of each of the preceding embodiments, in Formula (I):

$R^2$ is selected from pyrrolidinyl and mono-, di- or tri-substituted pyrrolidinyl, wherein each said optional substituent on said pyrrolidinyl group is independently selected from ($C_1$-$C_3$)alkyl and oxo wherein the alkyl in —($C_1$-$C_3$)alkyl is optionally substituted with 1, 2, or 3 substituents independently selected from halogen, OH, $(CH_2)_nO(C_1$-$C_3)$alkyl, and —$(O)_{0-1}(C_1$-$C_3)$haloalkyl, wherein n is 0-2.

In another alternative of each of the preceding embodiments, in Formula (I):

$R^2$ is $C(O)NR^{2A}R^{2B}$, wherein:

$R^{2A}$ is selected from H and —($C_1$-$C_3$)alkyl, and $R^{2B}$ is selected from H and —($C_1$-$C_3$)alkyl.

In another alternative of each of the preceding embodiments, in Formula (I):

$R^2$ is selected from $CH_3$, cyclopropyl, cyclopropyl substituted with fluoro, cyclobutyl, cyclobutyl substituted with fluoro, $C(O)NH(C_1$-$C_3$alkyl), ($C_1$-$C_3$alkyl), ($C_1$-$C_3$haloalkyl),

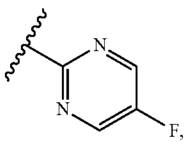

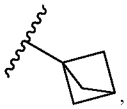

,

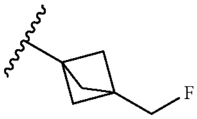

,

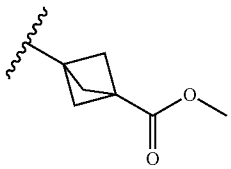

,

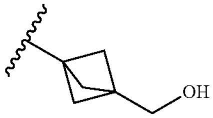

, and

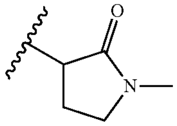

.

In an alternative of each of the preceding embodiments, in Formula (I):

the moiety

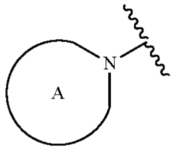

is selected from:

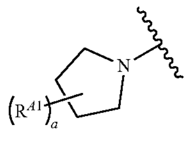

,

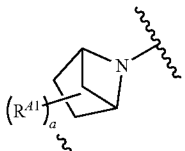

, and

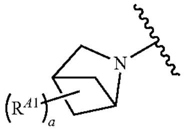

, wherein a is 0, 1, or 2; and each $R^{A1}$ is independently selected from halogen, OH, —($C_1$-$C_6$)alkyl, —($C_1$-$C_6$)alkyl-OH, and —($C_1$-$C_6$)alkyl-CN.

In another alternative of each of the preceding embodiments, in Formula (I):

the moiety

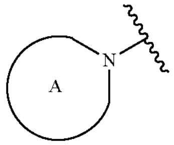

is selected from:

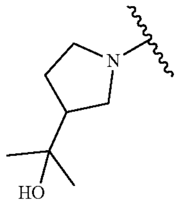

,

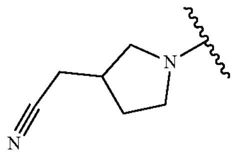

,

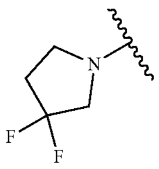

,

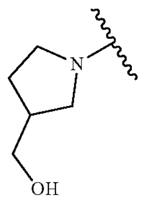

,

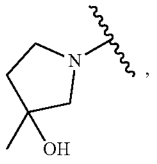

, and

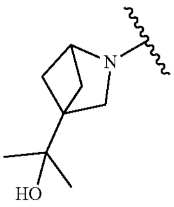

.

In another alternative of each of the preceding embodiments, in Formula (I):

the moiety

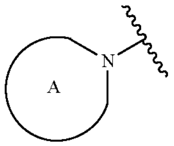

is selected from:

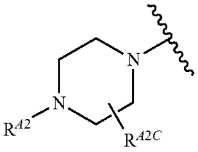,
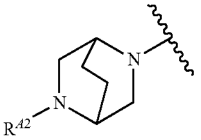,
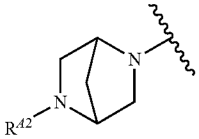,
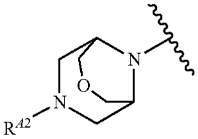,
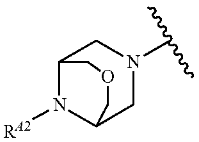, and
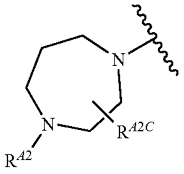, wherein $R^{A2}$ is selected from H, —($C_1$-$C_6$)alkyl, —($C_1$-$C_6$)alkyl-OH, —($C_1$-$C_6$)alkyl-CN, $S(O)_2$($C_1$-$C_3$)alkyl, optionally substituted cyclopropyl, optionally substituted cyclobutyl, optionally substituted cyclopentyl, optionally substituted oxetanyl, optionally substituted tetrahydrofuranyl, optionally substituted thietanyl dioxide, optionally substituted tetrahydrothiophenyl dioxide, wherein each said optional substituent is 1, 2, or 3 substituents independently selected from halogen, oxo, —($C_1$-$C_3$)alkyl, and —($C_1$-$C_3$)haloalkyl; and $R^{A2C}$ is selected from H and —($C_1$-$C_6$)alkyl.

In one such embodiment, $R^{A2C}$ is selected from H and $CH_3$. In another such embodiment, $R^{A2C}$ is H. In another such embodiment, $R^{A2C}$ is $CH_3$.

In another alternative of each of the preceding embodiments, in Formula (I):

the moiety

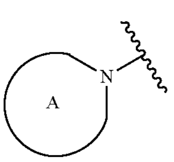 is 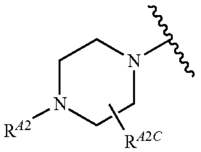.

A subembodiment of this aspect of the invention is realized when $R^{A2}$ is:

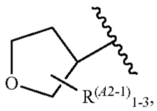

wherein $R^{(A2\text{-}1)}$ is selected from the group consisting of OH, $C_1$-$C_3$ alkyl, $OCH_3$, F, and CN. A further subembodiment of this aspect of the invention is realized when and $R^{A2C}$ is hydrogen or $CH_3$.

In another alternative of each of the preceding embodiments, in Formula (I):

the moiety

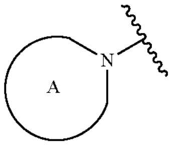

is selected from:

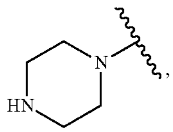,
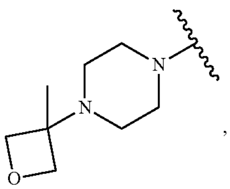,
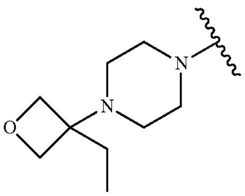,
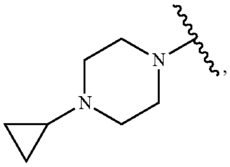,
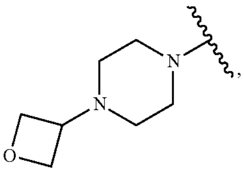,
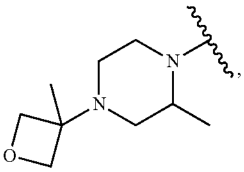,
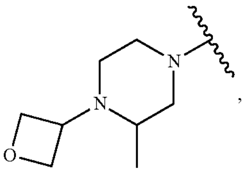,
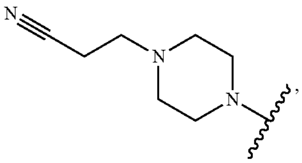,
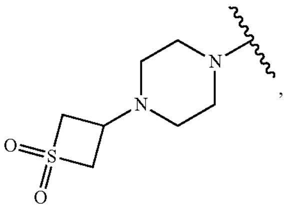,
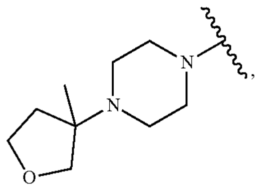,
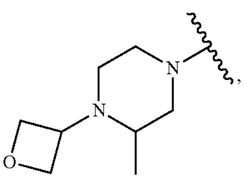,
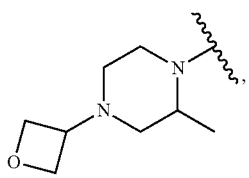, -continued

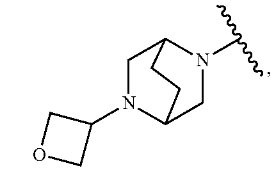,
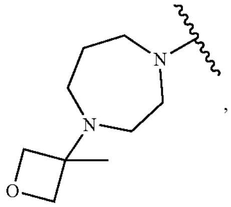,
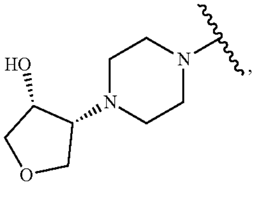,
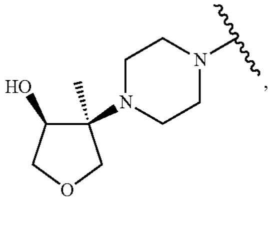,
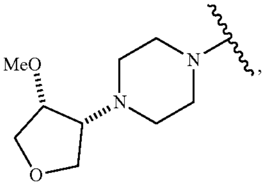,
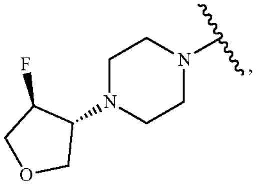,
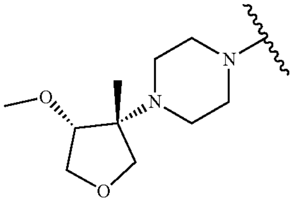,
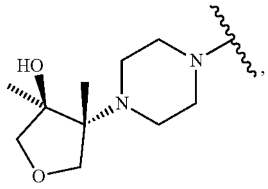,
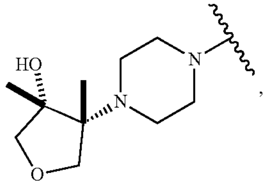,
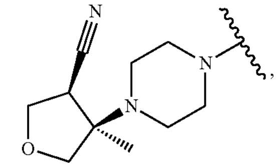,
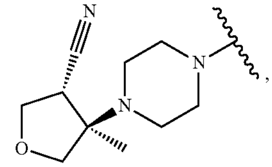,
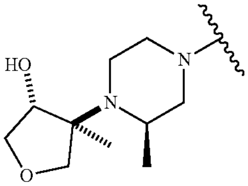,
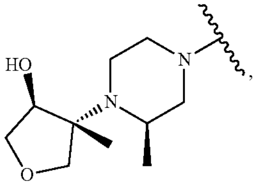,
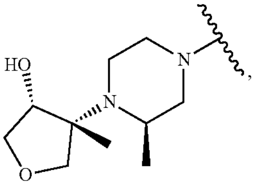,
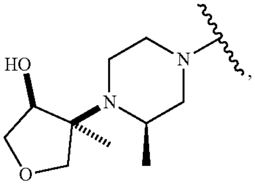,
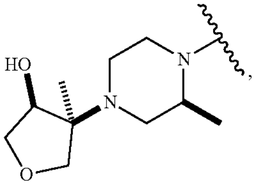, -continued

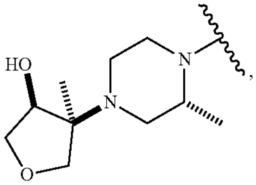,
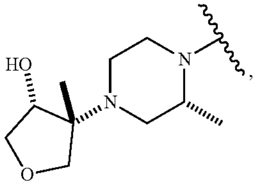, and
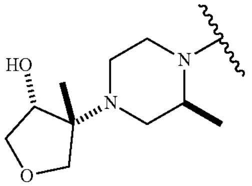

In another alternative of each of the preceding embodiments, in Formula (I):

the moiety

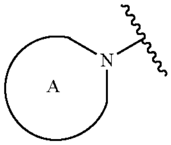

is selected from:

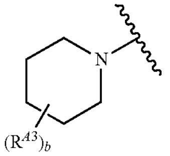,
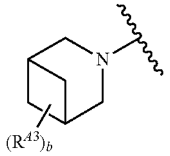,
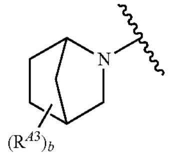,
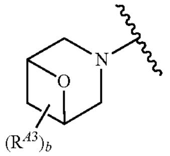,
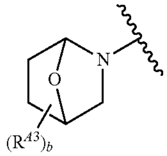,
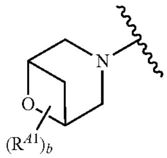 and
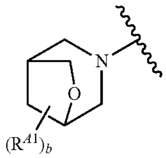

wherein:

b is 0, 1, 2, or 3; and each $R^{A3}$ is independently selected from H, halogen, $NH_2$, OH, oxo, —$(C_1$-$C_3)$alkyl, —$(C_1$-$C_3)$alkyl-OH, —$(C_1$-$C_3)$alkyl-CN, —$(C_1$-$C_3)$haloalkyl, $O(C_1$-$C_3)$alkyl, $S(O)_2(C_1$-$C_3)$alkyl, optionally substituted cyclopropyl, optionally substituted cyclobutyl, optionally substituted cyclopentyl, optionally substituted azetidinyl, optionally substituted oxetanyl, optionally substituted tetrahydrofuranyl, optionally substituted thietanyl dioxide, optionally substituted tetrahydrothiophenyl dioxide, and optionally substituted heteroaryl, wherein each said optional substituent is 1, 2, or 3 substituents independently selected from halogen, oxo, OH, —$(C_1$-$C_3)$alkyl, and —$(C_1$-$C_3)$haloalkyl.

In another alternative of each of the preceding embodiments, in Formula (I):

the moiety
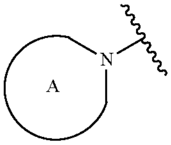
is
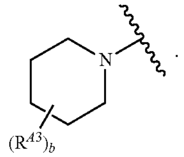
.
In another alternative of each of the preceding embodiments, in Formula (I):
the moiety
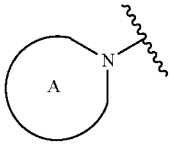
is selected from:
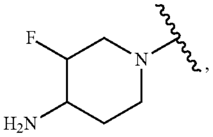, 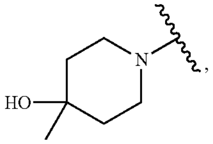, 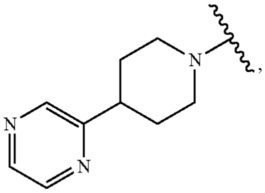, 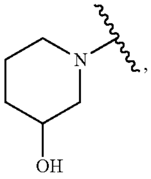, 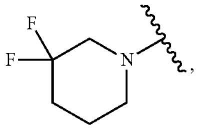, 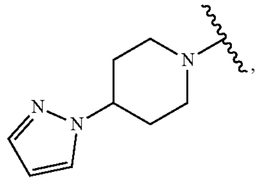, 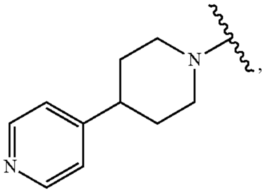, 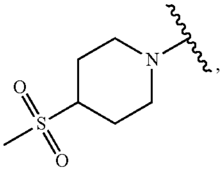, 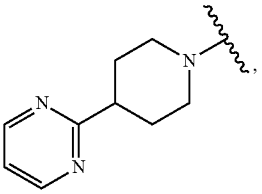, 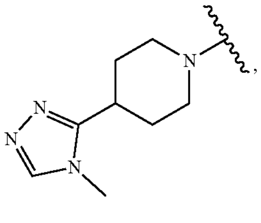,
-continued
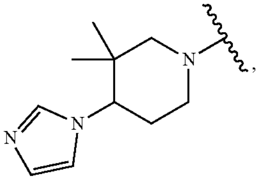, 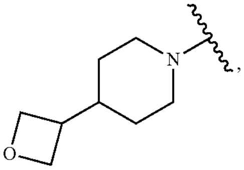, 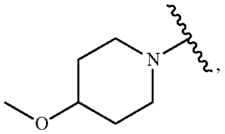, 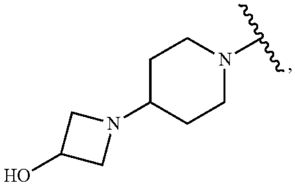, and 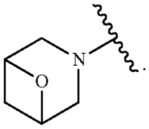.
In another alternative of each of the preceding embodiments, in Formula (I):
the moiety
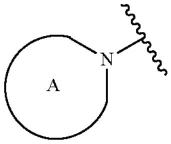
is a fused bicyclic moiety selected from:
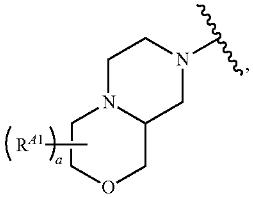, 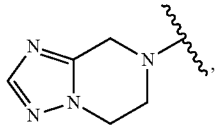, 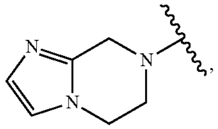, 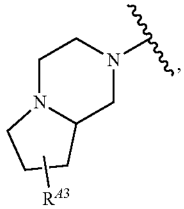, 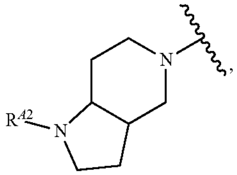, 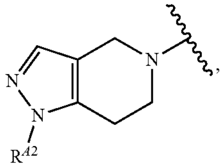, 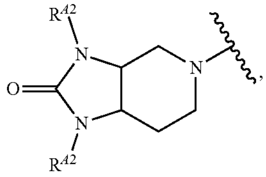, 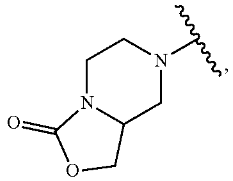, -continued

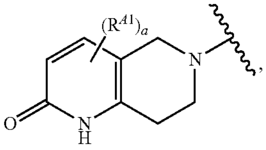,
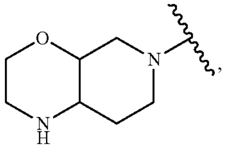,

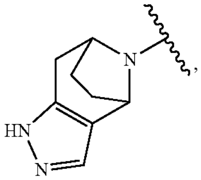,
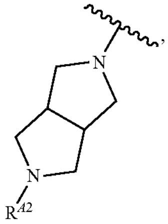,

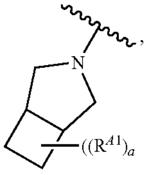,
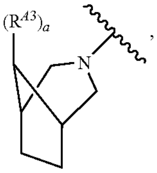,
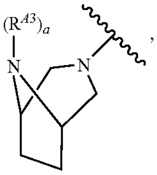, and

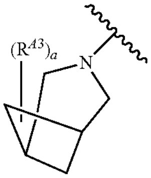, wherein a, $R^{A1}$, $R^{A2}$, and $R^{A3}$ are as defined in Formula (I).

In another alternative of each of the preceding embodiments, in Formula (I):

the moiety

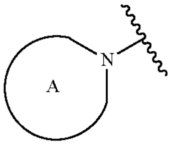

is a moiety selected from:

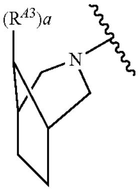,
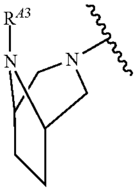, and
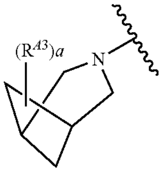, wherein a, $R^{A1}$, $R^{A2}$, and $R^{A3}$ are as defined in Formula (I).

In another alternative of each of the preceding embodiments, in Formula (I):

the moiety

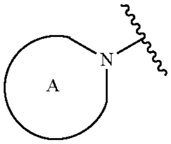

is a moiety selected from:

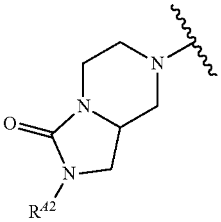,
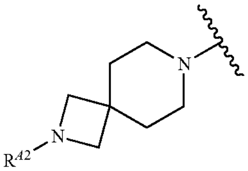,
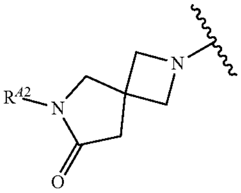,
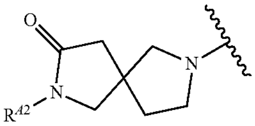,
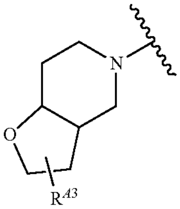,
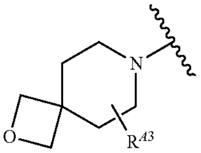,
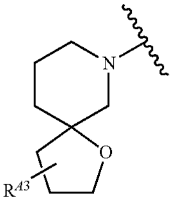,
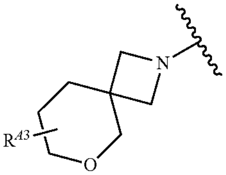, and
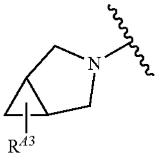, wherein $R^{A2}$ and $R^{A3}$ are as defined in Formula (I).

In another alternative of each of the preceding embodiments, in Formula (I):

the moiety

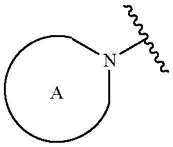

is selected from

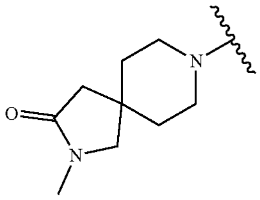, 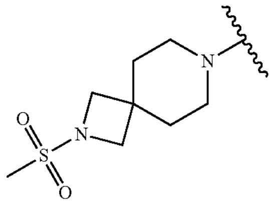,

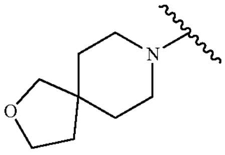, 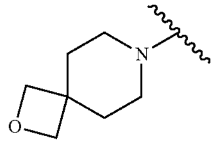,

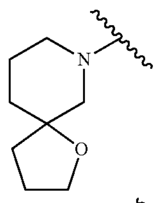, 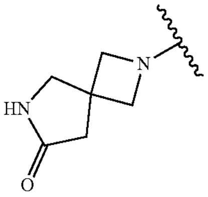,

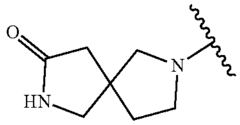, 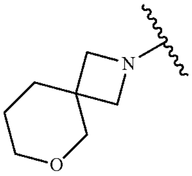, and

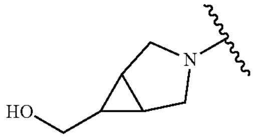.

In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below.—

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^{1}H$) and deuterium ($^{2}H$), also abbreviated as D herein. Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl $—CH_2C(O)—$ groups (keto forms) may undergo tautomerism to form hydroxyl —CH═C(OH)— groups (enol forms). Both keto and enol forms, where present, are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

"$(C_1-C_n)$Alkyl" means an aliphatic hydrocarbon group, which may be straight or branched, comprising 1 to n carbon atoms. Thus, for example, "$(C_1-C_6)$alkyl" means an aliphatic hydrocarbon group, which may be straight or branched, comprising 1 to 6 carbon atoms. Similarly, for example, "$(C_1-C_3)$alkyl" means an aliphatic hydrocarbon group, which may be straight or branched, comprising 1 to 3 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halogen atom. As appreciated by those of skill in the art, "halo" or "halogen" as used herein is intended to include chloro (Cl), fluoro (F), bromo (Br) and iodo (I). Chloro (Cl) and fluoro(F) halogens are generally preferred.

"Halogen" (or "halo") means fluorine (F), chlorine (Cl), bromine (Br), or iodine (I). Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain. Non-limiting examples of suitable alkyl groups include methyl (Me), ethyl (Et), n-propyl, isopropyl, n-butyl, i-butyl, and t-butyl.

"Aryl" means an aromatic monocyclic or multicyclic ring system comprising 6 to 14 carbon atoms, preferably 6 to 10 carbon atoms. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridone, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclo pentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

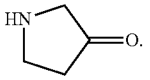

As used herein, the term "monocyclic heterocycloalkyl" refers to monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and $S(O)_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

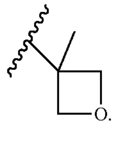 [SMILES: *C1(C)COC1]

It should be noted that in hetero-atom containing ring systems of this invention, there are no hydroxyl groups on carbon atoms adjacent to a N, O or S, as well as there are no N or S groups on carbon adjacent to another heteroatom.

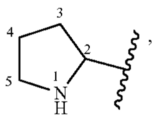

there is no —OH attached directly to carbons marked 2 and 5.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means unsubstituted or substituted and that optional substitution of an available hydrogen atom of the relevant moiety with the specified groups, radicals or moieties.

When a variable appears more than once in a group, e.g., $R^6$ in $—N(R^6)_2$, or a variable appears more than once in a structure presented herein, the variables can be the same or different.

The line ——, as a bond generally indicates a mixture of, or either of, the possible isomers, e.g., containing (R)- and (S)-stereochemistry. For example:

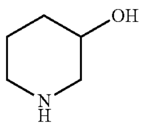 means containing both 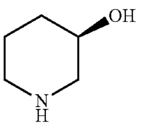 and

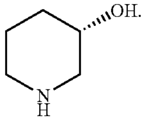

The wavy line, as used herein, indicates a point of attachment to the rest of the compound. Lines drawn into the ring systems, such as, for example:

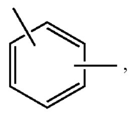

indicate that the indicated line (bond) may be attached to any of the substitutable ring carbon atoms.

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

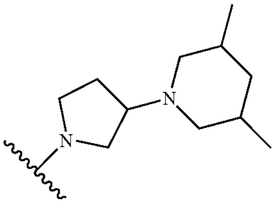

represents

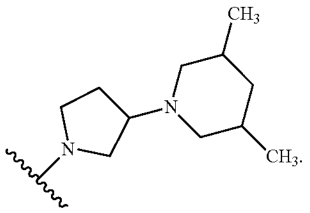

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of the invention contain one or more acidic groups or basic groups, the invention includes the corresponding pharmaceutically acceptable salts.

Thus, the compounds of the invention that contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of the invention which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of the invention simultaneously contain acidic and basic groups in the molecule the invention also includes, in addition to the salt forms mentioned, inner salts or betaines (zwitterions). Salts can be obtained from the compounds of the invention by customary methods which are known to the person skilled in the art, for example by combination with an organic or inorganic acid or base in a solvent or dispersant, or by anion exchange or cation exchange from other salts. The present invention also includes all salts of the compounds of the invention which, owing to low physiological compatibility, are not directly suitable for use in pharmaceuticals but which can be used, for example, as intermediates for chemical reactions or for the preparation of pharmaceutically acceptable salts.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof "Treatment" as used herein also refers to control, amelioration, or reduction of risks to the subject afflicted with a disease, disorder or condition in which LRRK2 is involved. The terms "preventing", or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The compounds of the present invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanthin and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanthin, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

PREPARATIVE EXAMPLES

The compounds of the invention can be prepared according to the following schemes and specific examples, or modifications thereof, using readily available starting materials, reagents and conventional synthesis procedures. In these reactions, it is also possible to make use of variants which are themselves known to those of ordinary skill in this art but are not mentioned in detail. General procedures for making the compounds claimed in this invention can be readily understood and appreciated by one skilled in the art from viewing the following schemes and descriptions.

Abbreviations used in the experimentals include the following:

| | |
|---|---|
| AcOH | Acetic Acid |
| ACN | Acetonitrile |
| aq | Aqueous |
| BHT | 3,5-Di-tert-4-butylhydroxytoluene |
| rac-BINAP | (±)-2,2'-Bis(diphenylphosphino)-1,1'-binaphthalene |
| BnBr | Benzyl bromide |
| BOC (or Boc) | tert-Butyloxycarbonyl |
| (Boc)2O | Di-tert-butyl dicarbonate |
| CDI | 1,1'-Carbonyldiimidazole |
| m-CPBA | meta-Chloroperoxybenzoic acid |
| CuTC | Copper(I) thiophene-2-carboxylate |
| DAST | (Diethylamino)sulfur trifluoride |
| DCE | Dichloroethane |
| DCM | Dichloromethane |
| DIBAL | Diisobutylaluminum hydride |
| DIEA, Hunig's Base | N,N-Diisopropylethylamine |
| DIPA | N,N-Diisopropylamine |
| DIPEA | N,N-Diisopropylethylamine |
| DMA | Dimethylacetamide |
| DMAP | N,N-dimethylpyridin-4-amine |
| DMEA | Dimethylethylamine |
| DMF | Dimethylformamide |
| DMP | Dess-Martin periodinane |
| DMSO | Dimethyl sulfoxide |
| DPPA | Diphenylphosphoryl azide |
| EtOAc | Ethyl acetate |
| EI or ESI | Electrospray ionization |
| $Et_3N$ | Triethylamine |
| H or h or hrs | Hours |
| HPLC | High performance liquid chromatography |
| $In(OTf)_3$ | Indium(III) trifluoromethanesulfonate |
| IPA | Isopropyl alcohol |
| $Ir[dF(Me)ppy]_2(dtbbpy)PF_6$ | Iridium(III) bis[2-(2,4-difluorophenyl)-5-methylpyridine-N,$C_{20}$]-4,40-di-tert-butyl-2,20-bipyridine hexafluorophosphate |
| LCMS | Liquid chromatography-mass spectrometry |

-continued

| | |
|---|---|
| MeCN | Acetonitrile |
| MeOH | Methanol |
| MS | Mass spectrometry |
| MTBA | Methyl tert-butyl ether |
| NBS | N-Bromosuccinimide |
| NCS | N-Chlorosuccinimide |
| NIS | N-Iodosuccinimide |
| NMP | N-Methyl-2-pyrrolidone |
| Oxone | Potassium peroxymonosulfate |
| PdCl2(dtbpf) | [1,1'-Bis(di-tert-butylphosphino)ferrocene] dichloropalladium(II) |
| $Pd_2dba_3$ | Tris(dibenzylideneacetone)dipalladium(0) |
| Pd/C | Palladium on Carbon |
| PE | Petroleum Ether |
| psi | Pounds per square inch |
| Pd-PEPPSI$^{2Me}$-IPent | Dichloro[1,3-bis(2,6-Di-3-pentylphenyl)imidazol-2-ylidene](2-methylpyridyl)palladium(II) |
| QuadraPure TU | MFCD07785601 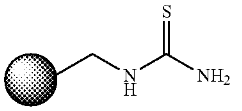 |
| Rac-BINAP Pd-G3 | (±)-2,2'-Bis(diphenylphosphino)-1,1'-binaphthalene [2-(2'-amino-1,1'-biphenyl)]palladium(II) methanesulfonate |
| rpm | revolutions per minute |
| RuPhos-Pd-G3 | (2-Dicyclohexylphosphino-2',6'-diisopropoxy-1,1'-biphenyl)[2-(2'-amino-1,1'-biphenyl)]palladium(II) methanesulfonate |
| RuPhos Pd G4 | (2-Dicyclohexylphosphino-2',6'-diisopropoxy-1,1'-biphenyl)[2-(2'-methyl amino-1,1'-biphenyl)]palladium(II) methanesulfonate |
| RT | Retention time |
| rt | Room temperature |
| SFC | Supercritical Fluid Chromatography |
| TBAF | Tetra-n-butylammonium fluoride |
| TBDPSCl | tert-Butyldiphenylchlorosilane |
| TFA | Trifluoroacetic acid |
| THF | Tetrahydrofuran |
| TLC | Thin Layer Chromatography |
| TMSCN | Trimethylsilyl cyanide |
| TsCl | 4-Toluenesulfonyl chloride |
| TsOH | p-Toluenesulfonic acid |

General Synthetic Schemes

The compounds of the invention may be prepared by methods known in the art, or according to the following general schemes and specific examples. Starting materials are available commercially or may readily be made by known methods.

General Scheme 1

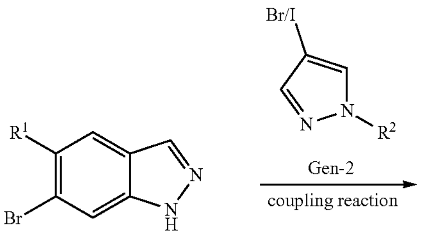

Gen-1

-continued

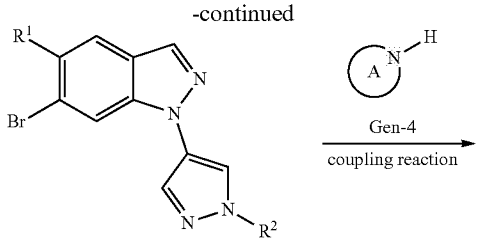

Gen-3

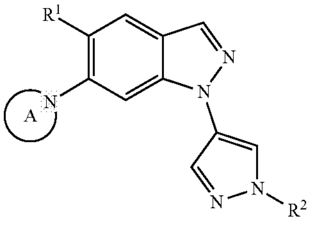

Gen-5

In General Scheme 1, commercially available (or synthetically prepared in accordance with the examples below) Gen-1 is coupled with commercially available or synthetically prepared Gen-2 through palladium or copper catalyzed chemistry to generated Gen-3. Gen-3 is coupled with diverse commercially available or synthetically prepared amines Gen-4 through a palladium catalyzed coupling reaction to generate Gen-5. A preparation of the representative compounds is described in more detail below.

General Scheme 2

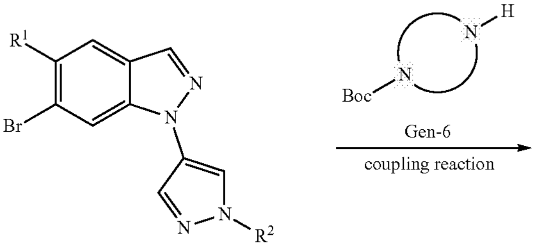

Gen-3

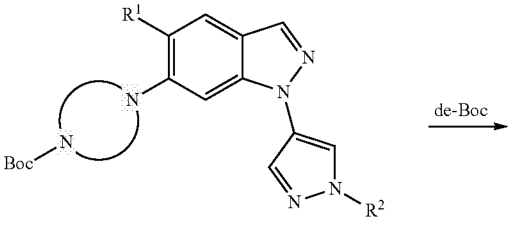

Gen-7

-continued

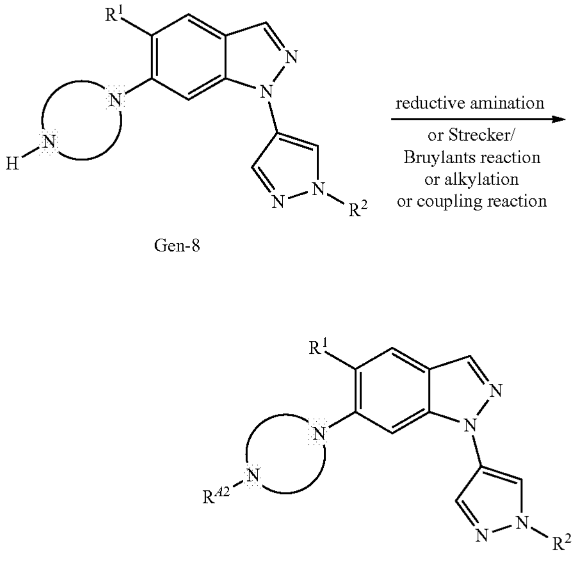

Gen-8

Gen-9

In General Scheme 2, Gen-3 is coupled with commercially available Gen-6 through a palladium catalyzed reaction to generate Gen-7. The Boc group is then removed under acidic conditions to form Gen-8. Gen-8 is then elaborated to Gen-9 through reductive amination or through a Strecker reaction following Bruylant's reaction or by an alkylation reaction or through palladium catalyzed coupling reaction. The preparation of representative compounds of the invention made by this process are described in more detail below.

General Scheme 3

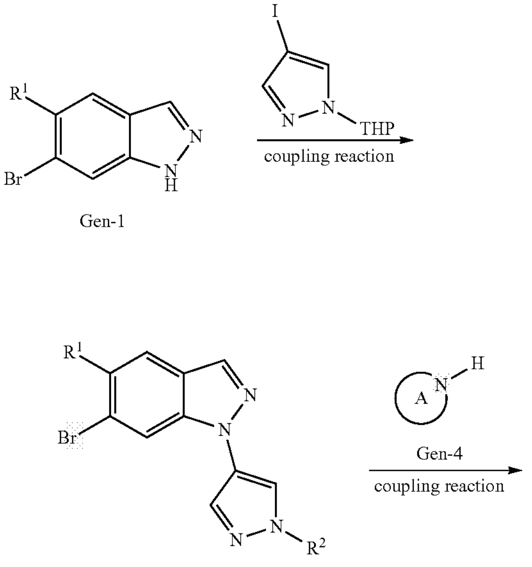

Gen-1

Gen-10

-continued

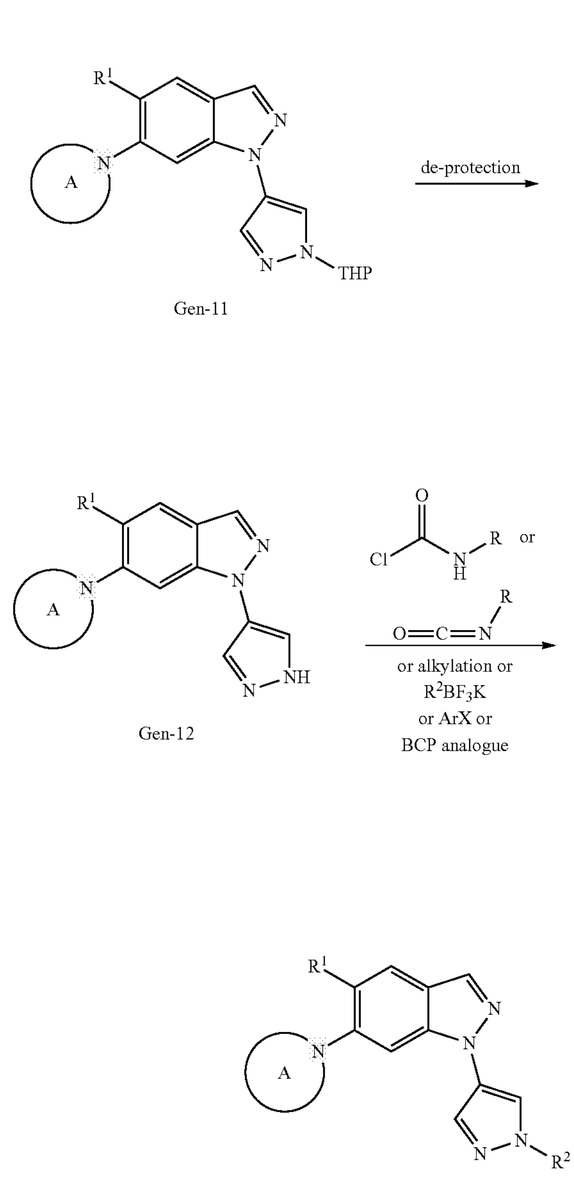

Gen-11

Gen-12

Gen-13

In General Scheme 3, Gen-1 is coupled with commercially available 4-iodo-1-(tetrahydro-2H-pyran-2-yl)-1H-pyrazole through a copper catalyzed coupling reaction to generate Gen-10, which is converted to Gen-11 by coupling with commercially available or synthetically prepared amines (Gen-4) under palladium catalyzed conditions. Gen-11 is deprotected under acidic conditions to generate Gen-12, which is then elaborated to Gen-13 by reacting with diverse substitute amino formyl chlorides, or diverse isocyanates, or with diverse alkylation reagents, or reacted with diverse aryl chloride or by coupling with diverse aryl halide or by Chan-Lan coupling with diverse aryl potassium trifluoroborate or react with bicycloalkyl bromide or iodide analogue through photoredox chemistry. Representative compounds of the invention which were made by this process are described in more detail below.

General Scheme 4

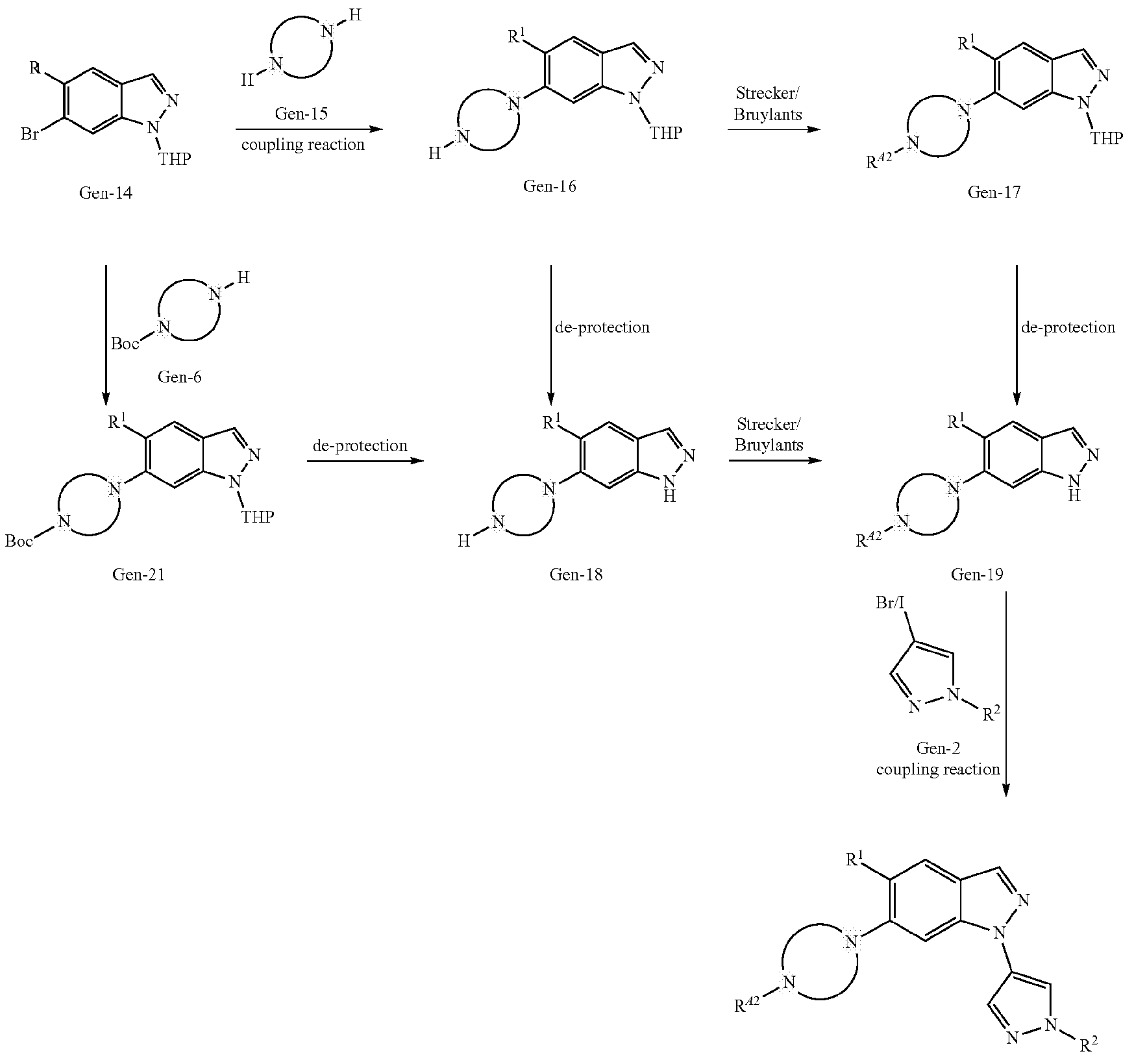

Gen-20

In General Scheme 4, Gen-14 is coupled with commercially available Gen-15 through a palladium catalyzed reaction to generate Gen-16, which is converted to Gen-17 by the Strecker reaction following Bruylants' reaction. Gen-17 may then be deprotected to form Gen-19. Gen-19 is then coupled with commercially available or synthetically prepared Gen-2 to generate Gen-20 through copper catalyzed conditions. Representative compounds of the invention which were made by this process are described in more detail below.

In General Scheme 4, Gen-16 also can be deprotected to form Gen-18. Gen-18 is then converted to Gen-19 through the Strecker reaction, followed by Bruylants' reaction.

In General Scheme 4, Gen-14 also can coupled with a commercially available Gen-6 through a palladium catalyzed reaction to generate Gen-21, which is then deprotected under acidic conditions to form Gen-18.

General Scheme 5

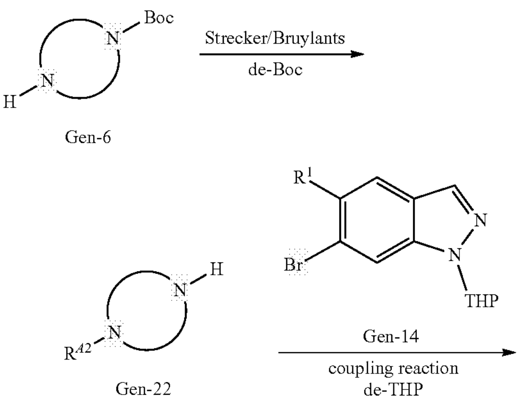

-continued

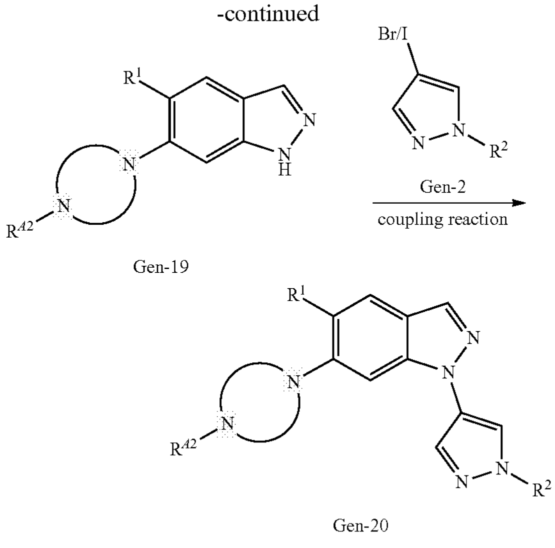

Gen-19

Gen-20

In General Scheme 5, Gen-6 can be converted to Gen-22 through the Strecker reaction followed by Bruylants' reaction, then Boc group deprotection. Gen-22 coupling with Gen-14, then deprotection of the THP group provided Gen-19. Gen-19 can be coupled with commercially available or synthetically prepared Gen-2 to generate Gen-20 through copper catalyzed conditions. Representative compounds of the invention which were made by this process are described in more detail below.

General Scheme 6

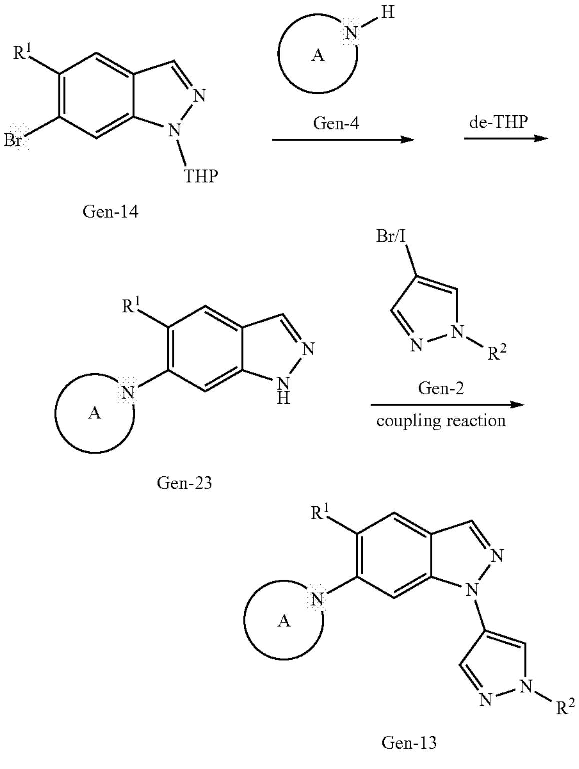

Gen-14

Gen-23

Gen-13

In General Scheme 6, Gen-14 is converted to Gen-23 by coupling with commercially available or synthetically prepared amines (Gen-4) under palladium catalyzed conditions followed by deprotection of the THP group. Coupling of Gen-23 with commercially available or synthetically prepared pyrazole bromides or iodides (Gen-2) through copper catalyzed conditions yield Gen-13. Representative compounds of the invention which were made by this process are described in more detail below.

General Scheme 7

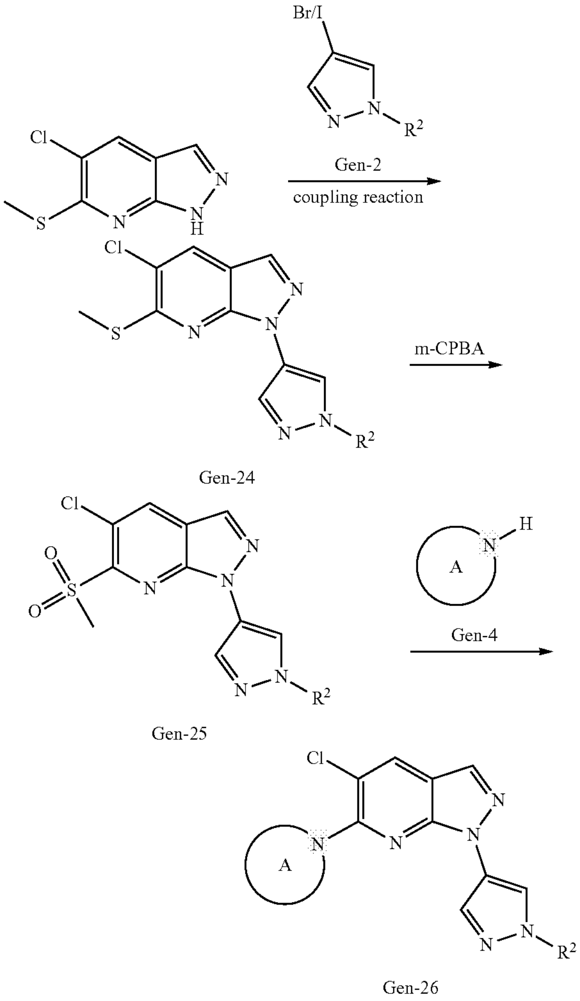

Gen-24

Gen-25

Gen-26

In General Scheme 7, synthetically prepared 5-chloro-6-(methylthio)-1H-pyrazolo[3,4-b]pyridine can be coupled with commercially available or synthetically prepared Gen-2 through copper catalyzed chemistry to generate Gen-24. Gen-24 was oxidized to Gen-25, and then coupled with diverse commercially available or synthetically prepared amines Gen-4 through a palladium catalyzed coupling reaction to provide Gen-26. A preparation of the representative compounds is described in more detail below.

General Experimental Information:

Unless otherwise noted, all reactions were magnetically stirred.

Unless otherwise noted, when diethyl ether was used in the experiments described below, the diethyl ether was Fisher ACS-certified material stabilized with BHT.

Unless otherwise noted, "concentrated" means evaporating the solvent from a solution or mixture using a rotary evaporator or vacuum pump.

Unless otherwise noted, flash chromatography was carried out on an Isco®, Analogix®, or Biotage® automated chromatography system using a commercially available cartridge as the column. Columns may be purchased from Isco, Analogix, Biotage, Varian, or Supelco and were generally filled with silica gel as the stationary phase. Aqueous solutions were concentrated on a Genevac® or were lyophilized.

Unless otherwise noted, all LRRK2 $IC_{50}$ data presented in tables refers to the LRRK2 G2019S Km ATP LanthaScreen™ Assay that is described in the Biological Assay section below.

Synthesis of Common Intermediates

Synthesis of Common Intermediates I-1: 6-bromo-5-chloro-1-(1-methyl-1H-pyrazol-4-yl)-1H-indazole Scheme 1

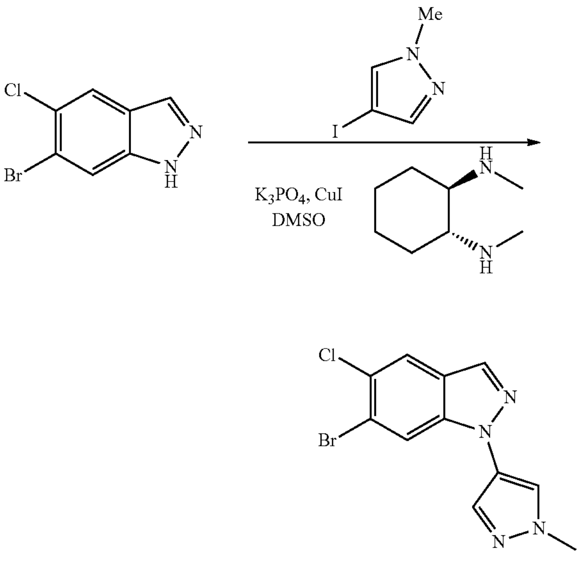

I-1

To a 5 L 4-necked round-bottom flask was added 6-bromo-5-chloro-1H-indazole (200 g, 864 mmol, 1.00 equiv.), 4-iodo-1-methyl-1H-pyrazole (269 g, 1296 mmol, 1.50 equiv.), (1R,2R)—N1,N2-dimethylcyclohexane-1,2-diamine (61.4 g, 432 mmol, 0.50 equiv.), CuI (32.9 g, 172 mmol, 0.20 equiv.), $K_3PO_4$ (550 g, 2592 mmol, 3.00 equiv.) and DMSO (2 L). The resulting mixture was stirred at 90° C. under a nitrogen atmosphere for 5 h. The mixture was allowed to cool to room temperature. The resulting mixture was diluted with water (5 L) and extracted with EtOAc (3×3 L). The combined organic layers were washed with brine, dried over anhydrous $Na_2SO_4$, and concentrated in vacuo to afford a residue which was purified by column chromatography on silica gel (EtOAc:petroleum ether=1:1) to afford the title compound (I-1). $^1$H NMR (400 MHz, DMSO-$d_6$) δ 8.40 (s, 1H), 8.32-8.27 (m, 1H), 8.16 (s, 1H), 8.15-8.10 (m, 1H), 7.92 (s, 1H), 3.94 (s, 3H). MS (EI) m/z: 313 $[M+H]^+$.

Synthesis of Common Intermediates I-2: 6-bromo-5-chloro-1-(1-cyclopropyl-1H-pyrazol-4-yl)-1H-indazole Scheme 2

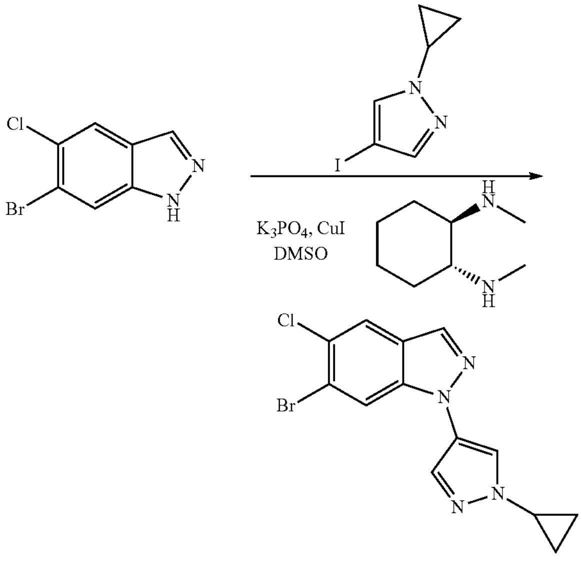

I-2

To a 5 L 4-necked round-bottom flask was added 6-bromo-5-chloro-1H-indazole (150 g, 648 mmol, 1.00 equiv.), 1-cyclopropyl-4-iodopyrazole (166 g, 712 mmol, 1.10 equiv.), (1R,2R)—N1,N2-dimethylcyclohexane-1,2-diamine (46.1 g, 324 mmol, 0.50 equiv.), CuI (24.7 g, 129 mmol, 0.20 equiv.), $K_3PO_4$ (412 g, 1944 mmol, 3.00 equiv.) and DMSO (3 L). The resulting mixture was stirred under a nitrogen atmosphere at 90° C. for 18 h. The mixture was allowed to cool to room temperature and diluted with water (5 L). The resulting mixture was extracted with EtOAc (3×3 L). The combined organic layers were washed with brine and dried over anhydrous $Na_2SO_4$. After filtration, the filtrate was concentrated in vacuo to afford a residue which was purified by column chromatography on silica gel (EtOAc:petroleum ether=1:2) to afford the title compound (I-2). $^1$HNMR (300 MHz, DMSO-$d_6$) δ 8.48 (s, 1H), 8.30 (s, 1H), 8.22-8.11 (m, 2H), 7.92 (s, 1H), 3.83 (tt, J=7.5, 3.9 Hz, 1H), 1.17 (q, J=4.0 Hz, 2H), 1.10-0.90 (m, 2H). MS (EI) m/z: 337 $[M+H]^+$.

Synthesis of Common Intermediates I-3: 5-chloro-1-(1-cyclopropyl-1H-pyrazol-4-yl)-6-(piperazin-1-yl)-1H-indazole Scheme 3

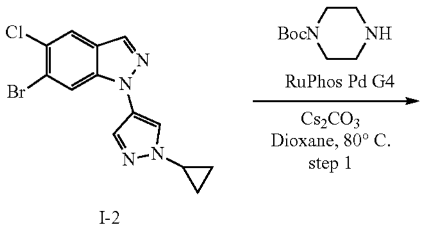

I-2

-continued

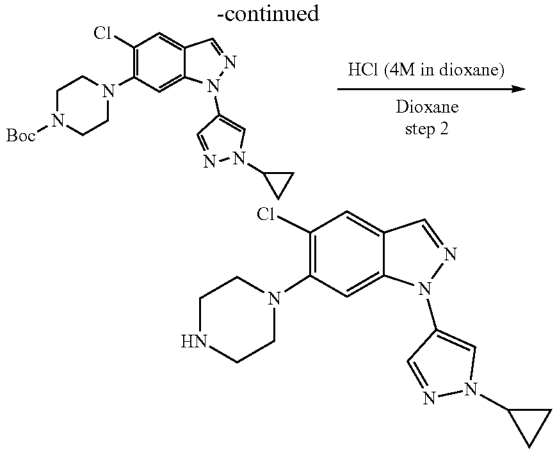

I-3

Step 1: tert-butyl 4-(5-chloro-1-(1-cyclopropyl-1H-pyrazol-4-yl)-1H-indazol-6-yl)piperazine-1-carboxylate To a vial was added I-2 (2.0 g, 5.9 mmol), tert-butyl piperazine-1-carboxylate (1.38 g, 7.43 mmol), RuPhos Pd G4 (0.50 g, 0.59 mmol), $Cs_2CO_3$ (3.86 g, 11.8 mmol) and dioxane (30 ml). The mixture was evacuated and back-filled with N2 five times, then stirred at 80° C. for 18 h. The mixture was diluted with EtOAc and water. The aqueous layer was washed with EtOAc (3×). The combined organic layers were washed with brine, dried over $MgSO_4$, filtered and concentrated in vacuo to afford a residue which was purified by column chromatography on silica gel (EtOAc in hexane: 0-50% gradient) to afford tert-butyl 4-(5-chloro-1-(1-cyclopropyl-1H-pyrazol-4-yl)-1H-indazol-6-yl)piperazine-1-carboxylate.

Step 2: 5-chloro-1-(1-cyclopropyl-1H-pyrazol-4-yl)-6-(piperazin-1-yl)-1H-indazole (I-3)

To the flask containing tert-butyl 4-(5-chloro-1-(1-cyclopropyl-1H-pyrazol-4-yl)-1H-indazol-6-yl)piperazine-1-carboxylate (1.37 g, 3.09 mmol) was added dioxane (15 ml) and HCl (4 M in dioxane) (5.0 ml, 20 mmol). The mixture was stirred at rt for 20 h, then evaporated in vacuo to afford the title compound as HCl salt (I-3), which was used in next step directly. $^1$H NMR (600 MHz, DMSO-$d_6$) δ 8.41 (s, 1H), 8.15 (s, 1H), 7.92 (s, 1H), 7.89 (s, 1H), 7.18 (s, 1H), 3.85 (tt, J=7.4, 3.8 Hz, 1H), 3.54 (s, 1H), 3.03-2.93 (m, 4H), 2.92-2.79 (m, 4H), 1.16 (p, J=4.8 Hz, 2H), 1.07-0.97 (m, 2H). MS (EI) m/z: 343 $[M+H]^+$.

Synthesis of Common Intermediates I-4: 6-bromo-5-chloro-1-(1-(tetrahydro-2H-pyran-2-yl)-1H-pyrazol-4-yl)-1H-indazole Scheme 4

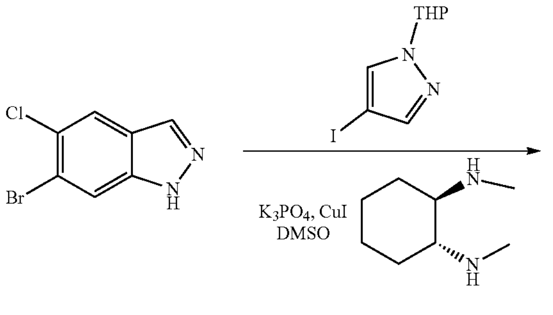

-continued

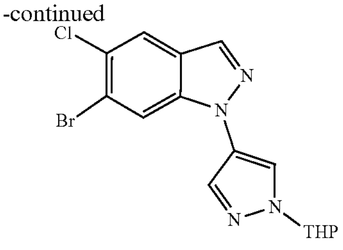

I-4

A flask was charged with CuI (18.8 g, 98.9 mmol), (1R,2R)—N1,N2-dimethylcyclohexane-1,2-diamine (35.2 g, 247 mmol) and DMSO (1.0 L). The mixture was stirred at rt for 5 min to form a pale blue solution. Another 2 L bottle flask was charged with $K_3PO_4$ (315 g, 1.48 mol), 6-bromo-5-chloro-1H-indazole (143 g, 494 mmol) and 4-iodo-1-(tetrahydro-2H-pyran-2-yl)-1H-pyrazole (165 g, 593 mmol). The catalyst solution was then added to this flask. The flask was then sealed, removed from the hood and then heated at 70° C. for 16 h. The mixture was then allowed to cool to rt, then diluted with water and extracted with EtOAc three times. The combined organic layers were washed with brine, dried over $Na_2SO_4$, filtered and concentrated in vacuo to give a residue which was purified by column chromatography (EtOAc in petroleum ether: 10-100% gradient) to afford the title compound. $^1$HNMR (400 MHz, DMSO-$d_6$) δ: 8.07 (s, 1H), 8.00 (s, 1H), 7.89 (s, 1H), 7.88 (s, 1H), 7.86 (s, 1H), 5.46-5.49 (m, 1H), 4.10-4.14 (m, 1H), 3.73-3.80 (m, 1H), 2.07-2.18 (m, 3H), 1.64-1.76 (m, 3H). MS (EI) m/z: 383 $[M+H]^+$.

Synthesis of Common Intermediates I-5: 5-chloro-6-(4-(3-methyloxetan-3-yl)piperazin-1-yl)-1-(1H-pyrazol-4-yl)-1H-indazole Scheme 5

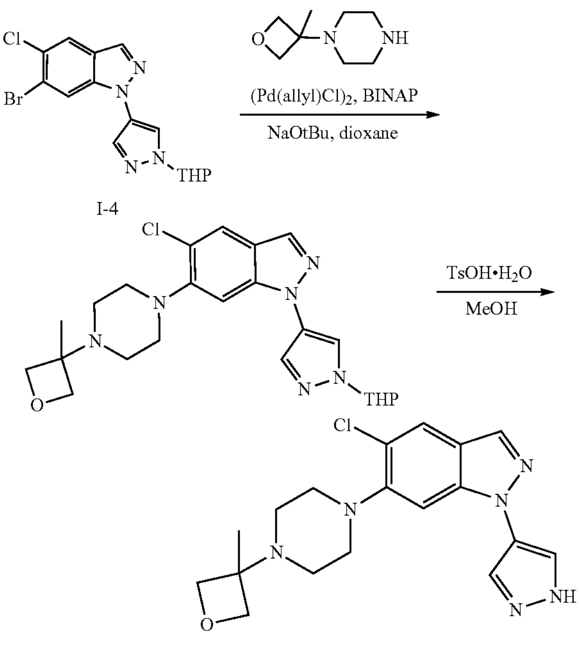

I-4

I-5

Step 1: 5-chloro-6-(4-(3-methyloxetan-3-yl)piperazin-1-yl)-1-(1-(tetrahydro-2H-pyran-2-yl)-1H-pyrazol-4-yl)-1H-indazole To a flask 1 was added $(Pd(allyl)Cl)_2$ (4.79 g, 13.1 mmol) and BINAP (16.3 g, 26.2 mmol). The the mixture was then evacuated and back-filled with N2 for three times, then degassed dioxane (400 mL) was added to the flask. The mixture was stirred at rt.

To another flask 2 was added I-4 (100 g, 262 mmol, 1.00 eq) and 1-(3-methyloxetan-3-yl)piperazine (60.6 g, 393 mmol, 1.50 eq). The mixture was then evacuated and back-filled with N2 for three times, then degassed dioxane (300 mL) and DIEA (68.5 mL, 393 mmol, 1.50 eq) were added. The mixture was then stirred at rt for 15 min. The suspension from flask 1 was added to a second bottle under N2. To this mixture was added NaOt-Bu (2 M, 262 mL, 524 mmol, 2.00 eq) (2M in THF) under an ice/water bath. The mixture was stirred at 40° C. for 14 h. Then the reaction was cooled to rt, diluted with water and extracted with EtOAc three times. The combined organic layers were washed with brine, dried over $Na_2SO_4$, filtered and concentrated in vacuo to give a crude product, which was used into the next step without further purification. MS (EI) m/z: 457 $[M+H]^+$.

Step 2: 5-chloro-6-(4-(3-methyloxetan-3-yl)piperazin-1-yl)-1-(1H-pyrazol-4-yl)-1H-indazole (I-5)

To a 2 L flask was added 5-chloro-6-(4-(3-methyloxetan-3-yl)piperazin-1-yl)-1-(1-(tetrahydro-2H-pyran-2-yl)-1H-pyrazol-4-yl)-1H-indazole (106 g, 232 mmol, 1.00 eq) and MeOH (1.0 L). To this suspension was added $TsOH{\cdot}H_2O$ (110 g, 580 mmol, 2.50 eq). The reaction mixture was stirred at 30° C. for 3 h, then cooled to rt. The mixture was filtered. The solid was dissolved in water (2.0 L), then the solution was adjusted to pH>12 by adding $Na_2CO_3$ (sat.). Some precipitate formed. After filtration, the solid was washed with water (500 mL) and EtOAc (300 mL), then dried in vacuo to afford the title compound I-5. $^1$HNMR (400 MHz, DMSO-$d_6$) δ: 8.17-8.15 (m, 3H), 7.93 (s, 1H), 7.24 (s, 1H), 4.45-4.43 (m, 2H), 4.16-4.15 (m, 2H), 3.40-2.90 (m, 4H), 2.48-2.42 (m, 4H), 1.33 (s, 3H). MS (EI) m/z: 373 $[M+H]^+$.

Synthesis of Common Intermediates I-6: 3-methyl-1-(3-methyloxetan-3-yl)piperazine Scheme 6

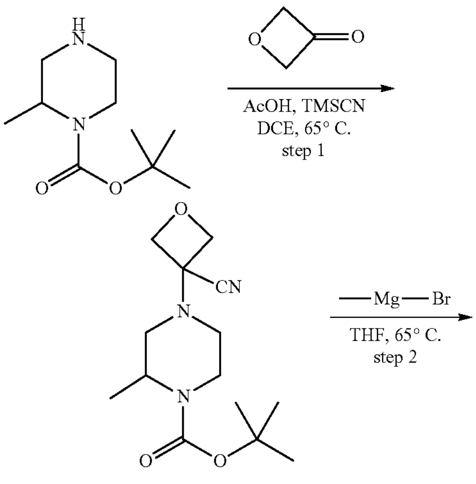

-continued

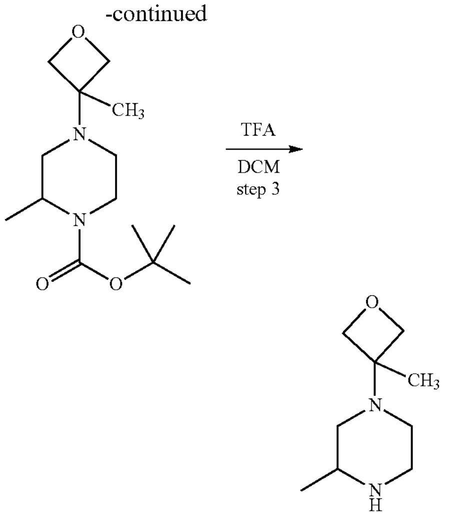

I-6

Step 1: tert-butyl 4-(3-cyanooxetan-3-yl)-2-methylpiperazine-1-carboxylate tert-Butyl 2-methylpiperazine-1-carboxylate (409 mg, 2.04 mmol) was added to a 20 mL vial. DCE (8 ml) was added under $N_2$. 3-oxetanone (200 μl, 3.12 mmol) was then added, followed by the addition of AcOH (180 μl, 3.14 mmol). The solution was then stirred at 65° C. for 30 min, then TMSCN (330 μl, 2.462 mmol) was added. The reaction mixture was stirred at 65° C. for 16 h, then diluted with DCM and 1M NaOH. The aqueous layer was extracted with DCM three times. The combined organic layers were washed with brine, dried over $MgSO_4$, filtered and concentrated in vacuo to afford tert-butyl 4-(3-cyanooxetan-3-yl)-2-methylpiperazine-1-carboxylate, which was used in next step directly. MS (EI) m/z: 226 $[M-56+H]^+$.

Step 2: tert-butyl 2-methyl-4-(3-methyloxetan-3-yl)piperazine-1-carboxylate

To a vial containing tert-butyl 4-(3-cyanooxetan-3-yl)-2-methylpiperazine-1-carboxylate (509.5 mg, 1.811 mmol), THF (9 ml) was added. To this solution was added methylmagnesium bromide (2.8 ml, 9.5 mmol) dropwise. The mixture was then heated at 65° C. for 6 h, allowed to cool to room temperature, and then quenched with 1 M NaOH. The aqueous phase was extracted twice with DCM. The combined organic layers were washed with brine, dried over $Na_2SO_4$, filtered and concentrated in vacuo to afford a residue which was then purified by column chromatography on silica gel (EtOAc in hexane: 0-100% gradient, ELSD detector) to give tert-butyl 2-methyl-4-(3-methyloxetan-3-yl)piperazine-1-carboxylate. $^1$H NMR (600 MHz, Chloroform-d) δ 4.71-4.55 (m, 2H), 4.09 (dd, J=16.6, 5.2 Hz, 2H), 4.00-3.59 (m, 2H), 2.99-2.79 (m, 1H), 2.65-2.46 (m, 1H), 2.44-2.31 (m, 1H), 2.30-2.18 (m, 1H), 2.11 (t, J=10.4 Hz, 1H), 1.50-1.35 (m, 12H), 0.79 (d, J=6.3 Hz, 3H).

Step 3: 3-methyl-1-(3-methyloxetan-3-yl)piperazine (I-6)

To a vial containing tert-butyl 2-methyl-4-(3-methyloxetan-3-yl)piperazine-1-carboxylate (240 mg, 0.888 mmol) was added DCM (5000 μl) and TFA (1000 μl, 12.98 mmol). The mixture was stirred at rt for 4 h. The solvent was then evaporated to afford the title compound as a TFA salt, which was used in next step directly. $^1$H NMR (600 MHz, DMSO-$d_6$) δ 4.60 (d, J=5.4 Hz, 2H), 4.14 (dd, J=43.6, 5.7 Hz, 2H), 3.42-3.18 (m, 2H), 3.10-2.96 (m, 1H), 2.95-2.84 (m, 1H), 2.84-2.63 (m, 2H), 2.61-2.50 (m, 1H), 1.47 (s, 3H), 0.89 (d, J=6.3 Hz, 3H).

Synthesis of Common Intermediates I-7: 6-bromo-5-chloro-1-(1-(5-fluoropyrimidin-2-yl)-1H-pyrazol-4-yl)-1H-indazole Scheme 7

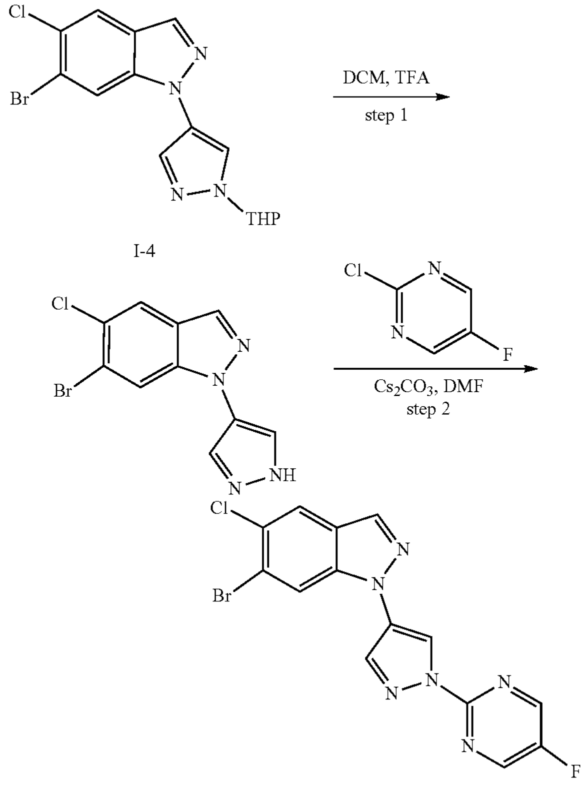

I-7

Step 1: 6-bromo-5-chloro-1-(1H-pyrazol-4-yl)-1H-indazole

I-4 (547 mg, 1.43 mmol) was dissolved in DCM (5 mL) in a 2 dram vial. HCl in dioxane (4M, 5 mL, 20 mmol) was added. The reaction mixture was heated at 50° C. for 18 h, then 1.5 mL of concentrated HCl was added, and then heated further at 50° C. for 6 h. The reaction was then quenched with 1M NaOH and extracted with 3:1 $CHCl_3$:IPA (3×). The combined organic layers were washed with brine, dried over $Na_2SO_4$, filtered and concentrated in vacuo to afford 6-bromo-5-chloro-1-(1H-pyrazol-4-yl)-1H-indazole. MS (EI) m/z: 297 [M+H]$^+$.

Step 2: 6-bromo-5-chloro-1-(1-(5-fluoropyrimidin-2-yl)-1H-pyrazol-4-yl)-1H-indazole (I-7)

6-bromo-5-chloro-1-(1H-pyrazol-4-yl)-1H-indazole (50 mg, 0.17 mmol) and $Cs_2CO_3$ (164 mg, 0.504 mmol) were added to a 2-5 mL microwave vial, then DMF (1.0 ml) and 2-chloro-5-fluoropyrimidine (0.020 ml, 0.22 mmol) were added via syringes. The reaction mixture was stirred at 100° C. for 2 h. The reaction was then diluted with water and extracted with $CHCl_3$/IPA (3:1). The combined organic layers were washed with water and brine, then dried over $Na_2SO_4$, filtered and concentrated in vacuo to afford the title compound (I-7). $^1$H NMR (400 MHz, DMSO-$d_6$): δ 9.20 (s, 1H), 9.05 (s, 2H), 8.45 (s, 1H), 8.41 (s, 1H), 8.35 (s, 1H), 8.22 (s, 1H); MS (EI) m/z: 395 [M+H]$^+$.

Synthesis of Common Intermediates I-8: 5-chloro-6-(4-(3-methyloxetan-3-yl)piperazin-1-yl)-1H-indazole Scheme 8

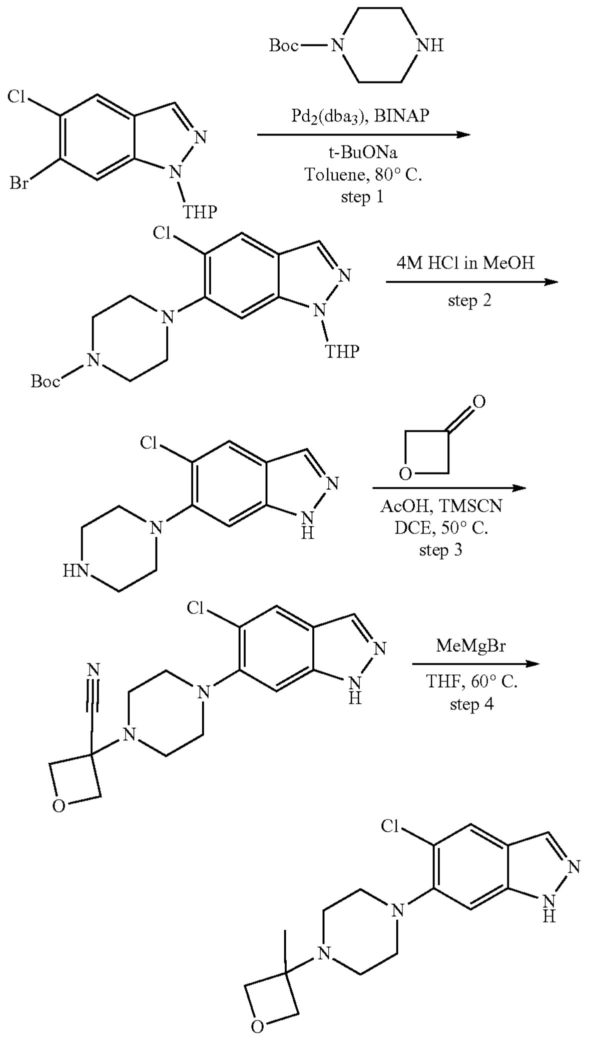

I-8

Step 1: tert-butyl 4-(5-chloro-1-(tetrahydro-2H-pyran-2-yl)-1H-indazol-6-yl)piperazine-1-carboxylate To a solution of 6-bromo-5-chloro-1-(tetrahydro-2H-pyran-2-yl)-1H-indazole (15.0 g, 47.5 mmol) in anhydrous Toluene (150 mL) was added tert-butyl piperazine-1-carboxylate (9.74 g, 52.3 mmol), t-BuONa (13.7 g, 143 mmol), BINAP (2.96 g, 4.75 mmol) and $Pd_2(dba)_3$ (2.2 g, 2.4 mmol). The reaction mixture was stirred at 80° C. for 16 h under N2 atmosphere. The mixture was then diluted with EtOAc and water. The aqueous layer was washed with EtOAc (30 mL). The combined organic layers were washed with brine, dried over $Na_2SO_4$, filtered and concentrated in vacuo to afford a residue which was then purified by column chromatography on silica gel (EtOAc in petroleum ether, 0-10% gradient) to afford tert-butyl 4-(5-chloro-1-(tetrahydro-2H-pyran-2-yl)-1H-indazol-6-yl)piperazine-1-carboxylate. MS (EI) m/z: 421 $[M+H]^+$ Step 2: 5-chloro-6-(piperazin-1-yl)-1H-indazole Tert-butyl 4-(5-chloro-1-(tetrahydro-2H-pyran-2-yl)-1H-indazol-6-yl)piperazine-1-carboxylate (10.0 g, 23.8 mmol) was added to a solution of 4M HCl in MeOH (100 mL). The resulting mixture was stirred at 15° C. for 1.5 h, then concentrated in vacuo to give the crude product, which was diluted with water and the pH adjusted to 7~8 by adding saturated aq. $NaHCO_3$. The aqueous solution was extracted with EtOAc (100 mL×3). The combined organic layers were washed with brine, dried over $Na_2SO_4$, filtered and concentrated in vacuo to afford 5-chloro-6-(piperazin-1-yl)-1H-indazole, which was used in next step directly. MS (EI) m/z: 237 $[M+H]^+$ Step 3: 3-(4-(5-chloro-1H-indazol-6-yl)piperazin-1-yl)oxetane-3-carbonitrile In a 250 mL three neck flask, 5-chloro-6-(piperazin-1-yl)-1H-indazole (5.0 g, 21 mmol), oxetan-3-one (7.0 g, 97 mmol) and acetic acid (3.0 mL, 21 mmol) were added in DCE (120 mL) at 20° C. under $N_2$. The reaction was stirred at 50° C. for 30 min. Then, TMSCN (9.0 g, 91 mmol) was added slowly to the mixture. The resulting mixture was then stirred at 50° C. for 3 h, cooled to rt, and then poured into water. The resulting solution was treated with KOH (1M) to adjust pH to 7-8, then extracted with EtOAc (300 mL×2). The combined organic layers were washed with brine, dried over $Na_2SO_4$, filtered and concentrated in vacuo to afford a residue which was then purified by column chromatography on silica gel (EtOAc in petroleum ether, 0-20% gradient) to afford 3-(4-(5-chloro-1H-indazol-6-yl)piperazin-1-yl)oxetane-3-carbonitrile. MS (ESI) m/z: 318 $[M+H]^+$ Step 4: 5-chloro-6-(4-(3-methyloxetan-3-yl)piperazin-1-yl)-1H-indazole (I-8)

Methyl magnesium bromide (25 mL, 75 mmol) was added dropwise to a solution of 3-(4-(5-chloro-1H-indazol-6-yl)piperazin-1-yl)oxetane-3-carbonitrile (4.5 g, 14 mmol) in anhydrous THF (50 mL). The resulting mixture was stirred at 60° C. under $N_2$ for 3 h. The reaction was quenched with $NH_4Cl$ (sat.) and extracted with EtOAc (300 mL×2). The combined organic layers were washed with brine, dried over $Na_2SO_4$, filtered and concentrated in vacuo to afford residue, which was purified by column chromatography on silica gel (EtOAc in petroleum ether, 0-70% gradient) to afford the title compound (I-8). MS (ESI) m/z: 307 $[M+H]^+$.

Synthesis of Common Intermediates I-9: 1-((1r,3r)-3-fluorocyclobutyl)-4-iodo-1H-pyrazole Scheme 9

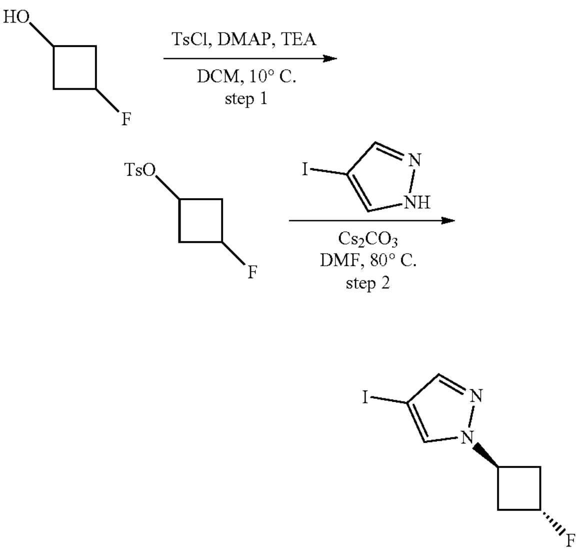

I-9

Step 1: 3-fluorocyclobutyl 4-methylbenzenesulfonate

DMAP (33.9 mg, 0.277 mmol), TEA (1.2 mL, 8.6 mmol) and TsCl (582 mg, 3.05 mmol) at 0° C. was added to a solution of 3-fluorocyclobutanol (250 mg, 2.77 mmol) in anhydrous DCM (5 mL). The resulting mixture was then stirred at 10° C. for 16 h. The resulting mixture was diluted with DCM and water. The aqueous layer was extracted with DCM (100 mL). The combined organic layers were washed with brine, dried over $Na_2SO_4$, filtered and concentrated in vacuo to afford a residue which was then purified by column chromatography on silica gel (EtOAc in petroleum ether, 0-5% gradient) to afford 3-fluorocyclobutyl 4-methylbenzenesulfonate. $^1H$ NMR (500 MHz, $CDCl_3$): δ 7.68 (d, J=8.24 Hz, 2H), 7.25 (d, J=8.09 Hz, 2H), 4.44-4.63 (m, 1H), 4.29-4.31 (m, 1H), 2.60-2.72 (m, 2H), 2.36 (s, 3H), 2.25-2.34 (m, 2H).

Step 2: 1-((1r,3r)-3-fluorocyclobutyl)-4-iodo-1H-pyrazole (I-9)

$Cs_2CO_3$ (1.51 g, 4.64 mmol) and 3-fluorocyclobutyl 4-methylbenzenesulfonate (425 mg, 1.74 mmol) was added to a solution of 4-iodo-1H-pyrazole (300 mg, 1.55 mmol) in anhydrous DMF (5 mL). The resulting mixture was stirred at 80° C. for 3 h. The mixture was then diluted with EtOAc and water. The aqueous layer was extracted with EtOAc (50 mL). The combined organic layers were washed with brine, dried over $Na_2SO_4$, filtered and concentrated in vacuo to afford residue, which was purified by column chromatography on silica gel (EtOAc in petroleum ether, 0-12% gradient) to afford the title compound. MS (EI) m/z: 267 $[M+H]^+$

Synthesis of Common Intermediates I-10: 2-(2-azabicyclo[2.1.1]hexan-4-yl)propan-2-ol hydrochloride Scheme 10

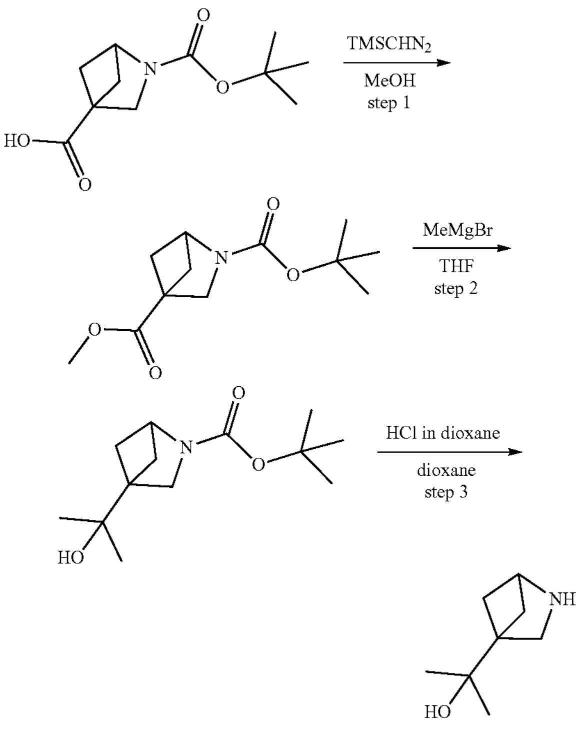

I-10

Step 1: 2-tert-butyl 4-methyl 2-azabicyclo[2.1.1]hexane-2,4-dicarboxylate (Trimethylsilyl)diazomethane (2.340 mL, 4.68 mmol) was added to a solution of 2-(tert-butoxycarbonyl)-2-azabicyclo[2.1.1]hexane-4-carboxylic acid (0.532 g, 2.34 mmol) in MeOH (5 mL) at room temperature. The mixture was stirred and allowed to react for 1 hour. Additional (trimethylsilyl) diazomethane (2.340 mL, 4.68 mmol) was added, and the resulting solution was stirred overnight. The reaction was then quenched with a few drops of acetic acid, and the pH was adjusted to 2 by the addition of a solution of citric acid (2M, 10 mL). The mixture was diluted with EtOAc (250 mL), the aqueous and organic layers were separated, and the organic layer was washed with aqueous sodium hydrogen carbonate (saturated, 2×250 mL) followed by brine (1×250 mL). The organic layer was dried ($Na_2SO_4$), filtered, and the solvent was evaporated under reduced pressure to provide the title compound, which was used without further purification in the following step.

Step 2: tert-butyl 4-(2-hydroxypropan-2-yl)-2-azabicyclo[2.1.1]hexane-2-carboxylate 2-tert-butyl 4-methyl 2-azabicyclo[2.1.1]hexane-2,4-dicarboxylate (4.16 g, 17.24 mmol) was dissolved in THF (69.0 ml) and cooled to 0° C. under nitrogen. After 10 minutes, approximately 3.4 M methylmagnesium bromide (13 ml, 44.2 mmol) was added in 2-methyl THF. The mixture was stirred for 1 h, then removed from the bath. The mixture was stirred for 24 hours, then the reaction was quenched with aq. $NH_4Cl$, then extracted with EtOAc. The organic layer was then washed with water followed by brine, then dried over sodium sulfate, filtered and evaporated. The crude was then pumped under vacuum overnight, then purified by silica gel chromatography, eluting with EtOAc/hexanes. The product containing fraction was evaporated to give the title compound. $^1H$ NMR (500 MHz, $CDCl_3$): δ 4.34 (br, 2H), 3.26 (s, 2H), 1.83 (d, J=4.5 Hz, 2H), 1.48 (s, 9H), 1.45 (d, J=4.5 Hz, 2H), 1.26 (s, 6H).

Step 3: 2-(2-azabicyclo[2.1.1]hexan-4-yl)propan-2-ol. HCl salt (I-10)

tert-Butyl 4-(2-hydroxypropan-2-yl)-2-azabicyclo[2.1.1]hexane-2-carboxylate (3.00 g, 12.43 mmol) was dissolved in dioxane (22 ml) followed by 4N HCl (11 ml, 44.0 mmol) in dioxane, then stirred. The reaction was monitored by TLC. At 1 hour, with the reaction partially completed, another 11 mL of 4N HCl in dioxane was added while stirring continued. TLC showed the total reaction completed at 4 hours with complete consumption of starting material and a baseline product (Hex/EtOAc). Subsequent evaporation by rotary evaporation gave the title compound. $^1H$ NMR (500 MHz, $CD_3OD$): δ 4.14 (s, 1H), 3.27 (s, 2H), 2.08 (m, 2H) 1.58 (m, 2H), 1.25 (s, 6H).

Synthesis of Common Intermediates I-11

Scheme 11

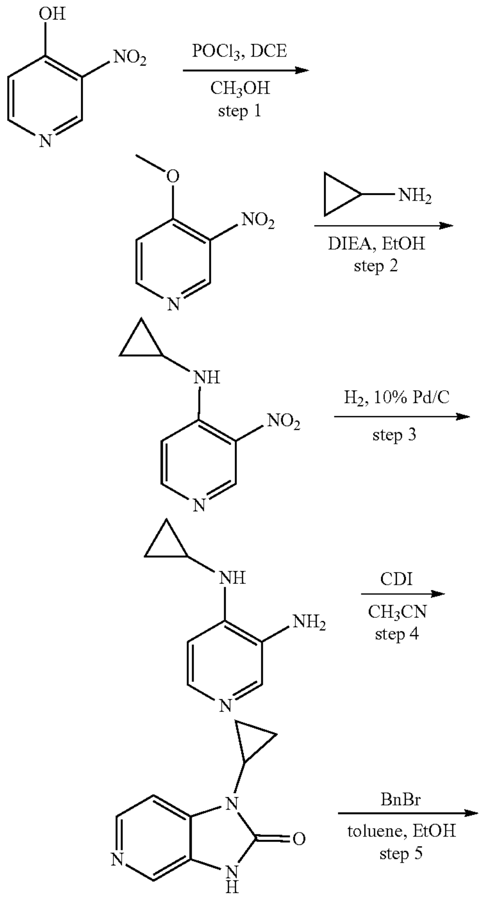

-continued

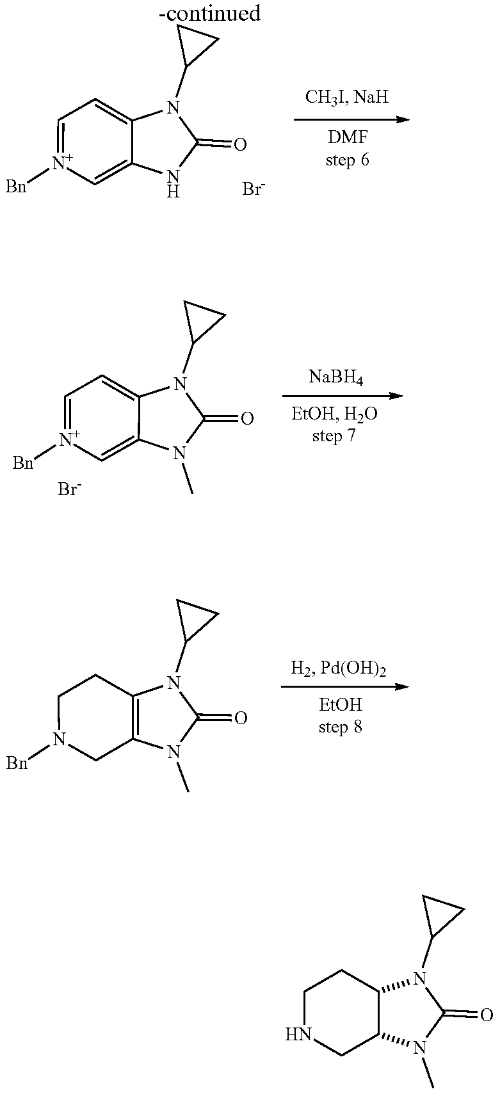

I-11

Step 1: 4-methoxy-3-nitropyridine

To a solution of 3-nitropyridin-4-ol (20 g, 0.14 mol) in 1, 2-dichloroethane (80 mL) was added $POCl_3$ (97.6 g, 0.630 mol) dropwise at 80° C. After this addition, the mixture was heated at 85° C. for 4 h, then cooled to 0° C. Anhydrous methanol (100 mL) was then added dropwise. The mixture was then heated at 65° C. for 1 h, then cooled to 0° C. The solid was collected and dissolved in water. $K_2CO_3$ was added slowly to adjust the pH to ~7, followed by extraction with EtOAc. The organic layer was dried over anhydrous sodium sulfate and concentrated in vacuo to 4-methoxy-3-nitropyridine. $^1$HNMR (300 MHz, DMSO-$d_6$): δ8.96 (s, 1H), 8.73 (d, J=6.0 Hz, 1H), 7.43 (d, J=6.0 Hz, 1H), 4.00 (s, 3H). MS (EI) m/z: 155 $[M+H]^+$.

Step 2: N-cyclopropyl-3-nitropyridin-4-amine

To a solution of 4-methoxy-3-nitropyridine (110 g, 0.714 mol) in absolute EtOH (400 mL) was added DIEA (152 g, 1.20 mol) and cyclopropylamine (84.0 g, 1.47 mol). The resulting solution was refluxed for 3 hours. After filtration, the filter cake was washed with cold ethanol. The mother liquor was concentrated and partitioned between water and ethyl acetate. The organic layer was concentrated to afford N-cyclopropyl-3-nitropyridin-4-amine. $^1$HNMR (400 MHz, DMSO-$d_6$): δ9.0 (s, 1H), 8.38 (d, J=6.8 Hz, 1H), 8.25 (s, 1H), 7.26 (d, J=6.8 Hz, 1H), 2.67-2.63 (m, 1H), 0.89-0.85 (m, 2H), 0.68-0.64 (m, 2H). MS (EI) m/z: 180 $[M+H]^+$.

Step 3: N4-cyclopropylpyridine-3,4-diamine

To a solution of N-cyclopropyl-3-nitropyridin-4-amine (100 g, 0.560 mol) in EtOH (800 mL) was added 10% Pd/C (8 g). The mixture was stirred under 50 psi of $H_2$ at 30° C. overnight. The catalyst was filtered, and the filtrate was concentrated to afford N4-cyclopropylpyridine-3,4-diamine. $^1$HNMR (400 MHz, DMSO-$d_6$): δ7.70-7.58 (m, 2H), 6.60 (d, J=7.2 Hz, 1H), 5.85 (s, 1H), 4.49 (s, 2H), 2.43-2.41 (m, 1H), 0.71-0.68 (m, 2H), 0.40-0.38 (m, 2H). MS (EI) m/z: 150 $[M+H]^+$.

Step 4: 1-cyclopropyl-1,3-dihydro-2H-imidazo[4,5-c]pyridin-2-one

To a solution of N-4-cyclopropylpyridine-3,4-diamine (75.0 g, 0.503 mol) in $CH_3CN$ (1 L) at 0° C., CDI (100 g, 0.617 mol) was added slowly, and the resulting mixture was warmed to 25° C. over 1 h. The precipitate was collected by filtration and dried in vacuo to give 1-cyclopropyl-1,3-dihydro-2H-imidazo[4,5-c]pyridin-2-one. $^1$HNMR (400 MHz, DMSO-$d_6$): δ10.90 (s, 1H), 8.20-8.10 (m, 2H), 7.17 (d, J=8.0 Hz, 1H), 2.90-2.87 (m, 1H), 1.01-0.99 (m, 2H), 0.86-0.84 (m, 2H). MS (EI) m/z: 176 $[M+H]^+$.

Step 5: 5-benzyl-1-cyclopropyl-2-oxo-2,3-dihydro-1H-imidazo[4,5-c]pyridin-5-ium bromide To a solution of 1-cyclopropyl-1,3-dihydro-2H-imidazo[4,5-c]pyridin-2-one (40.0 g, 0.228 mol) in toluene (300 mL) and EtOH (150 mL) was added BnBr (77.5 g, 0.456 mol), then the mixture was refluxed overnight. After concentration, the solid was washed with ethyl acetate to afford 5-benzyl-1-cyclopropyl-2-oxo-2,3-dihydro-1H-imidazo[4,5-c]pyridin-5-ium bromide. $^1$HNMR (400 MHz, DMSO-$d_6$): δ8.78-8.76 (m, 2H), 7.73 (d, J=6.4 Hz, 1H), 7.45-7.38 (m, 5H), 5.73 (s, 2H), 3.00-2.97 (m, 1H), 1.05-1.04 (m, 2H), 0.92-0.91 (m, 2H). MS (ESI) m/z: 266 $[M]^+$.

Step 6: 5-benzyl-1-cyclopropyl-3-methyl-2-oxo-23-dihydro-1H-imidazo[4,5-c]pyridin-5-ium bromide To a solution of 5-benzyl-1-cyclopropyl-2-oxo-2,3-dihydro-1H-imidazo[4,5-c]pyridin-5-ium bromide (20 g, 0.060 mol) in anhydrous DMF (200 mL), NaH (4.8 g, 0.12 mol, 60% in mineral oil) was added slowly at 0° C. The mixture was stirred for 30 min, then $CH_3I$ (17 g, 0.12 mol) was added dropwise at 0° C. The resulting mixture was stirred at room temperature overnight. Then most of DMF was removed in vacuo. DCM and water were added. The organic layer was washed with brine, dried over $Na_2SO_4$, filtered and concentrated in vacuo to afford 5-benzyl-1-cyclopropyl-3-methyl-2-oxo-2,3-dihydro-1H-imidazo[4,5-c]pyridin-5-ium bromide. MS (EI) m/z: 280 $[M]^+$.

Step 7: 5-benzyl-1-cyclopropyl-3-methyl-1,3,4,5,6,7-hexahydro-2H-imidazo[4,5-c] pyridin-2-one To a solution of 5-benzyl-1-cyclopropyl-3-methyl-2-oxo-2,3-dihydro-1H-imidazo[4,5-c] pyridin-5-ium bromide (40.0 g, 0.111 mol) in water (200 mL) and ethanol (200 mL) was added $NaBH_4$ (21.2 g, 0.555 mol) slowly at 0° C. The mixture was refluxed overnight. After filtration, most of ethanol was removed, and ethyl acetate was added. The organic layer was dried over $Na_2SO_4$, filtered and concentrated in vacuo to afford 5-benzyl-1-cyclopropyl-3-methyl-1,3,4,5,6,7-hexahydro-2H-imidazo[4,5-c]pyridin-2-one. $^1$H NMR (400 MHz, $CDCl_3$): δ7.39-7.17 (m, 5H), 3.79 (s, 2H), 3.22-3.18 (m, 2H), 2.91 (s, 3H), 2.70-2.68 (m, 2H), 2.60-2.55 (m, 1H), 2.51-2.45 (m, 2H), 0.83-0.75 (m, 4H). MS (EI) m/z: 284 $[M+H]^+$.

Step 8: (3aR,7aS)-1-cyclopropyl-3-methyloctahydro-2H-imidazo[4,5-c]pyridin-2-one (I-11)

To a solution of 5-benzyl-1-cyclopropyl-3-methyl-1,3,4,5,6,7-hexahydro-2H-imidazo, 4,5-c]pyridin-2-one (21 g, 0.074 mol) in ethanol (200 mL) was added 10% $Pd(OH)_2$ (2 g, 10%/w). The mixture was stirred under 50 psi of $H_2$ at 50° C. overnight. The catalyst was filtered, and the filtrate was concentrated in vacuo to afford the title compound (I-10) $^1$H NMR (400 MHz, $CDCl_3$): δ 3.44-3.41 (m, 1H), 3.08-3.04 (m, 2H), 2.89-2.84 (m, 2H), 2.70 (s, 3H), 2.56-2.50 (m, 1H), 2.32-2.30 (m, 1H), 2.24 (s, 1H), 1.98-1.93 (m, 1H), 1.65-1.56 (m, 1H), 0.87-0.75 (m, 1H), 0.69-0.67 (m, 1H), 0.51-0.48 (m, 2H). MS (EI) m/z: 196 $[M+H]^+$.

Synthesis of Common Intermediates I-12: O'1,O1-(mesityl-13-iodanediyl) 3,3'-dimethyl bis(bicyclo[1.1.1]pentane-1,3-dicarboxylate)

Scheme 12

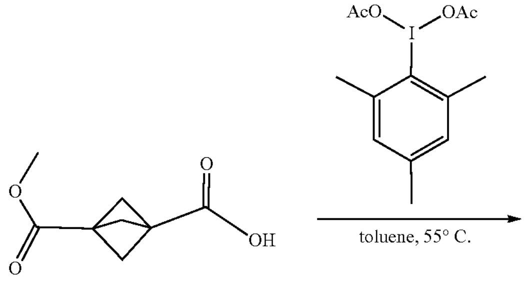

-continued

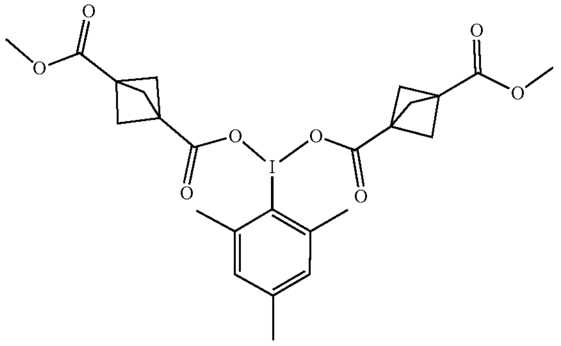

I-12

A 100 mL round-bottom flask was charged with iodomesitylene diacetate (475 mg, 1.30 mmol), 3-(methoxycarbonyl)bicyclo[1.1.1]pentane-1-carboxylic acid (460 mg, 2.70 mmol) and 25 mL toluene. The flask was attached to a rotary evaporator and a water bath heated to 55° C., and the solvent (and the generated acetic acid) was removed over a period of ~10 min. A second 18.5 mL aliquot of toluene was added to the flask and the evaporation step was repeated. The evaporation step was repeated two more times with 12.5 mL toluene each time. After further removal of residual toluene under high vacuum, the title compound (I-12) was generated and used in next step directly. $^1$H NMR (500 MHz, $CDCl_3$): δ 7.08 (s, 2H), 3.65 (s, 6H), 2.69 (s, 6H), 2.38 (s, 3H), 2.20 (s, 12H).

I-13 in Table 1 was prepared according to scheme 12 by using the corresponding starting material.

TABLE 1

| Intermediate | Structure | Name | NMR |
|---|---|---|---|
| I-13 | 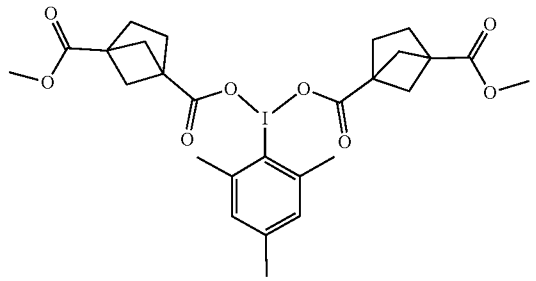 | O'1,O-(mesityl-λ$^3$-iodanediyl) 4,4'-dimethyl bis(bicyclo[2.1.1]hexane-1,4-dicarboxylate) | $^1$H NMR (499 MHz, Chloroform-d) δ 7.10 (s, 2H), 3.68 (s, 6H), 2.72 (s, 6H), 2.38 (s, 3H), 2.07 - 1.82 (m, 16H). |

Synthesis of Common Intermediates I-14: oxetan-3-one-d4

Scheme 13

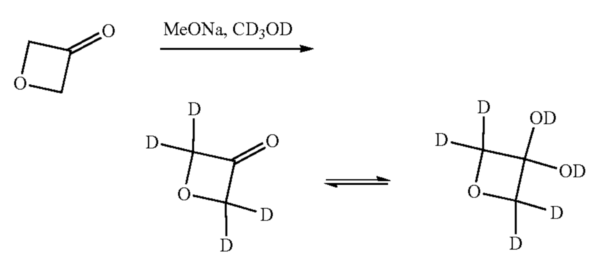

I-14

MeONa (15 mg, 0.28 mmol) was added to a solution of oxetan-3-one (100 mg, 1.4 mmol) in $CD_3OD$ (10 mL). The mixture was stirred at 45° C. overnight. The mixture was directly used in the next step as a solution (100 mg in 10 mL $CD_3OD$) without further purification. Intermediate I-14 exists in hydrate form. $^{13}C$ NMR (126 MHz, $CD_3OD$) δ 82.49, 79.81.

Synthesis of Common Intermediates I-15:

Scheme 14

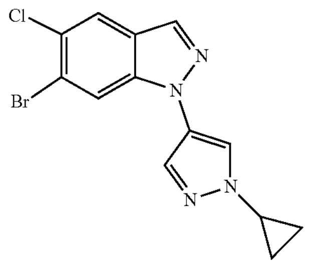

I-2

-continued

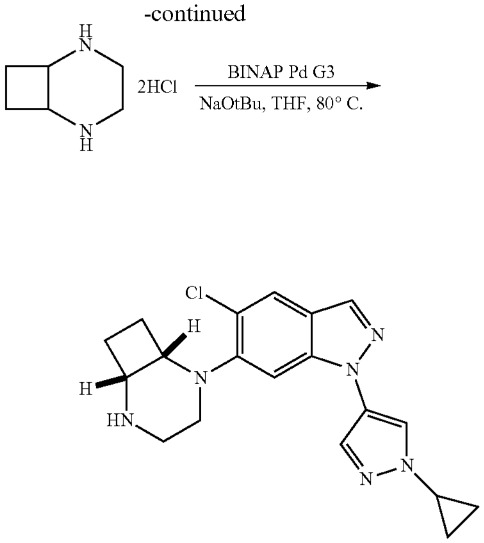

I-15

To a solution of I-2 (83 mg, 0.25 mmol) in anhydrous THF (4 mL) was added (1R,6S)-2,5-diazabicyclo[4.2.0]octane dihydrochloride (50 mg, 0.27 mmol), Sodium tert-butoxide (118 mg, 1.23 mmol) and rac-BINAP-Pd-G3 (12 mg, 0.010 mmol), and the resulting mixture was stirred at 80° C. under $N_2$ protection for 16 hours. After filtration and concentration, the crude product was purified by reversed phase HPLC, eluting with water (0.1% TFA)-ACN to give 6-((1S,6R)-2,5-diazabicyclo[4.2.0]octan-2-yl)-5-chloro-1-(1-cyclopropyl-1H-pyrazol-4-yl)-1H-indazole (I-15). MS (ESI) m/z: 369 $[M+H]^+$

Intermediate I-16: cis and trans methyl 3-(4-(5-chloro-6-(4-(3-methyloxetan-3-yl)piperazin-1-yl)-1H-indazol-1-yl)-1H-pyrazol-1-yl)cyclobutane-1-carboxylate Scheme 15

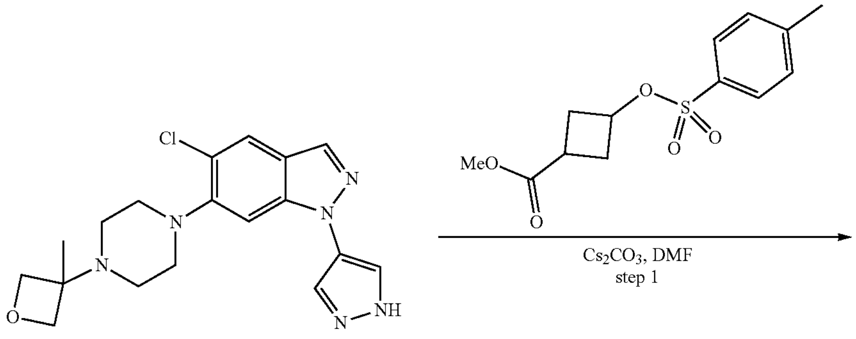

I-5

-continued

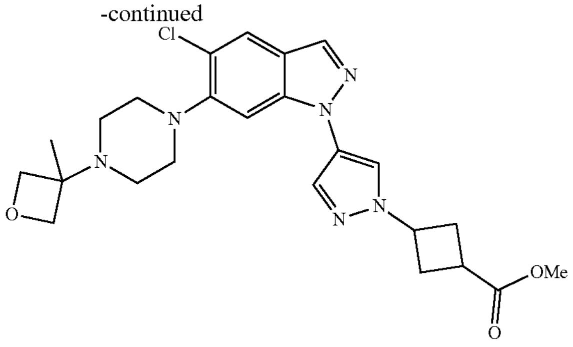

I-16

I-5 (1116 mg, 2.99 mmol), methyl 3-(tosyloxy)cyclobutane-1-carboxylate (851 mg, 2.99 mmol), $Cs_2CO_3$ (1950 mg, 5.99 mmol) and DMF (8.0 mL) were added to a vial. The mixture was stirred at 90° C. for 15 h. The mixture was cooled, diluted with sat. $NH_4Cl$ (20 mL) and extracted with 3:1 $CHCl_3$: IPA (4×25 mL). The organic extract was dried over $Na_2SO_4$, filtered and concentrated in vacuo to afford residue. The residue was purified by column chromatography on silica gel (3:1 EtOAc:EtOH in DCM, 0-100% gradient) to afford a mixture of both cis and trans methyl 3-(4-(5-chloro-6-(4-(3-methyloxetan-3-yl)piperazin-1-yl)-1H-indazol-1-yl)-1H-pyrazol-1-yl)cyclobutane-1-carboxylate (I-16). MS (EI) m/z 485 $[M+H]^+$.

Intermediate I-17: methyl 2-(4-(5-chloro-6-(4-(3-methyloxetan-3-yl)piperazin-1-yl)-1H-indazol-1-yl)-1H-pyrazol-1-yl)cyclopropane-1-carboxylate Scheme 16

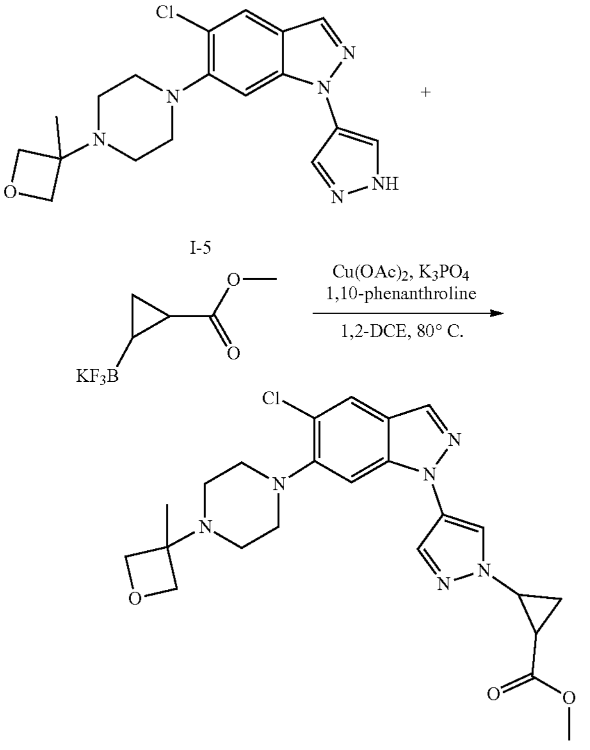

I-17

A 20 mL scintillation vial equipped with a magnetic stirrer was charged with copper (II) acetate (218 mg, 1.20 mmol) and 1,10-phenanthroline (216 mg, 1.20 mmol). Then, under a positive flow of argon DCE (9 mL) was added and stirring was commenced. The mixture was heated to 60° C. and maintained at this temperature for 20 min under a positive pressure of argon. A separate 20 mL oven-dried microwave vial equipped with a magnetic stirrer was charged with I-5 (373 mg, 1.00 mmol) and potassium trifluoro(2-(methoxycarbonyl)cyclopropyl)borate (206 mg, 1.00 mmol). The vial was sealed with a microwave cap. Then, potassium phosphate (1 M in $H_2O$, 3.0 mL, 3.0 mmol) was added and stirring was commenced. To the stirring mixture was added the Cu-phenanthroline complex (solution in DCE), and the reaction was heated to 80° C. overnight. The reaction mixture was allowed to cool to room temperature, diluted with EtOAc, dried over sodium sulfate, and filtered through Celite. The filtrate was then concentrated to dryness in vacuo to afford residue, which was purified by column chromatography on silica gel (0-25% MeOH in DCM gradient) to afford methyl 2-(4-(5-chloro-6-(4-(3-methyloxetan-3-yl)piperazin-1-yl)-1H-indazol-1-yl)-1H-pyrazol-1-yl)cyclopropane-1-carboxylate (I-17). MS (EI) m/z 471 $[M+H]^+$.

Synthesis of Common Intermediates I-18 and I-19: (trans)-3-(4-iodo-1H-pyrazol-1-yl)cyclobutan-1-ol (I-18) and 4-iodo-1-((trans)-3-methoxycyclobutyl)-1H-pyrazole (I-19)

Scheme 17

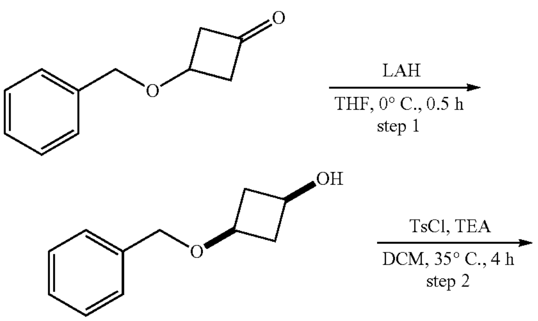

-continued

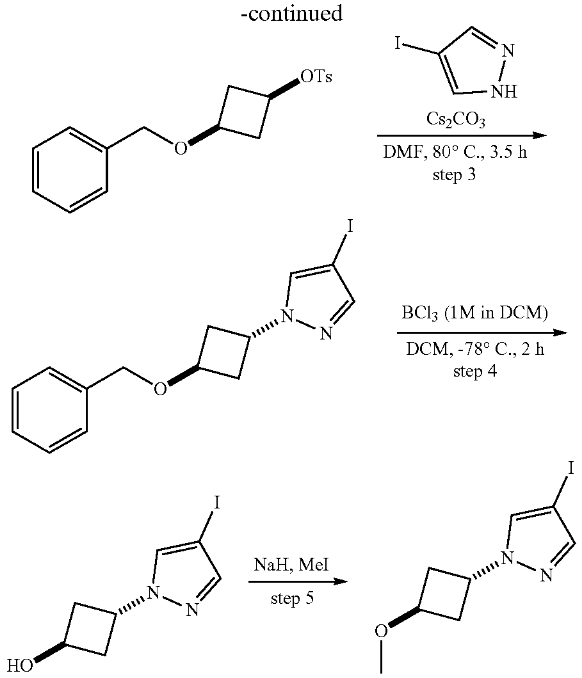

I-18 I-19

Step 1: (cis)-3-(benzyloxy)cyclobutan-1-ol

To a solution of 3-(benzyloxy)cyclobutanone (8.0 g, 45 mmol) in anhydrous THF (150 mL) was added slowly LAH (2.58 g, 68.0 mmol) at 0° C., and the resulting mixture was stirred at 0° C. for 0.5 hour. Water (8 mL) was added into the reaction mixture dropwise to quench the reaction. After filtration, the mixture was concentrated to give cis-3-(benzyloxy)cyclobutanol which was used to next step directly without further purification. $^1$H NMR (500 MHz, $CDCl_3$): δ 7.21-7.28 (m, 5H), 4.34 (s, 2H), 3.80-3.87 (m, 1H), 3.53-3.57 (m, 1H), 2.60-2.65 (m, 2H), 1.84-1.88 (m, 2H).

Step 2: (cis)-3-(benzyloxy)cyclobutyl 4-methylbenzenesulfonate

To a solution of cis-3-(benzyloxy)cyclobutanol (7.80 g, 43.8 mmol) in anhydrous DCM (120 mL) was added TEA (18.3 mL, 131 mmol) and DMAP (0.535 g, 4.38 mmol), then Ts-Cl (9.18 g, 48.1 mmol) was added into above the mixture at 0° C. and the resulting mixture was stirred at 35° C. for 4 hours. The reaction mixture was poured into water (100 mL) and extracted with DCM (100 mL×2). After filtration and concentration, the crude product was purified by flash silica gel chromatography (80 g, eluenting with 0~10% EtOAc in Petroleum ether gradient) to give cis-3-(benzyloxy)cyclobutyl 4-methylbenzenesulfonate. $^1$H NMR (500 MHz, $CDCl_3$): δ 7.75 (d, J=8.24 Hz, 2H), 7.24-7.34 (m, 7H), 4.44 (q, J=7.29 Hz, 1H), 4.34 (s, 2H), 3.60 (q, J=6.90 Hz, 1H), 2.57-2.60 (m, 2H), 2.42 (s, 3H), 2.12-2.18 (m, 2H).

Step 3: 1-((cis)-3-(benzyloxy)cyclobutyl)-4-iodo-1H-pyrazole

To a solution of 4-iodo-1H-pyrazole (7.0 g, 36 mmol) in anhydrous DMF (150 mL) was added 3-(benzyloxy)cyclobutyl 4-methylbenzenesulfonate (12 g, 36 mmol) and $Cs_2CO_3$ (35.3 g, 108 mmol), and the resulting mixture was stirred at 80° C. for 3.5 hours. The reaction mixture was poured into water (200 mL) and extracted with EtOAc (150 mL×3). The organic layer was washed with water (100 mL×2), dried over $Na_2SO_4$. After filtration and concentration, the crude product was purified by flash silica gel chromatography (120 g, 0~15% EtOAc in Petroleum ether gradient) to give trans-1-(3-(benzyloxy)cyclobutyl)-4-iodo-1H-pyrazole. MS (ESI) m/z: 355 $[M+H]^+$ Step 4: (trans)-3-(4-iodo-1H-pyrazol-1-yl)cyclobutan-1-ol (I-18)

To a solution of 1-(3-(benzyloxy)cyclobutyl)-4-iodo-1H-pyrazole (8 g, 22.59 mmol) in anhydrous DCM (100 mL) was added slowly boron trichloride (75 mL, 75 mmol) in DCM at −78° C., and the resulting mixture was stirred at −78° C. for 2 hours under $N_2$ protection. TLC (Pet.ether: EtOAc=3:1) showed the reaction was complete. The reaction mixture was poured into water (150 mL) and extracted with EtOAc (150 mL×2), dried over $Na_2SO_4$. After filtration and concentration, the crude product was purified by flash silica gel chromatography (80 g, eluenting with 0~22% EtOAc in Pet.ether gradient) to give trans-3-(4-iodo-1H-pyrazol-1-yl)cyclobutanol (I-18). $^1$H NMR (500 MHz, $CDCl_3$): δ 7.34 (s, 1H), 7.26 (s, 1H), 4.76 (m, 1H), 4.47-4.54 (m, 1H), 2.55-2.69 (m, 2H), 2.24-2.35 (m, 2H).

Step 5: 4-iodo-1-((trans)-3-methoxycyclobutyl)-1H-pyrazole (I-19)

To a solution of trans-3-(4-iodo-1H-pyrazol-1-yl)cyclobutanol (200 mg, 0.757 mmol) in THF (5 ml) was added sodium hydride (36.4 mg, 1.515 mmol) at 0° C. Then iodomethane (215 mg, 1.51 mmol) was added to the reaction mixture. The reaction mixture was stirred at 15° C. for 1 hour. The reaction mixture was poured into water (10 ml) and extracted with EtOAc (30 ml×3). The organic layer was washed with water (10 ml×3), dried over $Na_2SO_4$. After filtration and concentration, the crude product was purified by flash silica gel chromatography (4 g, eluenting with 0~20% EtOAc in Pet.ether gradient) to give trans-4-iodo-1-(3-methoxycyclobutyl)-1H-pyrazole (I-19). MS (ESI) m/z: 279 $[M+H]^+$ Synthesis of Common Intermediate I-20: 4-iodo-1-((1s,3s)-3-methoxycyclobutyl)-1H-pyrazole Scheme 18

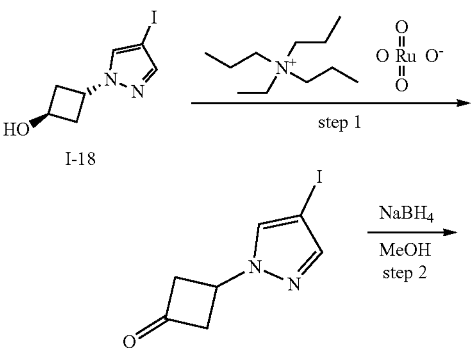

I-18

-continued

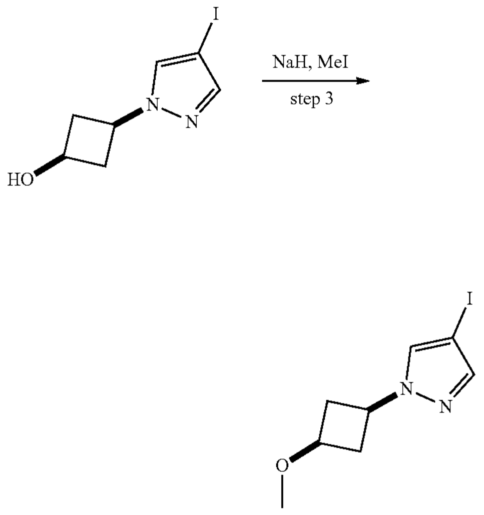

I-20

Step 1: 3-(4-iodo-1H-pyrazol-1-yl)cyclobutan-1-one

To a solution of I-18 (120 mg, 0.450 mmol) in anhydrous DCM (4 mL) was added tetrapropylammonium perruthenate (47.9 mg, 0.140 mmol) and 4-methylmorpholine N-oxide (160 mg, 1.36 mmol) at 25° C., the resulting mixture was stirred at 25° C. for 2 hours. The mixture quenched with $Na_2SO_3$ solution and extracted with EtOAc (10 mL×3). The organic layer was washed with water (10 mL×3), dried over $Na_2SO_4$. After filtration, the solvent was concentrated to give 3-(4-iodo-1H-pyrazol-1-yl)cyclobutan-1-one. MS (ESI) m/z: 263 $[M+H]^+$ Step 2: (1s,3s)-3-(4-iodo-1H-pyrazol-1-yl)cyclobutan-1-ol To a solution of 3-(4-iodo-1H-pyrazol-1-yl)cyclobutanone (400 mg, 1.53 mmol) in anhydrous MeOH (2 mL) was added $NaBH_4$ (87 mg, 2.3 mmol) at 25° C., the resulting mixture was stirred for 1 hour at 25° C. The mixture quenched with water. After filtration and concentration, the residue was purified by prep-TLC ($SiO_2$, Pet. ether:EtOAc=3:1) to give cis-3-(4-iodo-1H-pyrazol-1-yl)cyclobutanol. MS (ESI) m/z: 265 $[M+H]^+$ Step 3: 4-iodo-1-((1s,3s)-3-methoxycyclobutyl)-1H-pyrazole (I-20)

To a solution of cis-3-(4-iodo-1H-pyrazol-1-yl)cyclobutanol (200 mg, 0.76 mmol) in anhydrous THF (1 mL) was added NaH (45.4 mg, 1.14 mmol) at 0° C., the resulting mixture was stirred for 0.5 hour at 0° C., then warmed up to 25° C. followed by adding iodomethane (161 mg, 1.14 mmol). The mixture was stirred for 1 hour at 25° C. The mixture was quenched with water. After filtration and concentration, the residue was purified by prep-TLC ($SiO_2$, Pet. ether:EtOAc=3:1) to give cis-4-iodo-1-(3-methoxycyclobutyl)-1H-pyrazole (I-20). MS (ESI) m/z: 279 $[M+H]^+$ Synthesis of Common Intermediate I-21 and I-22: 4-bromo-1-((1R2R or 1S,2S)-2-(methoxymethyl)cyclopropyl)-1H-pyrazole (I-21) and 4-bromo-1-((1S,2S or 1R,2R)-2-(methoxymethyl)cyclopropyl)-1H-pyrazole (I-22)

Scheme 19

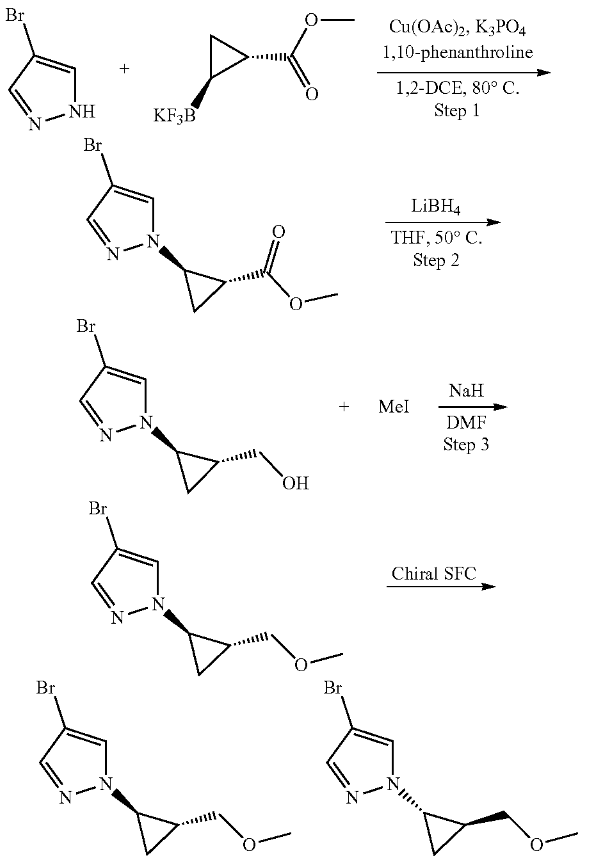

I-21 I-22

Step 1: methyl (1R,2R and 1S,2S)-2-(4-bromo-1H-pyrazol-1-yl)cyclopropane-1-carboxylate 4-bromo-1H-pyrazole (1.5 g, 10.2 mmol), potassium trifluoro((1R,2R and 1S,2S)-2-(methoxycarbonyl)cyclopropyl)borate (3 g, 14 mmol), copper(II) acetate (2.2 g, 12.11 mmol), 1,10-phenanthroline monohydrate (2.4 g, 12 mmol), and potassium phosphate, 1M in water (30.6 ml, 30.6 mmol) were combined in a 250 mL round bottom flask and dissolved in acetonitrile (40 mL). Stirred at 80° C. overnight. Cooled to room temperature and partitioned between 3:1 $CHCl_3$:IPA and water. Separated the phases using a phase separator. The organic solution was concentrated. Purified using an Isco Combiflash purification system using silica gel and a gradient of 25-50% ethyl acetate in hexanes. The desired fractions were pooled and concentrated to give methyl (1R,2R and 1S,2S)-2-(4-bromo-1H-pyrazol-1-yl)cyclopropane-1-carboxylate. MS (EI) m/z: 245 $[M+H]^+$.

Step 2: ((1R,2R and 1S,2S)-2-(4-bromo-1H-pyrazol-1-yl)cyclopropyl)methanol methyl 2-(4-bromo-1H-pyrazol-1-yl)cyclopropane-1-carboxylate (775 mg, 3.16 mmol) was dissolved in tetrahydrofuran (7.9 mL) in a 5 mL microwave vial followed by addition of lithium borohydride, 2M in THF (4.74 mL, 9.49 mmol). Stirred at 50° C. overnight. Cooled to room temperature and partitioned between water and 3:1 $CHCl_3$:IPA. The organic layer was separated using a phase separator and concentrated. Purified using an Isco Combiflash purification system using silica gel and a gradient of 0-10% methanol in dichloromethane. The desired fractions were pooled and concentrated to give ((1R,2R and 1S,2S)-2-(4-bromo-1H-pyrazol-1-yl)cyclopropyl)methanol. MS (EI) m/z: 217 $[M+H]^+$.

Step 3: 4-bromo-1-((1R,2R or 1S,2S)-2-(methoxymethyl)cyclopropyl)-1H-pyrazole (I-21) and 4-bromo-1-((1S,2S or 1R,2R)-2-(methoxymethyl)cyclopropyl)-1H-pyrazole (I-22)

((1R,2R and 1S,2S)-2-(4-bromo-1H-pyrazol-1-yl)cyclopropyl)methanol (495 mg, 2.28 mmol) was dissolved in N,N-Dimethylformamide (7.6 ml) and cooled to 0° C. Sodium hydride (201 mg, 5.02 mmol) was then added and the reaction stirred for 10 minutes. Iodomethane (284 μl, 4.56 mmol) was then added and the reaction allowed to warm to room temperature overnight. Quenched with water and extracted using dichloromethane and a phase separator. The organic Mobile phase A: liquid $CO_2$, Mobile phase B: 10% MeOH with 0.1% $NH_3$ modifier). The desired peaks were collected and concentrated to give 4-bromo-1-((1R,2R or 1S,2S)-2-(methoxymethyl)cyclopropyl)-1H-pyrazole (I-21) (retention time=2.5 min) and the desired enantiomer 4-bromo-1-((1S,2S or 1R,2R)-2-(methoxymethyl)cyclopropyl)-1H-pyrazole (I-22) (retention time=3.4 min). MS (EI) m/z: 231 $[M+H]^+$.

Synthesis of Common Intermediate I-23: methyl 3-(4-bromo-1H-pyrazol-1-yl)bicyclo[1.1.1]pentane-1-carboxylate Scheme 20

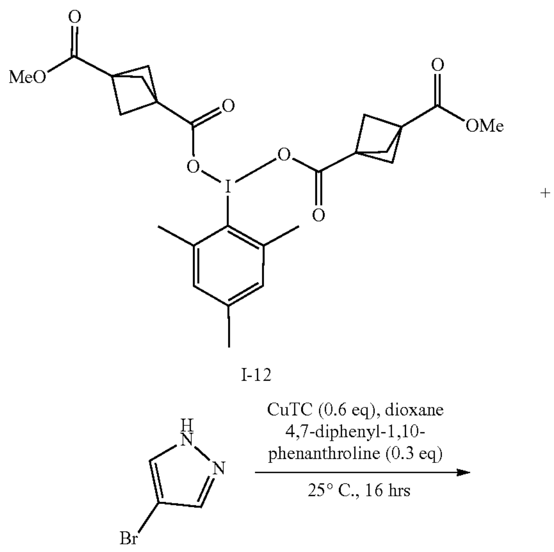

-continued

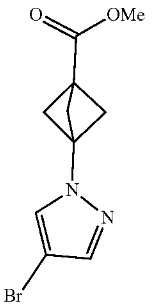

I-23

A flask was charged with 4-bromo-1H-pyrazole (100 g, 680 mmol, 2.00 eq), I-12 (497 g, 850 mmol, 2.50 eq) and 4,7-diphenyl-1,10-phenanthroline (33.9 g, 102 mmol, 0.300 eq), followed by dioxane (3.00 L). Thiophene-2-carbonyloxycopper (38.9 g, 204 mmol, 0.600 eq) was then added and the reaction stirred at 25° C. for 16 hrs. The reaction was then filtered and concentrated to give the crude product. The crude reaction mixture was then purified by column chromatography ($SiO_2$, Petroleum ether/Ethyl acetate=20/1 to 1/1) to afford methyl 3-(4-bromo-1H-pyrazol-1-yl)bicyclo[1.1.1]pentane-1-carboxylate. $^1$HNMR: (400 MHz, $CDCl_3$) δ 7.51 (s, 1H) 7.46 (s, 1H) 3.75 (s, 3H) 2.56 (s, 5H) 2.49-2.64 (m, 1H). MS (EI) m/z 271 $[M+H]^+$.

Synthesis of Common Intermediate I-24: methyl 3-(4-iodo-1H-pyrazol-1-yl)bicyclo[1.1.1]pentane-1-carboxylate Scheme 21

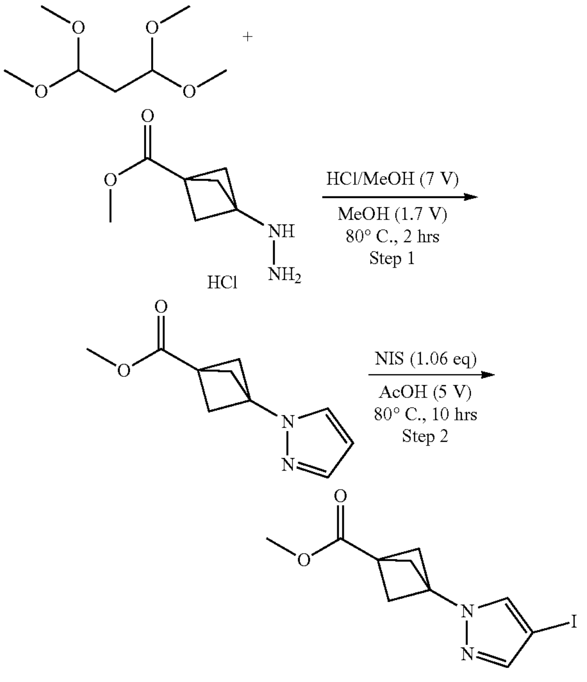

I-24

Step 1: methyl 3-(1H-pyrazol-1-yl)bicyclo[1.1.1]pentane-1-carboxylate

A flask was charged with methyl 3-hydrazinylbicyclo[1.1.1]pentane-1-carboxylate hydrochloride (227 g, 1.18 mol, prepared according to the literature procedure) and MeOH (400 mL), followed by HCl/MeOH (4 M, 1.4 L) and 1,1,3,3-tetramethoxypropane (213 g, 1.30 mol). The reaction was the warmed to 80° C. for 2 hours. The reaction mixture was concentrated under reduced pressure to remove MeOH. The residue was diluted with $H_2O$ (200 mL) and extracted with EtOAc (200 mL×2), the aqueous phase was extracted with DCM (100 mL×3). The combined organic layers were washed with brine (100 mL), dried over $Na_2SO_4$, filtered and concentrated under reduced pressure to give a residue. The residue was purified by column chromatography ($SiO_2$, Petroleum ether/Ethyl acetate=10/1 to 3/1) to afford methyl 3-(1H-pyrazol-1-yl)bicyclo[1.1.1]pentane-1-carboxylate. MS (EI) m z: 193 $[M+H]^+$ Step 2: methyl 3-(4-iodo-1H-pyrazol-1-yl)bicyclo[1.1.1]pentane-1-carboxylate (I-24)

A flask was charged with methyl 3-(1H-pyrazol-1-yl)bicyclo[1.1.1]pentane-1-carboxylate (95.0 g, 494 mmol) and AcOH (475 mL), followed by NIS (118 g, 524 mmol). The mixture was then stirred at 80° C. for 10 hours. The reaction mixture was concentrated under reduced pressure to remove AcOH, the resulting product was dissolved in DCM and filtered to removed solids, then the filtrate concentrated under reduced pressure to give a residue. The residue was purified by column chromatography ($SiO_2$, Petroleum ether/Ethyl acetate=20/1 to 10/1) to afford the title compound (I-24). $^1$HNMR: (400 MHz, $CDCl_3$) δ: 7.66-7.38 (m, 2H), 3.75 (s, 3H), 2.56 (s, 6H). MS (EI) m/z: 319 $[M+1]^+$ Synthesis of Common Intermediate I-25: (3-(4-bromo-1H-pyrazol-1-yl)bicyclo[1.1.1.]pentan-1-yl)methanol Scheme 22

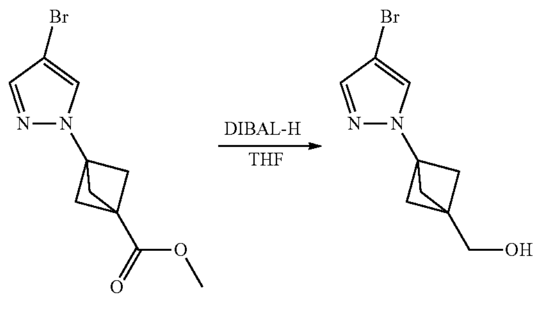

I-23 I-25

To a solution of I-23, (5.0 g, 18 mmol) in anhydrous THF (75 mL) cooled to 0° C. via ice/water bath was added via syringe 1.0 M DIBAL-H in hexane (55.3 mL, 55.3 mmol) and the resulting solution stirred at 0° C. for 2 hrs. The reaction was quenched by slowly pouring into aqueous $NH_4Cl$ solution (100 mL) and allowed to stir vigorously at room temperature, and the material is then filtered through celite. The organics were then separated and dried over sodium sulfate, filtered, and concentrated to dryness under reduced pressure. The residue was taken up into 10 mL of DCM and purified via ISCO (80 g silica gel), eluting with a gradient eluent of 0-80% ethyl acetate in hexane. The tubes containing the product were combined and the solvent removed under reduced pressure to afford the title compound (I-25). MS (EI) m/z: 243 $[M+H]^+$ I-26 in Table 2 was prepared from common intermediate I-24 according to Scheme 19 (step 2).

TABLE 2

| Intermediate | Structure | Name | Exact Mass [M + H]+ |
|---|---|---|---|
| I-26 | 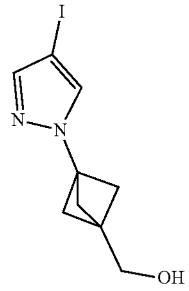 [SMILES: OCC12CC(n3cc(I)cn3)(C1)C2] | (3-(4-iodo-1H-pyrazol-1-yl)bicyclo[1.1.1]pentan-1-yl)methanol | Calc'd 291, found 291 |

Synthesis of Common Intermediate I-27: 4-bromo-1-(3-(methoxymethyl)bicyclo[1.1.1]pentan-1-yl)-1H-pyrazole Scheme 23

Scheme 23

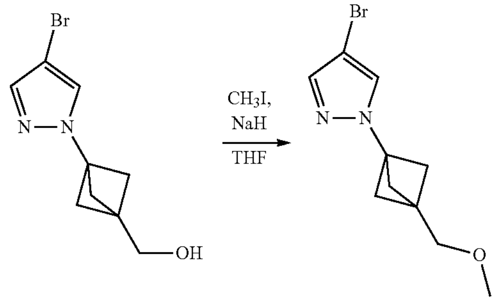

I-25 I-27

To a solution of I-25 (1.00 g, 4.11 mmol) in anhydrous THF (20 mL) cooled to 0° C. via ice/water bath was added in portions over 10 minutes NaH (200 mg, 5.00 mmol), and the resulting solution stirred for 30 minutes at 0° C. MeI (0.514 mL, 8.23 mmol) was then added via syringe dropwise and the solution stirred for an additional 2 h, allowing to warm to room temperature. The reaction was quenched with sat. aq. ammonium chloride (25 mL) and diluted with ethyl acetate (25 mL). The organics were separated, dried over sodium sulfate, filtered and the filtrate concentrated to dryness under reduced pressure. The residue was taken up into 5 mL DCM and purified by ISCO (40 g silica gel), eluting with a gradient eluant of 0-50% ethyl acetate in hexane to afford the title compound (I-27). MS (EI) m/z: 257 $[M+H]^+$ I-28 and I-29 in Table 3 were prepared from common intermediate I-26 according to Scheme 23 by using the corresponding alkylation reagents.

TABLE 3

| Intermediate | Structure | Name | Exact Mass [M + H]+ |
|---|---|---|---|
| I-28 | 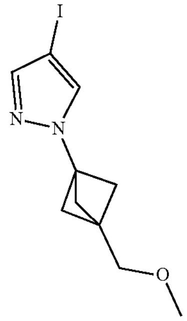 | 4-iodo-1-(3-(methoxymethyl)bicyclo [1.1.1]pentan-1-yl)-1H-pyrazole | Calc'd 305, found 305 |
| I-29 | 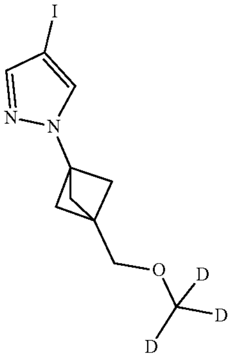 [SMILES: [2H]C([2H])([2H])OCC12CC(n3cc(I)cn3)(C1)C2] | 4-iodo-1-(3-((methoxy-d3)methyl)bicyclo[1.1.1] pentan-1-yl)-1H-pyrazole | Calc'd 308, found 308 |

Synthesis of Common Intermediate I-30: 3-bromo-1-(3-((difluoromethoxy)methyl)bicyclo[1.1.1]pentan-1-yl)-1H-pyrazole Scheme 24

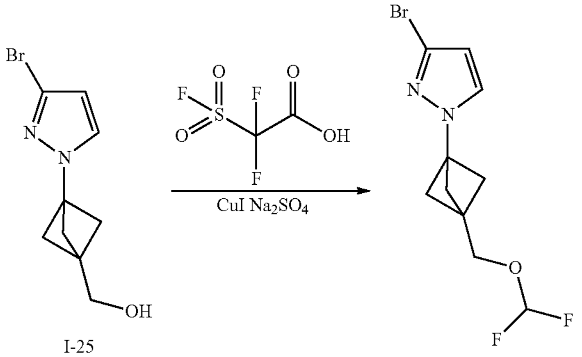

I-25

I-30

In a 5 mL microwave vial equipped with a magnetic stirrer was dissolved (3-(3-bromo-1H-pyrazol-1-yl)bicyclo [1.1.1]pentan-1-yl)methanol (250 mg, 1.03 mmol), Sodium sulfate (73.0 mg, 0.514 mmol) and copper iodide (98.0 mg, 0.514 mmol) in acetonitrile (3.5 mL). The mixture was then heated to 50° C. before 2,2-difluoro-2-(fluorosulfonyl)acetic acid (0.201 mg, 1.13 mmol) was added. Following the completion of addition, the resulting mixture was heated at 50° C. for 7 h. The crude reaction mixture was then concentrated in vacuo and the resulting residue was partitioned between diethyl ether and 1N aq. NaOH. The organic layer was separated and washed further with 1N aq. HCl, water and brine, dried over $Na_2SO_4$, filtered and the filtrate concentrated in vacuo. The material was dissolved in 2 mL of DCM and loaded onto the ISCO (GOLD 24 gram Silica gel column) eluting with a gradient of 0-50% ethyl acetate in hexane to afford the title compound (I-30). MS (EI) m/z: 293 $[M+H]^+$.

Synthesis of Common Intermediate I-31: 3-(4-bromo-1H-pyrazol-1-yl)bicyclo[1.1.1]pentane-1-carbaldehyde Scheme 25

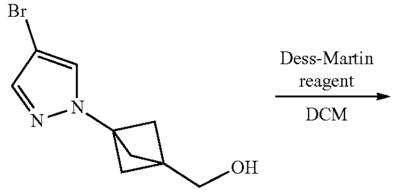

I-25

-continued

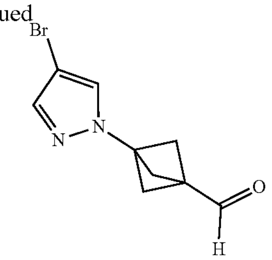

I-31

To a solution of I-25 (500 mg, 2.06 mmol) in 8 mL DCM cooled to 0° C. via ice/water bath was added Dess-Martin Periodinane (960 mg, 2.62 mmol) in portions over 4 minutes and the resulting mixture was stirred for 1 hr at 0° C. The mixture was quenched with aqueous sodium carbonate (1.0 M, 100 mL), and extracted with DCM (2×50 mL). The organics were combined, dried over sodium sulfate, filtered and the filtrate concentrated to dryness under reduced pressure. The residue was purified via ISCO (GOLD 40 gram silica gel column), eluting with a gradient of 0-100% ethyl acetate in hexane. The tubes containing the product were combined and concentrated under reduced pressure to afford the title compound (I-31). MS (EI) m/z: 241 $[M+H]^+$.

Synthesis of Common Intermediate I-32: 1-(3-(4-bromo-1H-pyrazol-1-yl)bicyclo[1.1.1]pentan-1-yl)-N,N-dimethylmethanamine Scheme 26

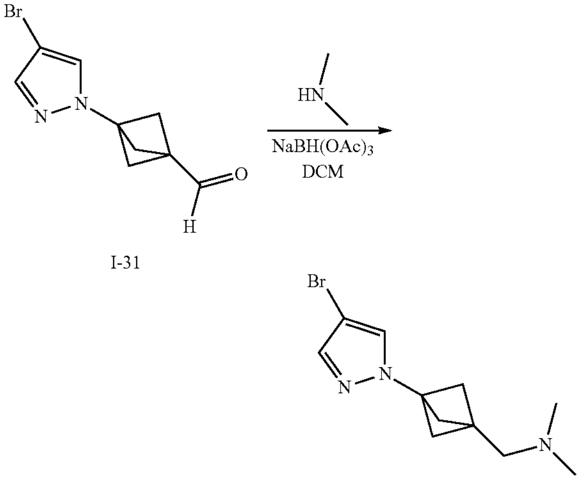

I-31

I-32

To a solution of I-31 (250 mg, 1.04 mmol) and dimethylamine (0.518 mL, 1.04 mmol, 2M in THF) in DCM (3 mL) was added crushed 4 A molecular sieves and the mixture stirred at room temperature for 1 hour. To this mixture was then added sodium triacetoxyborohydride (440 mg, 2.07 mmol) and the solution stirred at room temperature overnight. The solids were filtered off and washed with DCM (2×5 mL). The organics were then washed with sat'd aqueous sodium bicarbonate solution (2×10 mL), collected, dried over sodium sulfate, filtered, and the filtrate concentrated to dryness under reduced pressure. The residue was taken up into 3 mL DCM and placed onto the ISCO for purification.

The material was purified by ISCO 24 gram GOLD silica gel column, eluting with a gradient eluant of 0-100% 3:1 ethyl acetate:ethanol in hexane. The tubes containing the product were combined and the solvent removed under reduced pressure to afford the title compound (I-32). MS (EI) m/z: 270 $[M+H^+]$.

I-33 in Table 4 was prepared from common intermediate I-31 according to Scheme 26 by using the corresponding starting material.

TABLE 4

| Intermediate | Structure | Name | Exact Mass [M + H]+ |
|---|---|---|---|
| I-33 | 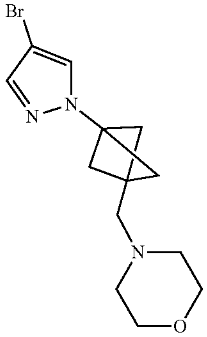 [SMILES: Brc1cnn(C23CC(CN4CCOCC4)(C2)C3)c1] | 4-((3-(4-bromo-1H-pyrazol-1-yl)bicyclo[1.1.1]pentan-1-yl)methyl)morpholine | Calc'd 312, found 312 |

Synthesis of Common Intermediate I-34: 4-bromo-1-(3-(difluoromethyl)bicyclo[1.1.1]pentan-1-yl)-1H-pyrazole Scheme 27

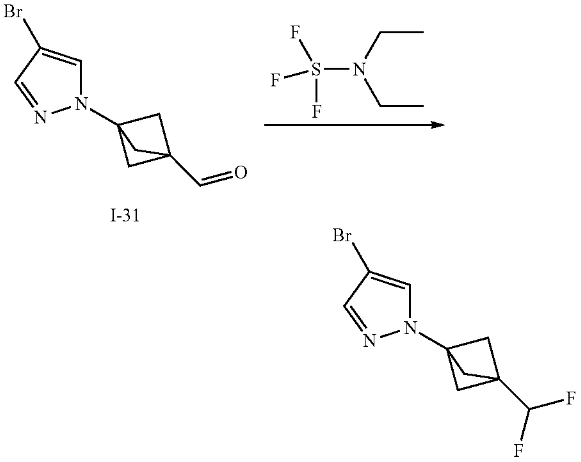

I-31

I-34

To a solution of I-31 (300 mg, 1.24 mmol) in DCM (12 ml) cooled −78° C. via dry ice/acetone bath was added DAST (0.658 ml, 4.98 mmol) and the resulting mixture was stirred at −78° C. for 30 min. The mixture was allowed to warm to room temperature before diluting with dichloromethane (15 mL). The mixture was then washed with water (20 mL), treated with 4M sodium hydroxide to PH=9, dried over sodium sulfate, filtered and the solvent was evaporated under reduced pressure. The residue was purified by column chromatography on silica gel (40 g, eluting with 0-40% ethyl acetate in hexane). The tubes containing the product were combined and the solvent removed under reduced pressure to afford the title compound (I-34). MS (EI) m/z 263 [M+H]$^+$.

Synthesis of Common Intermediate I-35: 4-bromo-1-(3-(1-methoxyethyl)bicyclo[1.1.1]pentan-1-yl)-1H-pyrazole Scheme 28

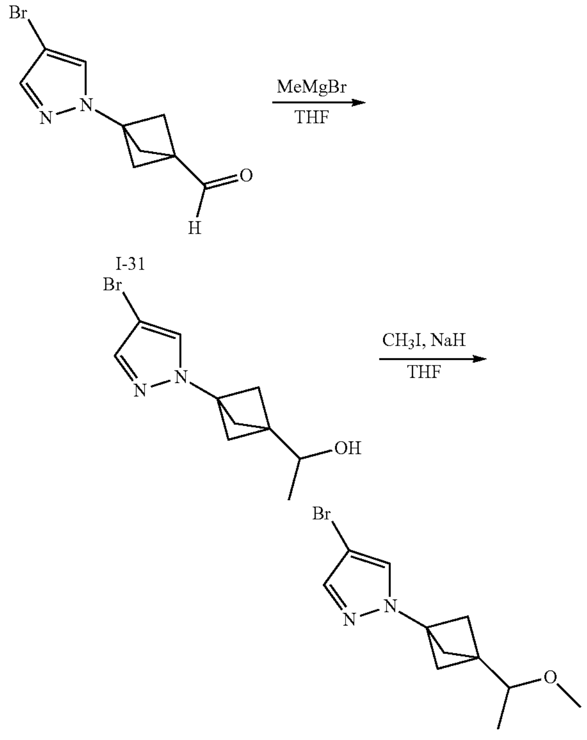

I-31

I-35

Step 1: 1-(3-(4-bromo-1H-pyrazol-1-yl)bicyclo[1.1.1]pentan-1-yl)ethan-1-ol

To a solution of I-31 (300 mg, 1.24 mmol) in THF (5.0 mL) cooled to 0° C. with ice/water bath was added via syringe 3.4M methylmagnesium chloride (in THF) (0.366 mL, 0.366 mmol) and the resulting mixture stirred at same temperature for 1 hr. The mixture was then allowed to warm to room temperature and an aliquot was taken for HPLC. LCMS proved the reaction was complete. The mixture was quenched with sat'd aqueous ammonium chloride (1 mL) and diluted with ethyl acetate (3 mL). The organics were separated and then dried over sodium sulfate, filtered and the filtrate concentrated to dryness under reduced pressure. The residue was taken up in 1 mL DCM and place onto the ISCO (24 g silica gel GOLD column) eluting with a gradient eluent of 0-60% ethyl acetate in hexane. The tubes containing the product were combined and the solvent removed under reduced pressure to afford 1-(3-(4-bromo-1H-pyrazol-1 yl)bicyclo [1.1.1]pentan-1-yl)ethan-1-ol. MS (EI) m/z: 257 [M+H]$^+$.

Step 2: 4-bromo-1-(3-(1-methoxyethyl)bicyclo[1.1.1]pentan-1-yl)-1H-pyrazole (I-35)

To a solution of 1-(3-(4-bromo-1H-pyrazol-1-yl)bicyclo[1.1.1]pentan-1-yl)ethan-1-ol (150 mg, 0.583 mmol) in anhydrous THF (3 mL) cooled to 0° C. via ice/water bath was added in portions over 2 minutes NaH (28 mg, 0.70 mmol) and the resulting solution stirred for 30 minutes at 0° C. MeI (0.073 mL, 1.2 mmol) was then added via syringe dropwise and the solution stirred for an additional 2 hrs allowing to warm to room temperature. The reaction was quenched with aq ammonium chloride (5 mL) and diluted with ethyl acetate (5 mL). The organic phase was separated, dried over sodium sulfate, filtered and the filtrate concentrated to dryness under reduced pressure. The residue was taken up into 2 mL DCM and purified by ISCO (12 g silica gel GOLD column) eluting with a gradient eluant of 0-50% ethyl acetate in hexane. The tubes containing the compound were combined and the solvent remove under reduced pressure to afford the title compound (I-35). MS (EI) m/z: 271 [M+H]$^+$.

Synthesis of Common Intermediate I-36: 1-(bicyclo[1.1.1]pentan-1-yl)-4-iodo-1H-pyrazole Scheme 29

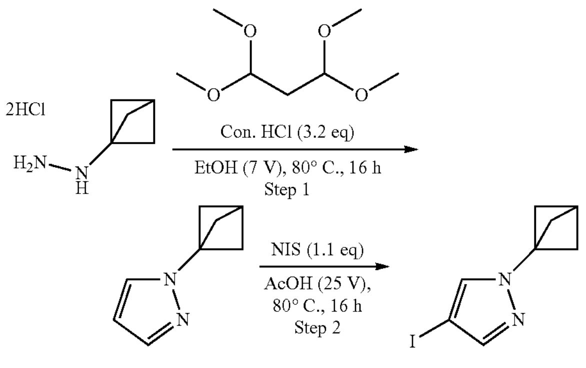

I-36

Step 1: 1-(bicyclo[1.1.1]pentan-1-yl)-1H-pyrazole

Bicyclo[1.1.1]pentan-1-ylhydrazine bis-HCl (20 g, 117 mmol), 1,1,3,3-tetramethoxypropane (19.2 g, 117 mmol) and EtOH (140 mL) were added to a 250 mL three-necked round-bottom flask. Concentrated hydrogen chloride (36.9 g, 374 mmol) was added to the suspension in one portion, and the suspension stirred at 80° C. for 16 hrs. The reaction was cooled and quenched with $H_2O$ (500 mL), then extracted with DCM (200 mL×5). The organics were dried over $Na_2SO_4$ and concentrated carefully (product is volatile) to give 1-(bicyclo[1.1.1]pentan-1-yl)-1H-pyrazole. The crude product was carried on to the next step without further purification. $^1$HNMR: (400 MHz, DMSO-$d_6$) δ 7.72 (d, J=2.2 Hz, 1H), 7.45 (s, 1H), 6.25 (t, J=2.0 Hz, 1H), 2.60 (s, 1H), 2.21 (s, 6H). GCMS m/z: 133 [M−H]$^-$.

Step 2: 1-(bicyclo[1.1.1]pentan-1-yl)-4-iodo-1H-pyrazole (I-36)

1-(bicyclo[1.1.1]pentan-1-yl)-1H-pyrazole (15.3 g, 114 mmol) and NIS (25.6 g, 114 mmol) were dissolved in Acetic Acid (381 mL). The reaction was then stirred at 80° C. for 2 hrs, then cooled, concentrated under reduced pressure, and purified by column chromatography on silica gel (Petroleum ether/EtOAc=100/1-30/1) to afford the title compound (I-36). $^1$HNMR: (400 MHz, DMSO-$d_6$) δ 7.98 (s, 1H), 7.54 (s, 1H), 2.60 (s, 1H), 2.20 (s, 6H). MS (EI) m/z: 261 [M+$H^+$].

Synthesis of Common Intermediate I-37: 4-bromo-1-(3-methoxybicyclo[1.1.1]pentan-1-yl)-1H-pyrazole Scheme 30

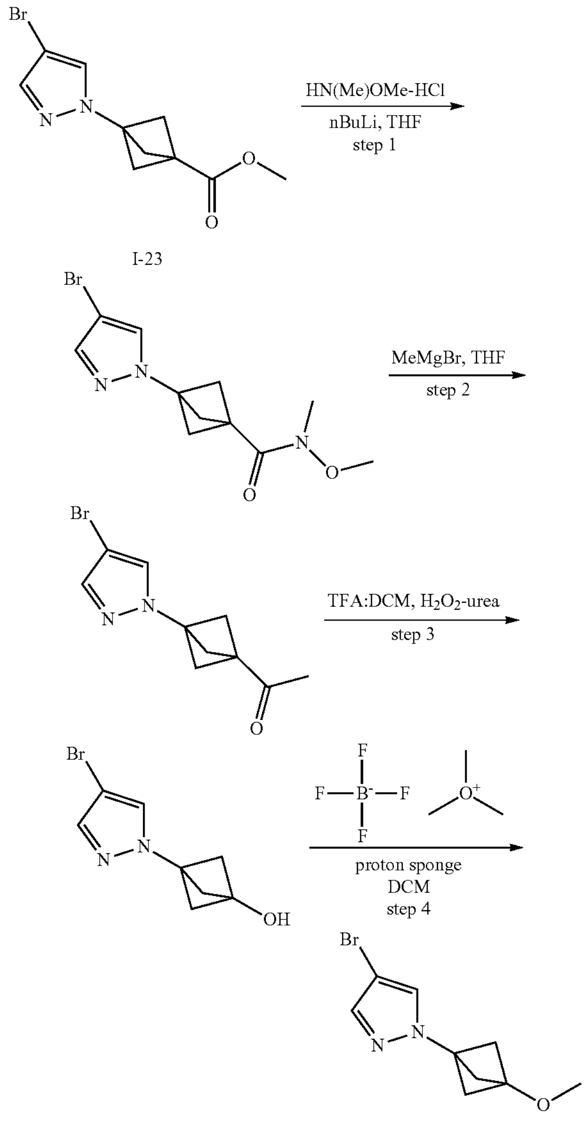

I-23

I-37

Step 1: 3-(4-bromo-1H-pyrazol-1-yl)-N-methoxy-N-methylbicyclo[1.1.1]pentane-1-carboxamide N,O-dimethylhydroxylamine, HCl (1.382 g, 14.16 mmol) was solvated in THF (75 mL) and cooled to −78 degrees celcius while under an atmosphere of nitrogen. Then, n-butyllithium (28.3 mmol, 11.3 mL of 2.5 M solution in hexanes) was slowly added via syringe. After stirring at −78 degrees celcius for 45 minutes, or until all solid is dissolved, intermediate I-23 (3.20 g, 11.8 mmol) was added as a solution in THF (5 mL) slowly over 5 minutes. The reaction was then allowed to slowly warm to room temperature. After 2 hours, The reaction was slowly quenched with saturated $NaHCO_3$(200 mL) and diluted with DCM (200 mL). The organic layer was retrieved, dried over $Na_2SO_4$, filtered, and concentrated. The crude residue was then purified by silica gel column chomotography using a gradient of 0-100% of 3:1 (EtOAc:EtOH) in hexanes to afford 3-(4-bromo-1H-pyrazol-1-yl)-N-methoxy-N methylbicyclo[1.1.1]pentane-1-carboxamide. MS (EI) m/z 300 [M+H]$^+$.

Step 2: 1-(3-(4-bromo-1H-pyrazol-1-yl)bicyclo[1.1.1]pentan-1-yl)ethan-1-one

A solution of 3-(4-bromo-1H-pyrazol-1-yl)-N-methoxy-N methylbicyclo[1.1.1]pentane-1-carboxamide (2.3 g, 7.7 mmol) in THF (50 mL) was cooled to −5 degrees celcius under a nitrogen atmosphere. Then, methylmagnesium bromide (9.2 mmol, 2.64 mL of 3.48 M solution in 2Me-THF) was added slowly via syringe. After stirring for 2 hours, the reaction was slowly quenched with saturated $NaHCO_3$(50 mL) while still at −5 degrees celcius. The mixture was diluted with DCM (100 mL) and the organic layer was extracted, dried over $Na_2SO_4$, filtered, and concentrated. The resulting residue was then purified by silica gel column chomotography using a gradient of 0-100% of 3:1 (EtOAc:EtOH) in hexanes to afford 1-(3-(4-bromo-TH-pyrazol-1-yl)bicyclo[1.1.1]pentan-1-yl)ethan-1-one. MS (EI) m/z 255 [M+H]$^+$.

Step 3: 3-(4-bromo-TH-pyrazol-1-yl)bicyclo[1.1.1]pentan-1-ol 1-(3-(4-bromo-1H-pyrazol-1-yl)bicyclo[1.1.1]pentan-1-yl)ethan-1-one (500 mg, 1.96 mmol) was solvated in DCM (10 mL) and TFA (10.5 mL) at room temperature in a 50 mL round bottom flask with a magnetic stir bar. Then, urea-hydrogen peroxide (1.10 g, 11.8 mmol) was added. The mixture was then warmed to 32 degrees celcius. After 5 hours, the reaction was diluted with water (15 mL) and stirred for 15 minutes. The organic layer was then extracted and washed with 10% sodium thiosulfate solution (50 mL). The organic layer was extracted, dried over $Na_2SO_4$, filtered, and concentrated. The resulting residue was purified by silica gel column chromatography using a gradient of 0-50% of 3:1 (EtOAc:EtOH) in hexanes to afford 3-(4-bromo-TH-pyrazol-1-yl)bicyclo[1.1.1]pentan-1-ol. MS (EI) m/z 229 [M+H]$^+$.

Step 4: 4-bromo-1-(3-methoxybicyclo[1.1.1]pentan-1-yl)-1H-pyrazole (I-37)

3-(4-bromo-TH-pyrazol-1-yl)bicyclo[1.1.1]pentan-1-ol (500 mg, 2.18 mmol), proton sponge (1.4 g, 6.6 mmol), and trimethyloxonium tetrafluoroborate (807 mg, 5.46 mmol) were combined in a dry 50 mL round bottom flask with stir bar and solvated in DCM (20 mL). The mixture was stirred at room temperature for 2 hours. Then, the reaction was diluted with 0.5 N HCl solution (15 mL) and stirred for 1 hour. The organic layer was extracted, dried over $Na_2SO_4$, filtered, and concentrated. The residue was then purified by silica gel column chomotography using a gradient of 0-50% of 3:1 (EtOAc:EtOH) in hexane to afford the title compound (I-37). MS (EI) m/z 243 $[M+H]^+$.

Synthesis of Common Intermediate I-38: 1-(3-fluorobicyclo[1.1.1]pentan-1-yl)-4-iodo-TH-pyrazole Scheme 31

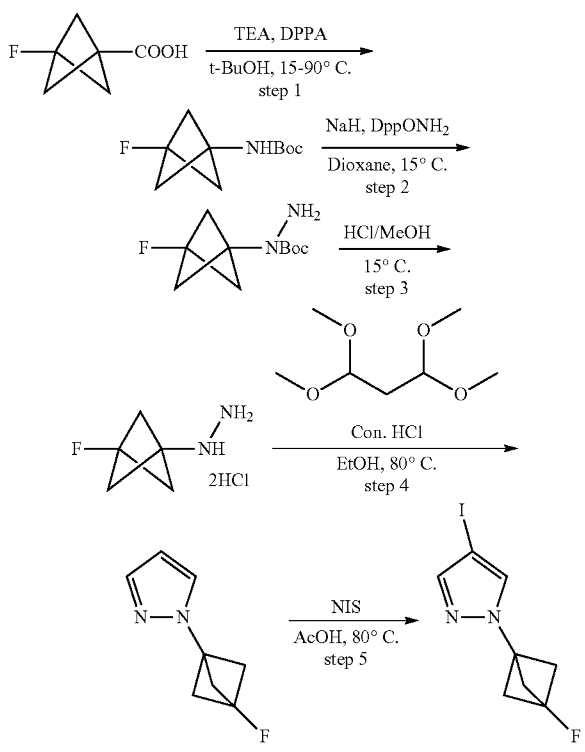

I-38

Step 1: tert-butyl (3-fluorobicyclo[1.1.1]pentan-1-yl)carbamate

Diphenyl azidooxyphosphonate (5.71 g, 19.6 mmol) was added over 20 mins into a mixture of triethylamine (2.04 g, 20.0 mmol) and fluorobicyclo[1.1.1]pentane-1-carboxylic acid (2.50 g, 19.2 mmol) in anhydrous t-BuOH (25 mL) at 15° C. The mixture was stirred at 15° C. for 2 h and then stirred at 90° C. for 3 h. The reaction mixture was concentrated under reduced pressure at 40° C. and the residue was diluted with MTBE. The resulting mixture was washed with aq. saturated $NaHCO_3$ solution 3 times. The organic layer was dried over $Na_2SO_4$, then filtered and concentrated under reduced pressure. The residue was purified by silica gel chromatography (Petroleum ether/EtOAc) to give tert-butyl (3-fluorobicyclo[1.1.1]pentan-1-yl)carbamate. $^1$HNMR: (400 MHz, $CDCl_3$) δ 2.33 (s, 6H), 1.45 (s, 9H).

Step 2: tert-butyl 1-(3-fluorobicyclo[1.1.1]pentan-1-yl)hydrazine-1-carboxylate

NaH (0.39 g, 9.94 mmol, 65% in mineral oil) was added to a solution of tert-butyl (3-fluorobicyclo[1.1.1]pentan-1-yl)carbamate (1.0 g, 4.97 mmol) in dioxane (20 mL) at 15° C. The reaction mixture was stirred at 15° C. for 3 h. Then O-(Diphenylphosphinyl)hydroxylamine (1.51 g, 6.46 mmol) was added. The resulting mixture was stirred at 15° C. for 21 h. $H_2O$ was added and the mixture was extracted with EtOAc 5 times. The combined organic layer was dried with $Na_2SO_4$, then filtered and filtrate was concentrated under reduced pressure. The residue was purified by silica gel chromatography (Petroleum ether/EtOAc) to give tert-butyl 1-(3-fluorobicyclo[1.1.1]pentan-1-yl)hydrazine-1-carboxylate. $^1$HNMR: (400 MHz, DMSO-$d_6$) δ 4.50 (s, 2H), 2.28 (d, J=2.1 Hz, 6H), 1.41 (s, 9H).

Step 3: (3-fluorobicyclo[1.1.1]pentan-1-yl)hydrazine, HCl salt

HCl (4 M solution in MeOH, 14.4 mL) was added to tert-butyl 1-(3-fluorobicyclo[1.1.1]pentan-1-yl)hydrazine-1-carboxylate (720 mg, 3.33 mmol) at 15° C. The reaction was stirred at 15° C. for 6 h. The reaction was concentrated in vacuum. The residue was used directly in the next step without further purification. $^1$HNMR (400 MHz, DMSO-$d_6$) δ 2.18 (d, J=2.1 Hz, 6H).

Step 4: 1-(3-fluorobicyclo[1.1.1]pentan-1-yl)-1H-pyrazole

Hydrogen chloride (834 mg, 8.46 mmol) was added to a mixture of (3-fluorobicyclo[1.1.1]pentan-1-yl)hydrazine, HCl salt (500 mg, 2.64 mmol) and 1,1,3,3-tetramethoxypropane (443 mg, 2.70 mmol) in EtOH (5 mL) at 15° C. The reaction mixture was stirred at 80° C. for 2 h. $H_2O$ was added and the mixture was extracted with DCM 5 times. The combined organic layer was dried over $Na_2SO_4$, then filtered and the filtrate was concentrated under reduced pressure (bath temperature 20-30° C.). The residue was used directly in the next step without further purification. MS (EI) m/z: 153 $[M+H]^+$.

Step 5: 1-(3-fluorobicyclo[1.1.1]pentan-1-yl)-4-iodo-1H-pyrazole (I-38)

NIS (2.00 g, 5.26 mmol) was added to a mixture of 1-(3-fluorobicyclo[1.1.1]pentan-1-yl)-1H-pyrazole (400 mg, 8.87 mmol) in acetic acid (10 mL) at 15° C. The mixture was stirred at 80° C. for 16 h. The mixture was concentrated in vacuum. The residue was purified by silica gel chromatography (Petroleum ether/EtOAc) to give the title compound (I-38). MS (EI) m/z: 279 $[M+H]^+$; $^1$HNMR: (400 MHz, DMSO-$d_6$) δ 8.05 (s, 1H), 7.62 (s, 1H), 2.61 (d, J=2.03 Hz, 6H).

Synthesis of Common Intermediate I-39

Scheme 32

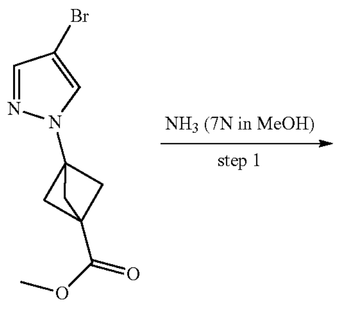

I-23

-continued

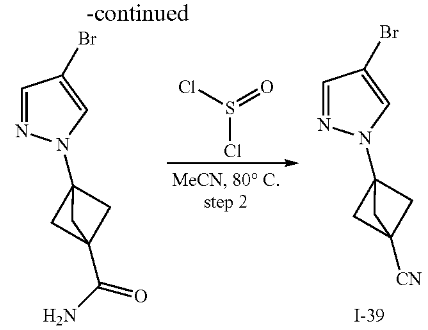

I-39

Step 1: 3-(4-bromo-1H-pyrazol-1-yl)bicyclo[1.1.1]pentane-1-carboxamide

I-23 (200 mg, 0.738 mmol), ammonia (2108 µl, 14.75 mmol, 7N in MeOH) were combined in a dry 20 mL vial with stir bar. The reaction was allowed to stir at room temperature for 18 h. The reaction mixture was concentrated in vacuo to give 3-(4-bromo-1H-pyrazol-1-yl)bicyclo[1.1.1]pentane-1-carboxamide. MS (EI) m/z 256 $[M+H]^+$.

Step 2: 3-(4-bromo-1H-pyrazol-1-yl)bicyclo[1.1.1]pentane-1-carbonitrile (I-39)

3-(4-bromo-1H-pyrazol-1-yl)bicyclo[1.1.1]pentane-1-carboxamide (189 mg, 0.738 mmol) was dissolved in MeCN (9 ml) and sulfurous dichloride (1.0 ml, 14 mmol) was added. The solution was heated to reflux for 3 hours. Then, the reaction was carefully concentrated in vacuo (HCl is released). The resulting material was azeotroped several times with THF to afford the title compound (I-39). MS (EI) m/z 238 $[M+H]^+$.

Intermediate I-40: 4-iodo-1-(3-iodobicyclo[1.1.1]pentan-1-yl)-1H-pyrazole

Scheme 33

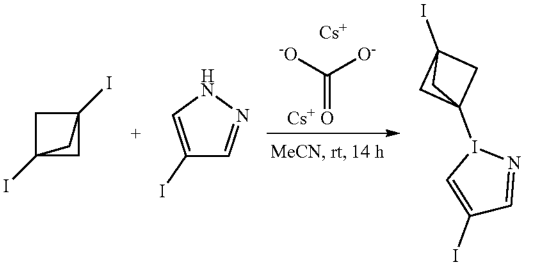

I-40

A 30-mL round-bottomed vial was charged with 4-iodo-1H-pyrazole (1.21 g, 6.25 mmol), 1,3-diiodobicyclo[1.1.1]pentane (2.0 g, 6.25 mmol) and cesium carbonate (6.11 g, 18.8 mmol), then MeCN (31.3 ml) was added and the reaction sealed and stirred at room temperature for 14 hours. The reaction was then filtered through a pad of celite (rinse with MeCN) and condensed, then loaded onto silica and purified by silica gel chromatography, eluting with 0-40% ethyl acetate in hexanes to afford the title compound (I-40). $^1H$ NMR (600 MHz, DMSO) δ 8.00 (s, 1H), 7.57 (s, 1H), 2.69 (s, 6H). MS (EI) m/z: 387 $[M+H]^+$

Intermediate I-41: 1-((2-(trimethylsilyl)ethoxy)methyl)-1,4,5,6,7,8-hexahydro-4,7-epiminocyclohepta[c]pyrazole Scheme 34

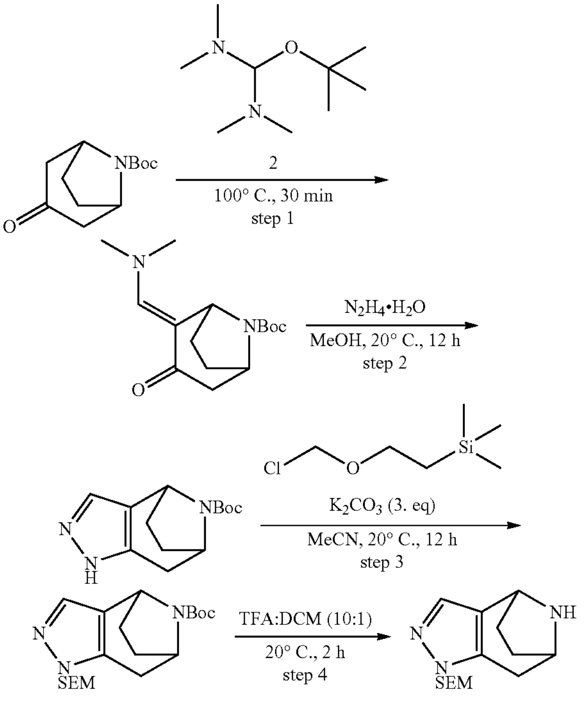

I-41

Step 1: tert-butyl (E)-2-((dimethylamino)methylene)-3-oxo-8-azabicyclo[3.2.1]octane-8-carboxylate Tert-butyl 3-oxo-8-azabicyclo[3.2.1]octane-8-carboxylate (0.50 g, 2.22 mmol) was dissolved in 1-tert-butoxy-N,N,N',N'-tetramethylmethanediamine (0.542 g, 3.11 mmol). The reaction vial was sealed with a septum and stirred for 1 h at 100° C. The reaction mixture was cooled to room temperature, diluted with water (60 mL) and extracted with ethyl acetate (3×100 mL). The combined organic layers were washed with brine, dried with $Na_2SO_4$, filtered and evaporated to give (E)-tert-butyl2-((dimethylamino)methylene)-3-oxo-8-azabicyclo[3.2.1]octane-8-carboxylate, which was used in the next step without further purification. MS (ESI) m/z: 281 $[M+H]^+$

Step 2: tert-butyl 1,4,5,6,7,8-hexahydro-4,7-epiminocyclohepta[c]pyrazole-9-carboxylate To a solution (E)-tert-butyl 2-((dimethylamino)methylene)-3-oxo-8-azabicyclo[3.2.1]octane-8-carboxylate (2.0 g, 7.1 mmol) in methanol (40 mL) was added $N_2H_4.H_2O$ (0.429 g, 8.56 mmol). The solution was stirred at 20° C. for 12 h. The reaction mixture was concentrated to give tert-butyl 1,4,5,6,7,8-hexahydro-4,7-epiminocyclohepta[c]pyrazole-9-carboxylate, which was used in the next step without purification. MS (ESI) m/z: 250 $[M+H]^+$ Step 3: tert-butyl 1-((2-(trimethylsilyl)ethoxy)methyl)-1,4,5,6,7,8-hexahydro-4,7-epiminocyclohepta[c]pyrazole-9-carboxylate To a solution of tert-butyl 1,4,5,6,7,8-hexahydro-4,7-epiminocyclohepta[c]pyrazole-9-carboxylate (200 mg, 0.802 mmol) in anhydrous Acetonitrile (20 mL) was added (2-(chloromethoxy)ethyl)trimethylsilane (267 mg, 1.60 mmol) and $K_2CO_3$ (222 mg, 1.60 mmol) at 20° C. The solution was stirred at 20° C. for 12 h. After concentration, $H_2O$ (40 mL) was added to the mixture. EtOAc (60 mL) was added into the mixture. The organic layer was separated. The aqueous layer was extracted with EtOAc (60 mL×2). The combined layers were concentrated, The crude mixture was purified by flash silica gel chromatography (4 g, eluenting with 0-10% EtOAc in Pet.ether gradient) to give tert-butyl 1-((2-(trimethylsilyl)ethoxy)methyl)-1,4,5,6,7,8-hexahydro-4,7-epiminocyclohepta[c]pyrazole-9-carboxylate. MS (ESI) m/z: 380 $[M+H]^+$ Step 4: 1-((2-(trimethylsilyl)ethoxy)methyl)-1,4,5,6,7,8-hexahydro-4,7-epiminocyclohepta[c]pyrazole (I-41)

To a solution of tert-butyl 1-((2-(trimethylsilyl)ethoxy)methyl)-1,4,5,6,7,8-hexahydro-4,7-epiminocyclohepta[c]pyrazole-9-carboxylate (1.0 g, 2.6 mmol) in DCM (20 mL) was added 2,2,2-trifluoroacetic acid (2.0 ml, 2.63 mmol), the mixture was stirred at 20° C. for 12 h. The mixture was concentrated to afford the crude product which was purified by Pre-HPLC (Mobile phase A: water (0.05% HCl), mobile phase B: acetonitrile. Gradient: 22-42% B, 10 min; 100% B, 2 min) to afford the title compound (I-41). MS (ESI) m/z: 280 $[M+H]^+$ Synthesis of Common Intermediates I-42: (1R,5S,8r)-8-methyl-3-azabicyclo[3.2.1]octan-8-ol Scheme 35

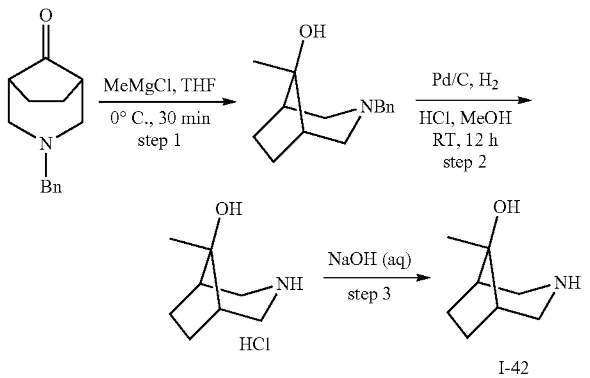

I-42

Step 1: (1R,5S,8r)-3-benzyl-8-methyl-3-azabicyclo[3.2.1]octan-8-ol [Endo —OH]

To a mixture of (1R,5S)-3-benzyl-3-azabicyclo[3.2.1]octan-8-one (220 g, 1.02 mol, 1.0 eq.) in THF (2200 ml) was added MeMgCl (1020 ml, 3 M in THF) dropwise at 0° C. The reaction was stirred at 0° C. for 30 min. After the reaction was completed, the saturated $NH_4Cl$ solution (2000 ml) was added at 0° C., then the solid was filtered out and the filter cake was wash with ethyl acetate (2000 ml). Two phases were separated, and the organic phase was wash with brine (3×500 ml), dried over $Na_2SO_4$ and concentrated under vacuum. The resulting residue was purified by silica gel column with ethyl acetate:petroleum ether=1:10 to afford (1R,5S,8r)-3-benzyl-8-methyl-3-azabicyclo[3.2.1]octan-8-ol [Endo —OH]. MS (EI) m/z 232 $[M+H]^+$.

Step 2: (1R,5S,8r)-8-methyl-3-azabicyclo[3.2.1]octan-8-ol hydrochloride

To a solution of (1R,5S,8r)-3-benzyl-8-methyl-3-azabicyclo[3.2.1]octan-8-ol (145 g, 0.63 mol, 1.0 eq.) in MeOH (1450 ml) was added Pd/C (70 g) and concentrated HCl (145 mL, 12M) under $H_2$ atmosphere. The reaction was stirred at RT for 12 h. After the reaction was completed. The solid was filtered out. The filtrate was concentrated and the EtOAc (145 mL) was added. The solids were collected by filtration to afford (1R,5S,8r)-8-methyl-3-azabicyclo[3.2.1]octan-8-ol hydrochloride. MS (EI) m/z: 142 $[M+H]^+$.

Step 3: (1R,5S,8r)-8-methyl-3-azabicyclo[3.2.1]octan-8-ol (I-42)

The free amino alcohol can be attained treating a solution of 8-methyl-3-azabicyclo[3.2.1]octan-8-ol hydrochloride (1.38 g, 7.77 mmol) in 20 ml of water with sodium hydroxide (7.77 ml, 7.77 mmol, 1 M), the free amino alcohol was extracted with 4:1 chloroform/IPA (75 ml×2). The combined organic extracts were dried over sodium sulfate, filtered and concentrated to afford the title compound (I-42), which was used without further purification. MS (EI) m/z 142 $[M+H]^+$.

Synthesis of Common Intermediate I-43: 4-((tert-butyldiphenylsilyl)oxy)dihydrofuran-3(2H)-one Scheme 36

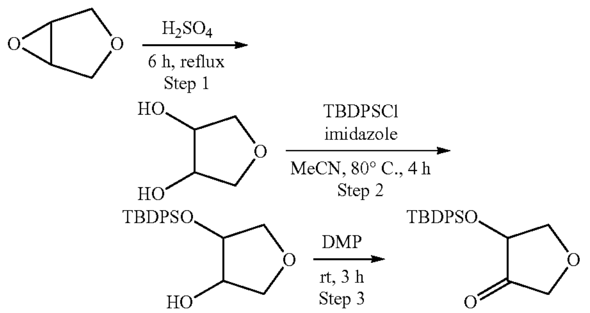

I-43

Step 1: tetrahydrofuran-3,4-diol

A 10-L 4-necked round-bottom flask was charged with 3,6-dioxabicyclo[3.1.0]hexane (409 g, 4751 mmol, 1.00 equiv) and $H_2SO_4$ (4 L, 1.5 mol/L). The resulting solution was stirred for 6 h at reflux. The reaction mixture was cooled to room temperature, and the pH of the solution was adjusted to 8 with $Na_2CO_3$, then extracted with 5 L of THF and concentrated to afford tetrahydrofuran-3,4-diol. $^1H$ NMR (400 MHz, $D_2O$, ppm) δ 4.23 (d, J=3.6 Hz, 2H), 3.95-4.03 (m, 2H), 3.72-3.77 (m, 2H).

Step 2: 4-((tert-butyldiphenylsilyl)oxy)tetrahydrofuran-3-ol

A 3-L 4-necked round-bottom flask was purged and maintained with an inert atmosphere of nitrogen and charged with tetrahydrofuran-3,4-diol (52 g, 499 mmol, 1.0 equiv), acetonitrile (1.5 L), imidazole (51 g, 749 mmol, 1.5 equiv) and TBDPSCl (137 g, 498 mmol, 1.0 equiv). The resulting solution was stirred for 4 h at 80° C. The resulting mixture was concentrated under vacuum then diluted with 1 L of ethyl acetate. The resulting mixture was washed with water (2×500 mL), dried over anhydrous sodium sulfate and concentrated under vacuum. The residue was purified by silica gel column, eluting with ethyl acetate in petroleum ether (1:100-1:30) to give 4-((tert-butyldiphenylsilyl)oxy) tetrahydrofuran-3-ol. $^1$H NMR (400 MHz, Chloroform-d, ppm) δ: 7.69-7.63 (m, 4H), 7.50-7.37 (m, 6H), 4.28 (q, J=6.3 Hz, 1H), 4.10-4.03 (m, 1H), 3.88-3.74 (m, 2H), 3.58 (d, J=6.3 Hz, 2H), 3.00 (d, J=4.3 Hz, 1H), 1.11 (s, 9H)

Step 3: 4-((tert-butyldiphenylsilyl)oxy)dihydrofuran-3(2H)-one (I-43)

A 2 L 3-necked round-bottom flask was purged and maintained with an inert atmosphere of nitrogen and charged with DMP (93 g, 219 mmol, 1.1 equiv), DCM (1.1 L) and 4-((tert-butyldiphenylsilyl)oxy)tetrahydrofuran-3-ol (71 g, 207 mmol, 1.0 equiv). The resulting solution was stirred for 3 h at 25-30° C., then diluted with 2 L of petroleum ether. The resulting mixture was washed with sat aq. $NaHCO_3$(2×1 L) and brine (1×1 L). The mixture was dried over anhydrous sodium sulfate and concentrated under vacuum. The residue was purified on silica gel column, eluting with ethyl acetate/petroleum ether (1:100-1:30) to afford the title compound (I-43). MS (EI) m/z 363 [M+Na]$^+$ I-44 in Table 5 was prepared according to Scheme 36 (step 2 and step 3) by using the corresponding reagent.

TABLE 5

| Intermediate | Structure | Name | NMR |
|---|---|---|---|
| I-44 | 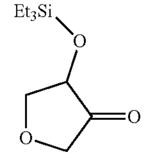 | 4-((triethylsilyl)oxy)dihydrofuran-3(2H)-one | $^1$H NMR (400 MHz, $CDCl_3$) δ 4.38 – 4.25 (m, 2H), 4.11 – 4.03 (m, 1H), 3.94 – 3.87 (m, 1H), 3.73 (t, J = 8.7 Hz, 1H), 0.95 (t, J = 7.9 Hz, 9H), 0.71 – 0.59 (m, 6H) |

Synthesis of Common Intermediate I-45: 5-chloro-6-(piperazin-1-yl)-1H-indazole Scheme 37

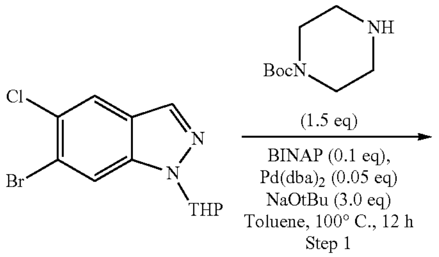

-continued

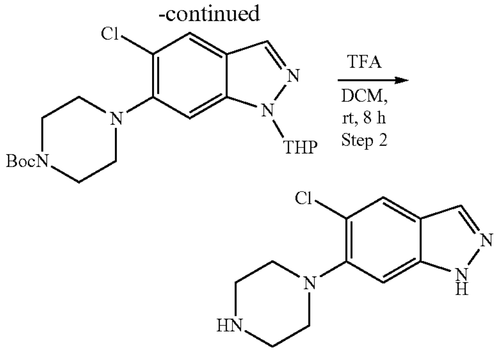

I-45

Step 1: tert-butyl 4-(5-chloro-1-(tetrahydro-2H-pyran-2-yl)-1H-indazol-6-yl)piperazine-1-carboxylate A three-necked flask was charged with 6-bromo-5-chloro-1-(tetrahydro-2H-pyran-2-yl)-1H-indazole (120 g, 380 mmol, 1.0 eq), tert-butyl piperazine-1-carboxylate (106.2 g, 570.3 mmol, 1.5 eq) and NaOtBu (109.6 g, 1.14 mol, 3.0 eq) under $N_2$. Toluene (3.60 L) was then added, and the resulting suspension sparged with nitrogen for 30 minutes. $Pd(dba)_2$ (17.41 g, 19.01 mmol, 0.05 eq) and BINAP (23.68 g, 38.02 mmol, 0.1 eq) were then added, and the reaction inerted with three $N_2$/vacuum cycles. The reaction was then stirred at 100° C. for 12 hours, then cooled to room temperature and filtered through a pad of celite. The reaction was then poured into 10 L of water and stirred for 10 minutes, then the aqueous phase extracted with ethyl acetate (5.0 L×2). The combined organic phase was washed with brine (2.0 L), dried with anhydrous $Na_2SO_4$, filtered and concentrated under vacuum. The residue was purified by column chromatography ($SiO_2$, Petroleum ether/Ethyl acetate to =10/1 to Dichloromethane: Methanol=1/1) to afford tert-butyl 4-(5-chloro-1-(tetrahydro-2H-pyran-2-yl)-1H-indazol-6-yl)piperazine-1-carboxylate. $^1$HNMR: (400 MHz, $CDCl_3$) δ: 7.89 (s, 1H), 7.73 (s, 1H), 7.13 (s, 1H), 5.63-5.66 (m, 1H), 4.00-4.03 (m, 1H), 3.75-4.00 (m, 1H), 3.65-3.75 (m, 4H), 3.06-3.07 (m, 4H), 2.52-2.55 (m, 1H), 2.04-2.16 (m, 1H), 1.67-1.76 (m, 4H), 1.50 (s, 9H).

Step 2: 5-chloro-6-(piperazin-1-yl)-1H-indazole (I-45)

Tert-butyl-4-(5-chloro-1-(tetrahydro-2H-pyran-2-yl)-1H-indazol-6-yl)piperazine-1-carboxylate (330 g, 783.9 mmol, 1.0 eq) and DCM (2.00 L) were added to a three-necked flask. TFA (1.28 kg, 11.24 mol, 831.9 mL, 14.33 eq) was then added dropwise into the solution, and the reaction mixture stirred for 8 hours at 20° C. The reaction was slowly quenched with sat. $NaHCO_3$(6.0 L), extracted with (3:1 $CHCl_3$:IPA), dried over $Na_2SO_4$ and concentrated. The crude 5-chloro-6-(piperazin-1-yl)-1H-indazole was used for subsequent steps without purification. $^1$HNMR: (400 MHz, MeOH) δ: 7.91 (s, 1H), 7.78 (s, 1H), 7.17 (s, 1H), 3.02-3.03 (m, 8H). MS (EI) m/z: 237 $[M+H]^+$.

I-46 in Table 6 was prepared according to Scheme 37 by using the corresponding starting materials

TABLE 6

| Intermediate | Structure | Name | Exact Mass [M + H]+ |
|---|---|---|---|
| I-46 | 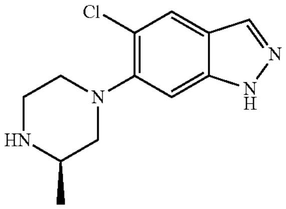 [SMILES: C[C@@H]1CN(c2cc3[nH]ncc3cc2Cl)CCN1] | (R)-5-chloro-6-(3-methylpiperazin-1-yl)-1H-indazole | Calc'd 251, found 251 |

Synthesis of Common Intermediates I-47: 5-chloro-6-(2-methylpiperazin-1-yl)-1H-indazole Scheme 38

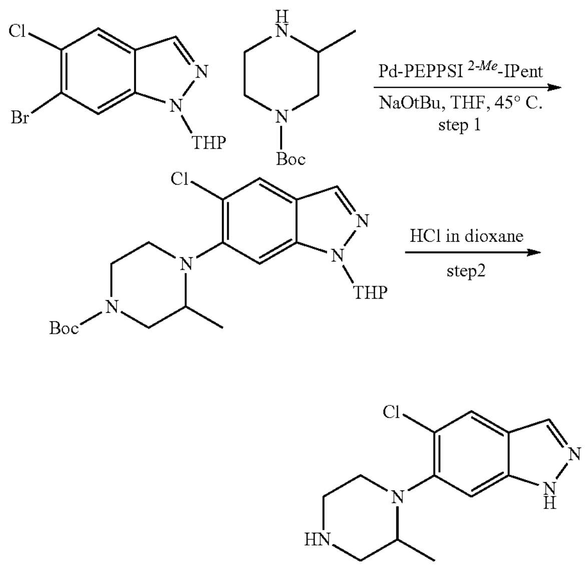

I-47

Step 1: tert-butyl 4-(5-chloro-1-(tetrahydro-2H-pyran-2-yl)-1H-indazol-6-yl)-3-methylpiperazine-1-carboxylate To a flask were added 6-bromo-5-chloro-1-(tetrahydro-2H-pyran-2-yl)-1H-indazole (5.0 g, 16 mmol), tert-butyl 3-methylpiperazine-1-carboxylate (6.35 g, 31.7 mmol), Pd-PEPPSI$^{2Me}$-IPent (0.532 g, 0.634 mmol) and THF (100 ml). The mixture was evacuate and backfilled with $N_2$ for 4 time, then NaOtBu (20 ml, 40.0 mmol, 2M in THF) was added dropwise. The mixture was evacuated and backfilled with $N_2$ for 4 times again. The mixture was heated at 45° C. for 18 h. The mixture was quenched with water and extracted with EtOAc. The combined organic layers was washed with brine, dried over $MgSO_4$, filtered and concentrated in vacuo. The residue was purified by column chromatography on silica (120 g, EtOAc in hexane, 0-60% gradient) to afford tert-butyl 4-(5-chloro-1-(tetrahydro-2H-pyran-2-yl)-1H-indazol-6-yl)-3-methylpiperazine-1-carboxylate. MS (EI) m/z: 435 $[M+H]^+$.

Step 2: 5-chloro-6-(2-methylpiperazin-1-yl)-1H-indazole (I-47)

To the solution of tert-butyl 4-(5-chloro-1-(tetrahydro-2H-pyran-2-yl)-1H-indazol-6-yl)-3-methylpiperazine-1-carboxylate (2.16 g, 4.96 mmol) in dioxane (20 ml), was added HCl in dioxane (16 ml, 64.0 mmol, 4N) at rt. The mixture was stirred at room temperature for 18 h. Then, the solvent was evaporated to afford the product as an HCl salt. This product was diluted with water, $NaHCO_3$ (sat.), extracted with $CHCl_3$/IPA (3/1) three times to give the title compound (I-47). MS (EI) m/z: 251 $[M+H^+]$.

Synthesis of Common Intermediate I-48 and I-49: 5-chloro-6-(4-((2S,3S and 2R,3R)-2,3-dimethyloxetan-3-yl)piperazin-1-yl)-1H-indazole and 5-chloro-6-(4-((2R,3S and 2S,3R)-2,3-dimethyloxetan-3-yl)piperazin-1-yl)-1H-indazole Scheme 39

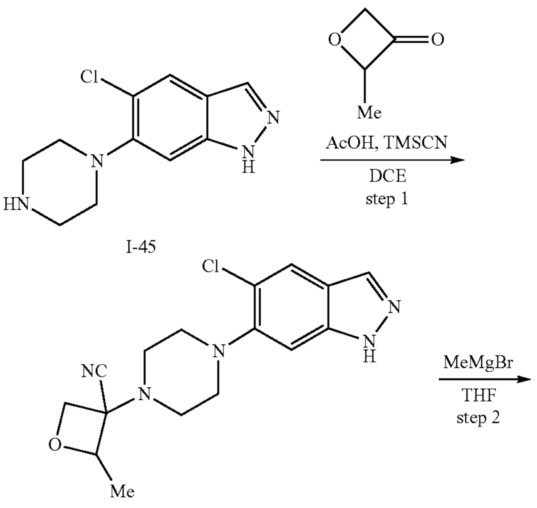

I-45

-continued

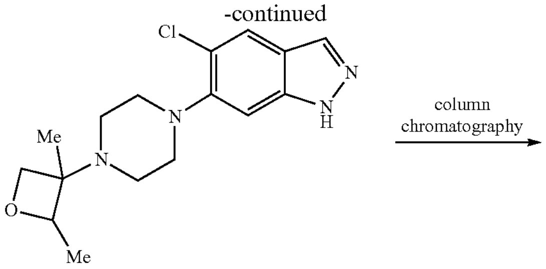

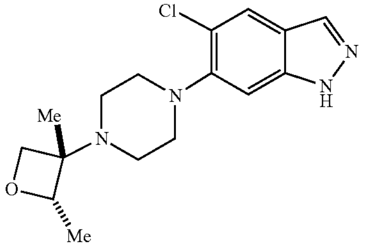

I-48

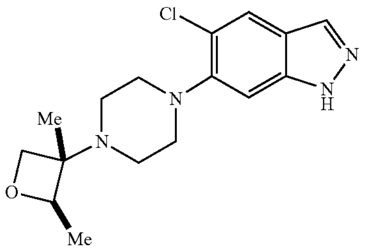

I-49

Step 1: cis and trans 3-(4-(5-chloro-1H-indazol-6-yl)piperazin-1-yl)-2-methyloxetane-3-carbonitrile I-45 (0.174 g, 0.734 mmol) was dissolved in DCE (5 mL) in a 20 mL vial under $N_2$. Acetic acid (0.063 mL, 1.1 mmol) was added followed by 2-methyloxetan-3-one (0.095 g, 1.1 mmol). After 10 minutes of stirring at room temperature, trimethylsilyl cyanide (0.138 mL, 1.101 mmol) was added via syringe. The reaction was then heated to 60° C. and stirred for 18 h. A second addition of 2-methyloxetan-3-one (0.02 g, 0.23 mmol) and trimethylsilyl cyanide (0.05 mL, 0.4 mmol) were added and the reaction was stirred for an additional 6 h at 60° C. The reaction was cooled to room temperature, diluted with sat. $NaHCO_3$(15 mL) and extracted with 3:1 $CHCl_3$:IPA (3×15 mL), dried over $Na_2SO_4$, filtered, and concentrated in vacuo to give a mixture of cis and trans-3-(4-(5-chloro-1H-indazol-6-yl)piperazin-1-yl)-2-methyloxetane-3-carbonitrile. MS (EI) m/z 332 $[M+H]^+$.

Step 2: 5-chloro-6-(4-((2S,3S and 2R,3R)-2,3-dimethyloxetan-3-yl)piperazin-1-yl)-1H-indazole (I-48) and 5-chloro-6-(4-((2R3S and 2S,3R)-2,3-dimethyloxetan-3-yl)piperazin-1-yl)-1H-indazole (I-49)

3-(4-(5-chloro-1H-indazol-6-yl)piperazin-1-yl)-2-methyloxetane-3-carbonitrile was dissolved in THF (4 mL) in a 50 mL RB flask under $N_2$. The flask was placed in an ice bath and cooled to 0° C. Methylmagnesium bromide (1.079 mL, 3.67 mmol, 3.4 M in 2-Me THF) was added down the side of the flask. The reaction was allowed to stir at 0° C. for 30 min then removed from the ice bath and allowed to warm to room temperature and stir for 1 h. The reaction was heated to 50° C. and stirred for 20 h. The reaction was cooled to 0° C. and slowly quenched with water (10 mL). The ice bath was removed and the resulting mixture was extracted with 3:1 $CHCl_3$:IPA (4×10 mL). The organic extract was dried over $Na_2SO_4$, filtered, and concentrated to give a residue, which was purified by column chromatography on silica gel (3:1 EtOAc:EtOH in DCM, 0-100% gradient) to afford the title compounds (I-48 and I-49).

I-48: MS (EI) m/z 321 $[M+H]^+$. Peak 1

I-49: MS (EI) m/z 321 $[M+H]^+$. Peak 2

I-50 and I-51 in Table 7 below were prepared from common intermediate I-46, I-47 according to Scheme 39 by using the I-44 and I-43 as ketone starting materials

TABLE 7

| Intermediate | Structure | Name | Exact Mass [M + H]+ |
|---|---|---|---|
| I-50 | 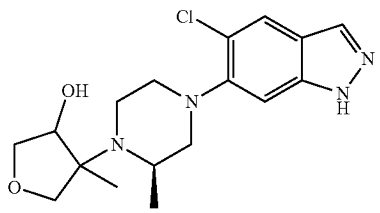 [SMILES: C[C@@H]1CN(c2cc3[nH]ncc3cc2Cl)CCN1C1(C)COCC1O] | 4-((R)-4-(5-chloro-1H-indazol-6-yl)-2-methylpiperazin-1-yl)-4-methyltetrahydrofuran-3-ol | Calc'd 351, found 351 |
| I-51 | 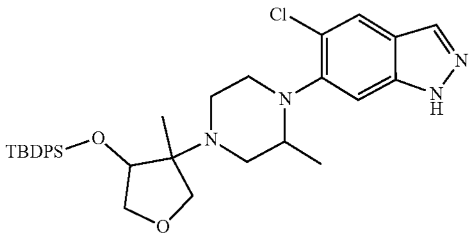 | 6-(4-(4-((tert-butyldiphenylsilyl)oxy)-3-methyltetrahydrofuran-3-yl)-2-methylpiperazin-1-yl)-5-chloro-1H-indazole | Calc'd 589, found 589 |

Synthesis of Common Intermediates I-52 and I-53: 6-(4-((3R,4R or 3S,4S)-4-((tert-butyldiphenylsilyl)oxy)tetrahydrofuran-3-yl)piperazin-1-Yl)-5-chloro-1H-indazole and 6-(4-((3S,4S or 3R,4R)-4-((tert-butyldiphenylsilyl)oxy)tetrahydrofuran-3-yl)piperazin-1-yl)-5-chloro-1H-indazole Scheme 40

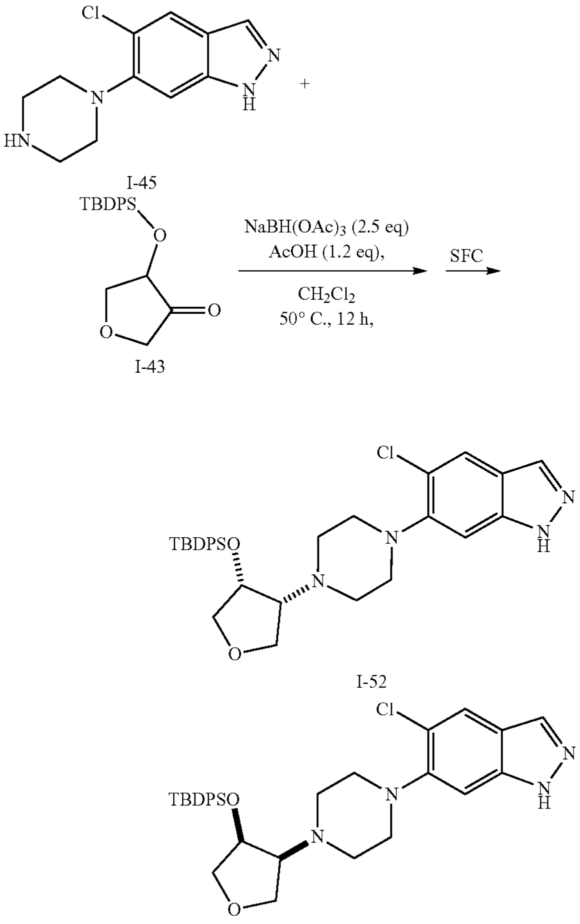

I-45

I-43

I-52

I-53

A 5 L three necked flask wash charged with I-45 (226 g, 955 mmol, 1.0 eq), I-43 (488 g, 1.43 mol, 1.5 eq) and DCE (4 L). The reaction mixture was stirred for 15 mins at 20° C., then $NaBH(OAc)_3$ (506 g, 2.40 mol, 2.5 eq) and AcOH (68.8 g, 1.15 mol, 65.5 mL, 1.2 eq) were added. The reaction was then stirred for 12 hours at 65° C. The reaction was then quenched with sat. $NaHCO_3$(6 L) and extracted with (3:1 $CHCl_3$:IPA). The combined organic extracts were dried over $Na_2SO_4$, and concentrated. The residue was purified by column chromatography ($SiO_2$, Petroleum ether/Ethyl acetate=20/1 to 0/1). The solids were further separated by SFC (column: DAICEL CHIRALPAK AD (250×50 mm); Mobile phase A: $CO_2$; Mobile phase B: EtOH with 0.1% $NH_4OH$) to give the title compounds (I-52 and I-53).

I-52: MS (EI) m/z 561 $[M+H]^+$. Retention time: 5.67 min.

I-53: MS (EI) m/z 561 $[M+H]^+$. Retention time: 7.83 min.

Synthesis of common intermediates I-54, I-55 and I-56: 1-(4-((tert-butyldiphenylsilyl)oxy)-3-methyltetrahydrofuran-3-yl)piperazine (I-54), 1-((3S,4S or 3R,4R)-4-((tert-butyldiphenylsilyl)oxy)-3-methyltetrahydrofuran-3-yl)piperazine (I-55) and 1-((3R,4R or 3S,4S)-4-((tert-butyldiphenylsilyl)oxy)-3-methyl-tetrahydrofuran-3-yl)piperazine (I-56)

Scheme 41

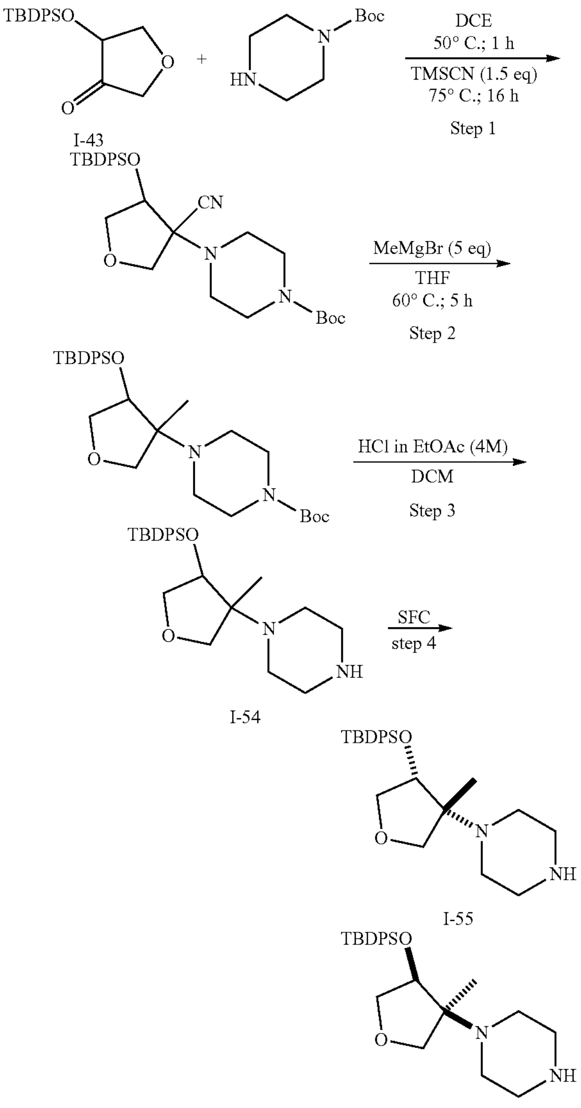

I-43

I-54

I-55

I-56

Step 1: tert-butyl 4-[4-[(tert-butyldiphenylsilyl)oxy]-3-cyanooxolan-3-yl]piperazine-1-carboxylate A 2-L 3-necked round-bottom flask purged and maintained with an inert atmosphere of nitrogen was charged with tert-butyl piperazine-1-carboxylate (250 g, 1.34 mol, 1.00 equiv), DCE (250 mL), I-43 (500 g, 1.47 mol, 1.10 equiv). The resulting solution was stirred for 1 h at 50° C. This was followed by the addition of TMSCN (160 g, 1.61 mol, 1.20 equiv) dropwise with stirring at 40° C. The resulting solution was stirred for 16 h at 75° C. The reaction mixture was cooled to room temperature. The resulting mixture was concentrated under vacuum and used crude in the subsequent step. MS (EI) m/z 536 $[M+1]^+$.

Step 2: tert-butyl 4-(4-((tert-butyldiphenylsilyl)oxy)-3-methyltetrahydrofuran-3-yl)piperazine-1-carboxylate A 5-L 4-necked round-bottom flask purged and maintained with an inert atmosphere of nitrogen was charged with tert-butyl 4-[4-[(tert-butyldiphenylsilyl)oxy]-3-cyanooxolan-3-yl]piperazine-1-carboxylate (600 g, 1.12 mmol, 1.00 equiv, crude) and THF (450 mL). This was followed by the addition of MeMgBr (4.2 L, 1 M solution in THF) dropwise with stirring at <10° C. The resulting solution was stirred for 3 h at 50° C. The reaction was then quenched by the addition of 1 L of sat. aq. $NaHCO_3$ then diluted with 10 L of ethyl acetate. The solids were filtered, and the resulting mixture was concentrated under vacuum. The residue was purified by flash chromatography over silica gel (0-20% ethyl acetate in petroleum ether) to afford tert-butyl 4-(4-((tert-butyldiphenylsilyl)oxy)-3-methyltetrahydrofuran-3-yl)piperazine-1-carboxylate. MS (EI) m/z 525 $[M+1]^+$.

Step 3: 1-(4-((tert-butyldiphenylsilyl)oxy)-3-methyltetrahydrofuran-3-yl)piperazine (I-54)

A 5-L 4-necked round-bottom flask purged and maintained with an inert atmosphere of nitrogen was charged with tert-butyl 4-[4-[(tert-butyldiphenylsilyl)oxy]-3-methyloxolan-3-yl]piperazine-1-carboxylate (220 g, 419 mmol, 1 equiv) and DCM (2.2 L). This was followed by the addition of HCl in ethyl acetate (470 mL) dropwise with stirring at 10 degrees C. The resulting solution was stirred for 16 h at room temperature. The resulting mixture was then diluted with 500 mL of MTBE, and the reaction was quenched with sat. aq. $NaHCO_3$ to give a pH value of 8. The resulting solution was extracted with dichloromethane (2×1 L) and the organic layers combined and dried over anhydrous sodium sulfate and concentrated under vacuum to afford 1-(4-((tert-butyldiphenylsilyl)oxy)-3-methyltetrahydrofuran-3-yl)piperazine. MS (EI) m/z 425 $[M+1]^+$.

Step 4: 1-((3S,4S or 3R,4R)-4-((tert-butyldiphenylsilyl)oxy)-3-methyltetrahydrofuran-3-yl)piperazine (I-55) and 1-((3R,4R or 3S,4S)-4-((tert-butyldiphenylsilyl)oxy)-3-methyltetrahydrofuran-3-yl)piperazine (I-56)

1-(4-((tert-butyldiphenylsilyl)oxy)-3-methyltetrahydrofuran-3-yl)piperazine was purified by Prep-SFC with the following conditions: Column, CHIRAL ART Amylose-SC, 5×25 cm; mobile phase A: $CO_2$; mobile phase B: MeOH (8 mmol/L $NH_3$.MeOH) to give I-55 and I-56.

I-55: MS (EI) m/z 425 $[M+H]^+$. Retention time: 4.63 min.

I-56: MS (EI) m/z 425 $[M+H]^+$. Retention time: 5.30 min.

Synthesis of Common Intermediates I-57 and I-58: 6-(4-((3S,4S or 3R,4R)-4-((tert-butyldiphenylsilyl)oxy)-3-methyltetrahydrofuran-3-yl)piperazin-1-yl)-5-chloro-1H-indazole (I-57) and 6-(4-((3R,4R or 3S,4S)-4-((tert-butyldiphenylsilyl)oxy)-3-methyltetrahydrofuran-3-yl)piperazin-1-yl)-5-chloro-1H-indazole (I-58)

Scheme 42

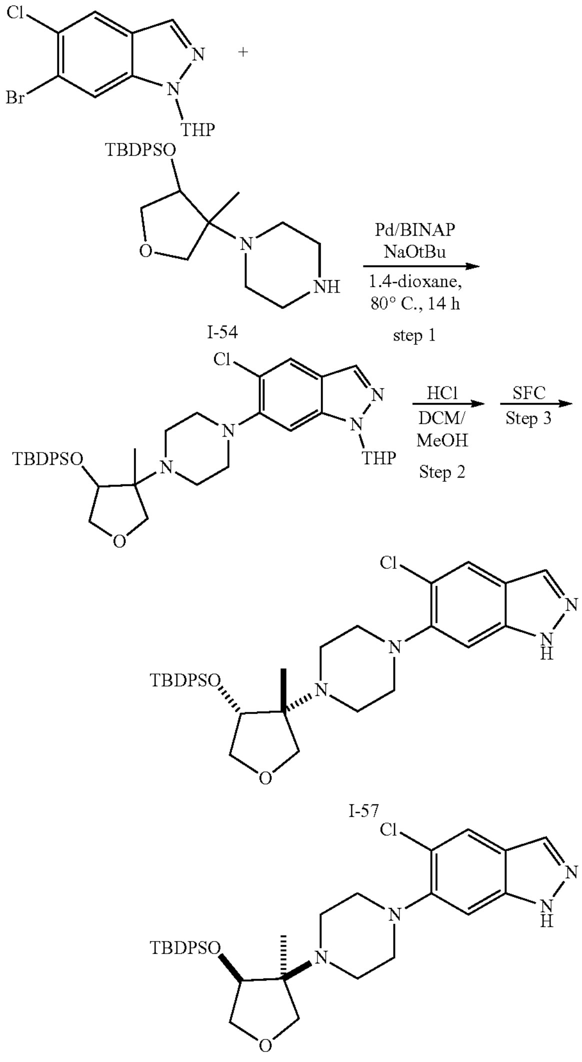

I-58

Step 1: 6-(4-(4-((tert-butyldiphenylsilyl)oxy)-3-methyltetrahydrofuran-3-yl)piperazin-1-yl)-5-chloro-1-(tetrahydro-2H-pyran-2-yl)-1H-indazole A 5-L 4-necked round-bottom flask purged and maintained with an inert atmosphere of nitrogen was charged with 6-bromo-5-chloro-1-(oxan-2-yl)indazole (300 g, 951 mmol, 1.00 equiv), I-54 (606 g, 1.43 mol, 1.50 equiv), dioxane (3.00 L) and t-BuONa (274 g, 2.85 mol, 3.00 equiv). The resulting solution was stirred for 20 min at 25 degrees C., then BINAP (296 g, 475 mmol, 0.50 equiv) and allylpalladium(II) chloride dimer (34.8 g, 95.1 mmol, 0.10 equiv) were added. The resulting solution was stirred at 80° C. overnight. The reaction was then cooled and quenched by the addition of water. The resulting solution was extracted with ethyl acetate (3×2 L), and the organic phase was washed with brine (1×3 L), dried over anhydrous sodium sulfate and concentrated to give 6-(4-(4-((tert-butyldiphenylsilyl)oxy)-3-methyltetrahydrofuran-3-yl)piperazin-1-yl)-5-chloro-1-(tetrahydro-2H-pyran-2-yl)-1H-indazole. MS (EI) m/z 659 $[M+1]^+$.

Step 2: 6-(4-(4-((tert-butyldiphenylsilyl)oxy)-3-methyltetrahydrofuran-3-yl)piperazin-1-yl)-5-chloro-1H-indazole A 5-L 4-necked round-bottom flask purged and maintained with an inert atmosphere of nitrogen was charged with 6-(4-(4-((tert-butyldiphenylsilyl)oxy)-3-methyltetrahydrofuran-3-yl)piperazin-1-yl)-5-chloro-1-(tetrahydro-2H-pyran-2-yl)-1H-indazole (350 g, 531 mmol, 1.00 equiv), DCM (1.5 L), MeOH (0.5 L), and HCl in 1,4-dioxane (77 g, 2.12 mol, 4.00 equiv). The resulting solution was stirred for 4 hr at 25° C. The reaction was then quenched by the addition of water, and the pH value of the solution was adjusted to 8 with $Na_2CO_3$. The resulting solution was extracted with dichloromethane (3×1 L). The organics were combined, washed with brine, dried over anhydrous sodium sulfate and concentrated. The residue was purified by flash chromatography over silica gel (30% EtOAc in PE) to afford 6-(4-(4-((tert-butyldiphenylsilyl)oxy)-3-methyltetrahydrofuran-3-yl)piperazin-1-yl)-5-chloro-1H-indazole. MS (EI) m/z 575 $[M+1]^+$.

Step 3: 6-(4-((3S,4S or 3R,4R)-4-((tert-butyldiphenylsilyl)oxy)-3-methyltetrahydrofuran-3-yl)piperazin-1-yl)-5-chloro-1H-indazole (I-57) and 6-(4-((3R,4R or 3S,4S)-4-((tert-butyldiphenylsilyl)oxy)-3-methyltetrahydrofuran-3-yl)piperazin-1-yl)-5-chloro-1H-indazole (I-58)

The racemic product was then chiral separated by Prep-SFC with the following conditions: Column: CHIRAL ART Amylose-SA, 5×25 cm; Mobile Phase A: $CO_2$, Mobile Phase B: IPA/DCM=5:1(0.1% 2M $NH_3$-MeOH) to give I-57 and I-58.

I-57: MS (EI) m/z 575 $[M+1]^+$. Retention time: 3.04 min.

I-58: MS (EI) m/z 575 $[M+1]^+$. Retention time: 3.61 min.

Synthesis of Common Intermediates I-59: 5-chloro-1-(1-cyclopropyl-1H-pyrazol-4-yl)-6-(methylsulfonyl)-1H-pyrazolo[3,4-b]pyridine Scheme 43

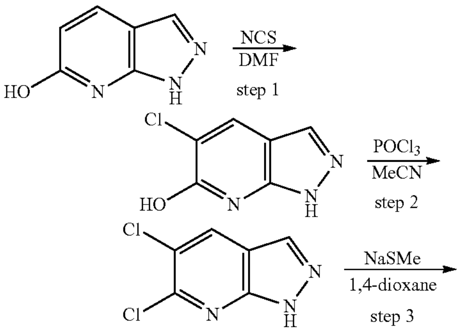

-continued

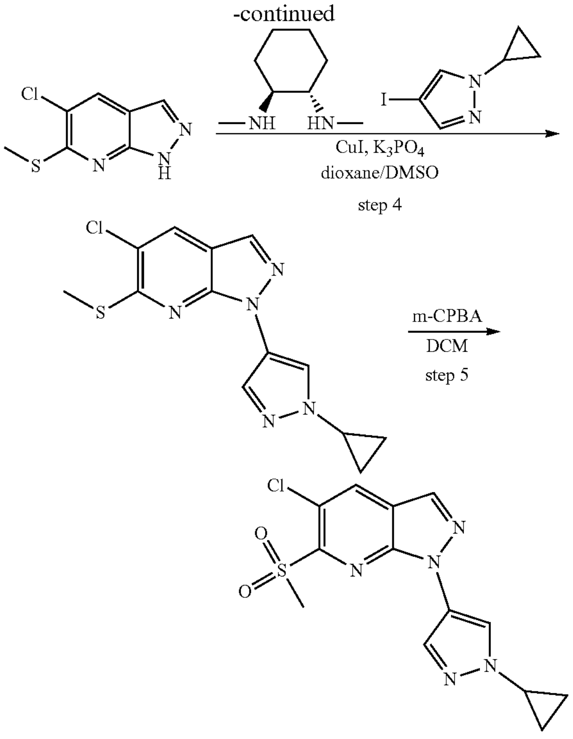

I-59

Step 1: 5-chloro-1H-pyrazolo[3,4-b]pyridin-6-ol

Into a 5 L 4-necked round-bottom flask were added 1H-pyrazolo[3,4-b]pyridin-6-ol (133 g, 981 mmol, 1.00 equiv.), DMF (2.50 L) and NCS (138 g, 1.03 mol, 1.05 equiv.). The resulting mixture was stirred overnight at room temperature. The resulting mixture was concentrated under vacuum. The residue was purified by trituration with ethyl acetate (1 L) to afford 5-chloro-1H-pyrazolo[3,4-b]pyridin-6-ol. MS (EI) m/z 170 $[M+1]^+$.

Step 2: 5,6-dichloro-1H-pyrazolo[3,4-b]pyridine

Into a 10 L 4-necked round-bottom flask were added 5-chloro-1H-pyrazolo[3,4-b]pyridin-6-ol (108 g, 637 mmol, 1.00 equiv.) and MeCN (3.50 L) under nitrogen atmosphere. To the above mixture was added $POCl_3$ (1.20 L, 12.9 mol, 20.2 equiv.) dropwise at room temperature. The resulting mixture was stirred overnight at 80° C. The resulting mixture was concentrated under vacuum. The resulting mixture was diluted with ACN (500 mL). The reaction was quenched by the addition of sat. $NaHCO_3$ aq. (3 L). The resulting mixture was extracted with $CH_3Cl$/IPA (3:1, 4×1.5 L). The combined organic layers were dried over anhydrous $Na_2SO_4$. After filtration, the filtrate was concentrated under reduced pressure to afford 5,6-dichloro-1H-pyrazolo[3,4-b]pyridine. MS (EI) m/z 188 $[M+1]^+$.

Step 3: 5-chloro-6-(methylthio)-1H-pyrazolo[3,4-b]pyridine

Into a 10 L 4-necked round-bottom flask were added 5,6-dichloro-1H-pyrazolo[3,4-b]pyridine (96 g, 511 mmol, 1.00 equiv.), 1,4-dioxane (4.00 L) and sodium thiomethoxide (192 g, 2.74 mol, 5.36 equiv.). The resulting mixture was stirred for 24 h at 100° C. The reaction was quenched by the addition of sat. $NaHCO_3$ aq. (4 L). The resulting mixture was extracted with $CH_2Cl_2$ (2×3 L). The combined organic layers were dried over anhydrous $Na_2SO_4$. After filtration, the filtrate was concentrated under reduced pressure to afford 5-chloro-6-(methylthio)-1H-pyrazolo[3,4-b]pyridine. MS (EI) m/z 200 $[M+1]^+$.

Step 4: 5-chloro-1-(1-cyclopropyl-1H-pyrazol-4-yl)-6-(methylthio)-1H-pyrazolo[3,4-b]pyridine Into a 2 L 4-necked round-bottom flask were added 5-chloro-6-(methylsulfanyl)-1H-pyrazolo[3,4-b]pyridine (61 g, 306 mmol, 1.00 equiv.), 1-cyclopropyl-4-iodopyrazole (83 g, 353 mmol, 1.15 equiv.), $K_3PO_4$ (195 g, 919 mmol, 3.00 equiv.), CuI (14.5 g, 76.1 mmol, 0.25 equiv.), trans-N1,N2-dimethylcyclohexane-1,2-diamine (13.0 g, 91.4 mmol, 0.30 equiv.), 1,4-dioxane (600 mL) and DMSO (600 mL). The resulting mixture was stirred overnight at 90° C. under nitrogen atmosphere. The reaction was quenched by the addition of water (2.5 L). The resulting mixture was extracted with $CH_2Cl_2$ (3×1 L). The combined organic layers were dried over anhydrous $Na_2SO_4$. After filtration, the filtrate was concentrated under reduced pressure. The residue was purified by silica gel column chromatography, eluted with PE/$CH_2Cl_2$/EtOAc (5:5:1) to afford 5-chloro-1-(1-cyclopropyl-1H-pyrazol-4-yl)-6-(methylthio)-1H-pyrazolo[3,4-b]pyridine. MS (EI) m/z 306 $[M+1]^+$.

Step 5: 5-chloro-1-(1-cyclopropyl-1H-pyrazol-4-yl)-6-(methylsulfonyl)-1H-pyrazolo[3,4-b]pyridine (I-59)

Into a 2 L 4-necked round-bottom flask were added 4-[5-chloro-6-(methylsulfanyl)pyrazolo[3,4-b]pyridin-1-yl]-1-cyclopropylpyrazole (50.0 g, 164 mmol, 1.00 equiv.) and DCM (1.25 L). To the above mixture was added m-CPBA (113 g, 655 mmol, 4.00 equiv.) at 0° C. The resulting mixture was stirred for additional 2 h at room temperature. The reaction was quenched by the addition of sat. $Na_2SO_3$ aq. (1 L). The resulting mixture was extracted with $CH_3Cl$/IPA (3:1, 3×1 L). The combined organic layers were washed with sat.$NaHCO_3$ aq. (2×1 L), dried over anhydrous $Na_2SO_4$. After filtration, the filtrate was concentrated under reduced pressure to afford the title compound (I-59). $^1$H-NMR: (400 MHz, DMSO-$d_6$, ppm) δ 8.84 (s, 1H), 8.55-8.51 (m, 2H), 8.08 (s, 1H), 3.91-3.86 (m, 1H), 3.69 (s, 3H), 1.17-1.13 (m, 2H), 1.10-1.04 (m, 2H). MS (EI) m/z 338 $[M+H]^+$.

I-60 in Table 8 below was prepared according to scheme 44 by using the I-35 in step 4

TABLE 8

| Intermediate | Structure | IUPAC Name | Exact Mass [M + H]+ |
|---|---|---|---|
| I-60 | 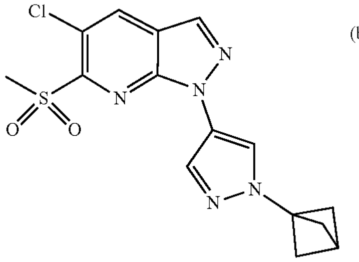 | (1-(1-(bicyclo[1.1.1]pentan-1-yl)-1H-pyrazol-4-yl)-5-chloro-6-(methylsulfonyl)-1H-pyrazolo[3,4-b]pyridine | Calc'd 364, found 364 |

Synthesis of Common Intermediates I-61 and I-62: 1-((3S,4S or 3R,4R)-4-((tert-butyldiphenylsilyl)oxy)tetrahydrofuran-3-yl)piperazine (I-61) and 1-((3R,4R or 3S,4S)-4-((tert-butyldiphenylsilyl)oxy)tetrahydrofuran-3-yl)piperazine (I-62)

Scheme 44

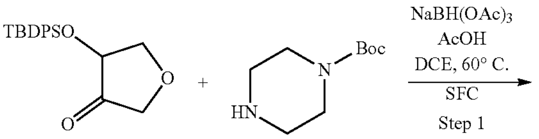

I-43

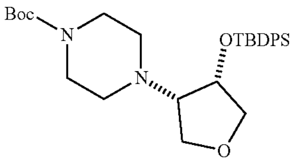

Peak 1

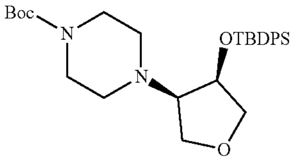

Peak 2

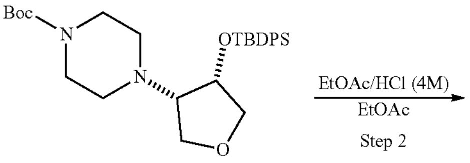

Peak 1

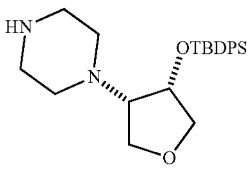

I-61

-continued

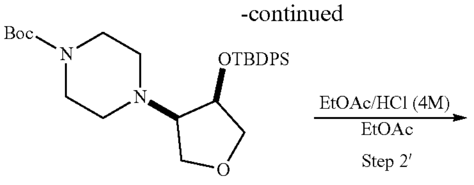

Peak 2

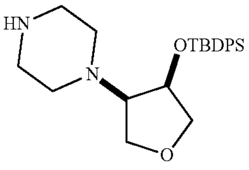

I-62

Step 1: tert-butyl 4-((3S,4S or 3R,4R)-4-((tert-butyldiphenylsilyl)oxy)tetrahydrofuran-3-yl)piperazine-1-carboxylate and tert-butyl 4-((3R,4R or 3S,4S)-4-((tert-butyldiphenylsilyl) oxy)tetrahydrofuran-3-yl)piperazine-1-carboxylate A flask was charged with I-43 (262 g, 0.77 mol, 1.0 eq) and DCE (2.0 L), followed by addition of tert-butyl piperazine-1-carboxylate (215 g, 1.15 mol, 1.15 eq) and NaBH$(OAc)_3$ (326 g, 1.54 mol, 2.0 eq) to the reaction mixture at 20° C. Acetic acid (92.4 g, 1.54 mol, 2.0 eq) was then added dropwise into the reaction mixture at 20° C., then the reaction heated to 60° C. for 2.5 hours. The reaction was then cooled to room temperature, and poured into 3 L of vigorously stirring sat. $NaHCO_3$. 1 L DCM was then added, and the resulting mixture extracted with DCM (1.5 L×2). The organics were dried and condensed, then purified by column chromatography on silica gel (PE:EtOAc=1:0 to 0:1) to afford tert-butyl 4-(4-((tert-butyldiphenylsilyl)oxy) tetrahydrofuran-3-yl)piperazine-1-carboxylate. $^1$HNMR: (400 MHz, $CDCl_3$) 7.39-7.79 (m, 10H), 4.27 (s, 1H), 3.93-4.02 (m, 2H), 3.68-3.83 (m, 2H), 3.37 (s, 4H), 2.59-2.60 (m, 1H), 2.34-2.41 (m, 4H), 1.46 (s, 9H), 1.09 (s, 9H). The racemic mixture was subjected to SFC chiral separation (column & dimensions: (DAICEL CHIRALCEL OJ (250 mm×50 mm; Mobile phase A: $CO_2$; Mobile phase B: EtOH with 0.1% $NH_4OH$) to afford tert-butyl 4-((3S,4S or 3R,4R)-4-((tert-butyldiphenylsilyl)oxy)tetrahydrofuran-3-yl)piperazine-1-carboxylate (Peak1, retention time: 3.40 min) and tert-butyl 4-((3R,4R or 3S,4S)-4-((tert-butyldiphenylsilyl) oxy)tetrahydrofuran-3-yl)piperazine-1-carboxylate (Peak2, retention time: 4.61).

Step 2: 1-((3S,4S or 3R,4R)-4-((tert-butyldiphenylsilyl)oxy)tetrahydrofuran-3-yl)piperazine (I-61) and 1-((3R,4R or 3S,4S)-4-((tert-butyldiphenylsilyl)oxy) tetrahydrofuran-3-yl)piperazine (I-62

A flask was charged with tert-butyl 4-((3S,4S or 3R,4R)-4-((tert-butyldiphenylsilyl)oxy) tetrahydrofuran-3-yl)piperazine-1-carboxylate (peak 1 from step 1, 110 g, 0.22 mol, 1.0 eq) and ethyl acetate (2 L). HCl/EtOAc (0.35 L, 4M) was then added dropwise into the reaction mixture at 0° C., then warmed to 20° C. for 36 hrs. The reaction was then quenched with sat. aq. $NaHCO_3$ (aq. pH 8) and then extracted with EtOAc (2×1 L). The organic layers were then washed with sat. NaCl (1.0 L), dried over $Na_2SO_4$, filtered and concentrate under reduced pressure to give a residue, which was triturated with MTBE and concentrated to afford the title compound (I-61). $^1$HNMR: (400 MHz, $CDCl_3$) δ: 7.73 (d, J=6.8 Hz, 2H), 7.64 (d, J=6.8 Hz, 2H), 7.39-7.46 (m, 6H), 4.29 (s, 1H), 3.97-4.00 (m, 1H), 3.91-3.93 (m, 1H), 3.84 (d, J=9.6 Hz, 1H), 3.70-3.74 (m, 1H), 3.05 (s, 4H), 2.66-2.73 (m, 5H), 1.08 (s, 9H). MS (EI) m/z: 411 $[M+H]^+$.

I-62 was obtained in the same way as I-61 from Peak 2 in step 1. MS (EI) m/z: 411 $[M+H]^+$.

EXAMPLES

Preparation of Example 1.1: 5-chloro-1-(1-methyl-1H-pyrazol-4-yl)-6-(4-(oxetan-3-yl)piperazin-1-yl)-1H-indazole (Ex. 1.1)

Scheme 45

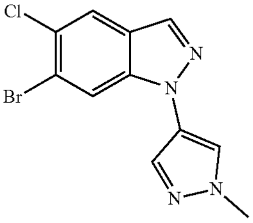

I-1

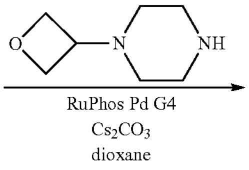

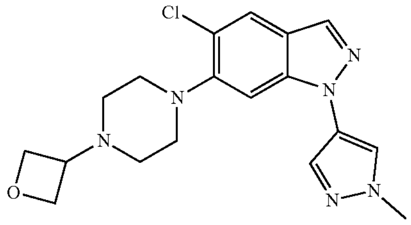

Ex. 1.1

To a vial was added I-1 (100 mg, 0.321 mmol), 1-(oxetan-3-yl)piperazine (68.5 mg, 0.481 mmol), RuPhos Pd G4 (27 mg, 0.032 mmol), $Cs_2CO_3$ (209 mg, 0.642 mmol) and dioxane (3 mL). The mixture was evacuated and back-filled with $N_2$ five times, then heated at 80° C. for 18 h. The mixture was filtered and purified by reversed phase HPLC, with water elution (0.10% TFA)-ACN to afford the title compound as the TFA salt (Ex. 1.1). $^1$H NMR (600 MHz, DMSO-$d_6$) δ 8.32 (s, 1H), 8.20 (s, 1H), 8.01 (s, 1H), 7.95 (s, 1H), 7.25 (s, 1H), 4.85-4.73 (m, 4H), 4.61-4.48 (m, 1H), 3.95 (s, 3H), 3.72-3.41 (m, 4H), 3.29-2.99 (m, 4H). MS (EI) m/z: 373 $[M+H]^+$.

Compounds in Table 9 below were prepared from common intermediate I-1 according to general Scheme 45 by using the corresponding starting materials.

TABLE 9

| Ex | Structure | Name | Exact Mass [M + H]+ |
|---|---|---|---|
| Ex 1.2 | 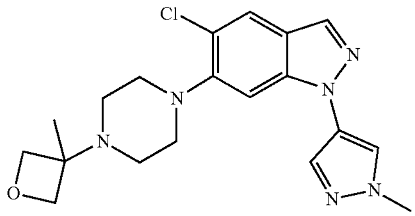 [SMILES: Cn1cc(-n2ncc3cc(Cl)c(N4CCN(C5(C)COC5)CC4)cc32)cn1] | 5-chloro-6-[4-(3-methyloxetan-3-yl)piperazin-1-yl]-1-(1-methyl-1H-pyrazol-4-yl)-1H-indazole | Calc'd 387, found 387 |
| Ex. 1.3 | 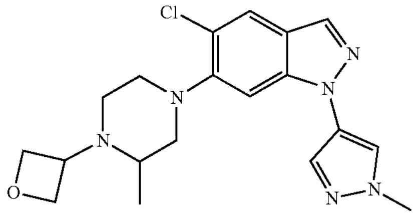 [SMILES: CC1CN(c2cc3c(cnn3-c3cnn(C)c3)cc2Cl)CCN1C1COC1] | 5-chloro-6-[3-methyl-4-(oxetan-3-yl)piperazin-1-yl]-1-(1-methyl-1H-pyrazol-4-yl)-1H-indazole | Calc'd 387, found 387 |

Preparation of Example 1.4 and 1.5: (S or R)-5-chloro-1-(1-methyl-1H-pyrazol-4-yl)-6-(2-methyl-4-(oxetan-3-yl)piperazin-1-yl)-1H-indazole and (R or S)-5-chloro-1-(1-methyl-TH-pyrazol-4-yl)-6-(2-methyl-4-(oxetan-3-yl)piperazin-1-yl)-1H-indazole Scheme 46

Scheme 46

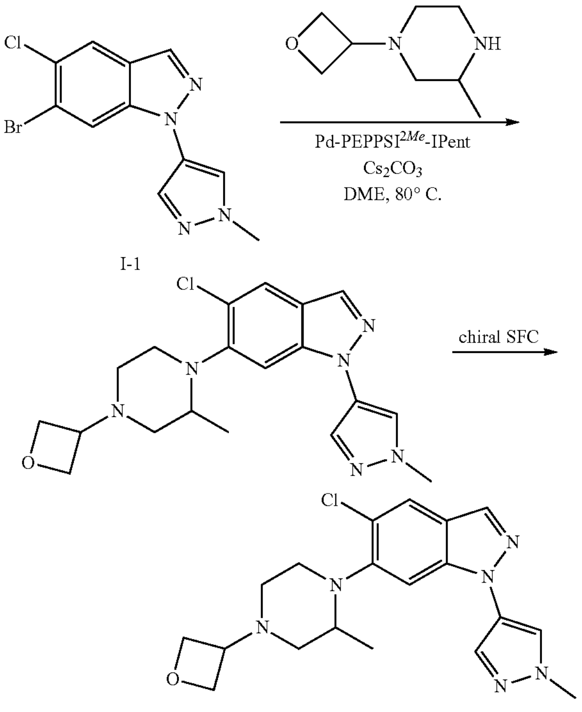

Ex. 1.4

-continued

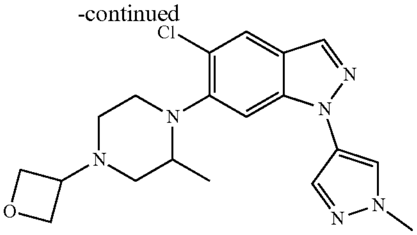

Ex. 1.5

To a vial was added I-1 (140 mg, 0.449 mmol), Pd-PEPPSI$^{2Me}$-IPent (26 mg, 0.031 mmol), $Cs_2CO_3$ (220 mg, 0.674 mmol), 3-methyl-1-(oxetan-3-yl)piperazine (104 mg, 0.666 mmol) and DME (2500 μl). The mixture was evacuated and back-filled with $N_2$ four times, then heated at 80° C. for 21 h. The mixture was diluted with water and EtOAc. The aqueous layer was extracted with EtOAc (3×). The combined organic layers were washed with brine, dried over $MgSO_4$, filtered and concentrated in vacuo to afford a residue which was then purified by column chromatography on silica (MeOH in DCM, 0-5% gradient) to afford 5-chloro-1-(1-methyl-1H-pyrazol-4-yl)-6-(2-methyl-4-(oxetan-3-yl)piperazin-1-yl)-1H-indazole. The product was subjected to SFC chiral separation (column & dimensions: AD-H, 21×250 mm; Mobile phase A: $CO_2$; Mobile phase B: MeOH with 0.1% $NH_4OH$) to afford the title compounds (examples 1.4 and 1.5).

Example 1.4

$^1$H NMR (600 MHz, DMSO-$d_6$) δ 8.37 (s, 1H), 8.18 (s, 1H), 7.96 (s, 1H), 7.90 (s, 1H), 7.40 (s, 1H), 4.58 (dt, J=10.4, 6.5 Hz, 2H), 4.47 (dt, J=23.7, 6.1 Hz, 2H), 3.96 (s, 3H), 3.68-3.58 (m, 1H), 3.47 (p, J=6.3 Hz, 1H), 3.32-3.28 (m, 1H), 3.26-3.19 (m, 1H), 2.85-2.78 (m, 1H), 2.69-2.60 (m, 1H), 2.39-2.29 (m, 1H), 2.12-2.00 (m, 1H), 0.87 (d, J=6.1 Hz, 3H); MS (EI) m/z: 387 [M+H]$^+$. Retention time: 3.4 min.

Example 1.5

$^1$H NMR (600 MHz, DMSO-$d_6$) δ 8.37 (s, 1H), 8.18 (s, 1H), 7.96 (s, 1H), 7.90 (s, 1H), 7.40 (s, 1H), 4.58 (dt, J=10.4, 6.5 Hz, 2H), 4.47 (dt, J=23.7, 6.1 Hz, 2H), 3.96 (s, 3H), 3.68-3.58 (m, 1H), 3.47 (p, J=6.3 Hz, 1H), 3.32-3.28 (m, 1H), 3.26-3.19 (m, 1H), 2.85-2.78 (m, 1H), 2.69-2.60 (m, 1H), 2.39-2.29 (m, 1H), 2.12-2.00 (m, 1H), 0.87 (d, J=6.1 Hz, 3H); MS (EI) m/z: 387 $[M+H]^+$. Retention time: 4.3 min.

Preparation of Example 1.6: 2-(5-chloro-1-(1-methyl-1H-pyrazol-4-yl)-1H-indazol-6-yl)-5-(oxetan-3-yl)-2,5-diazabicyclo[2.2.2]octane Scheme 47

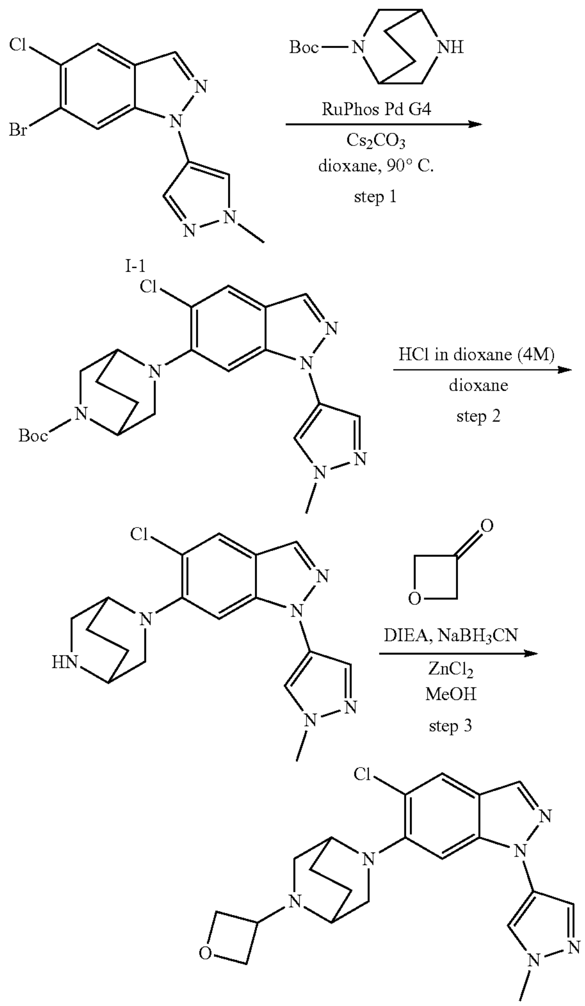

I-1

Ex. 1.6

Step 1: tert-butyl 5-(5-chloro-1-(1-methyl-1H-pyrazol-4-yl)-1H-indazol-6-yl)-2,5-diazabicyclo [2.2.2] octane-2-carboxylate To a vial was added I-1 (200 mg, 0.642 mmol), tert-butyl 2,5-diazabicyclo[2.2.2]octane-2-carboxylate (204 mg, 0.963 mmol), RuPhos Pd G4 (55 mg, 0.064 mmol), $Cs_2CO_3$ (837 mg, 2.57 mmol) and dioxane (5 ml). The mixture was evacuated and back-filled with $N_2$ four times and then heated at 90° C. for 21 h. The reaction mixture was filtered, and then the filtrate was concentrated in vacuo to afford residue, which was purified by column chromatography on silica gel (EtOAc in hexane: 0-100% gradient) to afford tert-butyl 5-(5-chloro-1-(1-methyl-1H-pyrazol-4-yl)-1H-indazol-6-yl)-2,5-diazabicyclo[2.2.2]octane-2-carboxylate. MS (EI) m/z: 443 $[M+H]^+$.

Step 2: 2-(5-chloro-1-(1-methyl-1H-pyrazol-4-yl)-1H-indazol-6-yl)-2,5-diazabicyclo [2.2.2] octane To a vial containing tert-butyl 5-(5-chloro-1-(1-methyl-1H-pyrazol-4-yl)-1H-indazol-6-yl)-2,5-diazabicyclo[2.2.2] octane-2-carboxylate (126 mg, 0.284 mmol) was added dioxane (1 ml) and HCl (4M in dioxane, 1 ml, 4 mmol). The mixture was stirred at rt for 1.5 h. The solvent was evaporated in vacuo to afford crude product 2-(5-chloro-1-(1-methyl-1H-pyrazol-4-yl)-1H-indazol-6-yl)-2,5-diazabicyclo[2.2.2]octane, 2HCl. MS (EI) m/z: 343 $[M+H]^+$.

Step 3: 2-(5-chloro-1-(1-methyl-1H-pyrazol-4-yl)-1H-indazol-6-yl)-5-(oxetan-3-yl)-2,5-diazabicyclo [2.2.2]octane (Ex. 1.6)

To a vial was added 2-(5-chloro-1-(1-methyl-1H-pyrazol-4-yl)-1H-indazol-6-yl)-2,5-diazabicyclo[2.2.2]octane, 2HCl (20 mg, 0.048 mmol), MeOH (500 μl) and DIEA (40 μl, 0.23 mmol). The mixture was stirred at rt for 20 min. Then oxetan-3-one (17.3 mg, 0.241 mmol), $NaBH_3CN$ (15.1 mg, 0.241 mmol) and $ZnCl_2$ (32.8 mg, 0.241 mmol) were added. The mixture was stirred at rt for 1 h. The mixture was filtered and purified by reversed phase HPLC, with water elution (0.1% TFA)-ACN to afford the title compound as a TFA salt (EX. 1.6). $^1$H NMR (600 MHz, DMSO-$d_6$) δ 8.29 (d, J=8.9 Hz, 1H), 8.16 (s, 1H), 7.96 (s, 2H), 7.29 (d, J=14.3 Hz, 1H), 4.86-4.62 (m, 4H), 3.95 (s, 3H), 3.89-3.33 (m, 7H), 2.36-1.78 (m, 4H); MS (EI) m/z: 399 $[M+H]^+$.

Preparation of Example 1.7: 5-chloro-1-(1-methyl-1H-pyrazol-4-yl)-6-(4-(3-methyloxetan-3-yl)-1,4-diazepan-1-yl)-1H-indazole Scheme 48

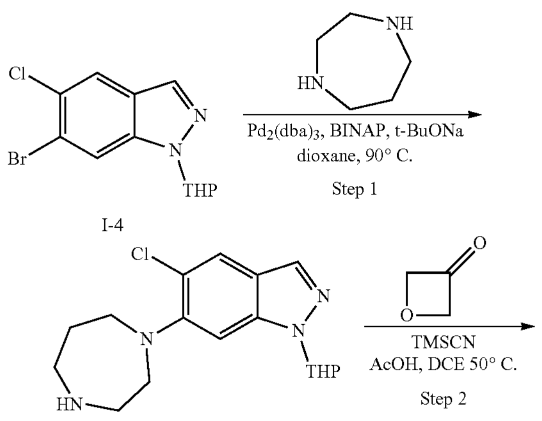

I-4

-continued

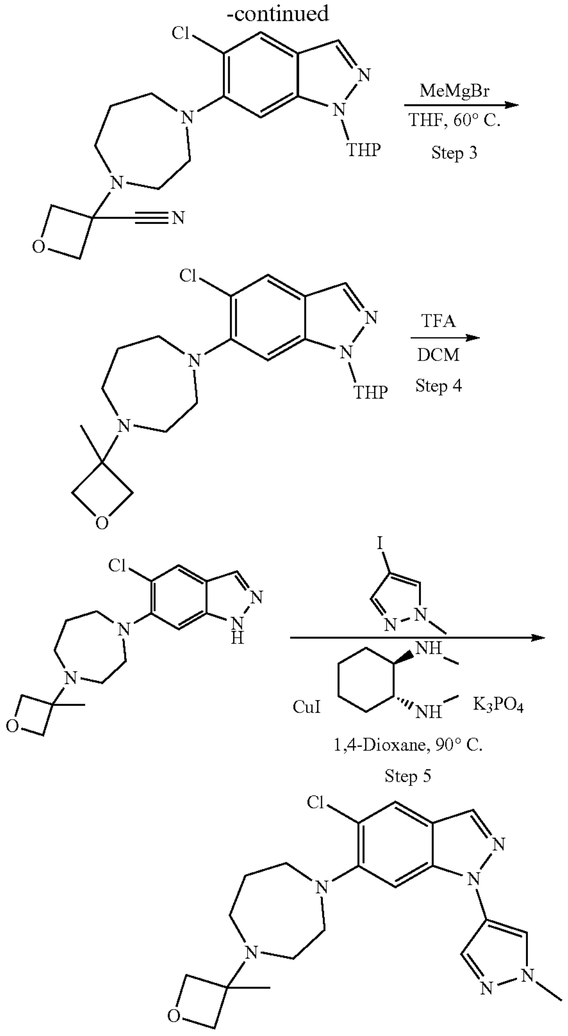

Ex. 1.7

Step 1: 5-chloro-6-(1,4-diazepan-1-yl)-1-(tetrahydro-2H-pyran-2-yl)-1H-indazole

A mixture of I-4 (1.0 g, 3.2 mmol), $Pd_2(dba)_3$ (0.290 g, 0.317 mmol), BINAP (0.197 g, 0.317 mmol), sodium tert-butoxide (0.609 g, 6.34 mmol) and 1,4-diazepane (0.476 g, 4.75 mmol) in toluene (20 ml) was stirred at 80° C. for 16 h under $N_2$ atmosphere. The mixture was then filtered. The filtrate was concentrated in vacuo to afford a residue which was purified by column chromatography on silica gel (EtOAc in hexane, 0-5% gradient) to afford 5-chloro-6-(1,4-diazepan-1-yl)-1-(tetrahydro-2H-pyran-2-yl)-1H-indazole. MS (EI) m/z: 335 $[M+H]^+$.

Step 2: 3-(4-(5-chloro-1-(tetrahydro-2H-pyran-2-yl)-1H-indazol-6-yl)-1,4-diazepan-1-yl)oxetane-3-carbonitrile A mixture of 5-chloro-6-(1,4-diazepan-1-yl)-1-(tetrahydro-2H-pyran-2-yl)-1H-indazole (500 mg, 1.49 mmol), oxetan-3-one (161 mg, 2.24 mmol) and acetic acid (137 mg, 2.24 mmol) in DCE (25 ml) was stirred at 50° C. for 30 min. Then, trimethylsilyl cyanide (222 mg, 2.24 mmol) was added slowly to the mixture. The mixture was then stirred at 50° C. for 16 h, then treated with KOH (1M, 10 ml) to adjust the pH to 7-8, followed by extraction with EtOAc (50 mL×3). The combined organic layers were washed with water (20 mL×3), and then dried over $Na_2SO_4$, filtered and concentrated in vacuo to afford a residue which was then purified by column chromatography on silica gel (EtOAc in hexane, 0-7% gradient) to afford 3-(4-(5-chloro-1-(tetrahydro-2H-pyran-2-yl)-1H-indazol-6-yl)-1,4-diazepan-1-yl)oxetane-3-carbonitrile. MS (EI) m/z 416 $[M+H]^+$.

Step 3: 5-chloro-6-(4-(3-methyloxetan-3-yl)-1,4-diazepan-1-yl)-1-(tetrahydro-2H-pyran-2-yl)-1H-indazole To a solution of 3-(4-(5-chloro-1-(tetrahydro-2H-pyran-2-yl)-1H-indazol-6-yl)-1,4-diazepan-1-yl)oxetane-3-carbonitrile (100 mg, 0.240 mmol) in anhydrous THF (4 ml) was added methylmagnesium bromide (28.7 mg, 0.240 mmol) at 60° C. under $N_2$ protection. The mixture was then stirred for 3 h, then quenched by saturated $NH_4Cl$. The reaction mixture was extracted with EtOAc (30 mL). The organic layer was washed with water (20 mL), dried over $Na_2SO_4$, filtered and concentrated in vacuo to afford a residue which was then purified by preparative TLC (eluting with EtOAc) to give 5-chloro-6-(4-(3-methyloxetan-3-yl)-1,4-diazepan-1-yl)-1-(tetrahydro-2H-pyran-2-yl)-1H-indazole. MS (EI) m/z 405 $[M+H]^+$.

Step 4: 5-chloro-6-(4-(3-methyloxetan-3-yl)-1,4-diazepan-1-yl)-1H-indazole

To a mixture of 5-chloro-6-(4-(3-methyloxetan-3-yl)-1,4-diazepan-1-yl)-1-(tetrahydro-2H-pyran-2-yl)-1H-indazole (50 mg, 0.12 mmol) in DCM (4 ml) was added TFA (0.2 ml). The reaction mixture was stirred at 25° C. for 16 h. After concentration, the pH of the residue was adjusted to 7-8 with saturated $NaHCO_3$. The residue was extracted with EtOAc (30 mL). The organic layer was washed with water (20 mL), dried over $Na_2SO_4$, filtered and concentrated in vacuo to afford a residue which was then purified by preparative TLC (DCM:MeOH=10:1) to give 5-chloro-6-(4-(3-methyloxetan-3-yl)-1,4-diazepan-1-yl)-1H-indazole. MS (EI) m/z 321 $[M+H]^+$.

Step 5: 5-chloro-1-(1-methyl-1H-pyrazol-4-yl)-6-(4-(3-methyloxetan-3-yl)-1,4-diazepan-1-yl)-1H-indazole (Ex. 1.7)

To a mixture of 5-chloro-6-(4-(3-methyloxetan-3-yl)-1,4-diazepan-1-yl)-1H-indazole (30 mg, 0.094 mmol) and 4-iodo-1-methyl-1H-pyrazole (30 mg, 0.14 mmol) in anhydrous 1,4-dioxane (3 ml) was added (1R,2R)—N1,N2-dimethylcyclohexane-1,2-diamine (2.0 mg, 0.014 mmol), copper(I) iodide (2.0 mg, 10 μmol) and $K_3PO_4$ (60 mg, 0.28 mmol). The resulting mixture was stirred at 90° C. under $N_2$ for 16 h. Then the mixture was filtered and concentrated in vacuo to afford a residue which was then purified by reversed phase HPLC, eluting with water (0.1% TFA)-ACN to afford the title compound (Ex. 1.7). $^1H$ NMR (500 MHz, $CDCl_3$) δ 8.01 (s, 1H), 7.79 (s, 2H), 7.77 (s, 1H), 7.18 (s, 1H), 5.26 (d, J=6.87 Hz, 2H), 4.30 (d, J=6.87 Hz, 2H), 4.03 (s, 3H), 3.63-3.65 (m, 2H), 3.33-3.37 (m, 6H), 2.43-2.45 (m, 2H), 1.83 (s, 3H). MS (EI) m/z: 401 $[M+H]^+$.

Preparation of Example 1.8: 5-chloro-6-(4-(3-ethyloxetan-3-yl)piperazin-1-yl)-1-(1-methyl-1H-pyrazol-4-yl)-1H-indazole Scheme 49

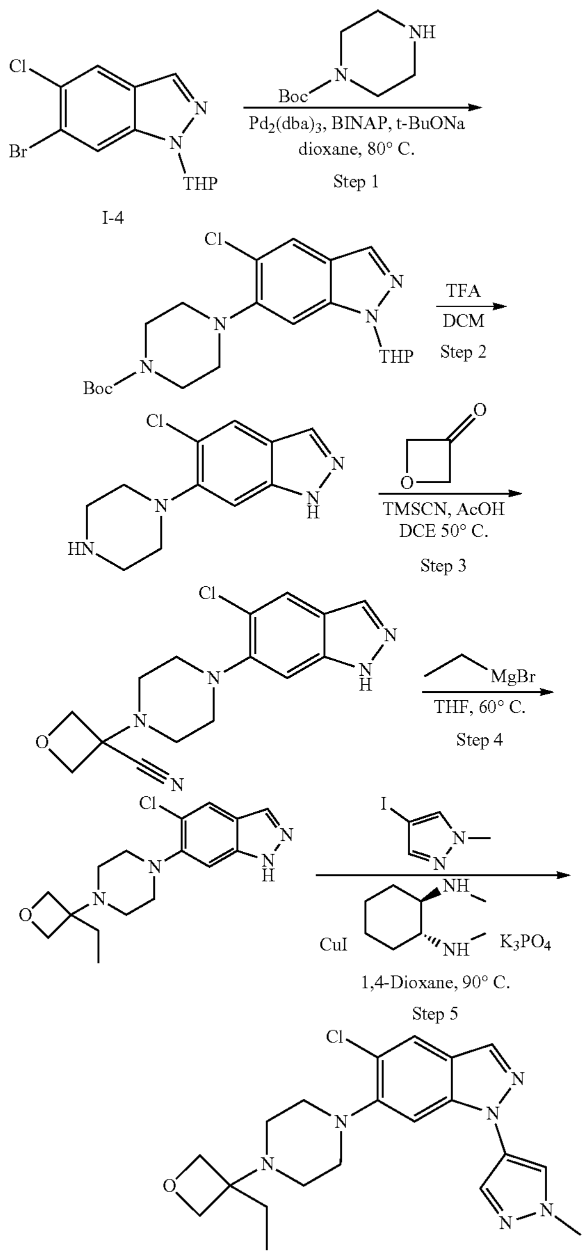

Ex. 1.8

Step 1: tert-butyl 4-(5-chloro-1-(tetrahydro-2H-pyran-2-yl)-1H-indazol-6-yl)piperazine-1-carboxylate To a mixture of I-4 (1.0 g, 3.2 mmol), sodium tert-butoxide (0.609 g, 6.34 mmol), BINAP (0.197 g, 0.317 mmol) and tert-butyl piperazine-1-carboxylate (0.649 g, 3.49 mmol) in dioxane (20 ml) was added Pd$_2$(dba)$_3$, (0.290 g, 0.317 mmol). The reaction mixture was stirred at 80° C. for 16 h under N$_2$ protection. After filtration and concentration, the residue was purified by column chromatography on silica gel (EtOAc in hexane, 0-5% gradient) to afford tert-butyl 4-(5-chloro-1-(tetrahydro-2H-pyran-2-yl)-1H-indazol-6-yl)piperazine-1-carboxylate. MS (EI) m/z: 421 [M+H]$^+$.

Step 2: 5-chloro-6-(piperazin-1-yl)-1H-indazole

To a mixture of tert-butyl 4-(5-chloro-1-(tetrahydro-2H-pyran-2-yl)-1H-indazol-6-yl)piperazine-1-carboxylate (590 mg, 1.40 mmol) in DCM (20 ml) was added TFA (1 ml). The reaction mixture was stirred at 30° C. for 16 h. Then the mixture was concentrated in vacuo to afford a residue. The residue was diluted with water and the pH was adjusted to 7-8 by adding saturated NaHCO$_3$. The solution was extracted with EtOAc (50 mL×3). The combined organic layers were washed with water (20 mL×3), dried over Na$_2$SO$_4$, filtered and concentrated in vacuo to afford a crude product, which was purified by column chromatography on silica gel (MeOH in EtOAc, 0-10% gradient) to afford 5-chloro-6-(piperazin-1-yl)-1H-indazole. MS (EI) m/z 237 [M+H]$^+$.

Step 3: 3-(4-(5-chloro-1H-indazol-6-yl)piperazin-1-yl)oxetane-3-carbonitrile

To a mixture of 5-chloro-6-(piperazin-1-yl)-1H-indazole (300 mg, 1.27 mmol) and acetic acid (116 mg, 1.90 mmol) in DCE (15 ml) at rt was added oxetan-3-one (137 mg, 1.90 mmol) under N$_2$ protection. The mixture was stirred at 50° C. for 30 min. Then, trimethylsilyl cyanide (189 mg, 1.90 mmol) was added dropwise. The mixture was then stirred at 50° C. for 16 h. The pH of the mixture was then adjusted to 7-8 by adding KOH (1M). The mixture was then extracted with EtOAc (30 mL). The organic layer was washed with water, dried over Na$_2$SO$_4$, filtered and concentrated in vacuo to afford a residue which was then purified by column chromatography on silica gel (EtOAc in hexane, 0-7% gradient) to give 3-(4-(5-chloro-1H-indazol-6-yl)piperazin-1-yl)oxetane-3-carbonitrile. MS (EI) m/z 318 [M+H]$^+$.

Step 4: 5-chloro-6-(4-(3-ethyloxetan-3-yl)piperazin-1-yl)-1H-indazole

To a mixture of 3-(4-(5-chloro-1H-indazol-6-yl)piperazin-1-yl)oxetane-3-carbonitrile (100 mg, 0.315 mmol) in anhydrous THF (4 ml) was added ethylmagnesium bromide (210 mg, 1.57 mmol) at 60° C. under N$_2$. The mixture was stirred at 60° C. for 3 h. Then NH$_4$Cl (sat.) was added to the mixture, and the residue was extracted with EtOAc (30 mL). The organic layer was washed with water, dried over Na$_2$SO$_4$, filtered and concentrated in vacuo to afford a residue which was then purified by column chromatography on silica gel (EtOAc in hexane, 0-100% gradient) to afford 5-chloro-6-(4-(3-ethyloxetan-3-yl)piperazin-1-yl)-1H-indazole. MS (EI) m/z 321 [M+H]$^+$.

Step 5: 5-chloro-6-(4-(3-ethyloxetan-3-yl)piperazin-1-yl)-1-(1-methyl-1H-pyrazol-4-yl)-1H-indazole (Ex. 1.8)

To a mixture of 5-chloro-6-(4-(3-ethyloxetan-3-yl)piperazin-1-yl)-1H-indazole (50 mg, 0.16 mmol) and 4-iodo-1-methyl-TH-pyrazole (50 mg, 0.240 mmol) in anhydrous 1,4-dioxane (3 ml) was added (1R,2R)—N1,N2-dimethylcyclohexane-1,2-diamine (3.0 mg, 0.021 mmol), copper(I)

iodide (3.0 mg, 0.016 mmol) and $K_3PO_4$ (100 mg, 0.471 mmol). The resulting mixture was stirred at 90° C. under $N_2$ for 16 h. After filtration and concentration, the residue was purified by reversed phase HPLC, eluting with water (0.1% TFA)-ACN to afford the title compound as TFA salt (Ex. 1.8). $^1H$ NMR (500 MHz, $CDCl_3$) δ 8.02 (s, 1H), 7.80 (s, 2H), 7.77 (s, 1H), 7.15 (s, 1H), 5.20 (d, J=7.78 Hz, 2H), 4.55 (d, J=7.78 Hz, 2H), 4.03 (s, 3H), 3.47-3.49 (m, 4H), 3.30-3.32 (m, 4H), 1.98 (q, J=7.50 Hz, 2H), 1.39 (t, J=7.40 Hz, 3H). MS (EI) m/z: 401 $[M+H]^+$.

Ex 1.9 in Table 10 was prepared from common intermediate I-2 according to Scheme 47 by using the corresponding starting materials.

-continued

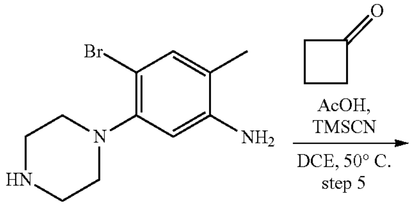

TABLE 10

| Ex | Structure | Name | Exact Mass [M + H]+ |
|---|---|---|---|
| Ex. 1.9 | 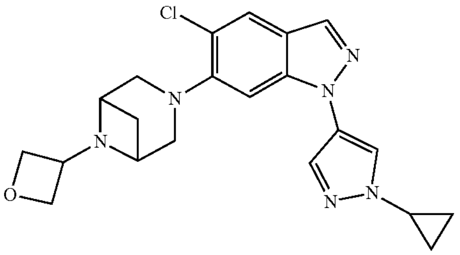 [SMILES: Clc1cc2cnn(-c3cnn(C4CC4)c3)c2cc1N1CC2CC(C1)N2C1COC1] | 5-chloro-1-(1-cyclopropyl-1H-pyrazol-4-yl)-6-[6-(oxetan-3-yl)-3,6-diazabicyclo[3.1.1]heptan-3-yl]-1H-indazole | Calc'd 411, found 411 |

Preparation of Example 2.1: 5-bromo-1-(1-methyl-1H-pyrazol-4-yl)-6-(4-(3-methyloxetan-3-yl)piperazin-1-yl)-1H-indazole Scheme 50

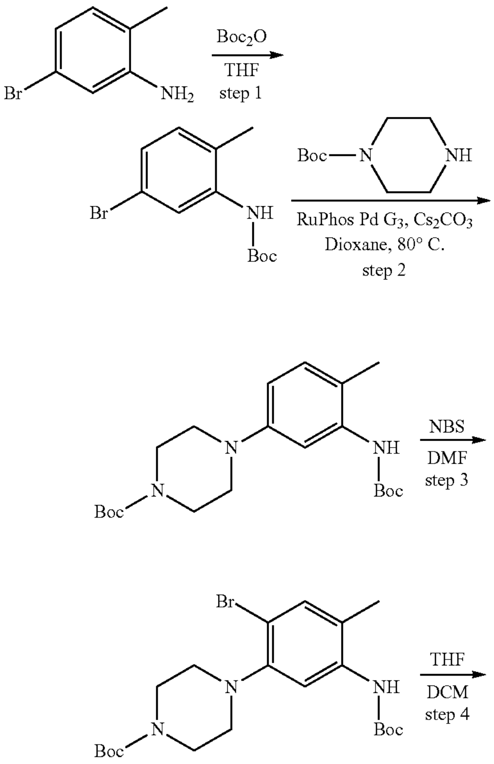

-continued

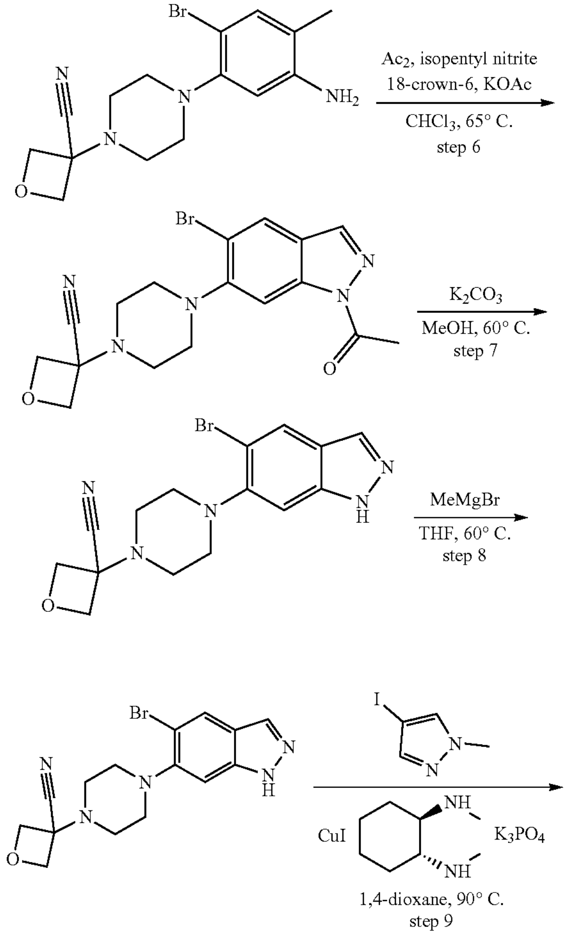

-continued

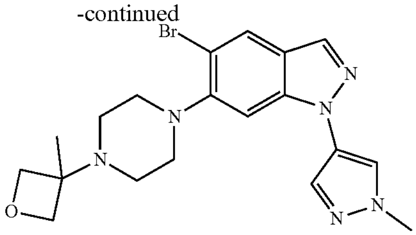

Ex. 2.1

Step 1: tert-butyl (5-bromo-2-methylphenyl)carbamate

A solution of $(Boc)_2O$ (18.7 mL, 81.0 mmol) and 5-bromo-2-methylaniline (10.0 g, 53.7 mmol) in THF (100 mL) was heated at 75° C. for 12 h. The resulting mixture was concentrated in vacuo to give the residue, which was purified by column chromatography on silica gel (EtOAc in petroleum ether: 0-8% gradient) to give tert-butyl (5-bromo-2-methylphenyl)carbamate. MS (EI) m/z 286 [M+H]+

Step 2: tert-butyl 4-(3-((tert-butoxycarbonyl) amino)-4-methylphenyl)piperazine-1-carboxylate To a solution of tert-butyl (5-bromo-2-methylphenyl) carbamate (4.0 g, 14 mmol), $Cs_2CO_3$ (13.7 g, 41.9 mmol) and tert-butyl piperazine-1-carboxylate (3.9 g, 21 mmol) in 1,4-dioxane (50 mL) was added RuPhos-Pd-G3 (1.169 g, 1.398 mmol) at room temperature. The mixture was stirred at 80° C. for 16 h under $N_2$ atmosphere. The mixture was filtered and concentrated in vacuo to afford a residue which was then purified by column chromatography on silica gel (EtOAc in petroleum ether: 0-8% gradient) to afford tert-butyl 4-(3-((tert-butoxycarbonyl)amino)-4-methylphenyl) piperazine-1-carboxylate. MS (EI) m/z: 392 $[M+H]^+$.

Step 3: tert-butyl 4-(2-bromo-5-((tert-butoxycarbonyl)amino)-4-methylphenyl)piperazine-1-carboxylate A solution of NBS (1.36 g, 7.66 mmol) and tert-butyl 4-(3-((tert-butoxycarbonyl)amino)-4-methylphenyl)piperazine-1-carboxylate (2.0 g, 5.1 mmol) in DMF (20 mL) was stirred at 15° C. for 16 h. The mixture was poured into EtOAc (50 mL) and washed with brine (40 mL×3). The organic layer was dried over $Na_2SO_4$, filtered and concentrated in vacuo to afford residue, which was purified by column chromatography on silica gel (EtOAc in petroleum ether: 0-12% gradient) to give tert-butyl 4-(2-bromo-5-((tert-butoxycarbonyl)amino)-4-methylphenyl) piperazine-1-carboxylate. MS (EI) m/z: 470 $[M+H]^+$

Step 4: 4-bromo-2-methyl-5-(piperazin-1-yl)aniline

To a solution of tert-butyl 4-(2-bromo-5-((tert-butoxycarbonyl)amino)-4-methylphenyl) piperazine-1-carboxylate (2.5 g, 5.3 mmol) in DCM (9 mL) was added TFA (4 mL) dropwise. The resulting mixture was stirred at rt for 3 h. Solvent was evaporated in vacuo and the residue was purified by reversed phase HPLC, eluting with water (0.1% TFA)-ACN to afford 4-bromo-2-methyl-5-(piperazin-1-yl) aniline. MS (EI) m/z: 270 $[M+H]^+$.

Step 5: 3-(4-(5-amino-2-bromo-4-methylphenyl) piperazin-1-yl)oxetane-3-carbonitrile To a solution of 4-bromo-2-methyl-5-(piperazin-1-yl)aniline (1.3 g, 4.8 mmol) in DCE (5 mL) was added oxetan-3-one (1.040 g, 14.44 mmol), followed by acetic acid (0.826 ml, 14.4 mmol) dropwise at 25° C. The mixture was then heated to 50° C. for 30 min. TMSCN (3.23 mL, 24.1 mmol) was then added to the mixture. The mixture was stirred at 50° C. for 16 h. KOH solution (1M, 10 mL) was added to the mixture. The mixture was extracted with EtOAc (10 mL×3). The combined organic layers were washed with brine, dried over $Na_2SO_4$, filtered and concentrated in vacuo to afford a residue which was then purified by column chromatography on silica gel (EtOAc in petroleum ether: 0-55% gradient) to give 3-(4-(5-amino-2-bromo-4-methylphenyl)piperazin-1-yl)oxetane-3-carbonitrile. MS (EI) m/z: 351 $[M+H]^+$

Step 6: 3-(4-(1-acetyl-5-bromo-1H-indazol-6-yl) piperazin-1-yl)oxetane-3-carbonitrile To a solution of 3-(4-(5-amino-2-bromo-4-methylphenyl) piperazin-1-yl)oxetane-3-carbonitrile (500 mg, 1.42 mmol) in $CHCl_3$ (10 mL) was added acetic anhydride (603 mg, 5.91 mmol) under ice bath. Then potassium acetate (279 mg, 2.85 mmol), 18-crown-6 (113 mg, 0.427 mmol) and isopentyl nitrite (334 mg, 2.85 mmol) were added. The resulting mixture was stirred at 65° C. for 16 h. The mixture was diluted with water (20 mL) and extracted with EtOAc (20 mL×3). The combined organic layers were washed with brine, dried over $Na_2SO_4$, filtered and concentrated in vacuo to afford residue, which was purified by column chromatography on silica gel (EtOAc in petroleum ether: 0-18% gradient) to give 3-(4-(1-acetyl-5-bromo-TH-indazol-6-yl) piperazin-1-yl)oxetane-3-carbonitrile. MS (EI) m/z: 404 $[M+H]^+$.

Step 7: 3-(4-(5-bromo-1H-indazol-6-yl)piperazin-1-yl)oxetane-3-carbonitrile $K_2CO_3$ (359 mg, 2.60 mmol) was added to a solution of 3-(4-(1-acetyl-5-bromo-1H-indazol-6-yl)piperazin-1-yl) oxetane-3-carbonitrile (350 mg, 0.866 mmol) in MeOH (8 mL). The resulting mixture was stirred at 60° C. for 45 min. The solvent was evaporated, and water (10 mL) was added. The mixture was extracted with EtOAc (10 mL×3). The combined organic layers were washed with brine, dried over $Na_2SO_4$, filtered and concentrated in vacuo to afford crude 3-(4-(5-bromo-1H-indazol-6-yl)piperazin-1-yl)oxetane-3-carbonitrile, which was used in next step directly. MS (EI) m/z: 362 $[M+H]^+$.

Step 8: 5-bromo-6-(4-(3-methyloxetan-3-yl)piperazin-1-yl)-1H-indazole

To a solution of 3-(4-(5-bromo-TH-indazol-6-yl)piperazin-1-yl)oxetane-3-carbonitrile (100 mg, 0.276 mmol) in THF (10 mL) methylmagnesium bromide (2.76 ml, 2.76 mmol) was added at 60° C. under a $N_2$ atmosphere. The resulting solution was stirred at 60° C. for 1.5 h. The reaction was quenched with $NH_4Cl$ (sat. 8 mL) and extracted with EtOAc (50 mL). The organic layer was washed with brine, dried over $Na_2SO_4$, filtered and concentrated in vacuo to afford a residue which was then purified by preparative TLC ($SiO_2$, eluting with EtOAc) to give 5-bromo-6-(4-(3-methyloxetan-3-yl)piperazin-1-yl)-1H-indazole. MS (EI) m/z: 351 $[M+H]^+$.

Step 9: 5-bromo-1-(1-methyl-1H-pyrazol-4-yl)-6-(4-(3-methyloxetan-3-yl)piperazin-1-yl)-1H-indazole (Ex. 2.1)

CuI (2.7 mg, 0.014 mmol) was added to a solution of 5-bromo-6-(4-(3-methyloxetan-3-yl)piperazin-1-yl)-1H-indazole (25 mg, 0.071 mmol), (1R,2R)—N1,N2-dimethylcyclohexane-1,2-diamine (4.0 mg, 0.028 mmol), 4-iodo-1-methyl-TH-pyrazole (22.2 mg, 0.107 mmol) and potassium phosphate (45.3 mg, 0.214 mmol) in anhydrous 1,4-dioxane (3 mL) under a $N_2$ atmosphere. The resulting mixture was stirred at 90° C. for 16 h. The mixture was filtered and concentrated in vacuo to afford a residue which was then purified by reversed phase HPLC, eluting with water (0.10% TFA)-ACN to afford the title compound as a TFA salt (Ex. 2.1). $^1H$ NMR (500 MHz, $CDCl_3$) δ8.02 (s, 1H), 8.00 (s, 1H), 7.80 (s, 1H), 7.79 (s, 1H), 7.19 (s, 1H), 5.25 (br d, J=7.32 Hz, 2H), 4.39 (d, J=7.17 Hz, 2H), 4.03 (s, 3H) 3.46-3.53 (m, 4H), 3.14-3.39 (m, 4H), 1.83 (s, 3H). MS (ESI) m/z: 431.2 $[M+H]^+$.

Preparation of Example 3.1: 5-fluoro-1-(1-methyl-TH-pyrazol-4-yl)-6-(4-(3-methyloxetan-3-yl)piperazin-1-yl)-1H-indazole Scheme 51

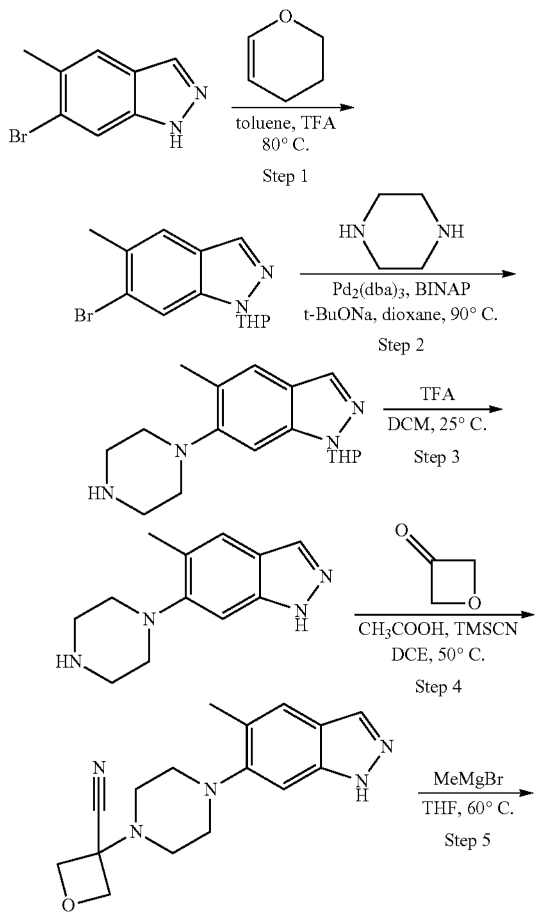

-continued

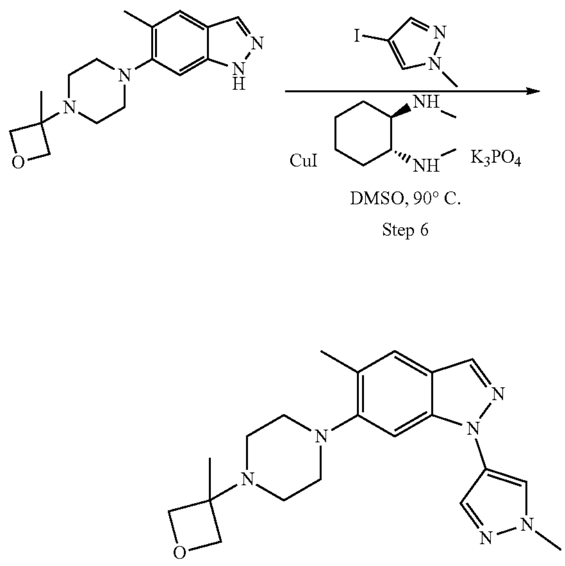

Ex. 3.1

Step 1: 6-bromo-5-methyl-1-(tetrahydro-2H-pyran-2-yl)-1H-indazole

To a solution of 6-bromo-5-methyl-1H-indazole (2.00 g, 9.48 mmol) in anhydrous toluene (20 mL) was added 3,4-dihydro-2H-pyran (0.877 g, 10.4 mmol) and 2,2,2-trifluoroacetic acid (0.10 mL, 1.30 mmol), and the resulting mixture was stirred at 80° C. for 4 hours. The reaction mixture was concentrated, and the residue was then purified by column chromatography on silica gel (EtOAc in petroleum ether: 0-10% gradient) to give 6-bromo-5-methyl-1-(tetrahydro-2H-pyran-2-yl)-1H-indazole. MS (EI) m/z: 295.0 $[M+H]^+$.

Step 2: 5-methyl-6-(piperazin-1-yl)-1-(tetrahydro-2H-pyran-2-yl)-1H-indazole Sodium tert-butoxide (260 mg, 2.71 mmol), BINAP (1688 mg, 2.71 mmol) and $Pd_2(dba)_3$ (248 mg, 0.271 mmol) were added to a solution of 6-bromo-5-methyl-1-(tetrahydro-2H-pyran-2-yl)-1H-indazole (800 mg, 2.71 mmol) and piperazine (233 mg, 2.71 mmol) in toluene (10 mL) at room temperature. The mixture was stirred at 90° C. under $N_2$ atmosphere for 12 h. Water (10 mL) was added to the mixture, and the mixture was extracted three times with EtOAc (20 mL). The combined organic layers were washed with brine (20 mL), dried over anhydrous $Na_2SO_4$ and filtered. The filtrate was concentrated in vacuo to give the residue, which was purified by column chromatography on silica gel (MeOH in DCM: 0-15% gradient) to give 5-methyl-6-(piperazin-1-yl)-1-(tetrahydro-2H-pyran-2-yl)-1H-indazole. MS (EI) m/z: 301.2 $[M+H]^+$.

Step 3: 5-methyl-6-(piperazin-1-yl)-1H-indazole

To a solution of 5-methyl-6-(piperazin-1-yl)-1-(tetra-hydro-2H-pyran-2-y-1)-1H-indazole (150 mg, 0.499 mmol) in DCM (4.0 mL) was added 2,2,2-trifluoroacetic acid (1.0 mL, 0.50 mmol) dropwise, and the resulting mixture was stirred at rt for 12 h. The mixture was concentrated in vacuo to give a residue which was then purified by reversed phase HPLC, eluting with water (0.1% TFA)-ACN to afford 5-methyl-6-(piperazin-1-yl)-1H-indazole. MS (EI) m/z: 217.1 $[M+H]^+$ Step 4: 3-(4-(5-methyl-TH-indazol-6-yl)piperazin-1-yl)oxetane-3-carbonitrile Oxetan-3-one (100 mg, 1.39 mmol) was added to a solution of 5-methyl-6-(piperazin-1-yl)-1H-indazole (150 mg, 0.694 mmol) in DCE (5.0 mL), followed by acetic acid (0.793 mL, 13.9 mmol) dropwise at rt. The mixture was then heated to 50° C. After 30 min, trimethylsilyl cyanide (0.871 ml, 6.94 mmol) was added to the mixture. The mixture was stirred at 50° C. for 12 h. Water (10 mL) was added to the mixture, and the mixture was then extracted with EtOAc (20 mL×3). The combined organic layers were washed with brine (20 mL), dried over anhydrous $Na_2SO_4$ and filtered. The filtrate was concentrated in vacuo to give the residue, which was purified by prep-TLC ($SiO_2$, PE:EtOAc=2:1, v/v) to give 3-(4-(5-methyl-TH-indazol-6-yl)piperazin-1-yl)oxetane-3-carbonitrile. MS (EI) m/z: 298.2 $[M+H]^+$.

Step 5: 5-methyl-6-(4-(3-methyloxetan-3-yl)piperaz-in-1-yl)-1H-indazole

A solution of 3-(4-(5-methyl-1H-indazol-6-yl)piperazin-1-yl)oxetane-3-carbonitrile (90.0 mg, 0.303 mmol) in THF (4.0 mL) was stirred at 60° C. for 30 min. Methylmagnesium bromide (722 mg, 6.05 mmol) was then added to the mixture while maintaining the temperature at 60° C., and the mixture was stirred for 4 h. The mixture was then allowed to cool to rt and the reaction was quenched with saturated $NH_4Cl$ (5 mL) and extracted with EtOAc (3×10 mL). The combined organic layers were washed with brine (20 mL), dried over anhydrous $Na_2SO_4$ and filtered. The filtrate was concentrated in vacuo to give a residue which was then purified by prep-TLC ($SiO_2$, EtOAc) to give 5-methyl-6-(4-(3-methyl-oxetan-3-yl)piperaz-in-1-yl)-1H-indazole. MS (EI) m/z: 287.0 $[M+H]^+$.

Step 6: 5-methyl-1-(1-methyl-TH-pyrazol-4-yl)-6-(4-(3-methyloxetan-3-yl)piperazin-1-yl)-1H-indazole (Ex. 3.1)

To a solution of 5-methyl-6-(4-(3-methyloxetan-3-yl)pip-erazin-1-yl)-1H-indazole (20 mg, 0.070 mmol) and 4-iodo-1-methyl-TH-pyrazole (21.7 mg, 0.105 mmol) in DMSO (1.0 mL) potassium phosphate (44.5 mg, 0.210 mmol), (1R,2R)—N1,N2-dimethylcyclohexane-1,2-diamine (9.9 mg, 0.070 mmol) and copper(I) iodide (13.3 mg, 0.070 mmol) were added at rt. The mixture was stirred at 90° C. under $N_2$ atmosphere for 16 h. Then the mixture was then concentrated in vacuo to give a residue which was then purified by reversed phase HPLC and eluted with water (0.1% $NH_4OH$)-ACN to afford the title compound (Ex. 3.1). $^1$H NMR (400 MHz, $CDCl_3$) δ: 7.97 (s, 1H), 7.83 (s, 1H), 7.74 (s, 1H), 7.54 (s, 1H), 7.13 (s, 1H), 4.65 (d, J=5.9 Hz, 2H), 4.28 (d, J=5.9 Hz, 2H), 4.02 (s, 3H), 3.08-2.98 (m, 4H), 2.57 (t, J=4.5 Hz, 4H), 2.41 (s, 3H), 1.46 (s, 3H). MS (EI) m/z: 367.2 $[M+H]^+$.

Preparation of Example 4.1: 5-chloro-1-(1-cyclo-propyl-1H-pyrazol-4-yl)-6-(4-(3-methyloxetan-3-yl)piperazin-1-yl)-1H-indazole Scheme 52

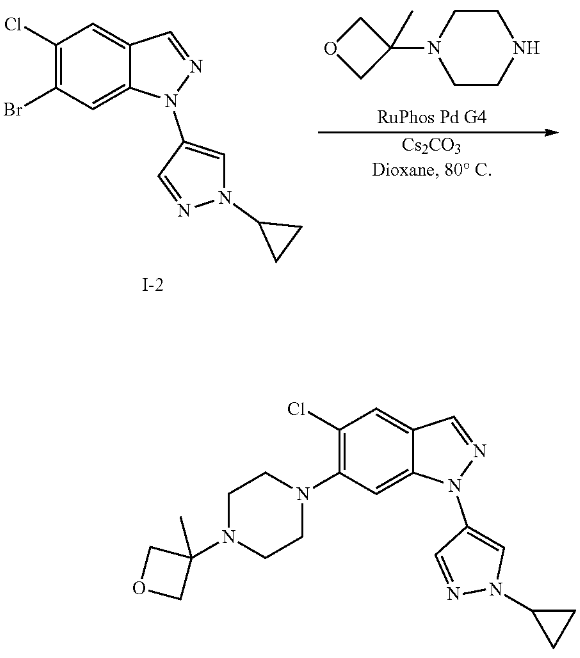

I-2

Ex. 4.1

To a vial was added I-2 (200 mg, 0.592 mmol), 1-(3-methyloxetan-3-yl)piperazine (111 mg, 0.711 mmol), RuPhos Pd G4 (50 mg, 0.059 mmol), $Cs_2CO_3$ (386 mg, 1.18 mmol) and dioxane (2500 µl). The mixture was evacuated and back-filled with $N_2$ five times, then stirred at 80° C. for 18 h. The mixture was diluted with EtOAc and water. The aqueous layer was extracted with EtOAc three times. The combined organic layers were washed with brine, dried over $MgSO_4$, filtered and concentrated in vacuo to afford a residue which was then dissolved in MeOH and purified by reversed phase HPLC, with water elution (0.1% $NH_4OH$)-ACN to afford the title compound (Ex. 4.1). $^1$H NMR (600 MHz, DMSO-$d_6$) δ 8.43 (s, 1H), 8.17-8.13 (m, 1H), 7.93 (s, 1H), 7.90 (s, 1H), 7.27 (s, 1H), 4.46 (d, J=5.6 Hz, 2H), 4.17 (d, J=5.6 Hz, 2H), 3.85 (tt, J=7.4, 3.8 Hz, 1H), 3.20-3.01 (m, 4H), 2.57-2.47 (m, 4H), 1.34 (s, 3H), 1.20-1.14 (m, 2H), 1.07-0.97 (m, 2H); MS (EI) m/z: 413 $[M+H]^+$.

Preparation of Example 4.2 and 4.3: (S or R)-5-chloro-1-(1-cyclopropyl-1H-pyrazol-4-yl)-6-(2-methyl-4-(3-methyloxetan-3-yl)piperazin-1-yl)-1H-indazole and (R or S)-5-chloro-1-(1-cyclopropyl-1H-pyrazol-4-yl)-6-(2-methyl-4-(3-methyloxetan-3-yl)piperazin-1-yl)-1H-indazole and (R or S)-5-chloro-1-(1-cyclopropyl-1H-pyrazol-4-yl)-6-(2-methyl-4-(3-methyloxetan-3-yl)piperazin-1-yl)-1H-indazole and (R or S)-5-chloro-1-(1-cyclopropyl-1H-pyrazol-4-yl)-6-(2-methyl-4-(3-methyloxetan-3-yl)piperazin-1-yl)-1H-indazole Scheme 53

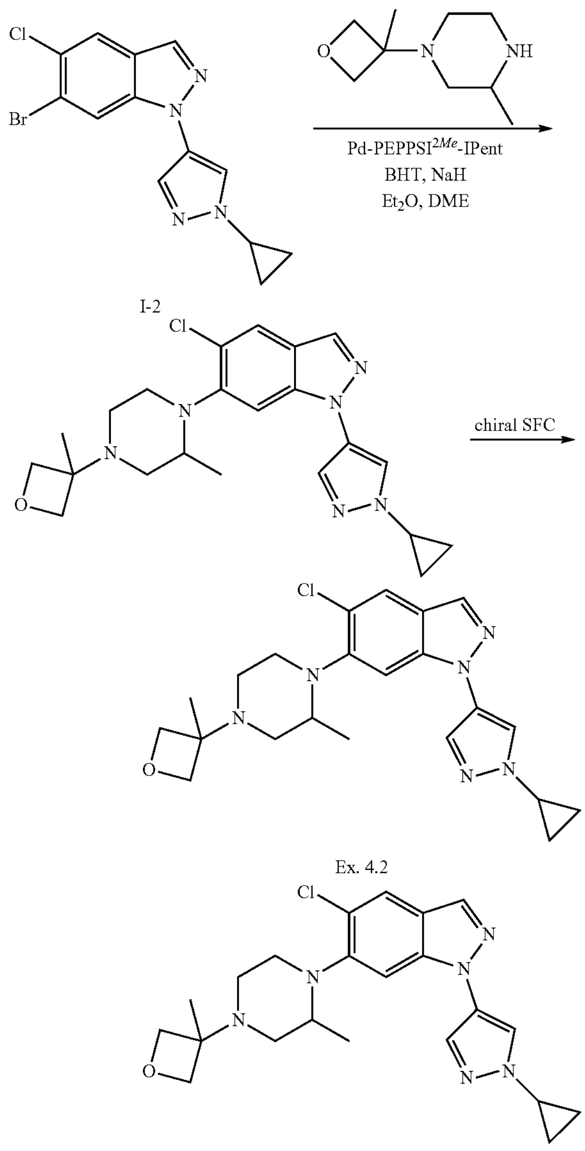

I-2

Ex. 4.2

Ex. 4.3

To a vial equipped with a stir bar, NaH (38.5 mg, 0.963 mmol) and 2,6-di-tert-butyl-4-methylphenol (BHT) (212 mg, 0.962 mmol) were added. The vial was then sealed with a septum, evacuated and back-filled with $N_2$ three times. The vial was then cooled to 0° C., and $Et_2O$ (1000 µl) was added by syringe. After the mixture was stirred for 15 min at 0° C., the solvent was then removed in vacuo to yield a solid. To this vial, Pd-PEPPSI$^{2Me}$-IPent (12 mg, 0.015 mmol) was added, followed by I-2 (100 mg, 0.296 mmol), I-6 (101 mg, 0.355 mmol), and DME (1000 µl). The vial was then evacuated and back-filled with $N_2$ three times and heated at 80° C. for 16 h. The mixture was filtered and purified by column chromatography on silica gel (EtOAc in hexane: 0-50% gradient) to afford 5-chloro-1-(1-cyclopropyl-1H-pyrazol-4-yl)-6-(2-methyl-4-(3-methyloxetan-3-yl)piperazin-1-yl)-1H-indazole. The product was subjected to SFC chiral separation (column & dimensions: OJ-H, 21×250 mm; Mobile phase A: $CO_2$; Mobile phase B: MeOH with 0.1% $NH_4OH$) to afford the title compounds (examples 4.2 and 4.3).

Example 4.2

$^1$H NMR (600 MHz, DMSO-$d_6$) δ 8.42 (s, 1H), 8.15 (s, 1H), 7.92 (s, 1H), 7.91 (s, 1H), 7.24 (s, 1H), 4.53 (dd, J=22.0, 5.3 Hz, 2H), 4.10 (dd, J=35.1, 5.1 Hz, 2H), 3.85 (tt, J=7.4, 3.8 Hz, 1H), 3.29-3.16 (m, 2H), 2.96-2.85 (m, 1H), 2.74-2.55 (m, 2H), 2.49-2.36 (m, 2H), 1.44 (s, 3H), 1.17 (p, J=4.8 Hz, 2H), 1.03 (td, J=7.2, 5.0 Hz, 2H), 0.84 (d, J=6.3 Hz, 3H); MS (EI) m/z: 427 $[M+H]^+$. Retention time: 2.8 min.

Example 4.3

$^1$H NMR (600 MHz, DMSO-$d_6$) δ 8.42 (s, 1H), 8.15 (s, 1H), 7.92 (s, 1H), 7.91 (s, 1H), 7.24 (s, 1H), 4.53 (dd, J=22.0, 5.3 Hz, 2H), 4.10 (dd, J=35.1, 5.1 Hz, 2H), 3.85 (tt, J=7.4, 3.8 Hz, 1H), 3.29-3.16 (m, 2H), 2.96-2.85 (m, 1H), 2.74-2.55 (m, 2H), 2.49-2.36 (m, 2H), 1.44 (s, 3H), 1.17 (p, J=4.8 Hz, 2H), 1.03 (td, J=7.2, 5.0 Hz, 2H), 0.84 (d, J=6.3 Hz, 3H); MS (EI) m/z: 427 $[M+H]^+$. Retention time: 7.7 min.

Preparation of Example 4.4 and 4.5: (S or R)-5-chloro-1-(1-cyclopropyl-1H-pyrazol-4-yl)-6-(4-(3-methyltetrahydrofuran-3-yl)piperazin-1-yl)-1H-indazole and (R or S)-5-chloro-1-(1-cyclopropyl-TH-pyrazol-4-yl)-6-(4-(3-methyltetrahydrofuran-3-yl)piperazin-1-yl)-1H-indazole Scheme 54

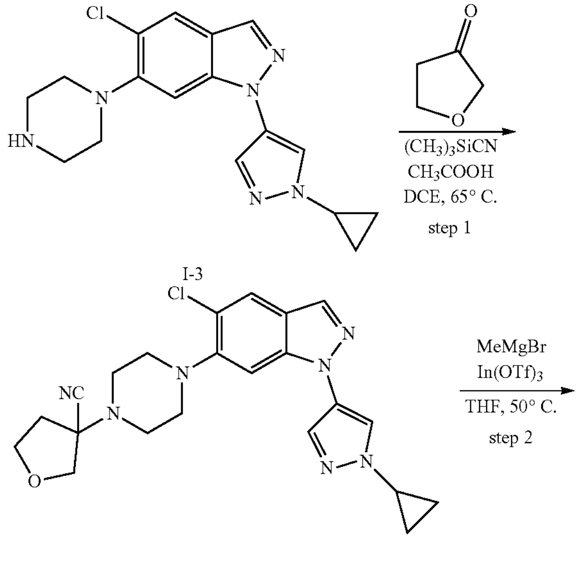

I-3

-continued

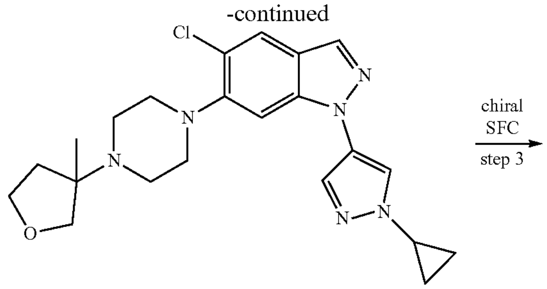

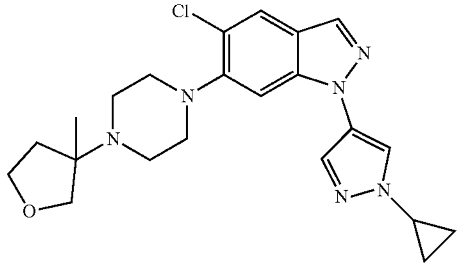

Ex. 4.4

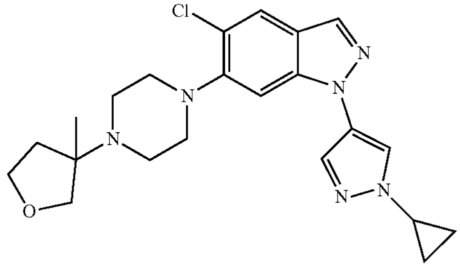

Ex. 4.5

Step 1: 3-(4-(5-chloro-1-(1-cyclopropyl-1H-pyrazol-4-yl)-1H-indazol-6-yl)piperazin-1-yl) tetrahydrofuran-3-carbonitrile To a vial containing I-3 (150 mg, 0.395 mmol), DCE (3800 μl) and DIEA (400 μl, 2.29 mmol) were added. To this mixture, 45 mg of 4 A molecular sieves (ground, activated in oven), acetic acid (150 μl, 2.62 mmol) and dihydrofuran-3(2H)-one (122 mg, 1.42 mmol) were added. The mixture was then stirred at 65° C. for 40 min, followed by the addition of trimethylsilyl cyanide (150 μl, 1.12 mmol). The mixture was stirred at 65° C. for 17 h, then diluted with DCM and saturated $NaHCO_3$. The aqueous layer was washed with DCM three times. The combined organic layers were washed with brine, dried over $MgSO_4$, filtered and concentrated in vacuo to afford residue. The residue was purified by column chromatography on silica gel (EtOAc in hexane, 0-100% gradient) to afford 3-(4-(5-chloro-1-(1-cyclopropyl-1H-pyrazol-4-yl)-1H-indazol-6-yl)piperazin-1-yl)tetrahydrofuran-3-carbonitrile. MS (EI) m/z 438 $[M+H]^+$.

Step 2: 5-chloro-1-(1-cyclopropyl-1H-pyrazol-4-yl)-6-(4-(3-methyltetrahydrofuran-3-yl)piperazin-1-yl)-1H-indazole A solution of THF (1500 μl) and $In(OTf)_3$ (17 mg, 0.030 mmol) was added to a vial containing 3-(4-(5-chloro-1-(1-cyclopropyl-1H-pyrazol-4-yl)-1H-indazol-6-yl)piperazin-1-yl)tetrahydrofuran-3-carbonitrile (65.8 mg, 0.150 mmol). The solution was cooled to 0° C., then MeMgBr (3.0 M in ether, 350 μl, 1.13 mmol) was added dropwise. The mixture was stirred at 0° C. for 1 h, then heated at 50° C. for 5 h. The reaction was then quenched with water, diluted with MeOH, filtered and purified by reversed phase HPLC, water elution (0.1% $NH_4OH$)-ACN to afford 5-chloro-1-(1-cyclopropyl-1H-pyrazol-4-yl)-6-(4-(3-methyltetrahydrofuran-3-yl)piperazin-1-yl)-1H-indazole. $^1H$ NMR (600 MHz, DMSO-$d_6$) δ 8.43 (s, 1H), 8.15 (s, 1H), 7.93 (s, 1H), 7.90 (s, 1H), 7.25 (s, 1H), 3.90-3.77 (m, 3H), 3.60-3.47 (m, 2H), 3.22-2.97 (m, 4H), 2.79-2.67 (m, 2H), 2.65-2.55 (m, 2H), 1.95-1.86 (m, 1H), 1.83-1.73 (m, 1H), 1.16 (p, J=4.8 Hz, 2H), 1.13 (s, 3H), 1.07-0.98 (m, 2H); MS (EI) m/z 427 $[M+H]^+$.

Step 3: (S or R)-5-chloro-1-(1-cyclopropyl-1H-pyrazol-4-yl)-6-(4-(3-methyltetrahydrofuran-3-yl) piperazin-1-yl)-1H-indazole and (R or S)-5-chloro-1-(1-cyclopropyl-1H-pyrazol-4-yl)-6-(4-(3-methyltetrahydrofuran-3-yl)piperazin-1-yl)-1H-indazole (Ex. 4.4 and Ex. 4.5)

5-chloro-1-(1-cyclopropyl-1H-pyrazol-4-yl)-6-(4-(3-methyltetrahydrofuran-3-yl)piperazin-1-yl)-1H-indazole was subjected to SFC chiral separation (column & dimensions: IA, 21×250 mm; Mobile phase A: $CO_2$; Mobile phase B: MeOH with 0.1% $NH_4OH$) to afford the title compounds (examples 4.4 and 4.5).

Example 4.4

$^1H$ NMR (600 MHz, DMSO-$d_6$) δ 8.43 (s, 1H), 8.15 (s, 1H), 7.93 (s, 1H), 7.90 (s, 1H), 7.25 (s, 1H), 3.90-3.77 (m, 3H), 3.60-3.47 (m, 2H), 3.22-2.97 (m, 4H), 2.79-2.67 (m, 2H), 2.65-2.55 (m, 2H), 1.95-1.86 (m, 1H), 1.83-1.73 (m, 1H), 1.16 (p, J=4.8 Hz, 2H), 1.13 (s, 3H), 1.07-0.98 (m, 2H); MS (EI) m/z 427 $[M+H]^+$. Retention time: 5.1 min.

Example 4.5

$^1H$ NMR (600 MHz, DMSO-$d_6$) δ 8.43 (s, 1H), 8.15 (s, 1H), 7.93 (s, 1H), 7.90 (s, 1H), 7.25 (s, 1H), 3.90-3.77 (m, 3H), 3.60-3.47 (m, 2H), 3.22-2.97 (m, 4H), 2.79-2.67 (m, 2H), 2.65-2.55 (m, 2H), 1.95-1.86 (m, 1H), 1.83-1.73 (m, 1H), 1.16 (p, J=4.8 Hz, 2H), 1.13 (s, 3H), 1.07-0.98 (m, 2H); MS (EI) m/z 427 $[M+H]^+$. Retention time: 5.8 min.

Preparation of Example 4.6: 3-(4-(5-chloro-1-(1-cyclopropyl-1H-pyrazol-4-yl)-1H-indazol-6-yl)piperazin-1-yl)propanenitrile Scheme 55

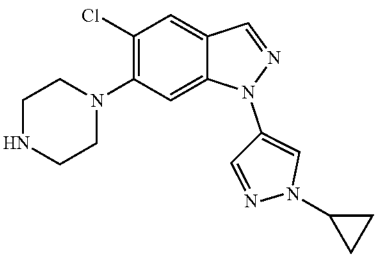

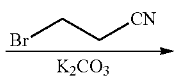

I-3

-continued

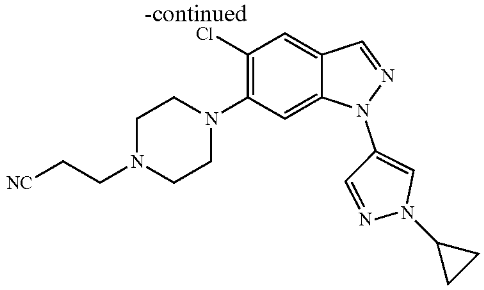

Ex. 4.6

-continued

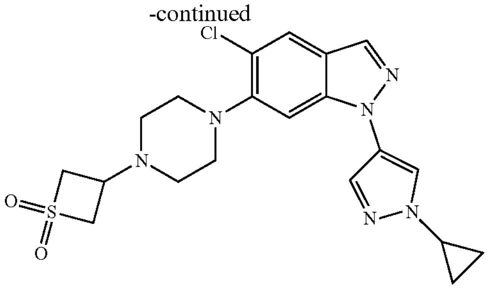

Ex. 4.7

To a vial was added I-3 (21 mg, 0.055 mmol), $K_2CO_3$ (38.1 mg, 0.276 mmol), MeCN (0.8 ml) and 3-bromopropanenitrile (24.4 mg, 0.182 mmol). The slurry was stirred at 100° C. for 20 h. The mixture was filtered and purified by reversed phase HPLC, with water elution (0.1% $NH_4OH$-ACN)) to afford the title compound (Ex. 4.6). $^1H$ NMR (600 MHz, DMSO-$d_6$) δ 8.43 (s, 1H), 8.16 (s, 1H), 8.00-7.84 (m, 2H), 7.27 (s, 1H), 3.92-3.78 (m, 1H), 3.45-3.22 (m, 3H), 3.21-2.98 (m, 3H), 2.86-2.58 (m, 6H), 1.25-1.10 (m, 2H), 1.10-0.96 (m, 2H); MS (EI) m/z 396 $[M+H]^+$.

Preparation of Example 4.7: 3-(4-(5-chloro-1-(1-cyclopropyl-1H-pyrazol-4-yl)-1H-indazol-6-yl)piperazin-1-yl)thietane 1,1-dioxide Scheme 56

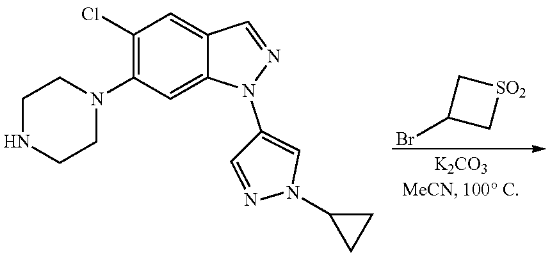

I-3

I-3 (21 mg, 0.055 mmol), 3-bromothietane 1,1-dioxide (23 mg, 0.12 mmol), $K_2CO_3$ (38.1 mg, 0.276 mmol) and MeCN (1 ml) were added to a vial. The slurry was stirred at 100° C. for 18 h. The mixture was filtered and purified by reversed phase HPLC, with water elution (0.1% TFA-ACN) to afford the title compound as the TFA salt (Ex. 4.7). $^1H$ NMR (600 MHz, DMSO-$d_6$) δ 8.42 (s, 1H), 8.17 (s, 1H), 7.96 (s, 1H), 7.92 (s, 1H), 7.26 (s, 1H), 4.47-4.24 (m, 4H), 3.84 (tt, J=7.4, 3.8 Hz, 1H), 3.71-3.51 (m, 1H), 3.29-3.06 (m, 4H), 2.98-2.70 (m, 4H), 1.20-1.11 (m, 2H), 1.08-0.97 (m, 2H); MS (EI) m/z 447 $[M+H]^+$.

Ex. 4.8 in Table 10 was prepared from common intermediate I-3 according to general Scheme 54 by using the I-14 and corresponding starting materials Ex. 4.9 and Ex. 4.10 in Table 11 were prepared from common intermediate I-3 according to general Scheme 54 by using I-15 and corresponding starting materials, then SFC chiral separation (column & dimensions: Chiralpak AD, 30×250 mm; Mobile phase A: $CO_2$; Mobile phase B: 55% MeOH) Retention time: Ex. 4.9: 1.780 min; Ex. 4.10: 2.725 min.

TABLE 11

| EX | Structure | Name | Exact Mass [M + H]+ |
|---|---|---|---|
| Ex. 4.8 | 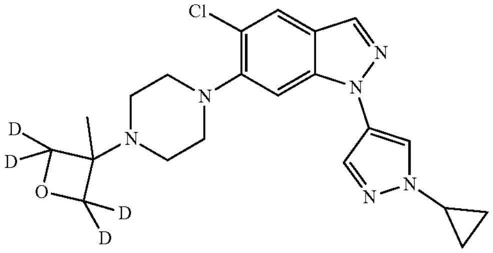 [SMILES: [2H]C1([2H])OC([2H])([2H])C1(C)N1CCN(c2cc3c(cnn3-c3cnn(C4CC4)c3)cc2Cl)CC1] | 5-chloro-1-(1-cyclopropyl-1H-pyrazol-4-yl)-6-{4-[3-methyl(~2~H_4_)oxetan-3-yl]piperazin-1-yl}-1H-indazole | Calc'd 417, found 417 |

TABLE 11-continued

| EX | Structure | Name | Exact Mass [M + H]+ |
|---|---|---|---|
| Ex. 4.9 | 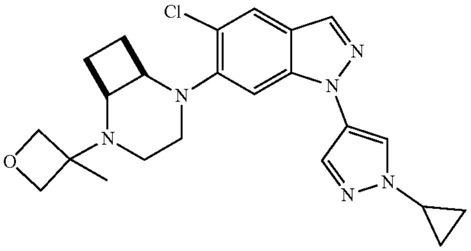 [SMILES: CC1(N2CCN(c3cc4c(cnn4-c4cnn(C5CC5)c4)cc3Cl)[C@@H]3CC[C@@H]32)COC1] | 5-chloro-1-(1-cyclopropyl-1H-pyrazol-4-yl)-6-((1R,6S or 1S,6R)-5-(3-methyloxetan-3-yl)-2,5-diazabicyclo[4.2.0]octan-2-yl)-1H-indazole | Calc'd 439, found 439 |
| Ex. 4.10 | 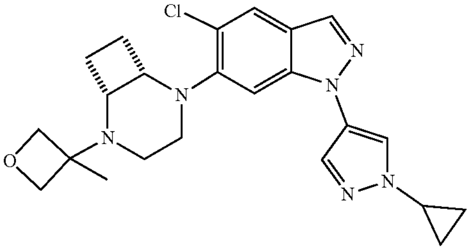 [SMILES: CC1(N2CCN(c3cc4c(cnn4-c4cnn(C5CC5)c4)cc3Cl)[C@H]3CC[C@H]32)COC1] | 5-chloro-1-(1-cyclopropyl-1H-pyrazol-4-yl)-6-((1S,6R or 1R,6S)-5-(3-methyloxetan-3-yl)-2,5-diazabicyclo[4.2.0]octan-2-yl)-1H-indazole | Calc'd 439, found 439 |

Preparation of Example 4.11 and 4.12: (1R,2R or 1S,2S)-2-(4-(5-chloro-1-(1-cyclopropyl-1H-pyrazol-4-yl)-1H-indazol-6-yl)piperazin-1-yl)cyclobutan-1-ol and (1S,2S or 1R,2R)-2-(4-(5-chloro-1-(1-cyclopropyl-1H-pyrazol-4-yl)-1H-indazol-6-yl)piperazin-1-yl)cyclobutan-1-ol Scheme 57

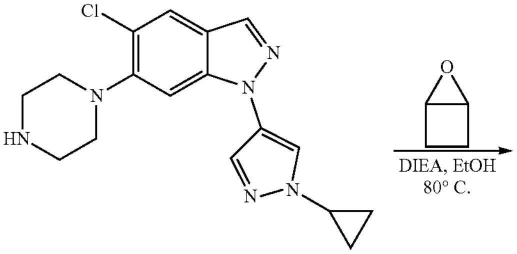

I-3

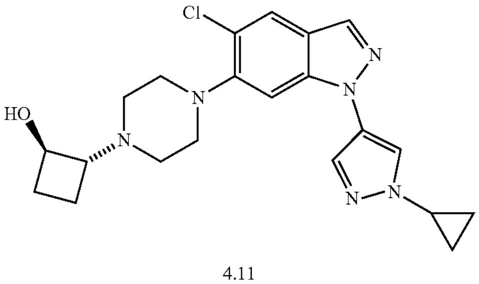

4.11

-continued

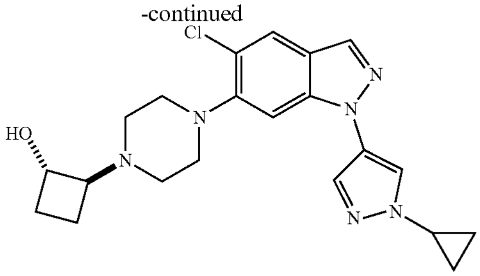

4.12

To a vial were added I-3 (90 mg, 0.23 mmol), ethanol (2.00 mL) and DIEA (200 μL, 1.14 mmol). To this solution was added 5-oxabicyclo[2.1.0]pentane (109 mg, 0.778 mmol). The mixture was heated at 80° C. for 18 h. The mixture was filtered and purified by reversed phase HPLC, eluting with water (0.1% TFA)-ACN to afford 2-(4-(5-chloro-1-(1-cyclopropyl-1H-pyrazol-4-yl)-1H-indazol-6-yl)piperazin-1-yl)cyclobutan-1-ol. The product was subjected to SFC chiral separation (column & dimensions: CCA, 21×250 mm; Mobile phase A: $CO_2$; Mobile phase B: MeOH with 0.1% $NH_4OH$) to afford the title compounds (examples 4.11 and 4.12).

Example 4.11

$^1$H NMR (600 MHz, DMSO-$d_6$) δ 8.41 (s, 1H), 8.15 (s, 1H), 7.93 (s, 1H), 7.90 (s, 1H), 7.25 (s, 1H), 5.15 (d, J=7.2 Hz, 1H), 3.92-3.72 (m, 2H), 3.18-2.96 (m, 4H), 2.63-2.53 (m, 5H), 1.98 (q, J=8.9 Hz, 1H), 1.75 (q, J=9.1 Hz, 1H), 1.42 (p, J=10.4 Hz, 1H), 1.22-1.11 (m, 3H), 1.07-0.99 (m, 2H). MS (EI) m/z: 413 $[M+H]^+$. Retention time: 2.8 min.

Example 4.12

$^1$H NMR (600 MHz, DMSO-$d_6$) δ 8.41 (s, 1H), 8.15 (s, 1H), 7.93 (s, 1H), 7.90 (s, 1H), 7.25 (s, 1H), 5.15 (d, J=7.2 Hz, 1H), 3.92-3.72 (m, 2H), 3.18-2.96 (m, 4H), 2.63-2.53

(m, 5H), 1.98 (q, J=8.9 Hz, 1H), 1.75 (q, J=9.1 Hz, 1H), 1.42 (p, J=10.4 Hz, 1H), 1.22-1.11 (m, 3H), 1.07-0.99 (m, 2H). MS (EI) m/z: 413 $[M+H]^+$. Retention time: 3.3 min.

Example 4.13: 3-(4-(5-chloro-1-(1-cyclopropyl-1H-pyrazol-4-yl)-1H-indazol-6-yl)piperazin-1-yl)tetrahydrothiophene 1,1-dioxide Scheme 58

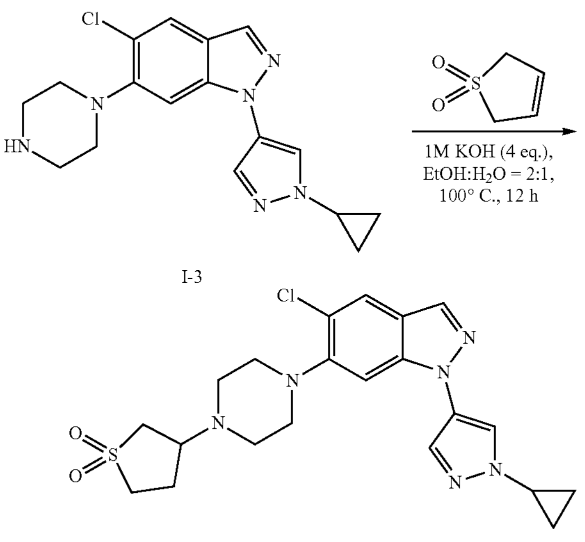

I-3

Ex. 4.13

To a solution of I-3 (60 mg, 0.175 mmol) and 2,5-dihydrothiophene 1,1-dioxide (62 mg, 0.52 mmol) in EtOH (2 mL) and water (1 mL) was added KOH (700 μL, 0.700 mmol). The reaction was heated to 100° C. and stirred for 12 h. Water (10 mL) was added to the mixture and the mixture was extracted with EtOAc (10 mL×3). The combined organic layers were washed with brine (10 mL), dried over anhydrous $Na_2SO_4$ and filtered. The filtrate was concentrated in vacuo to give the residue, which was purified by reversed phase HPLC, eluting with water (0.1% TFA)-ACN to afford the title compound (Ex. 4.13) $^1H$ NMR (500 MHz, MeOD) δ 8.18 (s, 1H), 8.08 (d, J=0.6 Hz, 1H), 7.89 (s, 1H), 7.84 (s, 1H), 7.21 (s, 1H), 4.20-4.10 (m, 1H), 3.76 (m, 1H), 3.71 (m, 1H), 3.54 (s, 2H), 3.50-3.39 (m, 6H), 3.38-3.30 (m, 2H), 3.22 (m, 1H), 2.80 (m, 1H), 2.46-2.28 (m, 1H), 1.20-1.16 (m, 2H), 1.11-1.06 (m, 2H); MS (EI) m/z: 461 $[M+H]^+$ Preparation of Example 4.14 and 4.15: (R or S)-3-(4-(5-chloro-1-(1-cyclopropyl-1H-pyrazol-4-yl)-1H-indazol-6-yl)piperazin-1-yl)-3-methyltetrahydrothiophene 1,1-dioxide and (S or R)-3-(4-(5-chloro-1-(1-cyclopropyl-1H-pyrazol-4-yl)-1H-indazol-6-yl) piperazin-1-yl)-3-methyltetrahydrothiophene 1,1-dioxide Scheme 59

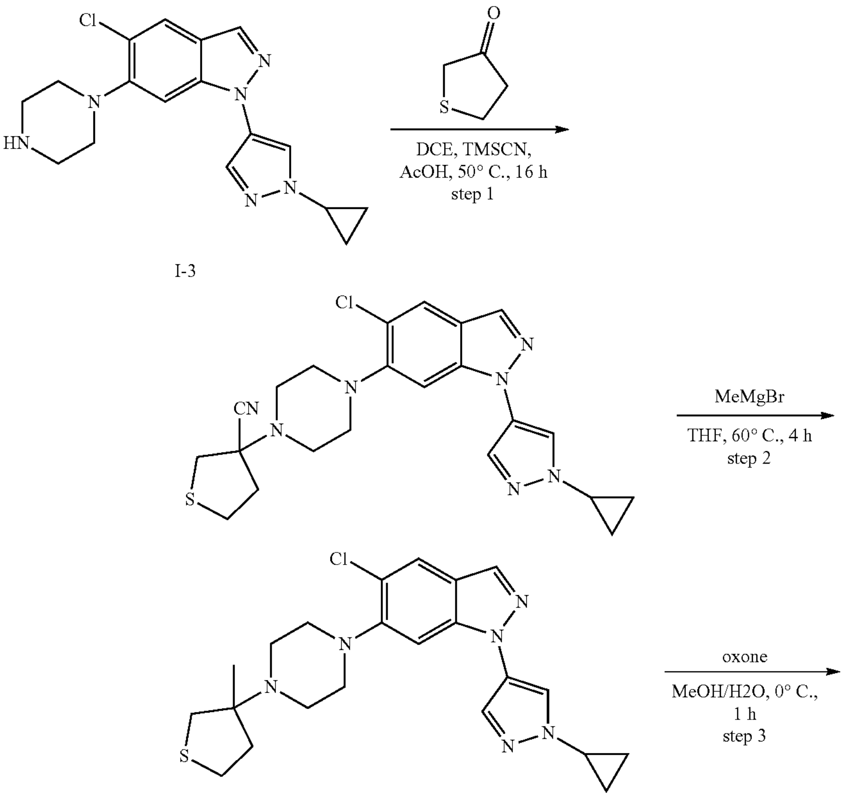

I-3

-continued

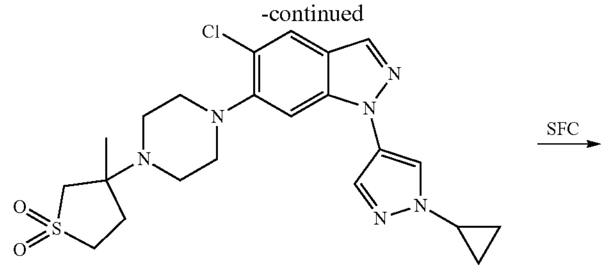

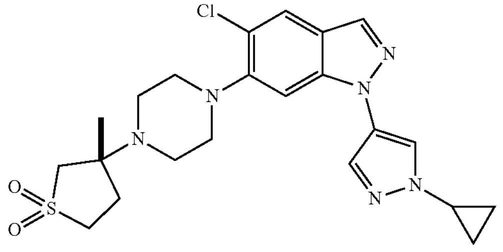

Ex. 4.14

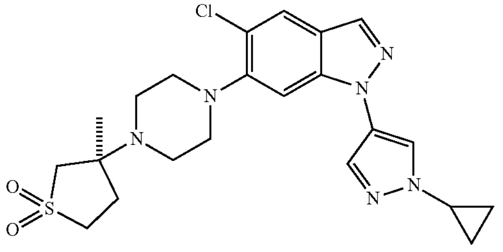

Ex. 4.15

Step 1: 3-(4-(5-chloro-1-(1-cyclopropyl-1H-pyrazol-4-yl)-1H-indazol-6-yl)piperazin-1-yl)tetrahydrothiophene-3-carbonitrile To a solution of I-3 (200 mg, 0.583 mmol) in DCE (8.0 mL) was added dihydrothiophen-3(2H)-one (596 mg, 5.83 mmol), followed by acetic acid (334 μL, 5.83 mmol) dropwise at 25° C. The reaction was headed to 50° C. After 30 min, trimethylsilyl cyanide (1.10 mL, 8.75 mmol) was added to the mixture. The mixture was stirred at 50° C. for 16 hours. Water (10 mL) was added to the mixture and the mixture was extracted with EtOAc (20 mL×3). The combined organic layers were washed with brine (20 mL), dried over anhydrous $Na_2SO_4$ and filtered. The filtrate was concentrated in vacuo to give the residue, which was purified by prep-TLC ($SiO_2$, DCM:MeOH=10:1, v/v) to give 3-(4-(5-chloro-1-(1-cyclopropyl-1H-pyrazol-4-yl)-1H-indazol-6-yl)piperazin-1-yl)tetrahydrothiophene-3-carbonitrile. MS (EI) m/z: 454 $[M+H]^+$ Step 2: 5-chloro-1-(1-cyclopropyl-1H-pyrazol-4-yl)-6-(4-(3-methyltetrahydrothiophen-3-yl)piperazin-1-yl)-1H-indazole A solution of 3-(4-(5-chloro-1-(1-cyclopropyl-1H-pyrazol-4-yl)-1H-indazol-6-yl)piperazin-1-yl)tetrahydrothiophene-3-carbonitrile (200 mg, 0.441 mmol) in THF (5.0 mL) was stirred at 60° C. for 30 min. Then methylmagnesium bromide (2.94 mL, 8.81 mmol, 3M in THF) was added to the mixture at 60° C. for 3 hours. The reaction was quenched with saturated $NH_4Cl$ (5.0 mL) and extracted with EtOAc (3×10 mL). The combined organic layers were washed with brine (10 mL), dried over anhydrous $Na_2SO_4$ and filtered. The filtrate was concentrated in vacuo to give the residue, which was purified by prep-TLC ($SiO_2$, DCM: MeOH=10:1, v/v) to give 5-chloro-1-(1-cyclopropyl-1H-pyrazol-4-yl)-6-(4-(3-methyltetrahydrothiophen-3-yl)piperazin-1-yl)-1H-indazole. MS (EI) m/z: 443 $[M+H]^+$ Step 3: 3-(4-(5-chloro-1-(1-cyclopropyl-1H-pyrazol-4-yl)-1H-indazol-6-yl)piperazin-1-yl)-3-methyltetrahydrothiophene 1,1-dioxide A solution of 5-chloro-1-(1-cyclopropyl-1H-pyrazol-4-yl)-6-(4-(3-methyltetrah-ydrothiophen-3-yl)piperazin-1-yl)-1H-indazole (100 mg, 0.226 mmol) in MeOH (5.0 mL) was stirred at 0° C. Oxone (416 mg, 0.677 mmol) in water (2.5 mL) was added to the mixture dropwise at 0° C. Then the mixture was stirred at 0° C. for 1 hour. LCMS showed the starting material was consumed completely. Water (10 mL) was added to the mixture and the mixture was extracted with EtOAc (20 mL×3). The combined organic layers were washed with brine (20 mL), dried over anhydrous $Na_2SO_4$ and filtered. The filtrate was concentrated in vacuo to give the residue, which was purified by prep-TLC ($SiO_2$, DCM: MeOH=20:1) to give 3-(4-(5-chloro-1-(1-cyclopropyl-1H-pyrazol-4-yl)-1H-indazol-6-yl)piperazin-1-yl)-3-methyltetrahy-drothiophene 1,1-dioxide. MS (EI) m/z: 475 $[M+H]^+$ Step 4: (R or S)-3-(4-(5-chloro-1-(1-cyclopropyl-1H-pyrazol-4-yl)-1H-indazol-6-yl)piperazin-1-yl)-3-methyltetrahydrothiophene 1,1-dioxide and (S or R)-3-(4-(5-chloro-1-(1-cyclopropyl-1H-pyrazol-4-yl)-1H-indazol-6-yl)piperazin-1-yl)-3-methyltetrahydrothiophene 1,1-dioxide (Ex. 4.14 and Ex. 4.15)

3-(4-(5-chloro-1-(1-cyclopropyl-1H-pyrazol-4-yl)-1H-indazol-6-yl)piperazin-1-yl)-3-methyltetrahydrothiophene 1,1-dioxide (40 mg, 0.084 mmol) was subjected to SFC chiral separation (column & dimensions: Chiralcel OD-3 150×4.6 mm; Mobile phase A: $CO_2$; Mobile phase B: ethanol with 0.05% DEA) to afford the title compounds (examples 4.14 and 4.15).

Ex. 4.14: $^1H$ NMR (400 MHz, $CDCl_3$) δ 7.99 (d, J=0.8 Hz, 1H), 7.83 (s, 1H), 7.79 (s, 1H), 7.77 (s, 1H), 7.06 (s, 1H), 3.71 (J=3.6, 7.2 Hz, 1H), 3.42-3.33 (m, 2H), 3.23-3.06 (m, 5H), 3.00 (d, J=13.2 Hz, 1H), 2.82 (d, J=5.6 Hz, 2H), 2.74 (d, J=6.0 Hz, 2H), 2.45 (m, 1H), 2.19 (J=7.2, 14.0 Hz, 1H), 1.35 (s, 3H), 1.25-1.22 (m, 2H), 1.14-1.08 (m, 2H). MS (ESI) m/z: 475 $[M+H]^+$. Retention time: 7.262 min Ex 4.15: $^1H$ NMR (400 MHz, $CDCl_3$) δ 7.99 (d, J=0.8 Hz, 1H), 7.83 (s, 1H), 7.79 (s, 1H), 7.77 (s, 1H), 7.07 (s, 1H), 3.71 (J=3.6, 7.2 Hz, 1H), 3.42-3.31 (m, 2H), 3.24-3.07 (m, 5H), 3.00 (d, J=12.8 Hz, 1H), 2.86-2.80 (m, 1H), 2.82 (d, J=5.6 Hz, 1H), 2.74 (d, J=5.6 Hz, 2H), 2.51-2.40 (m, 1H), 2.25-2.13 (m, 1H), 1.34 (s, 3H), 1.24 (td, J=1.6, 2.8 Hz, 2H), 1.15-1.08 (m, 2H); MS (ESI) m/z: 475 $[M+H]^+$. Retention time: 7.843 min Preparation of Example 5.1: 4-(5-chloro-6-(4-(3-methyloxetan-3-yl)piperazin-1-yl)-1H-indazol-1-yl)-N-methyl-1H-pyrazole-1-carboxamide Scheme 60

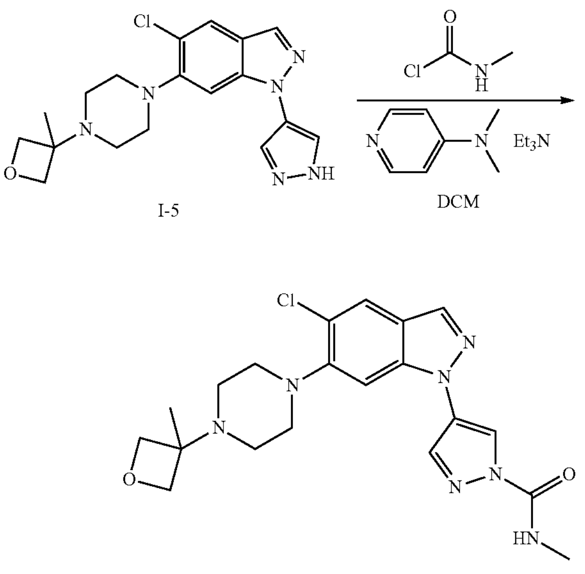

I-5

Ex. 5.1

To a vial containing I-5 (25 mg, 0.051 mmol), DMAP (4.0 mg, 0.033 mmol), methylcarbamic chloride (14 mg, 0.15 mmol), DCM (600 μl) and $Et_3N$ (50 μl, 0.36 mmol) were added. The mixture was stirred at rt for 1 h. The mixture was diluted with MeOH and water. The solvent was evaporated in vacuo to afford a residue which was then dissolved in MeOH and purified by reversed phase HPLC, with water elution (0.1% $NH_4OH$)-ACN to afford the title compound (Ex. 5.1). $^1H$ NMR (600 MHz, DMSO-$d_6$) δ 8.89 (s, 1H), 8.61 (q, J=4.4 Hz, 1H), 8.31 (s, 1H), 8.23 (s, 1H), 7.96 (s, 1H), 7.38 (s, 1H), 4.46 (d, J=5.6 Hz, 2H), 4.17 (d, J=5.6 Hz, 2H), 3.41-3.28 (m, 4H), 3.22-3.04 (m, 4H), 2.88 (d, J=4.7 Hz, 3H), 1.34 (s, 3H); MS (EI) m/z 430 $[M+H]^+$.

Preparation of Example 5.2: 4-(5-chloro-6-(4-(3-methyloxetan-3-yl)piperazin-1-yl)-1H-indazol-1-yl)-N-ethyl-1H-pyrazole-1-carboxamide Scheme 61

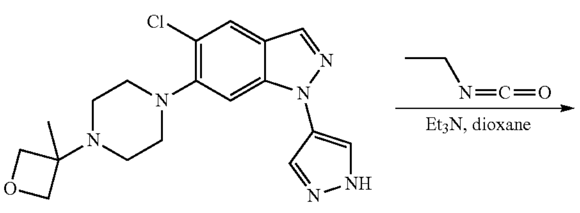

I-5

-continued

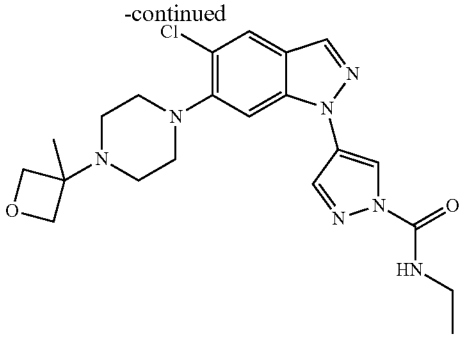

Ex. 5.2

I-5 (27 mg, 0.055 mmol), isocyanatoethane (37 mg, 0.52 mmol), dioxane (500 μl) and $Et_3N$ (80 μl, 0.57 mmol) were added to a vial. The mixture was stirred at rt for 1 h. To the mixture was added a few drops of $NaHCO_3$ (sat.), then the reaction was diluted with DMSO, filtered and purified by reversed phase HPLC, with water elution (0.1% $NH_4OH$-ACN) to afford the title compound (Ex. 5.2). $^1H$ NMR (600 MHz, DMSO-$d_6$) δ 8.89 (s, 1H), 8.72 (t, J=5.9 Hz, 1H), 8.30 (s, 1H), 8.23 (s, 1H), 7.96 (s, 1H), 7.38 (s, 1H), 4.46 (d, J=5.6 Hz, 2H), 4.17 (d, J=5.6 Hz, 2H), 3.44-3.26 (m, 6H), 3.21-3.04 (m, 4H), 1.34 (s, 3H), 1.18 (t, J=7.2 Hz, 3H); MS (EI) m/z 444 $[M+H]^+$.

Preparation of Example 5.3: 5-chloro-1-(1-((cis)-3-fluorocyclobutyl)-1H-pyrazol-4-yl)-6-(4-(3-methyloxetan-3-yl)piperazin-1-yl)-1H-indazole Scheme 62

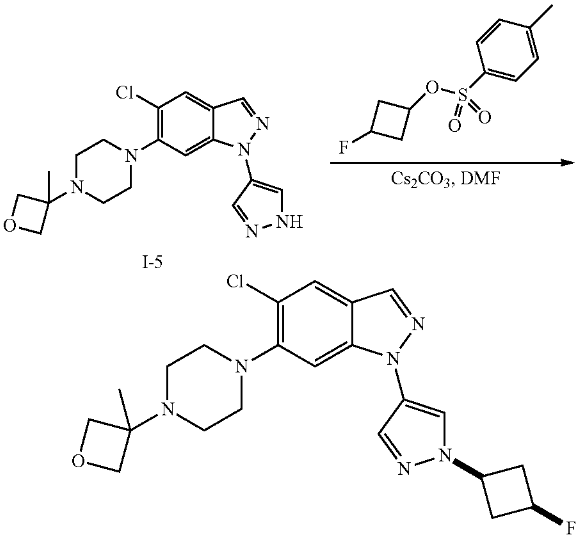

I-5

Ex. 5.3

I-5 (70 mg, 0.14 mmol), 3-fluorocyclobutyl 4-methylbenzenesulfonate (86.4 mg, 0.354 mmol), $Cs_2CO_3$ (187 mg, 0.575 mmol) and DMF (1000 μl) were added to a vial. The mixture was stirred at 80° C. for 3.5 h. To the mixture was added a few drops of $NaHCO_3$ (sat.), then the reaction was diluted with DMF, filtered and purified by reversed phase HPLC, with water elution (0.1% $NH_4OH$-ACN) to afford the title compound (Ex. 5.3). $^{1}$H NMR (600 MHz, DMSO-$d_6$) δ 8.47 (s, 1H), 8.22 (s, 1H), 8.06 (s, 1H), 8.01 (s, 1H), 7.26 (s, 1H), 5.05 (dp, J=56.6, 6.7 Hz, 1H), 4.99-4.77 (m, 2H), 4.56 (dt, J=14.8, 7.4 Hz, 1H), 4.41 (d, J=7.2 Hz, 2H), 3.78-3.07 (m, 8H), 3.05-2.93 (m, 2H), 2.86-2.71 (m, 2H), 1.70 (s, 3H); MS (EI) m/z 445 $[M+H]^+$.

Preparation of Example 5.4: 5-chloro-6-(4-(3-methyloxetan-3-yl)piperazin-1-yl)-1-(1-(2,2,2-trifluoroethyl)-1H-pyrazol-4-yl)-1H-indazole Scheme 63

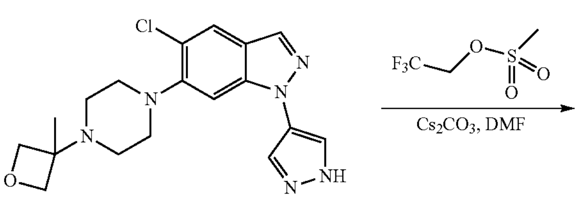

I-5

-continued

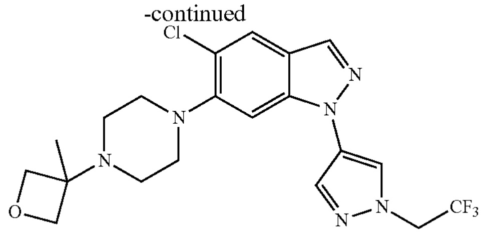

Ex. 5.4

I-5 (27 mg, 0.055 mmol), 2,2,2-trifluoroethyl methanesulfonate (19.5 mg, 0.109 mmol), $Cs_2CO_3$ (71 mg, 0.22 mmol) and DMF (600 μl) were added to a vial. The mixture was stirred at 90° C. for 3 h. The reaction was quenched with a few drops of water, diluted with MeOH, filtered and purified by reversed phase HPLC, with water elution (0.1% $NH_4OH$-ACN) to afford the title compound (Ex. 5.4). $^{1}$H NMR (600 MHz, DMSO-$d_6$) δ 8.53 (s, 1H), 8.20 (s, 1H), 8.15 (s, 1H), 7.96 (s, 1H), 7.29 (s, 1H), 5.24 (q, J=9.0 Hz, 2H), 4.45 (d, J=5.6 Hz, 2H), 4.17 (d, J=5.6 Hz, 2H), 3.38-3.28 (m, 4H), 3.20-3.01 (m, 4H), 1.34 (s, 3H); MS (EI) m/z 455 $[M+H]^+$.

Preparation of Example 5.5: 5-chloro-1-(1-(5-fluoropyrimidin-2-yl)-1H-pyrazol-4-yl)-6-(4-(3-methyloxetan-3-yl)piperazin-1-yl)-1H-indazole Scheme 64

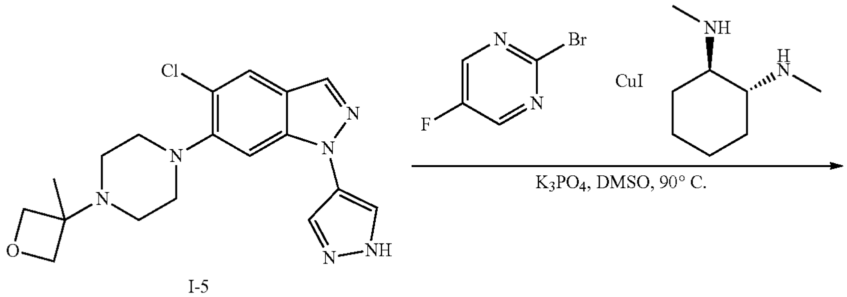

I-5

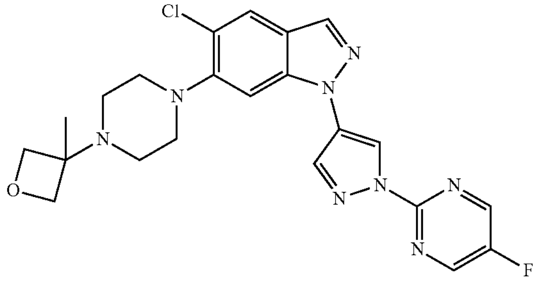

Ex. 5.5

I-5 (503 mg, 0.837 mmol), 2-bromo-5-fluoropyrimidine (279 mg, 1.58 mmol), CuI (47.8 mg, 0.251 mmol), (1R, 2R)—N1,N2-dimethylcyclohexane-1,2-diamine (0.040 ml, 0.25 mmol), potassium phosphate (711 mg, 3.35 mmol) and DMSO (6 ml) were charged to a vial. The mixture was evacuated and back-filled with $N_2$ 4 times and heated at 90° C. for 2 h. The mixture was diluted with water and EtOAc. The aqueous layer was extracted with EtOAc three times. The combined organic layers were washed with brine, dried over $MgSO_4$, filtered and concentrated in vacuo to afford a residue which was then purified by column chromatography on silica gel (EtOH/EtOAc(1/3) in hexane: 0-60% gradient) to afford the title compound (Ex. 5.5).

$^1$H NMR (600 MHz, DMSO-$d_6$) δ 9.14 (s, 1H), 9.05 (s, 2H), 8.44 (s, 1H), 8.26 (s, 1H), 7.97 (s, 1H), 7.43 (s, 1H), 4.45 (d, J=5.6 Hz, 2H), 4.17 (d, J=5.6 Hz, 2H), 3.39-3.27 (s, 4H), 3.21-3.08 (m, 4H), 1.34 (s, 3H); MS (EI) m/z 469 $[M+H]^+$.

Preparation of Example 5.6: 5-chloro-1-(1-((trans)-3-fluorocyclobutyl)-1H-pyrazol-4-yl)-6-(4-(3-methyloxetan-3-yl)piperazin-1-yl)-1H-indazole Scheme 65

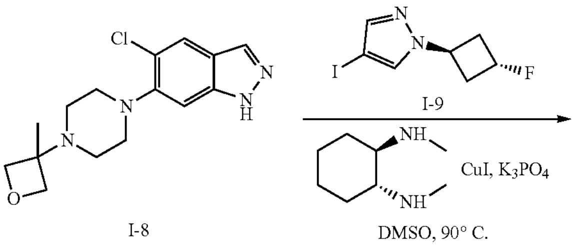

I-8

-continued

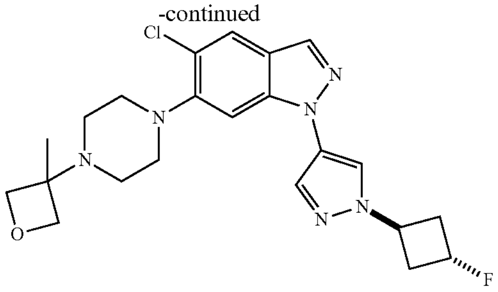

Ex. 5.6

I-9 (225 mg, 0.847 mmol), $K_3PO_4$ (540 mg, 2.54 mmol), (1R,2R)—N1,N2-dimethylcyclohexane-1,2-diamine (24.1 mg, 0.169 mmol) and CuI (16 mg, 0.085 mmol) were added to a solution of I-8 (260 mg, 0.847 mmol) in anhydrous DMSO (5 mL). The resulting mixture was stirred at 90° C. under $N_2$ for 16 h. The mixture was filtered, concentrated in vacuo to afford a residue which was then purified by reversed phase HPLC, eluting with water (0.10% TFA)-ACN to afford the title compound as a TFA salt (Ex. 5.6). $^1$H NMR (400 MHz, $CDCl_3$): δ 8.02 (s, 1H), 7.86 (s, 1H), 7.81 (s, 1H), 7.79 (s, 1H), 7.13 (s, 1H), 5.36-5.57 (m, 1H), 5.22-5.24 (m, 2H), 5.09-5.11 (m, 1H), 4.37-4.39 (m, 2H), 3.47-3.49 (m, 4H), 3.13-3.39 (m, 4H), 2.95-3.08 (m, 2H), 2.79-2.92 (m, 2H), 1.82 (s, 3H). MS (ESI) m/z: 445 $[M+H]^+$ Ex. 5.7 in Table 12 was prepared from common intermediate I-8 according to Scheme 65 by using the corresponding starting materials. Chiral separation was then achieved by SFC (column: DAICEL CHIRALPAK AD (250×50 mm); mobile phase A: $CO_2$; mobile phase B: IPA with 0.1% $NH_4OH$) gave two enantiomers: Ex 5.7 was the more potent enantiomer (retention time 0.779 min).

Ex. 5.8 and Ex. 5.9 were prepared from common intermediate I-8 according to Scheme 65 by using the corresponding intermediate I-19, I-20 and reagents Ex. 5.10 was prepared from common intermediate I-5, according to Scheme 62 by using 1-bromo-3-methoxycyclopentane as alkylation reagent.

TABLE 12

| EX | Structure | Name | Exact Mass [M + H]+ |
|---|---|---|---|
| Ex 5.7 | 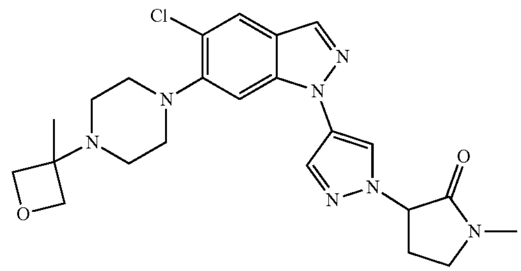 [SMILES: CN1CCC(n2cc(-n3ncc4cc(Cl)c(N5CCN(C6(C)COC6)CC5)cc43)cn2)C1=O] | (R or S)-3-(4-(5-chloro-6-(4-(3-methyloxetan-3-yl)piperazin-1-yl)-1H-indazol-1-yl)-1H-pyrazol-1-yl)-1-methylpyrrolidin-2-one | Calc'd 470, found 470 |

TABLE 12-continued

| EX | Structure | Name | Exact Mass [M + H]+ |
|---|---|---|---|
| Ex 5.8 | 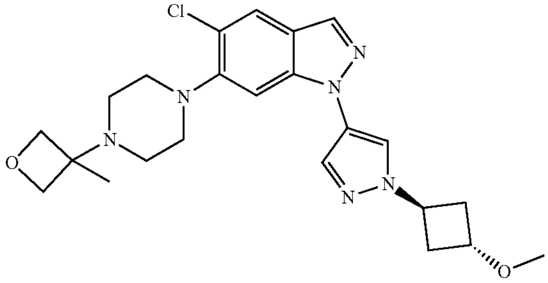 [SMILES: CO[C@H]1C[C@H](n2cc(-n3ncc4cc(Cl)c(N5CCN(C6(C)COC6)CC5)cc43)cn2)C1] | 5-chloro-1-[1-(trans-3-methoxycyclobutyl)-1H-pyrazol-4-yl]-6-[4-(3-methyloxetan-3-yl)piperazin-1-yl]-1H-indazole | Calc'd 457, found 457 |
| Ex 5.9 | 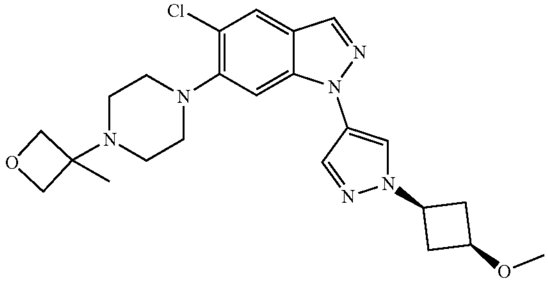 [SMILES: CO[C@H]1C[C@@H](n2cc(-n3ncc4cc(Cl)c(N5CCN(C6(C)COC6)CC5)cc43)cn2)C1] | 5-chloro-1-[1-(cis-3-methoxycyclobutyl)-1H-pyrazol-4-yl]-6-[4-(3-methyloxetan-3-yl)piperazin-1-yl]-1H-indazole | Calc'd 457, found 457 |
| Ex 5.10 | 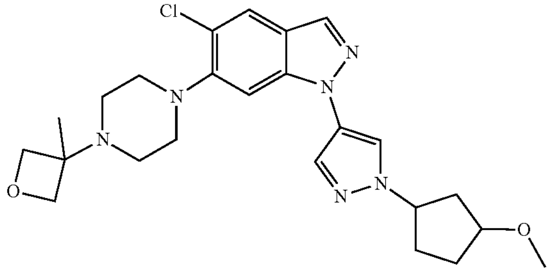 [SMILES: COC1CCC(n2cc(-n3ncc4cc(Cl)c(N5CCN(C6(C)COC6)CC5)cc43)cn2)C1] | 5-chloro-1-[1-(3-methoxycyclopentyl)-1H-pyrazol-4-yl]-6-[4-(3-methyloxetan-3-yl)piperazin-1-yl]-1H-indazole | Calc'd 471, found 471 |

Preparation of Example 5.11 and 5.12: 2-((1S,2S or 1R,2R)-2-(4-(5-chloro-6-(4-(3-methyloxetan-3-yl)piperazin-1-yl)-1H-indazol-1-yl)-1H-pyrazol-1-yl)cyclopropyl)propan-2-ol and 2-((1R,2R or 1S,2S)-2-(4-(5-chloro-6-(4-(3-methyloxetan-3-yl)piperazin-1-yl)-1H-indazol-1-yl)-1H-pyrazol-1-yl)cyclopropyl)propan-2-ol (Ex. 5.11 and Ex. 5.12)

Scheme 66

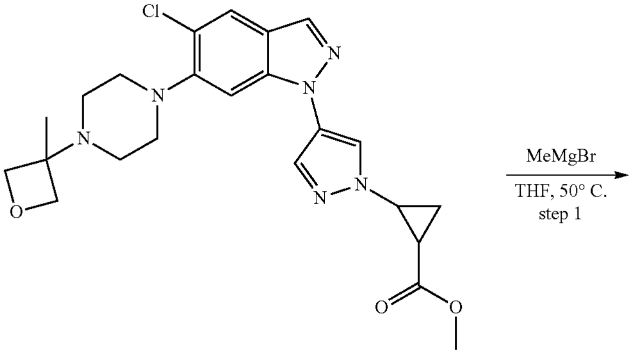

I-17

-continued

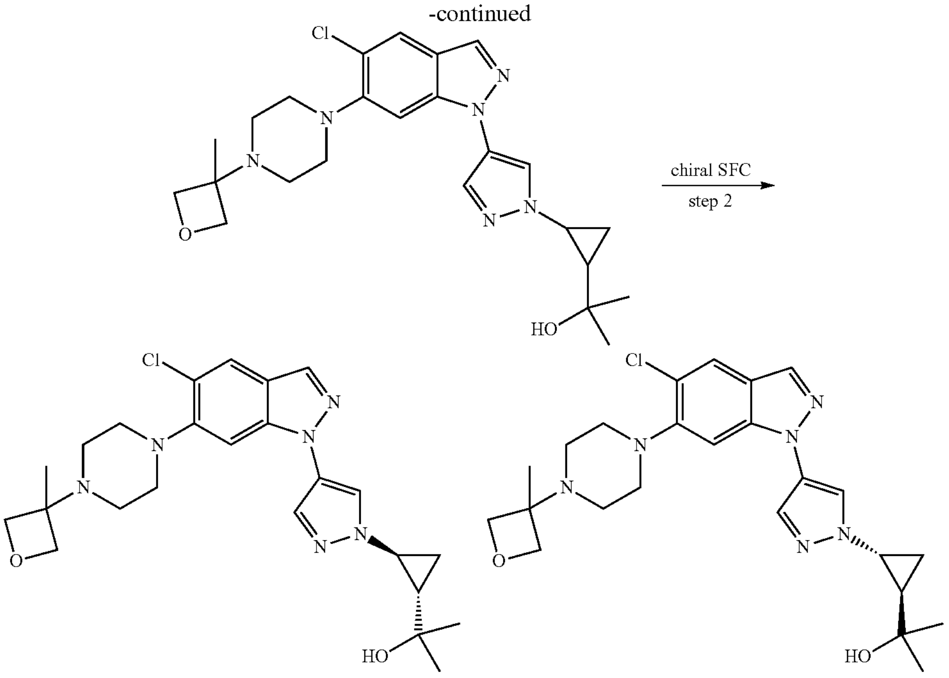

Ex. 5.11 Ex. 5.12

Step 1: 2-(2-(4-(5-chloro-6-(4-(3-methyloxetan-3-yl) piperazin-1-yl)-1H-indazol-1-yl)-1H-pyrazol-1-yl) cyclopropyl)propan-2-ol A 30 mL scintillation vial equipped with a magnetic stirrer was charged with I-17 (350 mg, 0.74 mmol). The vial was sealed with a rubber septum then evacuated and purged with argon (3×). Then, under a positive flow of argon, anhydrous THF (3.7 mL) was added and the stirring mixture cooled to 0° C. Methylmagnesium bromide (3.4 M solution in 2-MeTHF, 1.1 mL, 3.7 mmol) was added slowly. After 30 min, the reaction was stirred at 50° C. overnight. On cooling to rt, the reaction was quenched by careful addition of saturated aq. $NH_4Cl$ solution. The aqueous phase was extracted with DCM (3×15 mL), and the combined organic layers were dried over sodium sulfate, filtered, and the filtrate concentrated to dryness in vacuo. The residue was purified by achiral preparative SFC (Column & dimensions: methanesulfonamide, 250 mm×21 mm; Mobile phase A: $CO_2$; Mobile phase B: 0.1% $NH_3$-MeOH) to afford the 2-(2-(4-(5-chloro-6-(4-(3-methyloxetan-3-yl)piperazin-1-yl)-1H-indazol-1-yl)-1H-pyrazol-1-yl)cyclopropyl)propan-2-ol. MS (EI) m/z 471 $[M+H]^+$.

Step 2: 2-((1S,2S or 1R,2R)-2-(4-(5-chloro-6-(4-(3-methyloxetan-3-yl)piperazin-1-yl)-1H-indazol-1-yl)-1H-pyrazol-1-yl)cyclopropyl)propan-2-ol and 2-((1R,2R or 1S,2S)-2-(4-(5-chloro-6-(4-(3-methyloxetan-3-yl)piperazin-1-yl)-1H-indazol-1-yl)-1H-pyrazol-1-yl) cyclopropyl)propan-2-ol (Ex. 5.11 and Ex. 5.12)

2-(2-(4-(5-chloro-6-(4-(3-methyloxetan-3-yl)piperazin-1-yl)-1H-indazol-1-yl)-1H-pyrazol-1-yl)cyclopropyl)propan-2-ol was subjected to SFC chiral separation (Column & dimensions: CC4, 250 mm×21 mm; Mobile phase A: $CO_2$; Mobile phase B: 0.10% $NH_3$-MeOH) to afford the title compounds (Ex 5.11 and Ex. 5.12)

Ex. 5.11

$^1$H NMR (400 MHz, DMSO-d6, 25° C.) δ: 8.38 (s, 1H), 8.16 (s, 1H), 7.93 (s, 1H), 7.89 (s, 1H), 7.26 (s, 1H), 4.45 (br s, 2H), 4.35 (s, 1H), 4.17 (br s, 2H), 3.78 (s, 1H), 3.11 (s, 3H), 2.50 (s, overlap, 4H), 1.67 (s, 1H), 1.05-1.44 (m, overlap, 11H); MS (EI) m/z 471 $[M+H]^+$. Retention time: 7 min.

Ex. 5.12

$^1$H NMR (400 MHz, DMSO-d6, 25° C.) δ: 8.38 (s, 1H), 8.16 (s, 1H), 7.93 (s, 1H), 7.89 (s, 1H), 7.26 (s, 1H), 4.45 (br s, 2H), 4.35 (s, 1H), 4.17 (br s, 2H), 3.78 (s, 1H), 3.11 (s, 3H), 2.50 (s, overlap, 4H), 1.67 (s, 1H), 1.05-1.44 (m, overlap, 11H); MS (EI) m/z 471 $[M+H]^+$. Retention time: 9.5 min.

Preparation of Example 5.13 and 5.14: N-(((1R,2S or 1S,2R)-2-(4-(5-chloro-6-(4-(3-methyloxetan-3-yl) piperazin-1-yl)-1H-indazol-1-yl)-1H-pyrazol-1-yl) cyclopropyl)methyl)acetamide and N-(((1S,2R or 1R,2S)-2-(4-(5-chloro-6-(4-(3-methyloxetan-3-yl) piperazin-1-yl)-1H-indazol-1-yl)-1H-pyrazol-1-yl) cyclopropyl)methyl)acetamide Scheme 67

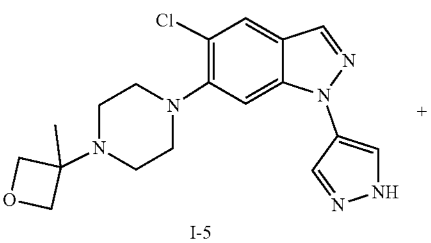

I-5

-continued

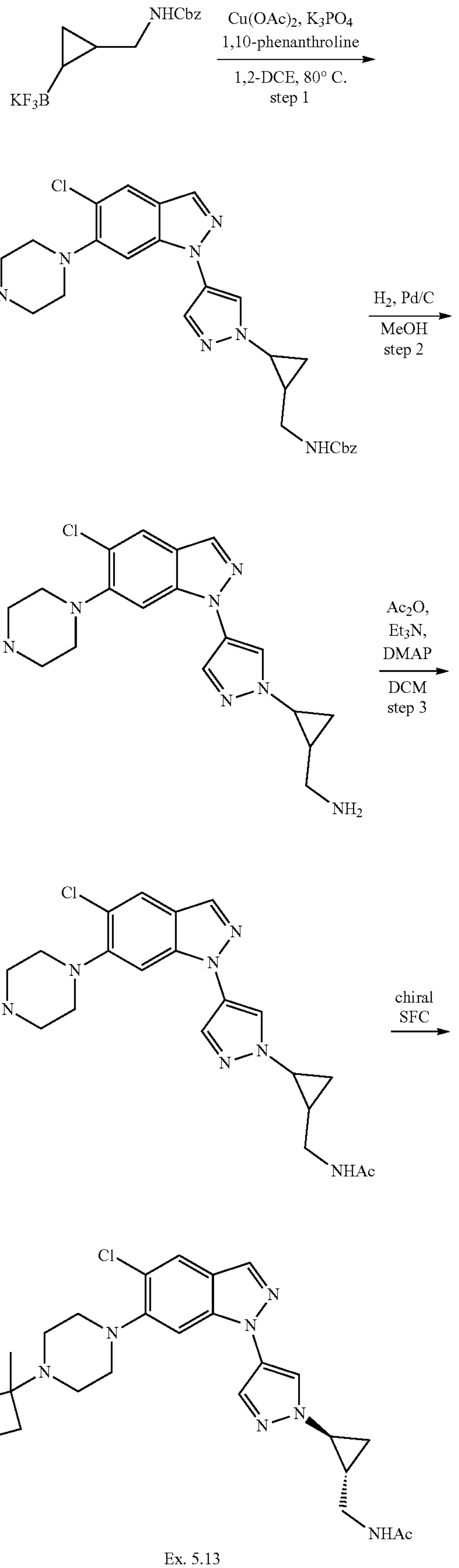

Ex. 5.13

-continued

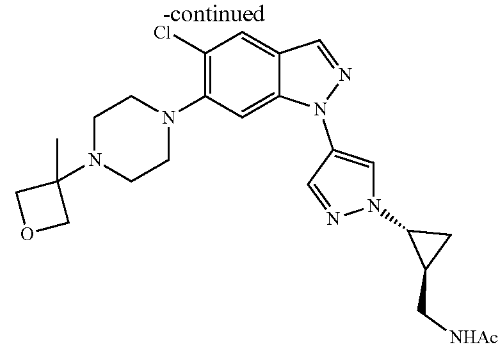

Ex. 5.14

Step 1: benzyl ((2-(4-(5-chloro-6-(4-(3-methyloxetan-3-yl)piperazin-1-yl)-1H-indazol-1-yl)-1H-pyrazol-1-yl)cyclopropyl)methyl)carbamate A 20 mL scintillation vial equipped with a magnetic stirrer was charged with copper (II) acetate (218 mg, 1.2 mmol) and 1,10-phenanthroline (216 mg, 1.2 mmol). Then, under a positive flow of argon DCE (9 mL) was added and stirring was commenced. The mixture was heated to 60° C. and maintained at this temperature for 20 min under a positive pressure of argon. A separate 20 mL oven-dried microwave vial equipped with a magnetic stirrer was charged with I-5 (373 mg, 1.0 mmol) and benzyl ((2-(trifluoro-$\lambda^4$-boranyl)cyclopropyl)methyl)carbamate, potassium salt (311 mg, 1.0 mmol). The vial was sealed with a microwave cap. Then, potassium phosphate (1 M solution in $H_2O$, 3.0 mL, 3.0 mmol) was added and stirring was commenced. To the stirring mixture was added the Cu-phenanthroline complex (solution in DCE prepared above), and the reaction was stirred at 80° C. overnight. The reaction mixture was allowed to cool to room temperature, diluted with EtOAc, dried over sodium sulfate, and filtered through Celite. The filtrate was then concentrated to dryness in vacuo. The crude residue was subjected to purification by reversed phase HPLC on C18 column, eluting with water (0.1% TFA)-MeCN, to afford the racemic intermediate benzyl ((2-(4-(5-chloro-6-(4-(3-methyloxetan-3-yl)piperazin-1-yl)-1H-indazol-1-yl)-1H-pyrazol-1-yl)cyclopropyl)methyl)carbamate. MS (EI) m/z 576 $[M+H]^+$.

Step 2: (2-(4-(5-chloro-6-(4-(3-methyloxetan-3-yl)piperazin-1-yl)-1H-indazol-1-yl)-1H-pyrazol-1-yl)cyclopropyl)methanamine A 30 mL scintillation vial equipped with a magnetic stirrer was charged with benzyl ((2-(4-(5-chloro-6-(4-(3-methyloxetan-3-yl)piperazin-1-yl)-1H-indazol-1-yl)-1H-pyrazol-1-yl)cyclopropyl)methyl)carbamate (55 mg, 0.095 mmol) and 10% wt Pd/C (100 mg). The vial was sealed with a rubber septum then evacuated and purged with argon (3×). Then, under a positive flow of argon anhydrous MeOH (4.0 mL) was added. The suspension was then sparged with an $H_2$ balloon for 20 minutes, and then stirred for 40 minutes under balloon pressure of $H_2$. The mixture was diluted with EtOAc and filtered through a pad of Celite. The filtrate was concentrated to dryness in vacuo to afford the racemic title compound, and the crude material was carried on directly to the next step. MS (EI) m/z 442 $[M+H]^+$.

Step 3: N-(((1R,2S or 1S,2R)-2-(4-(5-chloro-6-(4-(3-methyloxetan-3-Yl)piperazin-1-yl)-1H-indazol-1-yl)-1H-pyrazol-1-yl)cyclopropyl)methyl)acetamide and N-(((1S,2R or 1R,2S)-2-(4-(5-chloro-6-(4-(3-methyloxetan-3-yl)piperazin-1-yl)-1H-indazol-1-yl)-1H-pyrazol-1-yl)cyclopropyl)methyl)acetamide (Ex 5.13 and Ex. 5.14)

To the vial containing the free primary amine intermediate prepared above was added DMAP (12 mg, 0.095 mmol), and the mixture was dissolved in DCM (4.0 mL). To the stirring mixture at RT was added triethylamine (27 μL, 0.19 mmol), then acetic anhydride (0.011 mL, 0.12 mmol). After 30 minutes, the mixture was diluted with DCM and transferred to a separatory funnel containing saturated aq. $NaHCO_3$ solution. The phases were separated and the aqueous phase was extracted once more time with 3:1 $CHCl_3$/IPA. The combined organic layers were dried over $Na_2SO_4$, filtered, and concentrated to dryness in vacuo. The crude residue was subjected to purification by reversed phase HPLC on C18 column, eluting with water (0.1% TFA)-MeCN, to afford N-((2-(4-(5-chloro-6-(4-(3-methyloxetan-3-yl)piperazin-1-yl)-1H-indazol-1-yl)-1H-pyrazol-1-yl)cyclopropyl)methyl) acetamide. The racemic product was resolved to its component enantiomers by chiral preparative SFC (Column & dimensions: AS-H, 250 mm×21 mm; Mobile phase A: $CO_2$; Mobile phase B: 0.1% $NH_3$-MeOH) to afford the title compounds (Ex 5.13 and Ex. 5.14)

Ex. 5.13

$^1$H NMR (400 MHz, DMSO-d6, 25° C.) δ: 8.40 (s, 1H), 8.16 (s, 1H), 8.09 (s, 1H), 7.91 (br s, 2H), 7.27 (s, 1H), 4.46 (s, 2H), 4.18 (s, 2H), 3.72 (s, 1H), 2.95-3.25 (m, overlap, 6H), 1.85 (s, 3H), 1.70 (s, 2H), 0.8-1.5 (m, overlap, 8H); MS (EI) m/z 484 $[M+H]^+$; Retention time: 2.3 min.

Ex. 5.14

$^1$H NMR (400 MHz, DMSO-d6, 25° C.) δ: 8.40 (s, 1H), 8.16 (s, 1H), 8.09 (s, 1H), 7.91 (br s, 2H), 7.27 (s, 1H), 4.46 (s, 2H), 4.18 (s, 2H), 3.72 (s, 1H), 2.95-3.25 (m, overlap, 6H), 1.85 (s, 3H), 1.70 (s, 2H), 0.8-1.5 (m, overlap, 8H); MS (EI): m/z 484 $[M+H]^+$; Retention time: 3.6 min.

Preparation of Example 5.15 and 5.16: cis-3-(4-(5-chloro-6-(4-(3-methyloxetan-3-yl)piperazin-1-yl)-1H-indazol-1-yl)-1H-pyrazol-1-yl)-N-methylcyclobutane-1-carboxamide (Ex. 5.15) and trans-3-(4-(5-chloro-6-(4-(3-methyloxetan-3-yl)piperazin-1-yl)-1H-indazol-1-yl)-1H-pyrazol-1-yl)-N-methylcyclobutane-1-carboxamide (Ex. 5.16)

Scheme 68

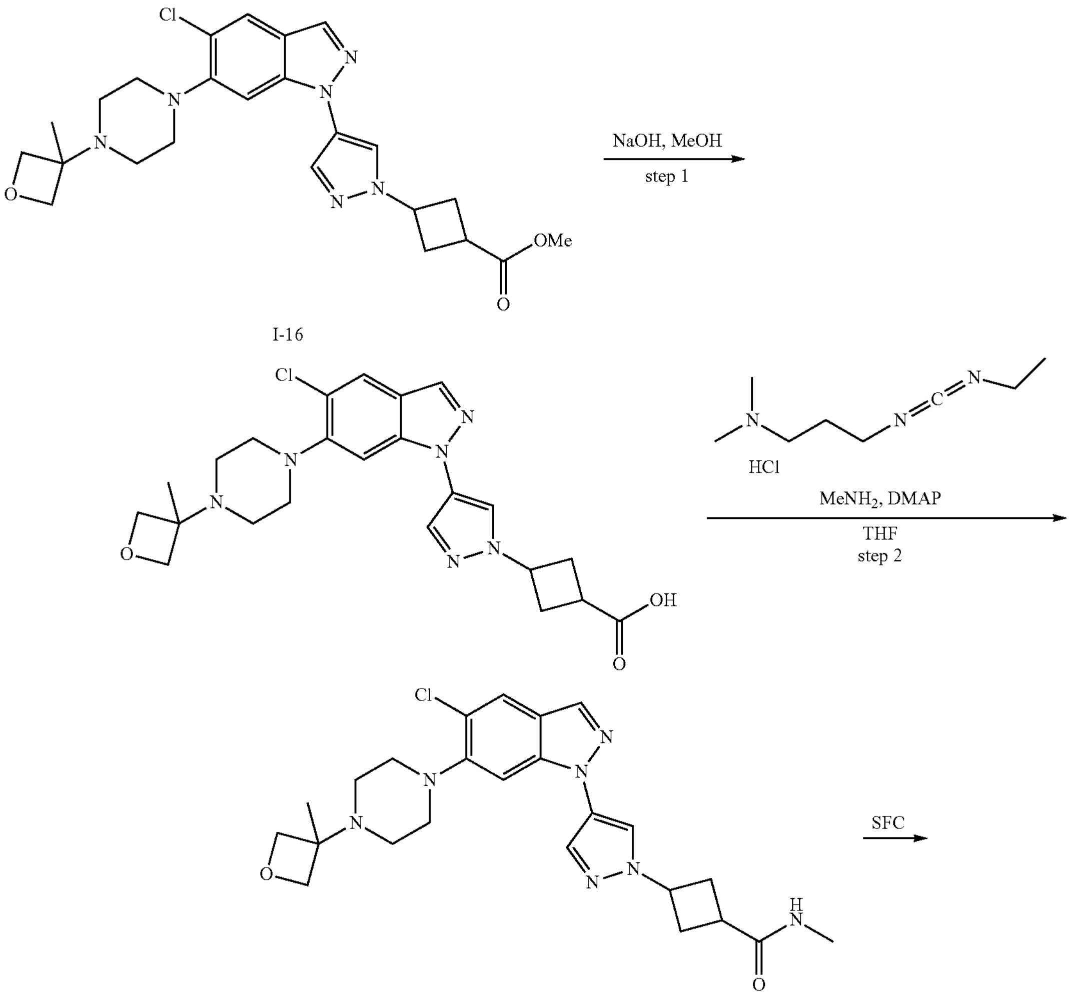

-continued

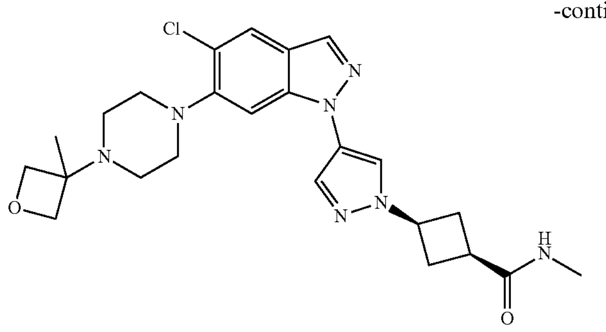

Ex. 5.15

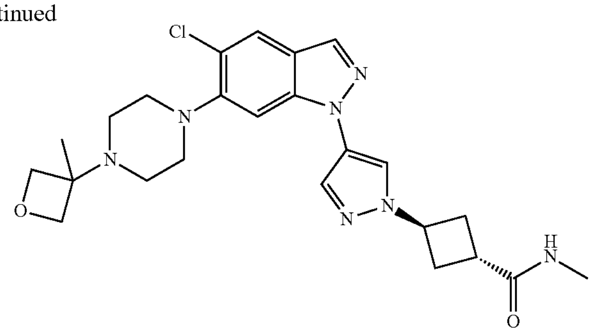

Ex. 5.16

Step 1: cis and trans 3-(4-(5-chloro-6-(4-(3-methyloxetan-3-yl)piperazin-1-yl)-1H-indazol-1-yl)-1H-pyrazol-1-yl)cyclobutane-1-carboxylic acid I-16 (200 mg, 0.41 mmol) was dissolved in Methanol (4.0 mL) in a vial then sodium hydroxide (0.20 mL, 2.0 mmol, 10 M solution in water) was added. The mixture was stirred at 50° C. for 18 h. The mixture was cooled, diluted with sat. $NH_4Cl$ solution (15 mL) and extracted with 3:1 $CHCl_3$: IPA (3x20 mL). The organic extract was dried over $Na_2SO_4$, filtered and concentrated in vacuo to afford a mixture of cis and trans 3-(4-(5-chloro-6-(4-(3-methyloxetan-3-yl)piperazin-1-yl)-1H-indazol-1-yl)-1H-pyrazol-1-yl)cyclobutane-1-carboxylic acid. MS (EI) m/z 471 $[M+H]^+$.

Step 2: cis-3-(4-(5-chloro-6-(4-(3-methyloxetan-3-yl)piperazin-1-yl)-1H-indazol-1-yl)-1H-pyrazol-1-yl)-N-methylcyclobutane-1-carboxamide (Ex. 5.15) and trans-3-(4-(5-chloro-6-(4-(3-methyloxetan-3-yl)piperazin-1-yl)-1H-indazol-1-yl)-1H-pyrazol-1-yl)-N-methylcyclobutane-1-carboxamide (Ex. 5.16)

3-(4-(5-chloro-6-(4-(3-methyloxetan-3-yl)piperazin-1-yl)-1H-indazol-1-yl)-1H-pyrazol-1-yl)cyclobutane-1-carboxylic acid (40 mg, 0.085 mmol), and 4-dimethylaminopyridine (12.5 mg, 0.10 mmol) were weighed into a 2 dram vial and placed under $N_2$. THF (1 mL) was added then the reaction was cooled to 0° C. in an ice bath. Methylamine (0.051 mL, 0.10 mmol, 2M solution in THF) was added then 1-(3-dimethylaminopropyl)-3-ethylcarbodiimide hydrochloride (19.5 mg, 0.10 mmol) was added. The reaction was removed from the ice bath and allowed to warm to rt and stir for 20 h at rt. The reaction was diluted with saturated aq. $NaHCO_3$(2.5 mL) solution and extracted with 3:1 $CHCl_3$: IPA (4x5 mL). The organic extract was filtered through a phase separator and concentrated in vacuo then purified by reversed phase HPLC, eluting with water (0.10% TFA)-ACN to afford the title compounds as a mixture of diastereomers. The mixture was resolved to its component diastereomers by chiral preparative SFC (Column & dimensions: OJ-H, 250 mmx21 mm; Mobile phase A: $CO_2$; Mobile phase B: 1:1 ACN:MeOH with 0.1% $NH_4OH$ to afford Ex 5.15 (cis) and Ex 5.16 (trans).

Ex. 5.15:

$^1H$ NMR (500 MHz, DMSO-$d_6$) δ 8.41 (s, 1H), 8.16 (s, 1H), 7.98 (s, 1H), 7.93 (s, 1H), 7.83 (s, 1H), 7.27 (s, 1H), 4.93-4.67 (m, 1H), 4.53-4.30 (m, 2H), 4.30-4.03 (m, 2H), 3.19-2.99 (m, 3H), 2.92-2.72 (m, 1H), 2.72-2.63 (m, 2H), 2.63-2.52 (m, 6H), 2.54-2.44 (m, 3H), 1.34 (s, 3H). MS (EI) m/z: 484 $[M+H]^+$. Retention time 3.4 min.

Ex. 5.16:

$^1H$ NMR (500 MHz, DMSO-$d_6$) δ 8.50 (s, 1H), 8.15 (s, 1H), 7.98 (s, 1H), 7.96-7.90 (m, 1H), 7.88 (s, 1H), 7.28 (s, 1H), 5.24-5.07 (m, 1H), 4.45 (d, J=5.4 Hz, 2H), 4.16 (d, J=5.4 Hz, 2H), 3.18-2.97 (m, 5H), 2.81-2.68 (m, 2H), 2.71-2.62 (m, 3H), 2.62-2.54 (m, 3H), 2.52-2.43 (m, 2H), 1.33 (s, 3H). MS (EI) m/z: 484 $[M+H]^+$. Retention time 4.4 min.

Ex. 5.17 and Ex. 5.18 in Table 13 were prepared from I-16 according to Scheme 19 (step 2 and step 3). Chiral separation was then achieved by SFC (Column & dimensions: OJ-H, 250 mmx21 mm; Mobile phase A: $CO_2$; Mobile phase B: 1:1 ACN:MeOH with 0.1% $NH_4OH$). Ex 5.17 (cis) (Retention time: 3.9 min) and Ex 5.18 (trans) (Retention time: 4.7 min).

TABLE 13

| Ex | Structure | Name | Exact Mass [M + H]+ |
|---|---|---|---|
| Ex. 5.17 | 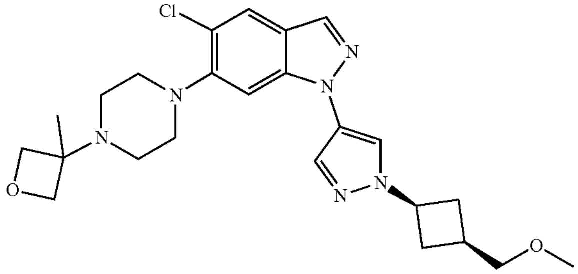 [SMILES: COC[C@H]1C[C@@H](n2cc(-n3ncc4cc(Cl)c(N5CCN(C6(C)COC6)CC5)cc43)cn2)C1] | 5-chloro-1-{1-[cis-3-(methoxymethyl)cyclobutyl]-1H-pyrazol-4-yl}-6-[4-(3-methyloxetan-3-yl)piperazin-1-yl]-1H-indazole | Calc'd 471, found 471 |

TABLE 13-continued

| Ex | Structure | Name | Exact Mass [M + H]+ |
|---|---|---|---|
| Ex. 5.18 | 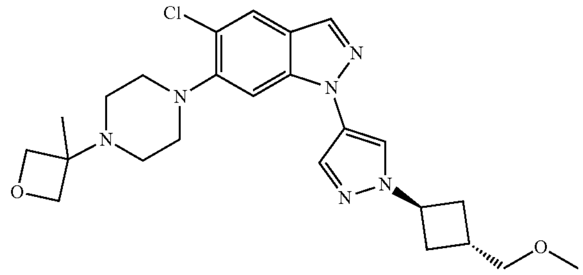 [SMILES: COC[C@H]1C[C@H](n2cc(-n3ncc4cc(Cl)c(N5CCN(C6(C)COC6)CC5)cc43)cn2)C1] | 5-chloro-1-{1-[trans-3-(methoxymethyl)cyclobutyl]-1H-pyrazol-4-yl}-6-[4-(3-methyloxetan-3-yl)piperazin-1-yl]-1H-indazole | Calc'd 471, found 471 |

Preparation of examples Ex. 5.19 and Ex. 5.20: (1R,2R or 1S,2S)-2-(4-(5-chloro-6-(4-(3-methyloxetan-3-yl)piperazin-1-yl)-1H-indazol-1-yl)-1H-pyrazol-1-yl)cyclopropane-1-carbonitrile and (1S,2S or 1R,2R)-2-(4-(5-chloro-6-(4-(3-methyloxetan-3-yl)piperazin-1-yl)-1H-indazol-1-yl)-1H-pyrazol-1-yl)cyclopropane-1-carbonitrile Scheme 69

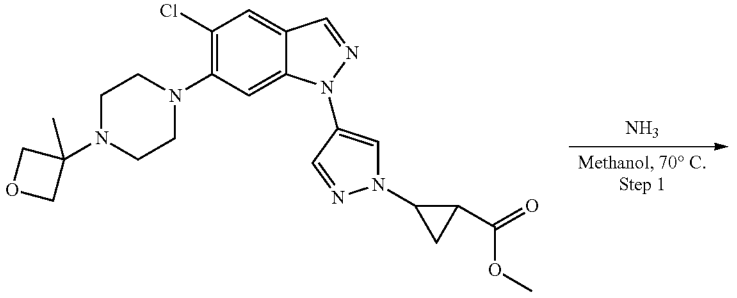

I-17

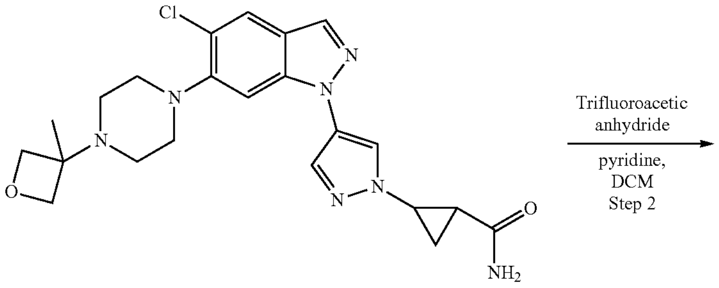

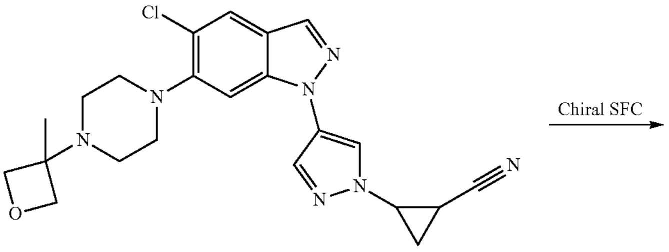

-continued

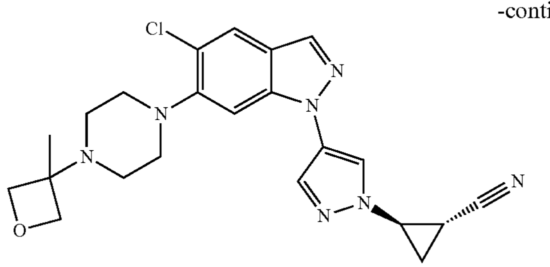

Ex. 5.19

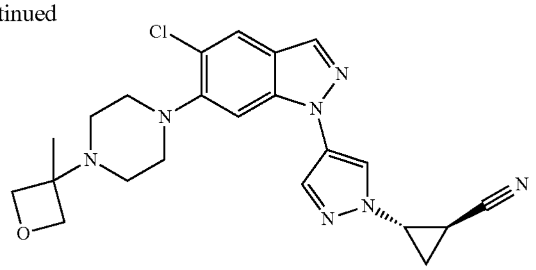

Ex. 5.20

Step 1: (1R,2R and 1S,2S)-2-(4-(5-chloro-6-(4-(3-methyloxetan-3-yl)piperazin-1-yl)-1H-indazol-1-yl)-1H-pyrazol-1-yl)cyclopropane-1-carboxamide I-17 (200 mg, 0.43 mmol) was dissolved in 7N ammonia in methanol (1.2 mL, 8.40 mmol) in a 20 mL microwave vial. The reaction was sealed and stirred at 70° C. for 3 days. Cooled to room temperature and concentrated to give the title compound, which was used in the next step without further purification. MS (EI) m/z: 456 $[M+H]^+$.

Step 2: (1R,2R or 1S,2S)-2-(4-(5-chloro-6-(4-(3-methyloxetan-3-yl)piperazin-1-yl)-1H-indazol-1-yl)-1H-pyrazol-1-yl)cyclopropane-1-carbonitrile (Ex. 5.19) and (1S,2S or 1R,2R)-2-(4-(5-chloro-6-(4-(3-methyloxetan-3-yl)piperazin-1-yl)-1H-indazol-1-yl)-1H-pyrazol-1-yl)cyclopropane-1-carbonitrile (Ex. 5.20)

(1R,2R and 1S,2S)-2-(4-(5-chloro-6-(4-(3-methyloxetan-3-yl)piperazin-1-yl)-1H-indazol-1-yl)-1H-pyrazol-1-yl)cyclopropane-1-carboxamide (180 mg, 0.40 mmol) was dissolved in dichloromethane (1 mL) in an 8 mL vial followed by addition of pyridine (0.16 mL, 1.97 mmol). Trifluoroacetic anhydride (0.126 mL, 0.910 mmol) was then slowly added. The mixture was stirred at room temperature overnight, quenched with saturated $NaHCO_3$ (aq) solution and extracted using 3:1 $CHCl_3$:IPA. The organic extract was filtered through a phase separator, concentrated and purified by column chromatography on silica gel (MeOH in DCM: 0-10% gradient). The desired fractions were pooled and concentrated to give racemic product. The racemic material was subjected to SFC chiral separation (Column & dimensions: CC4, 250 mm×21 mm; Mobile phase A: $CO_2$; Mobile phase B: MeOH with 0.1% $NH_3$ modifier) to afford the title compounds (Ex. 5.19 and Ex. 5.20).

Ex. 5.19:

$^1H$ NMR (500 MHz, DMSO-$d_6$) δ 8.58 (s, 1H), 8.18 (s, 1H), 8.01 (s, 1H), 7.94 (s, 1H), 7.30 (s, 1H), 4.63 (ddd, J=8.5, 5.2, 3.5 Hz, 1H), 4.46 (d, J=5.6 Hz, 2H), 4.17 (d, J=5.6 Hz, 2H), 3.12 (s, 3H), 2.54-2.48 (m, 6H), 2.11-2.03 (m, 1H), 1.90-1.82 (m, 1H), 1.35 (s, 3H). MS (EI) m/z: 438 $[M+H]^+$. Retention time: 6.1 min Ex. 5.20:

$^1H$ NMR (500 MHz, DMSO-$d_6$) δ 8.58 (s, 1H), 8.18 (s, 1H), 8.01 (s, 1H), 7.94 (s, 1H), 7.30 (s, 1H), 4.63 (ddd, J=8.5, 5.2, 3.5 Hz, 1H), 4.46 (d, J=5.6 Hz, 2H), 4.17 (d, J=5.6 Hz, 2H), 3.12 (s, 3H), 2.54-2.48 (m, 6H), 2.11-2.03 (m, 1H), 1.90-1.82 (m, 1H), 1.35 (s, 3H). MS (EI) m/z: 438 $[M+H]^+$. Retention time: 7.6 min Preparation of Example 5.21 5-chloro-1-(1-(4-(difluoromethyl)-5-fluoropyrimidin-2-yl)-1H-pyrazol-4-yl)-6-(4-(3-methyloxetan-3-yl)piperazin-1-yl)-1H-indazole Scheme 70

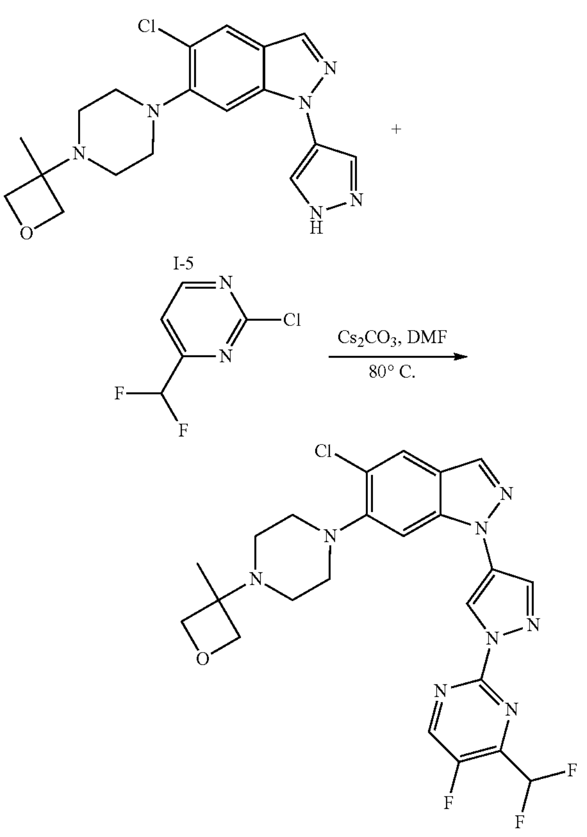

Ex. 5.21

To a solution of 5-chloro-6-(4-(3-methyloxetan-3-yl)piperazin-1-yl)-1-(1H-pyrazol-4-yl)-1H-indazole (I-5, 37 mg, 0.1 mmol) and 2-chloro-4-(difluoromethyl)pyrimidine (24 mg, 0.15 mmol) in DMF (1 mL) was added $Cs_2CO_3$ (65 mg, 0.20 mmol). The reaction was stirred at 80° C. for 4 h. The reaction mixture was cooled to rt and filtered. The resulting filtrate was diluted with DMSO and purified by reverse phase HPLC on C18 column, eluting with water and ACN (0.05% TFA) to afford the title compound. $^1H$ NMR (500 MHz, DMSO-$d_6$) δ 9.26 (d, J=1.7 Hz, 1H), 9.13 (d, J=0.8 Hz, 1H), 8.50 (d, J=0.9 Hz, 1H), 8.28 (d, J=0.9 Hz, 1H), 7.99

(s, 1H), 7.52-7.11 (m, 2H), 4.46 (d, J=5.7 Hz, 2H), 4.17 (d, J=5.6 Hz, 2H), 3.50-3.3 (m, 4H), 2.57-2.48 (m, 4H), 1.34 (s, 3H). MS (EI) m/z 519 $[M+H]^+$.

The compounds in Table 14 below was prepared from common intermediate I-5 according to Scheme 70 by using the corresponding starting materials.

TABLE 14

| Ex | Structure | Name | Exact Mass [M + H]+ |
|---|---|---|---|
| Ex. 5.22 | 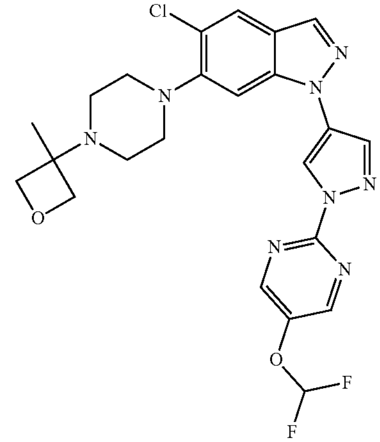 [SMILES: CC1(N2CCN(c3cc4c(cnn4-c4cnn(-c5ncc(OC(F)F)cn5)c4)cc3Cl)CC2)COC1] | 5-chloro-1-{1-[5-(difluoromethoxy) pyrimidin-2-yl]-1H-pyrazol-4-yl}-6-[4-(3-methyloxetan-3-yl)piperazin-1-yl]-1H-indazole | Calc'd 517, found 517 |
| Ex. 5.23 | 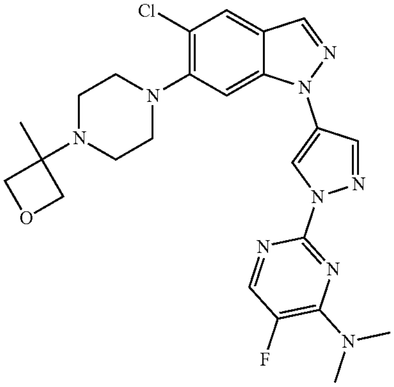 [SMILES: CN(C)c1nc(-n2cc(-n3ncc4cc(Cl)c(N5CCN(C6(C)COC6)CC5)cc43)cn2)ncc1F] | 2-(4-{5-chloro-6-[4-(3-methyloxetan-3-yl)piperazin-1-yl]-1H-indazol-1-yl}-1H-pyrazol-1-yl)-5-fluoro-N,N-dimethylpyrimidin-4-amine | Calc'd 512, found 512 |
| Ex. 5.24 | 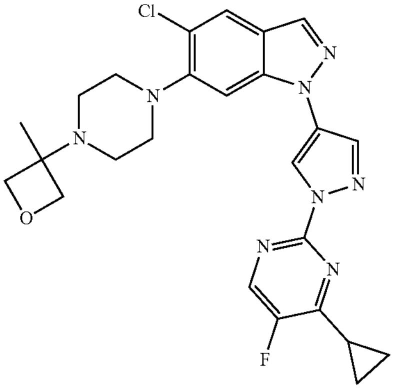 [SMILES: CC1(N2CCN(c3cc4c(cnn4-c4cnn(-c5ncc(F)c(C6CC6)n5)c4)cc3Cl)CC2)COC1] | 5-chloro-1-[1-(4-cyclopropyl-5-fluoropyrimidin-2-yl)-1H-pyrazol-4-yl]-6-[4-(3-methyloxetan-3-yl)piperazin-1-yl]-1H-indazole | Calc'd 509, found 509 |

TABLE 14-continued

| Ex | Structure | Name | Exact Mass [M + H]+ |
|---|---|---|---|
| Ex. 5.25 | 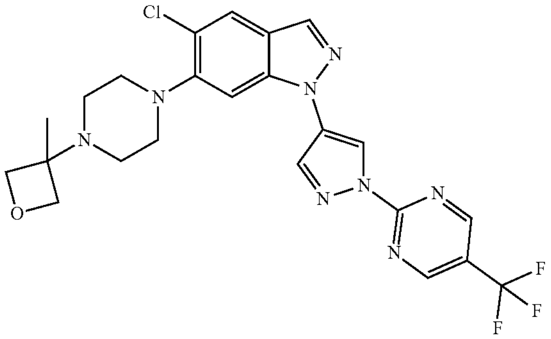 [SMILES: CC1(N2CCN(c3cc4c(cnn4-c4cnn(-c5ncc(C(F)(F)F)cn5)c4)cc3Cl)CC2)COC1] | 5-chloro-6-[4-(3-methyloxetan-3-yl)piperazin-1-yl]-1-{1-[5-(trifluoromethyl)pyrimidin-2-yl]-1H-pyrazol-4-yl}-1H-indazole | Calc'd 519, found 519 |

Preparation of Example 6.1: 1-(5-chloro-1-(1-cyclopropyl-1H-pyrazol-4-yl)-1H-indazol-6-yl)-4-methylpiperidin-4-ol Scheme 71

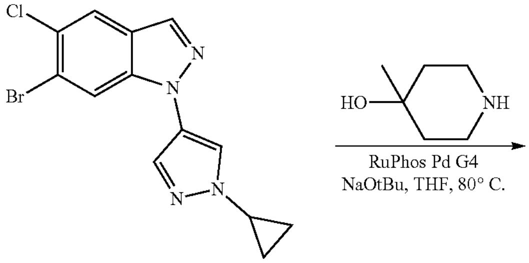

I-2

-continued

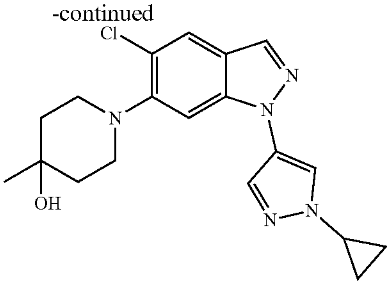

Ex. 6.1

I-2 (120 mg, 0.355 mmol), 4-methylpiperidin-4-ol, HCl (81 mg, 0.53 mmol), RuPhos Pd G4 (30 mg, 0.036 mmol) and THF (3000 μl) were added to a vial to form a mixture. To this mixture NaOtBu (711 μl, 1.42 mmol) was added. The mixture was then evacuated and back-filled with $N_2$ 5 times, then stirred at 80° C. for 17 h. The mixture was scavenged by QuadraPure TU™, then diluted with MeOH, filtered and purified by reversed phase HPLC, with water elution (0.10% $NH_4OH$-ACN) to afford the title compound (Ex. 6.1). $^1H$ NMR (600 MHz, DMSO-$d_6$) δ 8.42 (s, 1H), 8.13 (s, 1H), 7.91 (s, 1H), 7.89 (s, 1H), 7.21 (s, 1H), 4.33 (s, 1H), 3.85 (tt, J=7.4, 3.8 Hz, 1H), 3.12-3.00 (m, 4H), 1.74-1.58 (m, 4H), 1.21 (s, 3H), 1.16 (p, J=4.9 Hz, 2H), 1.07-0.98 (m, 2H); MS (EI) m/z 372 $[M+H]^+$.

Compounds in Table 15 below were prepared from common intermediate I-2 according to Scheme 71, using the corresponding starting materials.

TABLE 15

| EX | Structure | Name | Exact Mass [M + H]+ |
|---|---|---|---|
| Ex 6.2 | 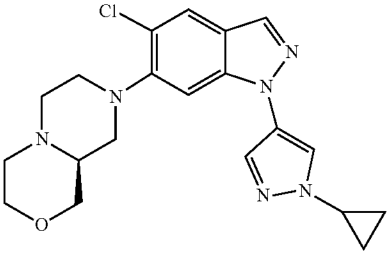 [SMILES: Clc1cc2cnn(-c3cnn(C4CC4)c3)c2cc1N1CCN2CCOC[C@@H]2C1] | (9aS)-8-[5-chloro-1-(1-cyclopropyl-1H-pyrazol-4-yl)-1H-indazol-6-yl]octahydropyrazino[2,1-c][1,4]oxazine | Calc'd 399 Found 399 |

TABLE 15-continued

| EX | Structure | Name | Exact Mass [M + H]+ |
|---|---|---|---|
| Ex. 6.3 | 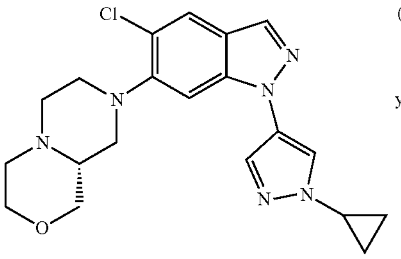 | (9aR)-8-[5-chloro-1-(1-cyclopropyl-1H-pyrazol-4-yl)-1H-indazol-6-yl]octahydropyrazino[2,1-c][1,4]oxazine | Calc'd 399 found 399 |

Preparation of Example 6.4 and Example 6.5: 9-(5-chloro-1-(1-cyclopropyl-1H-pyrazol-4-yl)-1H-indazol-6-yl)-7-methyl-3-oxa-7,9-diazabicyclo[3.3.1] nonane (Two Isomers)

Scheme 72

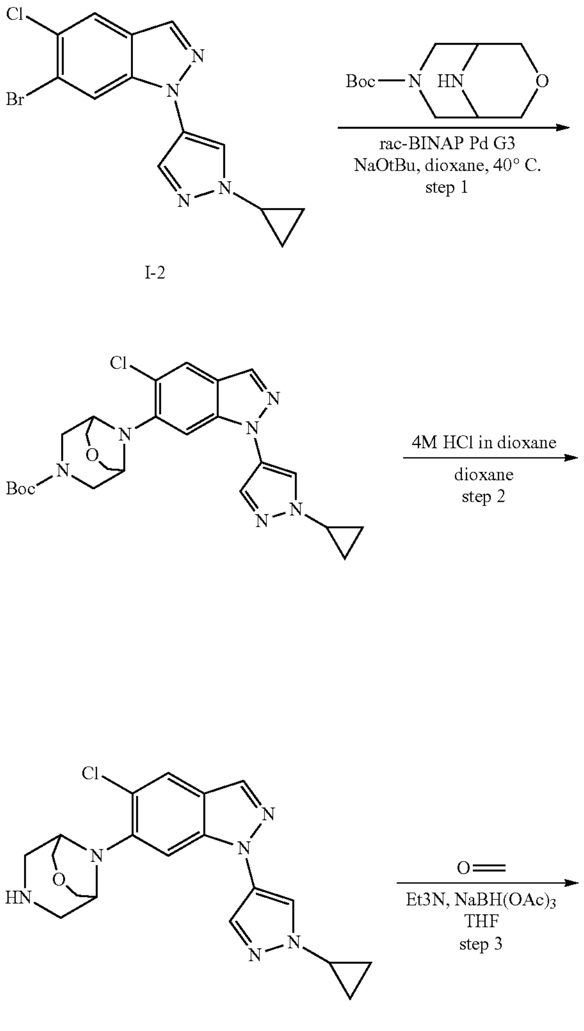

-continued

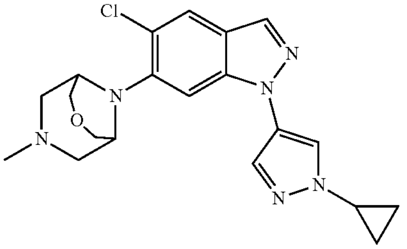

Ex. 6.4 and Ex 6.5

Step 1: tert-butyl 9-(5-chloro-1-(1-cyclopropyl-1H-pyrazol-4-yl)-1H-indazol-6-yl)-3-oxa-7,9-di azabicyclo[3.3.1]nonane-7-carboxylate (isomers 1 and 2)

I-2 (169 mg, 0.500 mmol), tert-butyl 3-oxa-7,9-diazabicyclo[3.3.1]nonane-7-carboxylate (152 mg, 0.667 mmol) and rac-BINAP-Pd-G3 (37 mg, 0.038 mmol) were added to a vial. The mixture was then evacuated and back-filled with nitrogen (3×). Dioxane (3.0 mL) was then added, and the mixture was evacuated and back-filled with nitrogen three more times. 2N sodium tert-butoxide (0.5 mL, 1 mmol) in THF was added. The mixture was heated at 60° C. for 5 h, then at 70° C. for 1 hour, then allowed to cool to 0° C., then quenched with aq. $NH_4Cl$, and then extracted with EtOAc. The organic phase was dried over $Na_2SO_4$, filtered and concentrated in vacuo to afford a residue which was then purified by column chromatography on silica gel (EtOAc in DCM: 0-45% gradient) to afford tert-butyl 9-(5-chloro-1-(1-cyclopropyl-1H-pyrazol-4-yl)-1H-indazol-6-yl)-3-oxa-7,9-diazabicyclo[3.3.1]nonane-7-carboxylate as two isomers.

Isomer 1: 1H NMR (500 MHz, $CD_3OD$) δ 8.19 (s, 1H), 8.05 (s, 1H), 7.869 (s, 1H), 7.866 (s, 1H), 7.16 (s, 1H), 4.18-4.05 (m, 4H), 3.87 (d, J=11.5 Hz, 2H), 3.82-3.78 (m, 1H), 3.68-3.63 (m, 2H) 3.21-3.15 (m, 2H), 1.51 (s, 9H), 1.24-1.21 (m, 2H), 1.14-1.10 (m, 2H). MS (EI) m/z 485 $[M+H]^+$.

Isomer 2: $^1$H NMR (500 MHz, $CD_3OD$) δ 8.25 (s, 1H), 8.06 (s, 1H), 7.89 (s, 1H), 7.85 (s, 1H), 7.22 (s, 1H), 4.17-4.07 (m, 4H), 3.94-3.89 (m, 2H), 3.83-3.78 (m, 3H), 3.70-3.60 (m, 2H), 1.45 (s, 9H), 1.24-1.21 (m, 2H), 1.15-1.10 (m, 2H). MS (EI) m/z 485 $[M+H]^+$.

Step 2: 9-(5-chloro-1-(1-cyclopropyl-1H-pyrazol-4-yl)-1H-indazol-6-yl)-3-oxa-7,9-diazabicyclo[3.3.1]nonane dihydrochloride Isomer 1 of tert-butyl 9-(5-chloro-1-(1-cyclopropyl-1H-pyrazol-4-yl)-1H-indazol-6-yl)-3-oxa-7,9-diazabicyclo[3.3.1]nonane-7-carboxylate (30 mg, 0.062 mmol) was dissolved in 1,4-dioxane (247 μl). To this solution was added 4M HCl in dioxane (231 μl, 0.925 mmol). The mixture was stirred at rt for 1.5 hours. The solvent was evaporated in vacuo to afford 9-(5-chloro-1-(1-cyclopropyl-1H-pyrazol-4-yl)-1H-indazol-6-yl)-3-oxa-7,9-diazabicyclo[3.3.1]nonane. MS (EI) m/z 385 $[M+H]^+$.

Step 3: 9-(5-chloro-1-(1-cyclopropyl-1H-pyrazol-4-yl)-1H-indazol-6-yl)-7-methyl-3-oxa-7,9-diazabicyclo[3.3.1]nonane hydrochloride (Ex. 6.4)

9-(5-chloro-1-(1-cyclopropyl-1H-pyrazol-4-yl)-1H-indazol-6-yl)-3-oxa-7,9-diazabicyclo[3.3.1]nonane dihydrochloride (28 mg, 0.061 mmol) was suspended in THF (612 μl). DIEA (21.4 μl, 0.122 mmol) was added. After 5 minutes, formaldehyde (36.4 μl, 0.489 mmol) was added through activated powdered molecular sieves (~30 mg). After 20 minutes, sodium triacetoxyborohydride (25.9 mg, 0.122 mmol) was added, and the mixture was stirred overnight. The reaction was quenched with aq. NaHCO3, diluted with water and extracted with EtOAc. The combined organic layers were washed with brine, dried over $Na_2SO_4$, filtered and concentrated in vacuo to afford a residue which was then purified by column chromatography on silica gel (EtOH in DCM: 0-50% gradient) to afford the title compound (Ex. 6.4) $^1H$ NMR (500 MHz, $CD_3OD$) δ 8.19 (s, 1H), 8.05 (s, 1H), 7.87 (s, 1H), 7.83 (s, 1H), 7.18 (s, 1H), 4.17 (d, J=11.5 Hz, 2H), 3.98 (d, J=11 Hz, 2H), 3.81-3.77 (m, 1H), 3.50-3.44 (m, 4H) 2.78 (s, 2H), 2.71 (s, 3H), 1.24-1.20 (m, 2H), 1.14-1.10 (m, 2H). MS (EI) m/z 399 $[M+H]^+$.

The compound of Example 6.5 (9-(5-chloro-1-(1-cyclopropyl-1H-pyrazol-4-yl)-1H-indazol-6-yl)-7-methyl-3-oxa-7,9-diazabicyclo[3.3.1]nonane hydrochloride) was prepared by repeating steps 2 and 3 above while replacing isomer 1 of step 1 with isomer 2 of step 1. $^1H$ NMR (500 MHz, $CD_3OD$) δ 8.19 (s, 1H), 8.05 (s, 1H), 7.87 (s, 1H), 7.83 (s, 1H), 7.21 (s, 1H), 4.15 (d, J=11.5 Hz, 2H), 3.96 (d, J=11.5 Hz, 2H), 3.87 (s, 2H) 3.82-3.78 (m, 1H), 3.08 (d, J=11 Hz, 2H), 2.76 (d, J=12 Hz, 2H), 2.30 (s, 3H), 1.23-1.18 (m, 2H), 1.14-1.10 (m, 2H). MS (EI) m/z 399 $[M+H]^+$.

The compound in Table 16 below was prepared from the corresponding starting materials and common intermediate I-2 according to Scheme 72.

TABLE 16

| Ex | Structure | Name | Exact Mass [M + H]+ |
|---|---|---|---|
| Ex 6.6 | 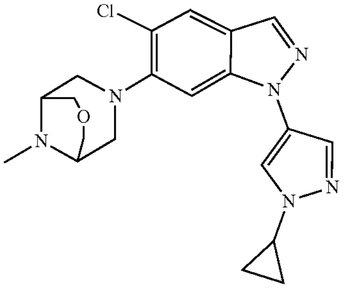 [SMILES: CN1C2COCC1CN(c1cc3c(cnn3-c3cnn(C4CC4)c3)cc1Cl)C2] | 7-[5-chloro-1-(1-cyclopropyl-1H-pyrazol-4-yl)-1H-indazol-6-yl]-9-methyl-3-oxa-7,9-diazabicyclo[3.3.1]nonane | Calc'd 399 found 399 |

Preparation of Example 6.7: (R)-1-(5-chloro-1-(1-cyclopropyl-1H-pyrazol-4-yl)-1H-indazol-6-yl)piperidin-3-ol Scheme 73

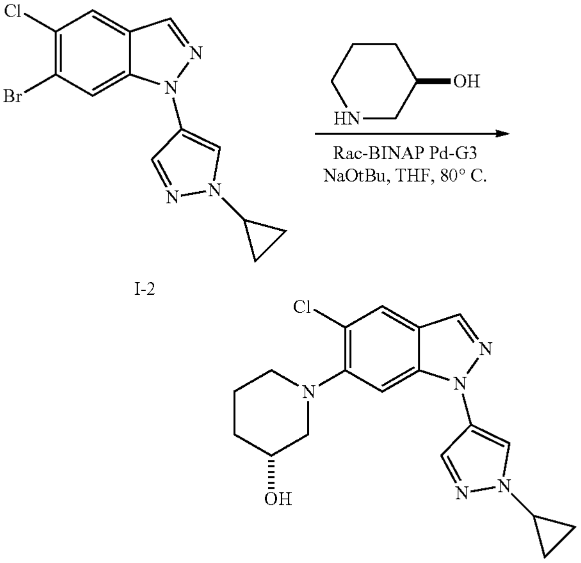

I-2

Ex. 6.7

I-2 (25 mg, 0.074 mmol), (R)-piperidin-3-ol (12.6 mg, 0.125 mmol), Rac-BINAP Pd G3 (7.35 mg, 7.41 μmol) and THF (500 μl) were added to a vial. To this mixture was added NaOtBu (150 μl, 0.300 mmol). The mixture was evacuated and back-filled with $N_2$ for five times, then stirred at 80° C. for 3 h. The mixture was scavenged by QuadraPure TU™ (metal scavenger resin) then diluted with MeOH, filtered and purified by reversed phase HPLC, with water elution (0.1% $NH_4OH$)-ACN to afford the title compound (Ex. 6.7). $^1H$ NMR (600 MHz, DMSO-$d_6$) δ 8.41 (s, 1H), 8.15 (s, 1H), 7.92 (s, 1H), 7.89 (s, 1H), 7.20 (s, 1H), 4.86 (d, J=4.7 Hz, 1H), 3.85 (tt, J=7.4, 3.8 Hz, 1H), 3.69 (tq, J=9.2, 4.4 Hz, 1H), 3.41 (dd, J=10.6, 3.7 Hz, 1H), 3.25-3.18 (m, 1H), 2.72-2.59 (m, 1H), 2.49-2.41 (m, 1H), 2.02-1.92 (m, 1H), 1.83-1.74 (m, 1H), 1.69-1.58 (m, 1H), 1.25 (qd, J=12.5, 4.2 Hz, 1H), 1.20-1.12 (m, 2H), 1.03 (td, J=7.3, 5.2 Hz, 2H); MS (EI) m/z 358 $[M+H]^+$.

Preparation of Example 6.8: 1-(5-chloro-1-(1-(5-fluoropyrimidin-2-yl)-1H-pyrazol-4-yl)-1H-indazol-6-yl)-4-methylpiperidin-4-ol Scheme 74

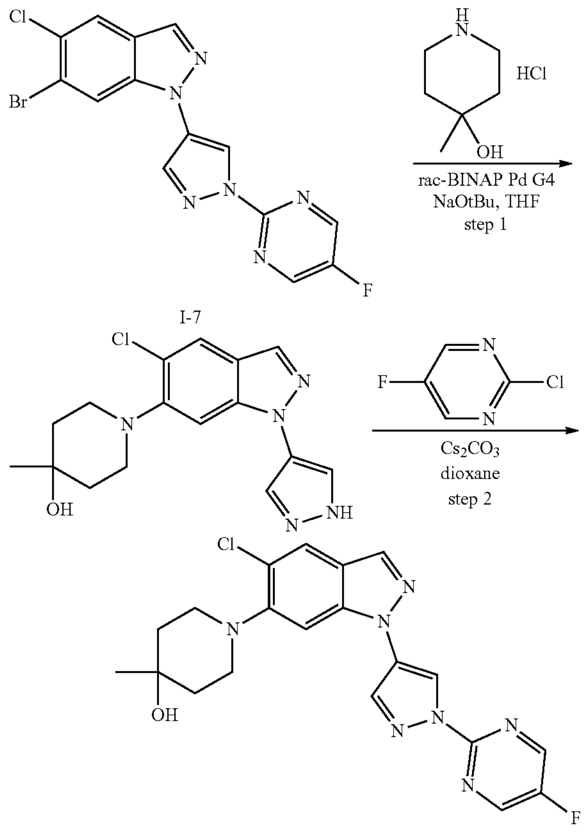

Ex. 6.8

Step 1: 1-(5-chloro-1-(1H-pyrazol-4-yl)-1H-indazol-6-yl)-4-methylpiperidin-4-ol

Rac-BINAP-Pd G4 (7.7 mg, 7.6 μmol), 6-bromo-5-chloro-1-(1-(5-fluoropyrimidin-2-yl)-1H-pyrazol-4-yl)-1H-indazole (30 mg, 0.076 mmol), and 4-methylpiperidine-4-ol HCl (17 mg, 0.11 mmol) were added to a vial. The vial was purged with argon and capped. Dry THF (1 mL) was added, followed by sodium tert-butoxide (0.15 mL, 0.30 mmol, 2 M in THF). The reaction was stirred at 80° C. overnight. The mixture was cooled, diluted with water (5 mL) and extracted with 3:1 $CHCl_3$:IPA (3×10 mL). The organic extract was filtered through a phase separator and concentrated in vacuo to afford 1-(5-chloro-1-(1H-pyrazol-4-yl)-1H-indazol-6-yl)-4-methylpiperidin-4-ol, which was used directly in next step. MS (EI) m/z 332 $[M+H]^+$.

Step 2: 1-(5-chloro-1-(1-(5-fluoropyrimidin-2-yl)-1H-pyrazol-4-yl)-1H-indazol-6-yl)-4-methylpiperidin-4-ol (Ex. 6.8)

Cesium carbonate (76 mg, 0.23 mmol) and 1-(5-chloro-1-(1H-pyrazol-4-yl)-1H-indazol-6-yl)-4-methylpiperidin-4-ol (26 mg, 0.078 mmol) were added to a 2-5 mL microwave vial, then dioxane (1 ml) and 2-chloro-5-fluoropyrimidine (20 μl, 0.22 mmol) were added by syringe. The reaction was stirred at 100° C. for 1 h. The mixture was cooled, diluted with water (5 mL), and extracted with 3:1 $CHCl_3$: IPA (3×10 mL). The organic extract was filtered through a phase separator and concentrated to afford residue, which was purified by reversed phase HPLC, with water elution (0.1% $NH_4OH$)-ACN to afford the title compound (Ex. 6.8). $^1H$ NMR (500 MHz, DMSO-$d_6$) δ 9.11 (s, 1H), 9.05 (s, 2H), 8.41 (s, 1H), 8.24 (s, 1H), 7.95 (s, 1H), 7.37 (s, 1H), 4.33 (s, 1H), 3.18-3.00 (m, 4H), 1.77-1.60 (m, 4H), 1.21 (s, 3H); MS (EI) m/z 428 $[M+H]^+$.

Compounds in Table 17 below were prepared from common intermediate I-2 according to Scheme 73 by using the corresponding starting materials. The amine starting material of Ex. 6.29 was I-11. The amine starting material of Ex. 6.40 was I-10. Ex. 6.48 was prepared from I-2 and I-41 according to Scheme 73, then deprotection. The amine starting material of Ex. 6.58 was I-42. All the other amine starting materials were commercially available.

TABLE 17

| Ex | Structure | Name | Exact Mass [M + H]+ |
|---|---|---|---|
| Ex 6.9 | 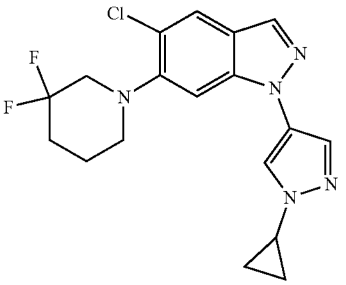 [SMILES: FC1(F)CCCN(c2cc3c(cnn3-c3cnn(C4CC4)c3)cc2Cl)C1] | 5-chloro-1-(1-cyclopropyl-1H-pyrazol-4-yl)-6-(3,3-difluoropiperidin-1-yl)-1H-indazole | Calc'd 378, found 378 |

TABLE 17-continued

| Ex | Structure | Name | Exact Mass [M + H]+ |
|---|---|---|---|
| Ex 6.10 | 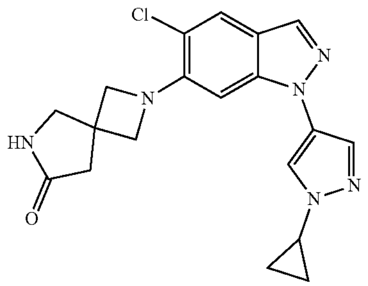 [SMILES: O=C1CC2(CN1)CN(c1cc3c(cnn3-c3cnn(C4CC4)c3)cc1Cl)C2] | 2-[5-chloro-1-(1-cyclopropyl-1H-pyrazol-4-yl)-1H-indazol-6-yl]-2,6-diazaspiro[3.4]octan-7-one | Calc'd 383, found 383 |
| Ex 6.11 | 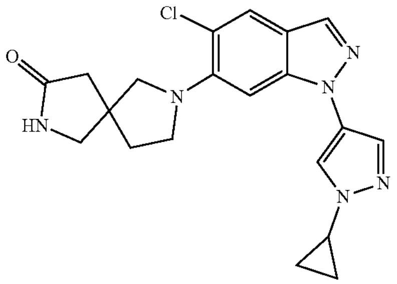 [SMILES: O=C1CC2(CCN(c3cc4c(cnn4-c4cnn(C5CC5)c4)cc3Cl)C2)CN1] | 7-[5-chloro-1-(1-cyclopropyl-1H-pyrazol-4-yl)-1H-indazol-6-yl]-2,7-diazaspiro[4.4]nonan-3-one | Calc'd 397, found 397 |
| Ex 6.12 | 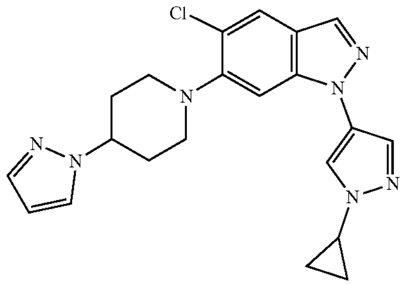 [SMILES: Clc1cc2cnn(-c3cnn(C4CC4)c3)c2cc1N1CCC(n2cccn2)CC1] | 5-chloro-1-(1-cyclopropyl-1H-pyrazol-4-yl)-6-[4-(1H-pyrazol-1-yl)piperidin-1-yl]-1H-indazole | Calc'd 408, found 408 |
| Ex 6.13 | 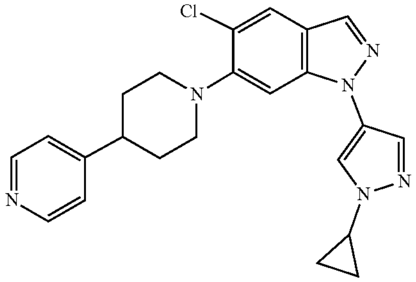 [SMILES: Clc1cc2cnn(-c3cnn(C4CC4)c3)c2cc1N1CCC(c2ccncc2)CC1] | 5-chloro-1-(1-cyclopropyl-1H-pyrazol-4-yl)-6-[4-(pyridin-4-yl)piperidin-1-yl]-1H-indazole | Calc'd 419, found 419 |
| Ex 6.14 | 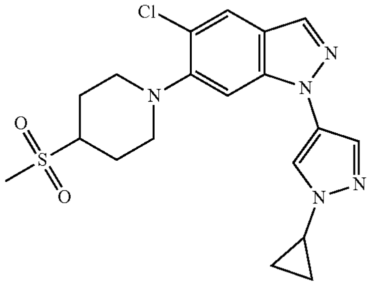 [SMILES: CS(=O)(=O)C1CCN(c2cc3c(cnn3-c3cnn(C4CC4)c3)cc2Cl)CC1] | 5-chloro-1-(1-cyclopropyl-1H-pyrazol-4-yl)-6-[4-(methylsulfonyl)piperidin-1-yl]-1H-indazole | Calc'd 420, found 420 |

TABLE 17-continued

| Ex | Structure | Name | Exact Mass [M + H]+ |
| --- | --- | --- | --- |
| Ex 6.15 | 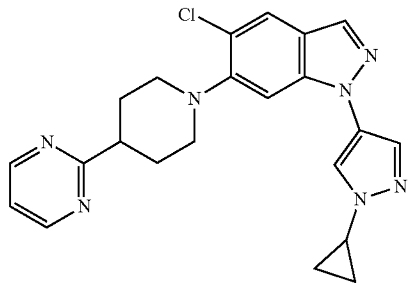 [SMILES: Clc1cc2cnn(-c3cnn(C4CC4)c3)c2cc1N1CCC(c2ncccn2)CC1] | 5-chloro-1-(1-cyclopropyl-1H-pyrazol-4-yl)-6-[4-(pyrimidin-2-yl)piperidin-1-yl]-1H-indazole | Calc'd 420, found 420 |
| Ex 6.16 | 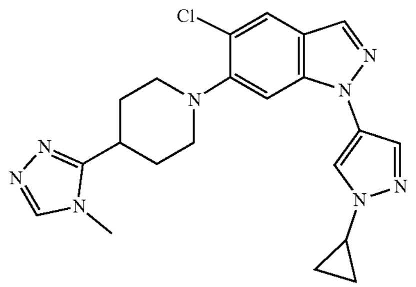 [SMILES: Cn1cnnc1C1CCN(c2cc3c(cnn3-c3cnn(C4CC4)c3)cc2Cl)CC1] | 5-chloro-1-(1-cyclopropyl-1H-pyrazol-4-yl)-6-[4-(4-methyl-4H-1,2,4-triazol-3-yl)piperidin-1-yl]-1H-indazole | Calc'd 423, found 423 |
| Ex 6.17 | 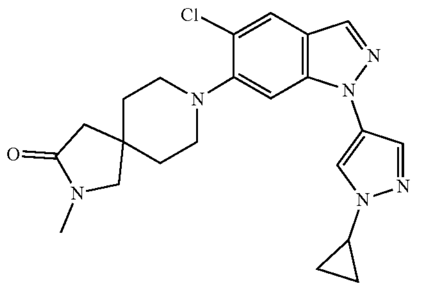 [SMILES: CN1CC2(CCN(c3cc4c(cnn4-c4cnn(C5CC5)c4)cc3Cl)CC2)CC1=O] | 8-[5-chloro-1-(1-cyclopropyl-1H-pyrazol-4-yl)-1H-indazol-6-yl]-2-methyl-2,8-diazaspiro[4.5]decan-3-one | Calc'd 425, found 425 |
| Ex 6.18 | 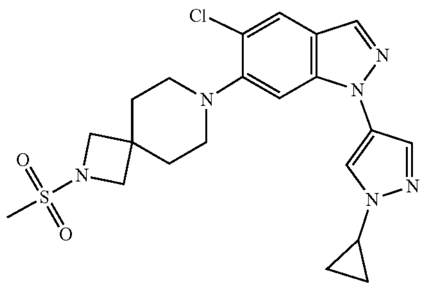 | 5-chloro-1-(1-cyclopropyl-1H-pyrazol-4-yl)-6-[2-(methylsulfonyl)-2,7-diazaspiro[3.5]nonan-7-yl]-1H-indazole | Calc'd 461, found 461 |

TABLE 17-continued

| Ex | Structure | Name | Exact Mass [M + H]+ |
|---|---|---|---|
| Ex 6.19 | 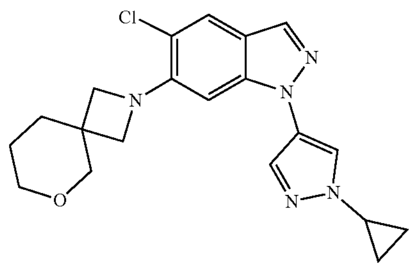 [SMILES: Clc1cc2cnn(-c3cnn(C4CC4)c3)c2cc1N1CC2(CCCOC2)C1] | 5-chloro-1-(1-cyclopropyl-1H-pyrazol-4-yl)-6-(6-oxa-2-azaspiro[3.5]nonan-2-yl)-1H-indazole | Calc'd 384, found 384 |
| Ex 6.20 | 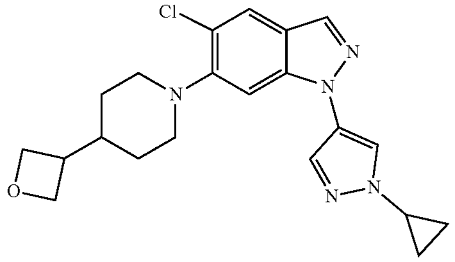 [SMILES: Clc1cc2cnn(-c3cnn(C4CC4)c3)c2cc1N1CCC(C2COC2)CC1] | 5-chloro-1-(1-cyclopropyl-1H-pyrazol-4-yl)-6-[4-(oxetan-3-yl)piperidin-1-yl]-1H-indazole | Calc'd 398, found 398 |
| Ex 6.21 | 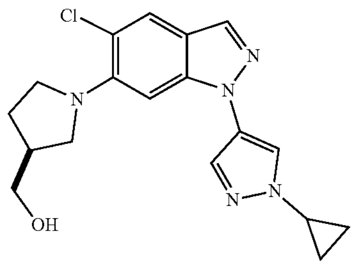 [SMILES: OC[C@H]1CCN(c2cc3c(cnn3-c3cnn(C4CC4)c3)cc2Cl)C1] | (S)-(1-(5-chloro-1-(1-cyclopropyl-1H-pyrazol-4-yl)-1H-indazol-6-yl)pyrrolidin-3-yl)methanol | Calc'd 358, found 358 |
| Ex 6.22 | 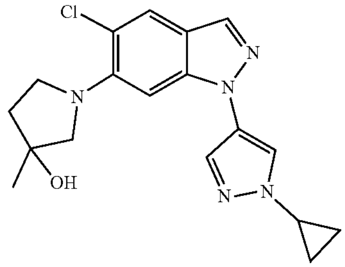 [SMILES: CC1(O)CCN(c2cc3c(cnn3-c3cnn(C4CC4)c3)cc2Cl)C1] | 1-[5-chloro-1-(1-cyclopropyl-1H-pyrazol-4-yl)-1H-indazol-6-yl]-3-methylpyrrolidin-3-ol | Calc'd 358, found 358 |
| Ex 6.23 | 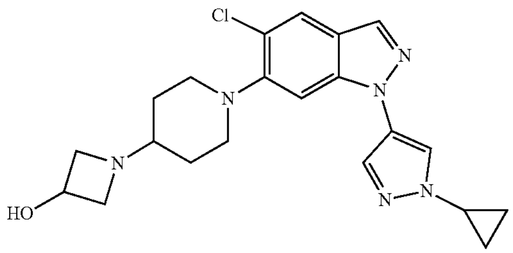 [SMILES: OC1CN(C2CCN(c3cc4c(cnn4-c4cnn(C5CC5)c4)cc3Cl)CC2)C1] | 1-{1-[5-chloro-1-(1-cyclopropyl-1H-pyrazol-4-yl)-1H-indazol-6-yl]piperidin-4-yl}azetidin-3-ol | Calc'd 413, found 413 |

TABLE 17-continued

| Ex | Structure | Name | Exact Mass [M + H]+ |
|---|---|---|---|
| Ex 6.24 | 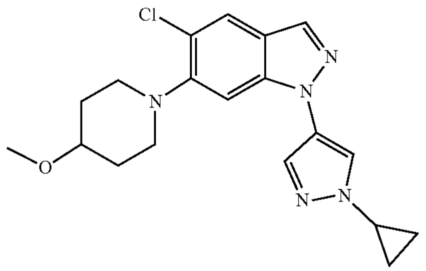 [SMILES: COC1CCN(c2cc3c(cnn3-c3cnn(C4CC4)c3)cc2Cl)CC1] | 5-chloro-1-(1-cyclopropyl-1H-pyrazol-4-yl)-6-(4-methoxypiperidin-1-yl)-1H-indazole | Calc'd 372, found 372 |
| Ex 6.25 | 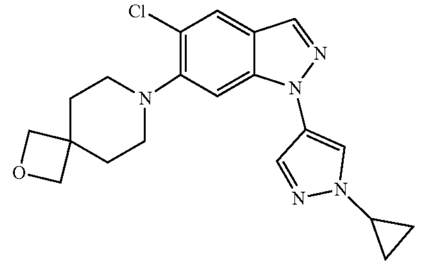 [SMILES: Clc1cc2cnn(-c3cnn(C4CC4)c3)c2cc1N1CCC2(CC1)COC2] | 5-chloro-1-(1-cyclopropyl-1H-pyrazol-4-yl)-6-(2-oxa-7-azaspiro[3.5]nonan-7-yl)-1H-indazole | Calc'd 384, found 384 |
| Ex 6.26 | 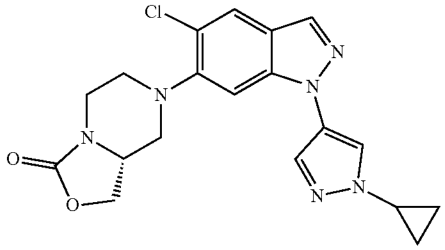 [SMILES: O=C1OC[C@H]2CN(c3cc4c(cnn4-c4cnn(C5CC5)c4)cc3Cl)CCN12] | (8aR)-7-[5-chloro-1-(1-cyclopropyl-1H-pyrazol-4-yl)-1H-indazol-6-yl]hexahydro-3H-[1,3]oxazolo[3,4-a]pyrazin-3-one | Calc'd 399, found 399 |
| Ex 6.27 | 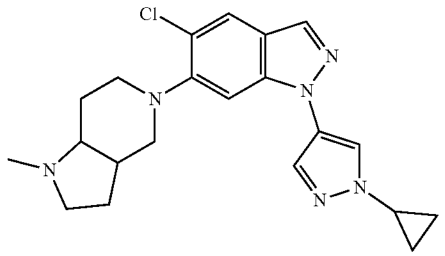 [SMILES: CN1CCC2CN(c3cc4c(cnn4-c4cnn(C5CC5)c4)cc3Cl)CCC21] | 5-chloro-1-(1-cyclopropyl-1H-pyrazol-4-yl)-6-[(cis, racemic)1-methyloctahydro-5H-pyrrolo[3,2-c]pyridin-5-yl]-1H-indazole | Calc'd 397, found 397 |
| Ex 6.28 | 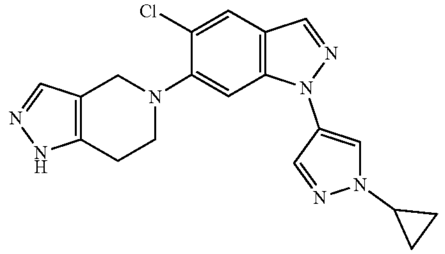 [SMILES: Clc1cc2cnn(-c3cnn(C4CC4)c3)c2cc1N1CCc2[nH]ncc2C1] | 5-[5-chloro-1-(1-cyclopropyl-1H-pyrazol-4-yl)-1H-indazol-6-yl]-4,5,6,7-tetrahydro-1H-pyrazolo[4,3-c]pyridine | Calc'd 380, found 380 |

TABLE 17-continued

| Ex | Structure | Name | Exact Mass [M + H]+ |
|---|---|---|---|
| Ex 6.29 | 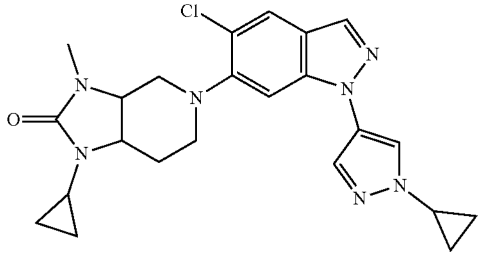 [SMILES: CN1C(=O)N(C2CC2)C2CCN(c3cc4c(cnn4-c4cnn(C5CC5)c4)cc3Cl)CC21] | (cis racemic)-5-[5-chloro-1-(1-cyclopropyl-1H-pyrazol-4-yl)-1H-indazol-6-yl]-1-cyclopropyl-3-methyloctahydro-2H-imidazo[4,5-c]pyridin-2-one | Calc'd 452, found 452 |
| Ex 6.30 | 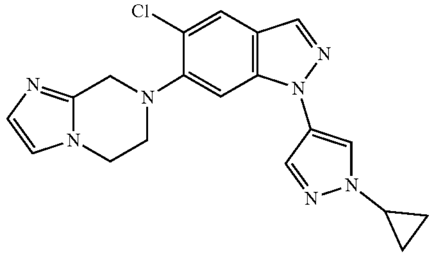 [SMILES: Clc1cc2cnn(-c3cnn(C4CC4)c3)c2cc1N1CCn2ccnc2C1] | 7-[5-chloro-1-(1-cyclopropyl-1H-pyrazol-4-yl)-1H-indazol-6-yl]-5,6,7,8-tetrahydroimidazo[1,2-a]pyrazine | Calc'd 380, found 380 |
| Ex 6.31 | 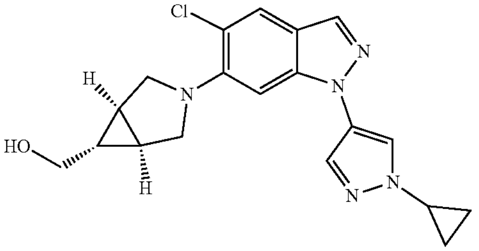 [SMILES: OC[C@@H]1[C@H]2CN(c3cc4c(cnn4-c4cnn(C5CC5)c4)cc3Cl)C[C@@H]12] | {(1R,5S,6r)-3-[5-chloro-1-(1-cyclopropyl-1H-pyrazol-4-yl)-1H-indazol-6-yl]-3-azabicyclo[3.1.0]hexan-6-yl}methanol | Calc'd 370, found 370 |
| Ex 6.32 | 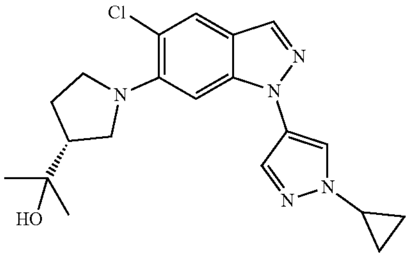 [SMILES: CC(C)(O)[C@@H]1CCN(c2cc3c(cnn3-c3cnn(C4CC4)c3)cc2Cl)C1] | 2-{(3R)-1-[5-chloro-1-(1-cyclopropyl-1H-pyrazol-4-yl)-1H-indazol-6-yl]pyrrolidin-3-yl}propan-2-ol | Calc'd 386, found 386 |
| Ex 6.33 | 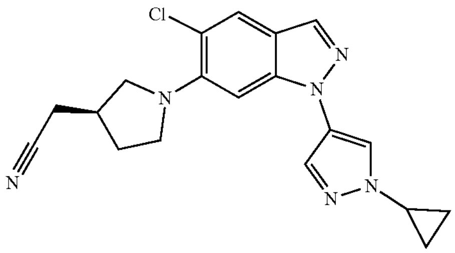 [SMILES: N#CC[C@@H]1CCN(c2cc3c(cnn3-c3cnn(C4CC4)c3)cc2Cl)C1] | {(3S)-1-[5-chloro-1-(1-cyclopropyl-1H-pyrazol-4-yl)-1H-indazol-6-yl]pyrrolidin-3-yl}acetonitrile | Calc'd 367, found 367 |
| Ex 6.34 | 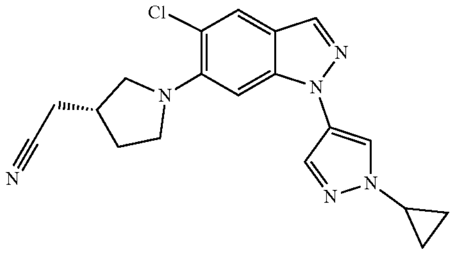 [SMILES: N#CC[C@H]1CCN(c2cc3c(cnn3-c3cnn(C4CC4)c3)cc2Cl)C1] | {(3R)-1-[5-chloro-1-(1-cyclopropyl-1H-pyrazol-4-yl)-1H-indazol-6-yl]pyrrolidin-3-yl}acetonitrile | Calc'd 367, found 367 |

TABLE 17-continued

| Ex | Structure | Name | Exact Mass [M + H]+ |
|---|---|---|---|
| Ex 6.35 | 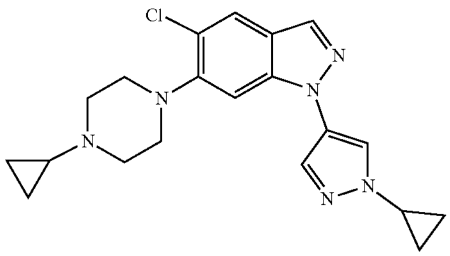 [SMILES: Clc1cc2cnn(-c3cnn(C4CC4)c3)c2cc1N1CCN(C2CC2)CC1] | 5-chloro-6-(4-cyclopropylpiperazin-1-yl)-1-(1-cyclopropyl-1H-pyrazol-4-yl)-1H-indazole | Calc'd 383, found 383 |
| Ex 6.36 | 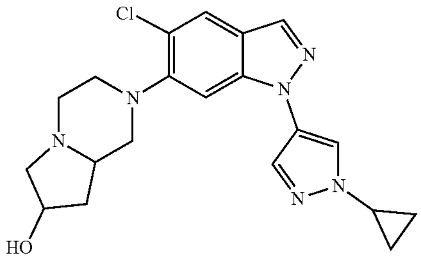 [SMILES: OC1CC2CN(c3cc4c(cnn4-c4cnn(C5CC5)c4)cc3Cl)CCN2C1] | 2-[5-chloro-1-(1-cyclopropyl-1H-pyrazol-4-yl)-1H-indazol-6-yl]octahydropyrrolo[1,2-a]pyrazin-7-ol | Calc'd 399, found 399 |
| Ex 6.37 | 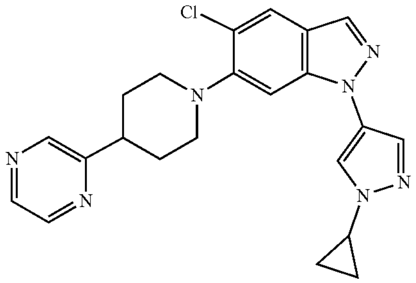 [SMILES: Clc1cc2cnn(-c3cnn(C4CC4)c3)c2cc1N1CCC(c2cnccn2)CC1] | 5-chloro-1-(1-cyclopropyl-1H-pyrazol-4-yl)-6-[4-(pyrazin-2-yl)piperidin-1-yl]-1H-indazole | Calc'd 420, found 420 |
| Ex. 6.40 | 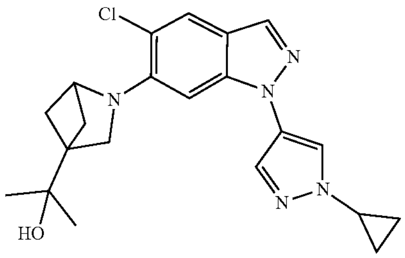 [SMILES: CC(C)(O)C12CC(C1)N(c1cc3c(cnn3-c3cnn(C4CC4)c3)cc1Cl)C2] | 2-{2-[5-chloro-1-(1-cyclopropyl-1H-pyrazol-4-yl)-1H-indazol-6-yl]-2-azabicyclo[2.1.1]hexan-4-yl}propan-2-ol | Calc'd 398, found 398 |
| Ex 6.41 | 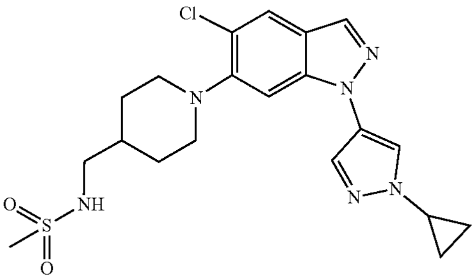 [SMILES: CS(=O)(=O)NCC1CCN(c2cc3c(cnn3-c3cnn(C4CC4)c3)cc2Cl)CC1] | N-({1-[5-chloro-1-(1-cyclopropyl-1H-pyrazol-4-yl)-1H-indazol-6-yl]piperidin-4-yl}methyl)methane-sulfonamide | Calc'd 449, found 449 |

TABLE 17-continued

| Ex | Structure | Name | Exact Mass [M + H]+ |
|---|---|---|---|
| Ex 6.42 | 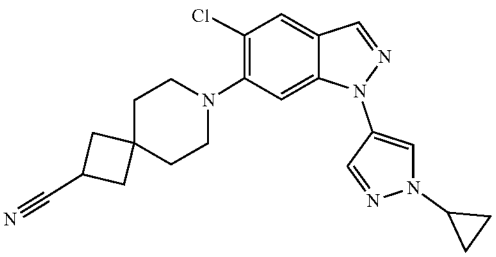 [SMILES: N#CC1CC2(CCN(c3cc4c(cnn4-c4cnn(C5CC5)c4)cc3Cl)CC2)C1] | 7-[5-chloro-1-(1-cyclopropyl-1H-pyrazol-4-yl)-1H-indazol-6-yl]-7-azaspiro[3.5]nonane-2-carbonitrile | Calc'd 407, found 407 |
| Ex 6.43 | 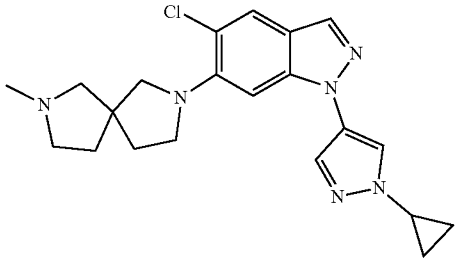 [SMILES: CN1CCC2(CCN(c3cc4c(cnn4-c4cnn(C5CC5)c4)cc3Cl)C2)C1] | 5-chloro-1-(1-cyclopropyl-1H-pyrazol-4-yl)-6-(7-methyl-2,7-diazaspiro[4.4]nonan-2-yl)-1H-indazole | Calc'd 397, found 397 |
| Ex 6.44 | 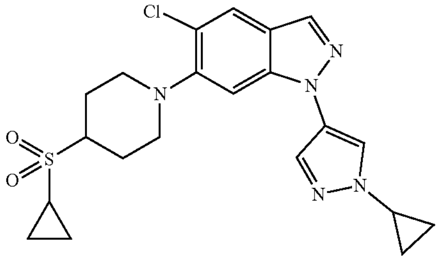 [SMILES: O=S(=O)(C1CC1)C1CCN(c2cc3c(cnn3-c3cnn(C4CC4)c3)cc2Cl)CC1] | 5-chloro-1-(1-cyclopropyl-1H-pyrazol-4-yl)-6-[4-(cyclopropylsulfonyl) piperidin-1-yl]-1H-indazole | Calc'd 446, found 446 |
| Ex 6.45 | 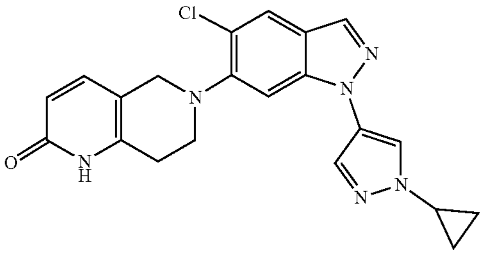 [SMILES: O=c1ccc2c([nH]1)CCN(c1cc3c(cnn3-c3cnn(C4CC4)c3)cc1Cl)C2] | 6-[5-chloro-1-(1-cyclopropyl-1H-pyrazol-4-yl)-1H-indazol-6-yl]-5,6,7,8-tetrahydro-1,6-naphthyridin-2(1H)-one | Calc'd 407, found 407 |
| Ex 6.46 | 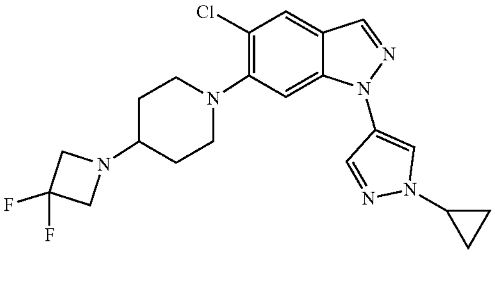 [SMILES: FC1(F)CN(C2CCN(c3cc4c(cnn4-c4cnn(C5CC5)c4)cc3Cl)CC2)C1] | 5-chloro-1-(1-cyclopropyl-1H-pyrazol-4-yl)-6-[4-(3,3-difluoroazetidin-1-yl)piperidin-1-yl]-1H-indazole | Calc'd 433, found 433 |

TABLE 17-continued

| Ex | Structure | Name | Exact Mass [M + H]+ |
|---|---|---|---|
| Ex 6.47 | 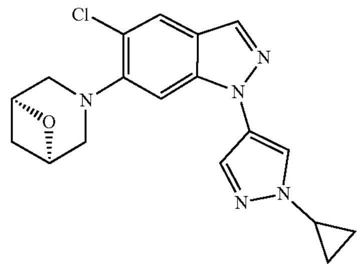 [SMILES: Clc1cc2cnn(-c3cnn(C4CC4)c3)c2cc1N1C[C@H]2C[C@@H](C1)O2] | 5-chloro-1-(1-cyclopropyl-1H-pyrazol-4-yl)-6-[(1R,5S)-6-oxa-3-azabicyclo[3.1.1]heptan-3-yl]-1H-indazole | Calc'd 356, found 356 |
| Ex 6.48 | 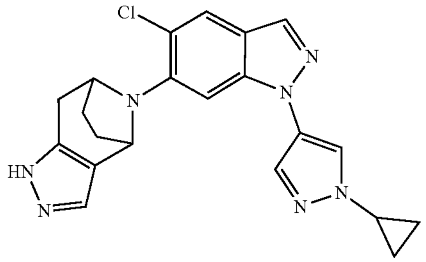 [SMILES: Clc1cc2cnn(-c3cnn(C4CC4)c3)c2cc1N1C2CCC1c1cn[nH]c1C2] | 9-[5-chloro-1-(1-cyclopropyl-1H-pyrazol-4-yl)-1H-indazol-6-yl]-1,4,5,6,7,8-hexahydro-4,7-epiminocyclohepta[c] pyrazole | Calc'd 406, found 406 |
| Ex 6.49 | 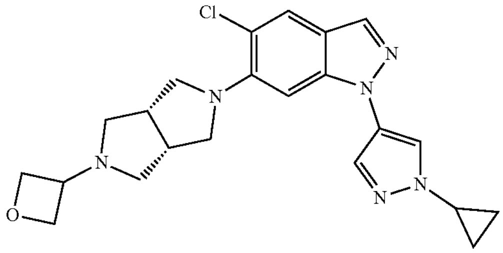 [SMILES: Clc1cc2cnn(-c3cnn(C4CC4)c3)c2cc1N1C[C@@H]2CN(C3COC3)C[C@@H]2C1] | 5-chloro-1-(1-cyclopropyl-1H-pyrazol-4-yl)-6-[(3aR,6aS)-5-(oxetan-3-yl)hexahydropyrrolo[3,4-c]pyrrol-2(1H)-yl]-1H-indazole | Calc'd 425, found 425 |
| Ex 6.50 | 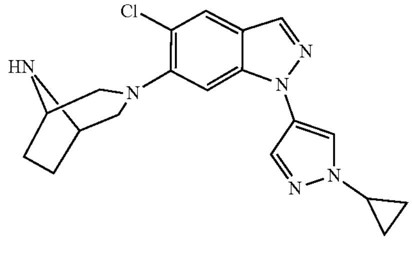 [SMILES: Clc1cc2cnn(-c3cnn(C4CC4)c3)c2cc1N1CC2CCC(C1)N2] | 5-chloro-1-(1-cyclopropyl-1H-pyrazol-4-yl)-6-(3,8-diazabicyclo[3.2.1]octan-3-yl)-1H-indazole | Calc'd 369, found 369 |
| Ex 6.51 | 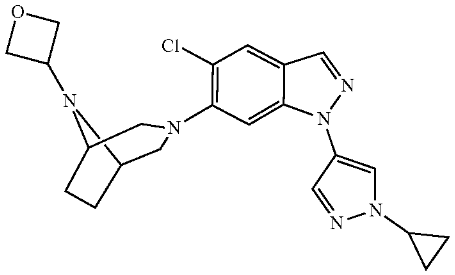 [SMILES: Clc1cc2cnn(-c3cnn(C4CC4)c3)c2cc1N1CC2CCC(C1)N2C1COC1] | 5-chloro-1-(1-cyclopropyl-1H-pyrazol-4-yl)-6-[8-(oxetan-3-yl)-3,8-diazabicyclo[3.2.1]octan-3-yl]-1H-indazole | Calc'd 425, found 425 |

TABLE 17-continued

| Ex | Structure | Name | Exact Mass [M + H]+ |
|---|---|---|---|
| Ex 6.52 | 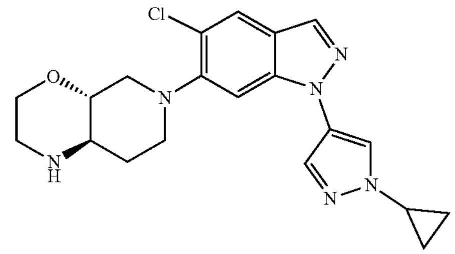 [SMILES: Clc1cc2cnn(-c3cnn(C4CC4)c3)c2cc1N1CC[C@H]2NCCO[C@@H]2C1] | (4aR,8aR)-6-[5-chloro-1-(1-cyclopropyl-1H-pyrazol-4-yl)-1H-indazol-6-yl]octahydro-1H-pyrido[3,4-b][1,4]oxazine | Calc'd 399, found 399 |
| Ex 6.53 | 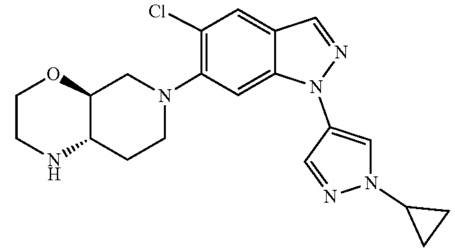 [SMILES: Clc1cc2cnn(-c3cnn(C4CC4)c3)c2cc1N1CC[C@@H]2NCCO[C@H]2C1] | (4aS,8aS)-6-[5-chloro-1-(1-cyclopropyl-1H-pyrazol-4-yl)-1H-indazol-6-yl]octahydro-1H-pyrido[3,4-b][1,4]oxazine | Calc'd 399, found 399 |
| Ex 6.54 | 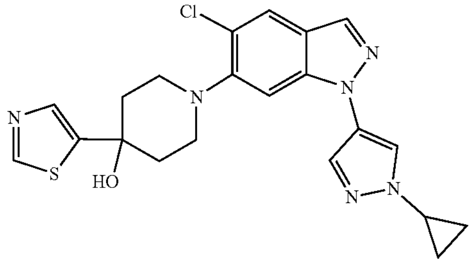 [SMILES: OC1(c2cncs2)CCN(c2cc3c(cnn3-c3cnn(C4CC4)c3)cc2Cl)CC1] | 1-[5-chloro-1-(1-cyclopropyl-1H-pyrazol-4-yl)-1H-indazol-6-yl]-4-(1,3-thiazol-5-yl)piperidin-4-ol | Calc'd 441, found 441 |
| Ex 6.55 | 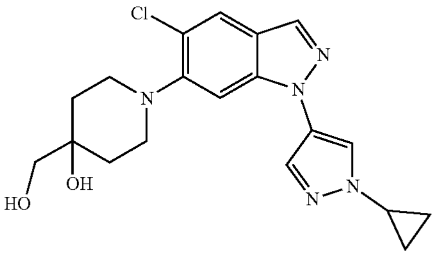 [SMILES: OCC1(O)CCN(c2cc3c(cnn3-c3cnn(C4CC4)c3)cc2Cl)CC1] | 1-[5-chloro-1-(1-cyclopropyl-1H-pyrazol-4-yl)-1H-indazol-6-yl]-4-(hydroxymethyl)piperidin-4-ol | Calc'd 388, found 388 |
| Ex 6.56 | 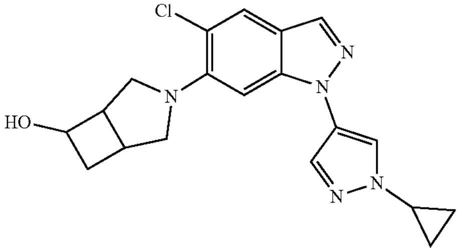 [SMILES: OC1CC2CN(c3cc4c(cnn4-c4cnn(C5CC5)c4)cc3Cl)CC12] | 3-[5-chloro-1-(1-cyclopropyl-1H-pyrazol-4-yl)-1H-indazol-6-yl]-3-azabicyclo[3.2.0]heptan-6-ol | Calc'd 370, found 370 |
| Ex 6.57 | 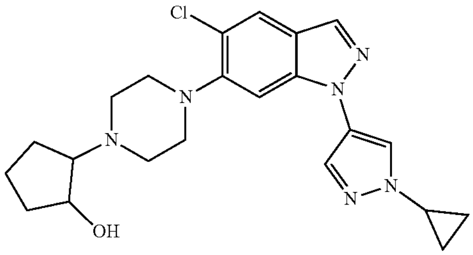 [SMILES: OC1CCCC1N1CCN(c2cc3c(cnn3-c3cnn(C4CC4)c3)cc2Cl)CC1] | 2-{4-[5-chloro-1-(1-cyclopropyl-1H-pyrazol-4-yl)-1H-indazol-6-yl]piperazin-1-yl}cyclopentan-1-ol | Calc'd 427, found 427 |

TABLE 17-continued

| Ex | Structure | Name | Exact Mass [M + H]+ |
|---|---|---|---|
| Ex 6.58 | 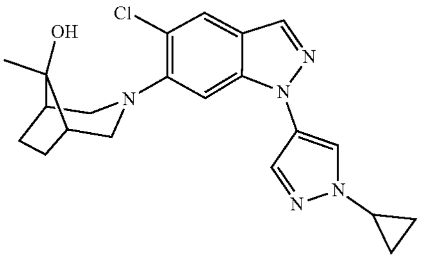 [SMILES: CC1(O)C2CCC1CN(c1cc3c(cnn3-c3cnn(C4CC4)c3)cc1Cl)C2] | (1R,5S)-3-[5-chloro-1-(1-cyclopropyl-1H-pyrazol-4-yl)-1H-indazol-6-yl]-8-methyl-3-azabicyclo[3.2.1]octan-8-ol | Calc'd 398, found 398 |

Preparation of Example 6.38: 1-(5-chloro-1-(1-cyclopropyl-1H-pyrazol-4-yl)-1H-indazol-6-yl)-3-fluoropiperidin-4-amine (Trans, Racemic)

Scheme 75

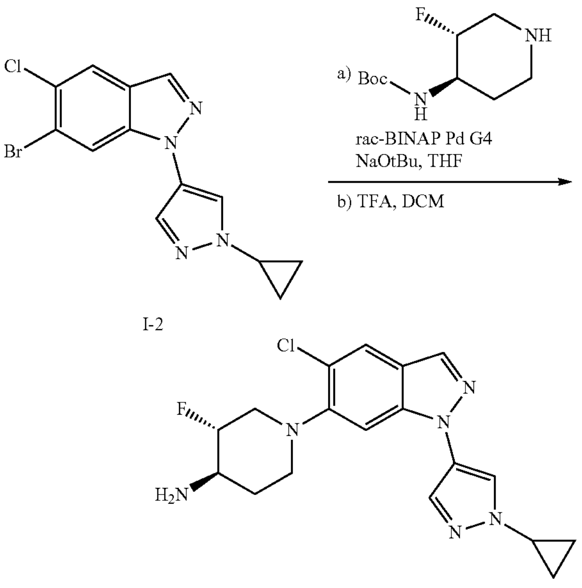

I-2

Ex. 6.38

I-2 (55 mg, 0.16 mmol), trans-4-(boc-amino)-3-fluoropiperidine (35.6 mg, 0.163 mmol), sodium tert-butoxide (39.1 mg, 0.407 mmol) and Rac-BINAP Pd G3 (16 mg, 0.016 mmol) in THF (800 μl) was degassed with a stream of $N_2$ for five minutes, then capped and heated at 90° C. overnight. The reaction was cooled and worked up with EtOAc/water. The separated organic phase was dried over $Na_2SO_4$, filtered and concentrated in vacuo. To the resulting mixture was added DCM (0.8 mL) followed by TFA (0.4 mL, 5 mmol). The reaction was stirred at room temp for 1 h, then concentrated in vacuo to afford a residue which was then purified by reversed phase HPLC, with water elution (0.1% TFA-ACN) to afford the title compound as the TFA salt (Ex. 6.38). $^1$H NMR (400 MHz, Chloroform-d) δ 7.97 (s, 1H), 7.84 (s, 1H), 7.81 (s, 1H), 7.69 (s, 1H), 6.99 (s, 1H), 4.95-4.77 (m, 1H), 3.84-3.74 (m, 1H), 3.70 (tt, J=7.2, 3.7 Hz, 1H), 3.46-3.36 (m, 2H), 2.83-2.72 (m, 2H), 2.33-2.23 (m, 1H), 2.15-1.97 (m, 1H), 1.18 (dd, J=5.4, 3.4 Hz, 2H), 1.12 (dd, J=11.3, 5.5 Hz, 2H); MS (EI) m/z 375 $[M+H]^+$.

Compounds in Table 18 below were prepared from common intermediate I-2 according to Scheme 75 by using the corresponding starting materials.

TABLE 18

| Ex | Structure | Name | Exact Mass [M + H]+ |
|---|---|---|---|
| Ex 6.39 | 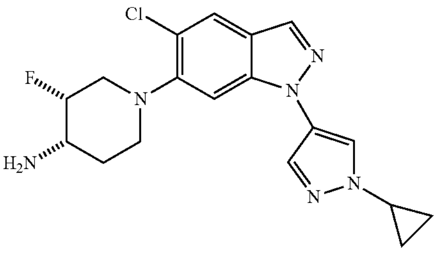 [SMILES: N[C@H]1CCN(c2cc3c(cnn3-c3cnn(C4CC4)c3)cc2Cl)C[C@H]1F] | (3S,4R) and (3R,4S)-1-[5-chloro-1-(1-cyclopropyl-1H-pyrazol-4-yl)-1H-indazol-6-yl]-3-fluoropiperidin-4-amine | Calc'd 375, found 375 |

TABLE 18-continued

| Ex | Structure | Name | Exact Mass [M + H]+ |
|---|---|---|---|
| Ex 6.59 | 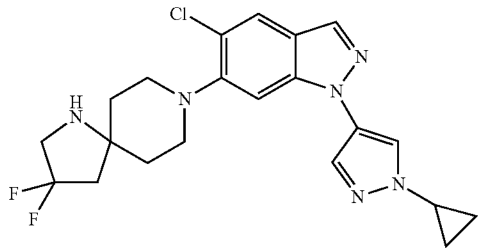 [SMILES: FC1(F)CNC2(CCN(c3cc4c(cnn4-c4cnn(C5CC5)c4)cc3Cl)CC2)C1] | 8-[5-chloro-1-(1-cyclopropyl-1H-pyrazol-4-yl)-1H-indazol-6-yl]-3,3-difluoro-1,8-diazaspiro[4.5]decane | Calc'd 433, found 433 |

Preparation of Example 6.60 and Example 6.61: (S or R)-1-(1-(1-(bicyclo[1.1.1]pentan-1-yl)-1H-pyrazol-4-yl)-5-chloro-1H-indazol-6-yl)-4-(tetrahydrofuran-3-yl)piperidin-4-ol (Ex. 6.60) and (R or S)-1-(1-(1-(bicyclo[1.1.1]pentan-1-yl)-1H-pyrazol-4-yl)-5-chloro-1H-indazol-6-yl)-4-(tetrahydrofuran-3-yl)piperidin-4-ol (Ex. 6.61)

Scheme 76

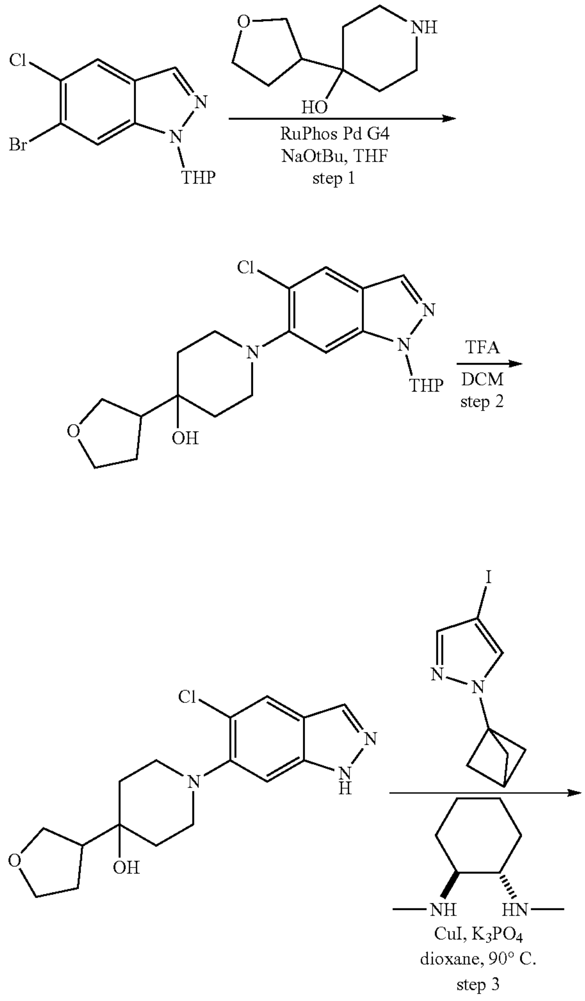

-continued

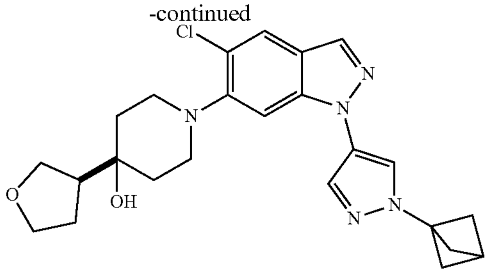

Ex. 6.60

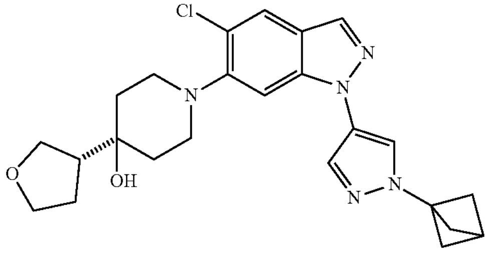

Ex. 6.61

Step 1: 1-(5-chloro-1-(tetrahydro-2H-pyran-2-yl)-1H-indazol-6-yl)-4-(tetrahydrofuran-3-yl)piperidin-4-ol To a vial were added 6-bromo-5-chloro-1-(tetrahydro-2H-pyran-2-yl)-1H-indazole (250 mg, 0.792 mmol), 4-(oxolan-3-yl)piperidin-4-ol (286 mg, 1.67 mmol), RuPhos Pd G4 (67.4 mg, 0.0790 mmol) and THF (4000 μl). To this mixture was added NaOtBu (1200 μl, 2.400 mmol). The mixture was evacuated and back filled with $N_2$ for 5 times, then stirred at 80° C. for 6 h. The mixture was dilute with $NH_4Cl$ (sat.) and extracted with EtOAc. The combined organic layers were washed with brine, dried over $MgSO_4$, filtered and concentrated in vacuo to afford residue, which was purified by column chromatography on silica (12 g, EtOAc in hexane, 0-100% gradient) to afford 1-(5-chloro-1-(tetrahydro-2H-pyran-2-yl)-1H-indazol-6-yl)-4-(tetrahydrofuran-3-yl)piperidin-4-ol. MS (EI) m/z 406 $[M+H]^+$.

Step 2: 1-(5-chloro-1H-indazol-6-yl)-4-(tetrahydrofuran-3-yl)piperidin-4-ol

To the solution of 1-(5-chloro-1-(tetrahydro-2H-pyran-2-yl)-1H-indazol-6-yl)-4-(tetrahydrofuran-3-yl)piperidin-4-ol (60 mg, 0.15 mmol) in DCM (1000 μl) was added TFA (100

μl, 1.30 mmol). After 16 h, more TFA (200 μl, 2.60 mmol) was added After 4 h, the solvent was evaporated to afford 122 mg of crude product as a TFA salt, which was used directly in next step. MS (EI) m/z: 322 $[M+H]^+$.

Step 3: (S or R)-1-(1-(1-(bicyclo[1.1.1]pentan-1-yl)-1H-pyrazol-4-yl)-5-chloro-1H-indazol-6-yl)-4-(tetrahydrofuran-3-yl)piperidin-4-ol and (R or S)-1-(1-(bicyclo[1.1.1]pentan-1-yl)-1H-pyrazol-4-yl)-5-chloro-1H-indazol-6-yl)-4-(tetrahydrofuran-3-yl)piperidin-4-ol (Ex. 6.60 and Ex. 6.61)

To a vial containing 1-(5-chloro-1H-indazol-6-yl)-4-(tetrahydrofuran-3-yl)piperidin-4-ol, TFA (64 mg, 0.15 mmol) were added (1S,2S)—N1,N2-dimethylcyclohexane-1,2-diamine (15 mg, 0.10 mmol), copper(I) iodide (10 mg, 0.053 mmol), 1-(bicyclo[1.1.1]pentan-1-yl)-4-iodo-1H-pyrazole (53.5 mg, 0.206 mmol), potassium phosphate (204 mg, 0.961 mmol) and dioxane (1500 μl). The mixture was evacuated and backfilled with $N_2$ for 3 times and heated at 90° C. for 5 h. The mixture was diluted with water and extracted with EtOAc three times. The combined organic layers was washed with brine, dried over $MgSO_4$, filtered and concentrated in vacuo to afford residue, which was purified by column chromatography on silica (4 g, EtOAc in hexane, 0-100%, gradient) to afford 1-(1-(1-(bicyclo[1.1.1]pentan-1-yl)-1H-pyrazol-4-yl)-5-chloro-1H-indazol-6-yl)-4-(tetrahydrofuran-3-yl)piperidin-4-ol, which was subjected to SFC chiral separation (column & dimensions: CCA, 21×250 mm; Mobile phase A: $CO_2$; Mobile phase B: MeOH with 0.1% $NH_4OH$) to afford the title compounds (Ex. 6.60 and Ex. 6.61).

Examples 6.60

$^1$H NMR (600 MHz, DMSO-$d_6$) δ 8.38 (s, 1H), 8.15 (s, 1H), 7.97 (s, 1H), 7.92 (s, 1H), 7.20 (s, 1H), 4.31 (s, 1H), 3.79-3.68 (m, 2H), 3.68-3.55 (m, 2H), 3.22-3.09 (m, 2H), 3.09-2.94 (m, 2H), 2.67 (s, 1H), 2.31 (s, 6H), 2.31-2.21 (m, 1H), 1.88-1.76 (m, 2H), 1.75-1.59 (m, 3H), 1.58-1.48 (m, 1H). MS (EI) m/z: 454 $[M+H]^+$. Retention time: 5.3 min.

Examples 6.61

$^1$H NMR (600 MHz, DMSO-$d_6$) δ 8.38 (s, 1H), 8.15 (s, 1H), 7.97 (s, 1H), 7.92 (s, 1H), 7.20 (s, 1H), 4.31 (s, 1H), 3.79-3.68 (m, 2H), 3.68-3.55 (m, 2H), 3.22-3.09 (m, 2H), 3.09-2.94 (m, 2H), 2.67 (s, 1H), 2.31 (s, 6H), 2.31-2.21 (m, 1H), 1.88-1.76 (m, 2H), 1.75-1.59 (m, 3H), 1.58-1.48 (m, 1H). MS (EI) m/z: 454 $[M+H]^+$. Retention time: 6.3 min.

Preparation of Example 6.62: (1R,5S,8r)-3-(5-chloro-1-(1-(3-methoxybicyclo[1.1.1]pentan-1-yl)-1H-pyrazol-4-yl)-1H-indazol-6-yl)-8-methyl-3-azabicyclo[3.2.1]octan-8-ol Scheme 77

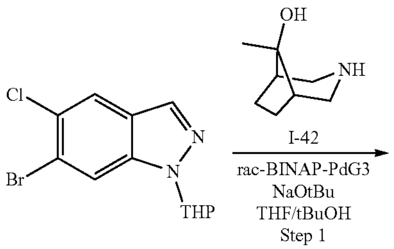

-continued

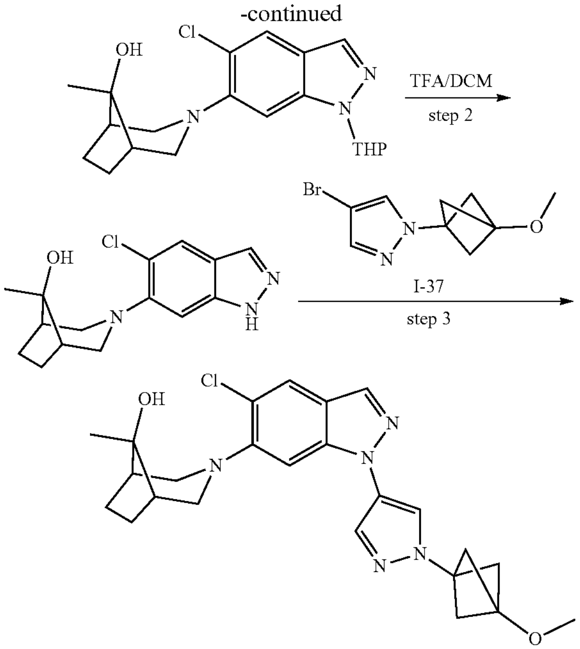

Ex. 6.62

Step 1: (1R,5S,8r)-3-(5-chloro-1-(tetrahydro-2H-pyran-2-yl)-1H-indazol-6-yl)-8-methyl-3-azabicyclo[3.2.1]octan-8-ol was prepared according to scheme 73. 6-bromo-5-chloro-1-(tetrahydro-2H-pyran-2-yl)-1H-indazole coupled with I-42 to give (1R,5S,8r)-3-(5-chloro-1-(tetrahydro-2H-pyran-2-yl)-1H-indazol-6-yl)-8-methyl-3-azabicyclo[3.2.1]octan-8-ol. MS (EI) m/z 376 $[M+H]^+$.

Step 2: (1R,5S,8r)-3-(5-chloro-1H-indazol-6-yl)-8-methyl-3-azabicyclo[3.2.1]octan-8-ol A solution of (1R,5S,8r)-3-(5-chloro-1-(tetrahydro-2H-pyran-2-yl)-1H-indazol-6-yl)-8-methyl-3-azabicyclo[3.2.1]octan-8-ol (110 mg, 0.293 mmol) in $CH_2Cl_2$ (1.56 mL) with TFA (390 μl, 5.07 mmol) was stirred at rt overnight and then concentrated. The residue was then partitioned between 5 mL of TN NaOH and DCM and the biphasic mixture stirred for 1 hour after which the DCM layer was separated, dried over sodium sulfate, filtered and concentrated to afford (1R,5S,8r)-3-(5-chloro-TH-indazol-6-yl)-8-methyl-3-azabicyclo[3.2.1]octan-8-ol, which was used without further purification. MS (EI) m/z: 292 $[M+H]^+$.

Step 3: (1R,5S,8r)-3-(5-chloro-1-(1-(3-methoxybicyclo[1.1.1]pentan-1-yl)-1H-pyrazol-4-yl)-1H-indazol-6-yl)-8-methyl-3-azabicyclo[3.2.1]octan-8-ol (Ex. 6.62)

Using exemplified procedure in Scheme 83 the title compound was made from (1R,5S,8r)-3-(5-chloro-TH-indazol-6-yl)-8-methyl-3-azabicyclo[3.2.1]octan-8-ol and I-37. $^1$H NMR (500 MHz, Chloroform-d) δ 7.99 (s, 1H), 7.89 (s, 1H), 7.80 (s, 1H), 7.75 (s, 1H), 7.23 (s, 1H), 4.14 (q, J=7.2 Hz, 1H),3.42 (m, 4H), 3.11 (m, 2H), 2.53 (s, 3H), 2.12 (m, 2H), 2.07 (s, 1H), 1.86 (bs, 2H), 1.80-1.75 (m, 2H), 1.38 (s, 3H), 0.89 (in, 3H); MS (EI) m/z: 454 [M+1].

Compounds in Table 19 below were prepared according to Scheme 77 by using the corresponding starting materials and I-28. All bridged tertiary alcohols are Endo stereochemistry, as drawn.

Ex. 6.67 and Ex. 6.68 were chiral separated by SFC (column: AS-H column; 21×250 mm), mobile phase A: $CO_2$; mobile phase B: IPA with 0.2% DIPA). Ex. 6.67 (retention time: 2.92 min); Ex. 6.68 (retention time: 3.48 min);

TABLE 19

| Ex | Structure | Name | Exact Mass [M + H]+ |
|---|---|---|---|
| Ex. 6.63 | 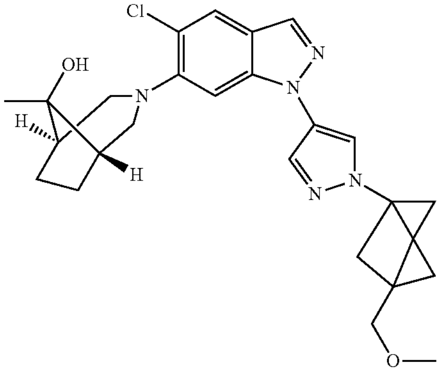 | (1R,5S)-3-[5-chloro-1-[1-[3-(methoxymethyl)-1-bicyclo[1.1.1]pentanyl] pyrazol-4-yl]indazol-6-yl]-8-methyl-3-azabicyclo[3.2.1]octan-8-ol | Calc'd 468, Found 468 |
| Ex. 6.64 | 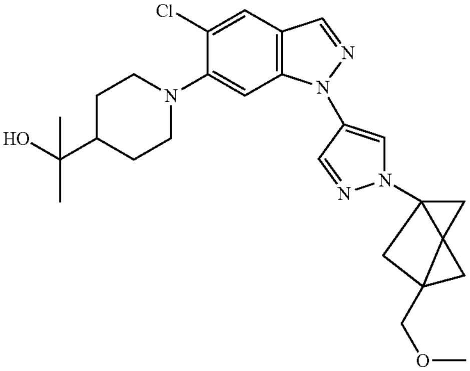 [SMILES: COCC12CC3(n4cc(-n5ncc6cc(Cl)c(N7CCC(C(C)(C)O)CC7)cc65)cn4)CC13C2] | 2-[1-[5-chloro-1-[1-[3-(methoxymethyl)-1-bicyclo[1.1.1]pentanyl] pyrazol-4-yl]indazol-6-yl]-4-piperidyl]propan-2-ol | Calc'd 470, Found 470 |
| Ex. 6.65 | 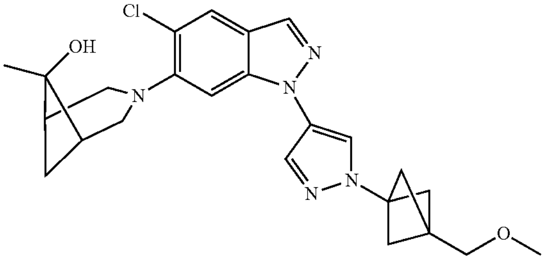 | (1S,5R)-3-[5-chloro-1-[1-[3-(methoxymethyl)-1-bicyclo[1.1.1]pentanyl] pyrazol-4-yl]indazol-6-yl]-6-methyl-3-azabicyclo[3.1.1]heptan-6-ol | Calc'd 454, Found 454. |
| Ex. 6.66 | 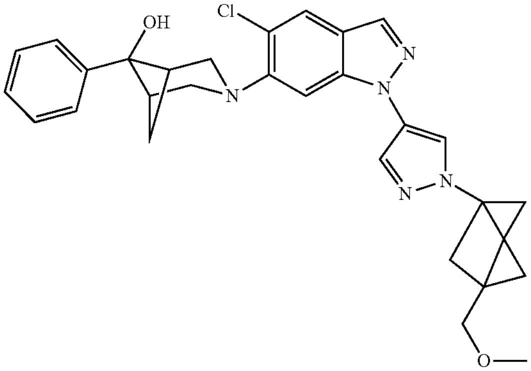 [SMILES: COCC12CC3(n4cc(-n5ncc6cc(Cl)c(N7CC8CC(C7)C8(O)c7ccccc7)cc65)cn4)CC13C2] | 3-[5-chloro-1-[1-[3-(methoxymethyl)-1-bicyclo[1.1.1]pentanyl] pyrazol-4-yl]indazol-6-yl]-6-phenyl-3-azabicyclo[3.1.1]heptan-6-ol | Calc'd 516, Found 516 |

TABLE 19-continued

| Ex | Structure | Name | Exact Mass [M + H]+ |
|---|---|---|---|
| Ex. 6.67 | 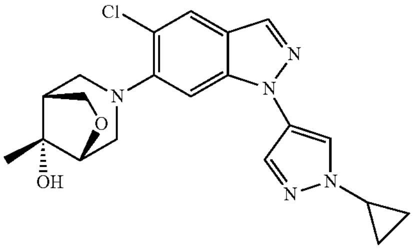 [SMILES: C[C@@]1(O)[C@H]2CO[C@@H]1CN(c1cc3c(cnn3-c3cnn(C4CC4)c3)cc1Cl)C2] | (1R,5R,8R)-3-[5-chloro-1-(1-cyclopropylpyrazol-4-yl)indazol-6-yl]-8-methyl-6-oxa-3-azabicyclo[3.2.1]octan-8-ol | Calc'd 400, Found 400 |
| Ex. 6.68 | 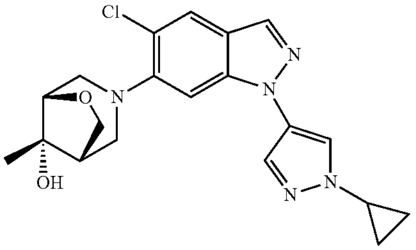 [SMILES: C[C@]1(O)[C@@H]2CO[C@H]1CN(c1cc3c(cnn3-c3cnn(C4CC4)c3)cc1Cl)C2] | (1S,5S,8S)-3-[5-chloro-1-(1-cyclopropylpyrazol-4-yl)indazol-6-yl]-8-methyl-6-oxa-3-azabicyclo[3.2.1]octan-8-ol | Calc'd 400, Found 400 |
| Ex. 6.69 | 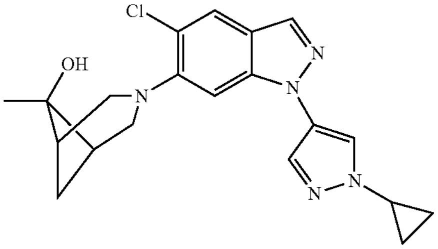 [SMILES: CC1(O)C2CC1CN(c1cc3c(cnn3-c3cnn(C4CC4)c3)cc1Cl)C2] | 3-[5-chloro-1-(1-cyclopropylpyrazol-4-yl)indazol-6-yl]-6-methyl-3-azabicyclo[3.1.1]heptan-6-ol | Calc'd 384, Found 384 |

Preparation of Example 6.70: 3-(5-chloro-1-(1-methyl-1H-pyrazol-4-yl)-1H-indazol-6-yl)-6-(pyridin-3-yl)-3-azabicyclo[3.1.1]heptan-6-ol Scheme 78

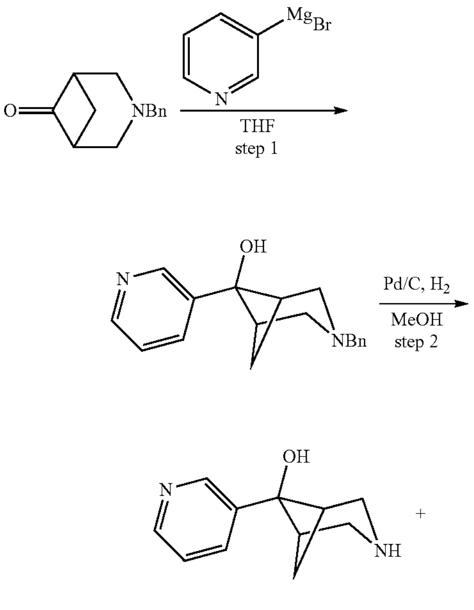

-continued

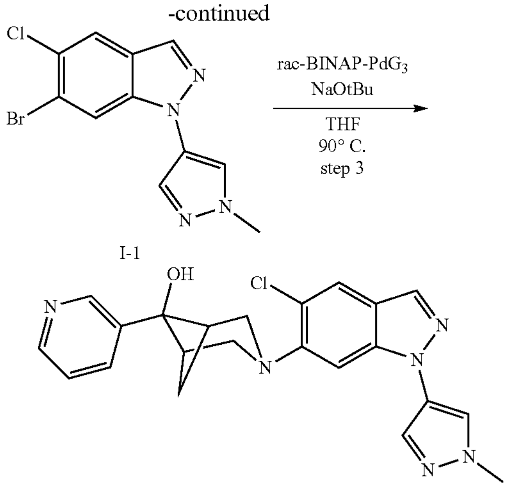

I-1

Ex. 6.70

Step 1: 3-benzyl-6-(pyridin-3-yl)-3-azabicyclo[3.1.1]heptan-6-ol 3-pyridylmagnesium bromide (16.0 ml, 4.00 mmol) was added into a cold (ice bath) solution of 3-benzyl-3-azabicyclo[3.1.1]heptan-6-one (700 mg, 3.48 mmol) in THF (20 ml). The reaction was stirred 0° C. for 30 min and quenched by adding sat. aq. $NH_4Cl$ solution then standard workup with EtOAc/water. The combined extracts were dried over $MgSO_4$, and concentrated. The residue was purified by flash chromatography ($SiO_2$, 40 g, 0-15% MeOH/DCM) to afford 3-benzyl-6-(pyridin-3-yl)-3-azabicyclo[3.1.1]heptan-6-ol. MS (EI) m/z: 281 $[M+H]^+$.

Step 2: 6-(pyridin-3-yl)-3-azabicyclo[3.1.1]heptan-6-ol

Pd/C (128 mg, 0.120 mmol) was added to a room temperature mixture of 3-benzyl-6-(pyridin-3-yl)-3-azabicyclo[3.1.1]heptan-6-ol (336 mg, 1.20 mmol) and MeOH (3 mL). The reaction was degassed via vacuum/$H_2$ cycles (×2) and stirred under a $H_2$ balloon at room temperature overnight. The reaction was filtered through a celite pad. The celite pad was rinsed with MeOH. The filtrate was concentrated under reduced pressure to afford 6-(pyridin-3-yl)-3-azabicyclo[3.1.1]heptan-6-ol. MS (EI) m/z: 191 $[M+H]^+$.

Step 3: 3-(5-chloro-1-(1-methyl-1H-pyrazol-4-yl)-1H-indazol-6-yl)-6-(pyridin-3-yl)-3-azabicyclo[3.1.1]heptan-6-ol (Ex. 6.70)

6-bromo-5-chloro-1-(1-methyl-1H-pyrazol-4-yl)-1H-indazole (I-1, 40 mg, 0.13 mmol), 6-(pyridin-3-yl)-3-azabicyclo[3.1.1]heptan-6-ol (26.9 mg, 0.14 mmol), sodium tert-butoxide (49.4 mg, 0.510 mmol) and rac-BINAP-Pd-G3 (12.7 mg, 0.013 mmol) in THF (1800 μl) was degassed with a stream of nitrogen for 1 minute and then capped and heated at 90° C. overnight. The crude mixture was worked up with water/EtOAc. The combined extracts were dried over $Na_2SO_4$, filtered and evaporated in vacuo. The resulting residue was purified by flash chromatography (40 g, eluting with MeOH in DCM, 0% to 10%). Related fractions were pooled and evaporated in vacuo to afford a colorless solid. This solid was further purified by prep-TLC eluting with 100% EtOAc to afford the title compound. $^1H$ NMR (400 MHz, Chloroform-d) δ 8.87 (s, 1H), 8.58 (s, 1H), 8.04 (s, 1H), 7.95 (d, J=7.9 Hz, 1H), 7.83 (d, J=1.3 Hz, 2H), 7.77 (s, 1H), 7.46 (s, 1H), 7.40-7.32 (m, 1H), 6.32 (s, 1H), 4.02 (s, 3H), 3.63 (d, J=10.3 Hz, 2H), 3.48 (s, 2H), 3.02 (s, 2H), 1.82 (m, 1H), 1.39 (d, J=10.2 Hz, 1H); MS (EI) m/z: 421 $[M+H]^+$.

Compounds in Table 20 below were prepared according to Scheme 78 by using the corresponding starting materials. All bridged tertiary alcohols are Endo stereochemistry, as drawn.

TABLE 20

| Ex | Structure | Name | Exact Mass [M + H]+ |
|---|---|---|---|
| Ex. 6.71 | 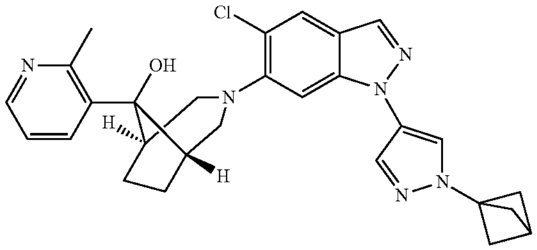 [SMILES: Cc1ncccc1C1(O)[C@@H]2CC[C@H]1CN(c1cc3c(cnn3-c3cnn(C45CC(C4)C5)c3)cc1Cl)C2] | (1S,5R)-3-[1-[1-(1-bicyclo[1.1.1]pentanyl)pyrazol-4-yl]-5-chloro-indazol-6-yl]-8-(2-methyl-3-pyridyl)-3-azabicyclo[3.2.1]octan-8-ol | Calc'd 501, Found 501 |
| Ex. 6.72 | 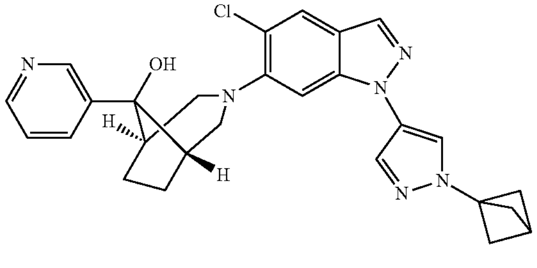 [SMILES: OC1(c2cccnc2)[C@@H]2CC[C@H]1CN(c1cc3c(cnn3-c3cnn(C45CC(C4)C5)c3)cc1Cl)C2] | (1R,5S)-3-[1-[1-(1-bicyclo[1.1.1]pentanyl)pyrazol-4-yl]-5-chloro-indazol-6-yl]-8-(3-pyridyl)-3-azabicyclo[3.2.1]octan-8-ol | Calc'd 487, Found 487 |
| Ex. 6.73 | 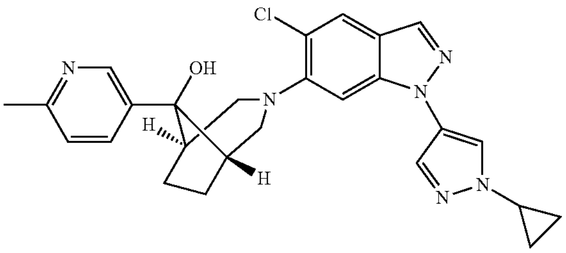 [SMILES: Cc1ccc(C2(O)[C@@H]3CC[C@H]2CN(c2cc4c(cnn4-c4cnn(C5CC5)c4)cc2Cl)C3)cn1] | (1R,5S)-3-[5-chloro-1-(1-cyclopropylpyrazol-4-yl)indazol-6-yl]-8-(6-methyl-3-pyridyl)-3-azabicyclo[3.2.1]octan-8-ol | Calc'd 475, Found 475 |

TABLE 20-continued

| Ex | Structure | Name | Exact Mass [M + H]+ |
|---|---|---|---|
| Ex. 6.74 | 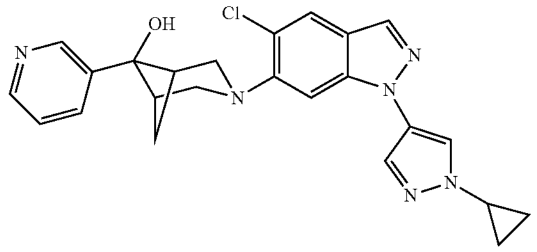 [SMILES: OC1(c2cccnc2)C2CC1CN(c1cc3c(cnn3-c3cnn(C4CC4)c3)cc1Cl)C2] | 3-[5-chloro-1-(1-cyclopropylpyrazol-4-yl)indazol-6-yl]-6-(3-pyridyl)-3-azabicyclo[3.1.1]heptan-6-ol | Calc'd 447, Found 447 |
| Ex. 6.75 | 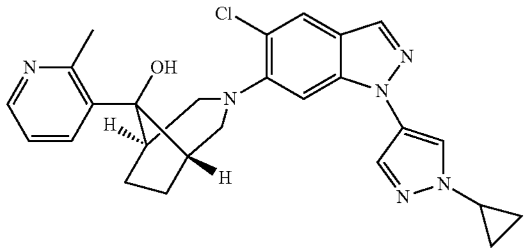 [SMILES: Cc1ncccc1C1(O)[C@@H]2CC[C@H]1CN(c1cc3c(cnn3-c3cnn(C4CC4)c3)cc1Cl)C2] | (1R,5S)-3-[5-chloro-1-(1-cyclopropylpyrazol-4-yl)indazol-6-yl]-8-(2-methyl-3-pyridyl)-3-azabicyclo[3.2.1]octan-8-ol | Calc'd 475, Found 475 |
| Ex. 6.76 | 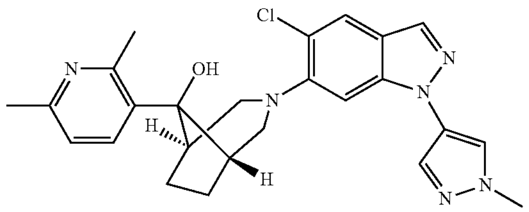 | (1R,5S)-3-[5-chloro-1-(1-methylpyrazol-4-yl)indazol-6-yl]-8-(2,6-dimethyl-3-pyridyl)-3-azabicyclo[3.2.1]octan-8-ol | Calc'd 463, Found 463 |
| Ex. 6.77 | 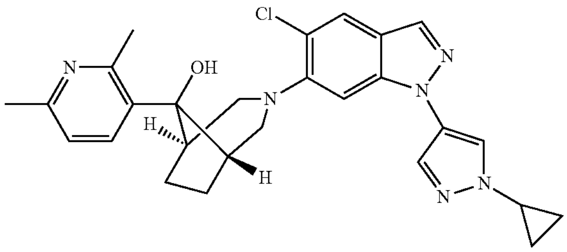 [SMILES: Cc1ccc(C2(O)[C@@H]3CC[C@H]2CN(c2cc4c(cnn4-c4cnn(C5CC5)c4)cc2Cl)C3)c(C)n1] | (1R,5S)-3-[5-chloro-1-(1-cyclopropylpyrazol-4-yl)indazol-6-yl]-8-(2,6-dimethyl-3-pyridyl)-3-azabicyclo[3.2.1]octan-8-ol | Calc'd 489, Found 489 |
| Ex. 6.78 | 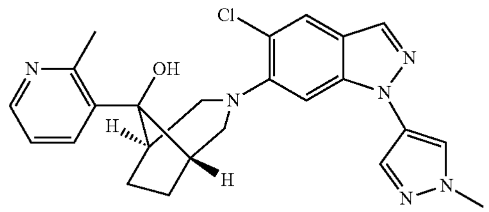 [SMILES: Cc1ncccc1C1(O)[C@@H]2CC[C@H]1CN(c1cc3c(cnn3-c3cnn(C)c3)cc1Cl)C2] | (1R,5S)-3-[5-chloro-1-(1-methylpyrazol-4-yl)indazol-6-yl]-8-(2-methyl-3-pyridyl)-3-azabicyclo[3.2.1]octan-8-ol | Calc'd 449, Found 449 |
| Ex. 6.79 | 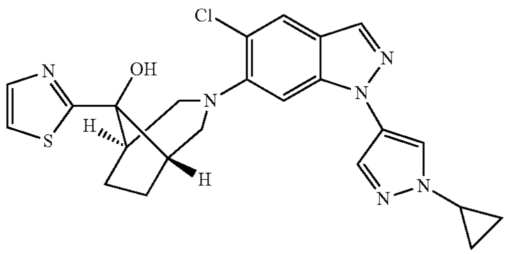 [SMILES: OC1(c2nccs2)[C@@H]2CC[C@H]1CN(c1cc3c(cnn3-c3cnn(C4CC4)c3)cc1Cl)C2] | (1R,5S)-3-[5-chloro-1-(1-cyclopropylpyrazol-4-yl)indazol-6-yl]-8-thiazol-2-yl-3-azabicyclo[3.2.1]octan-8-ol | Calc'd 467, Found 467 |

TABLE 20-continued

| Ex | Structure | Name | Exact Mass [M + H]+ |
|---|---|---|---|
| Ex. 6.80 | 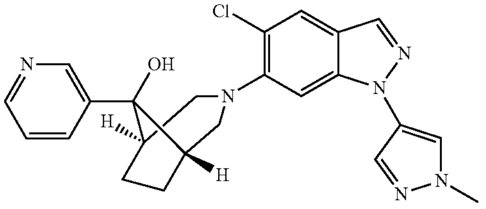 | (1S,5R)-3-[5-chloro-1-(1-methylpyrazol-4-yl)indazol-6-yl]-8-(3-pyridyl)-3-azabicyclo[3.2.1]octan-8-ol | Calc'd 435, Found 435 |
| Ex. 6.81 | 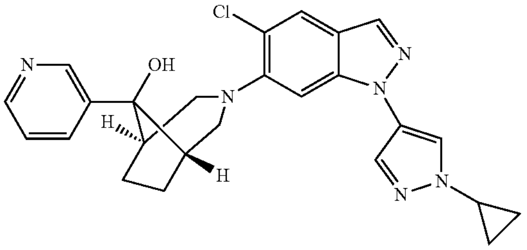 [SMILES: OC1(c2cccnc2)[C@@H]2CC[C@H]1CN(c1cc3c(cnn3-c3cnn(C4CC4)c3)cc1Cl)C2] | (1R,5S)-3-[5-chloro-1-(1-cyclopropylpyrazol-4-yl)indazol-6-yl]-8-(3-pyridyl)-3-azabicyclo[3.2.1]octan-8-ol | Calc'd 461, Found 461 |

Preparation of Example 6.82: 4-((1R,5S)-3-(5-chloro-1-(1-cyclopropyl-1H-pyrazol-4-yl)-1H-indazol-6-yl)-3,8-diazabicyclo[3.2.1]octan-8-yl)thiazole Scheme 79

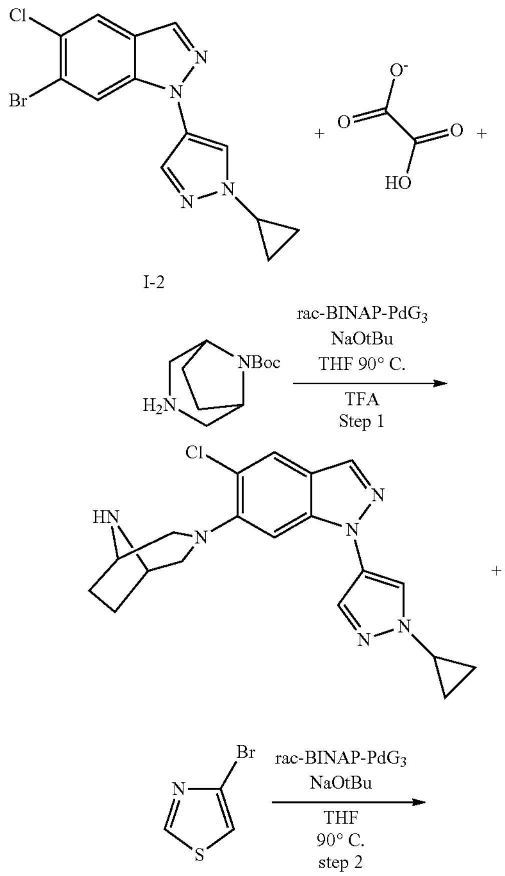

-continued

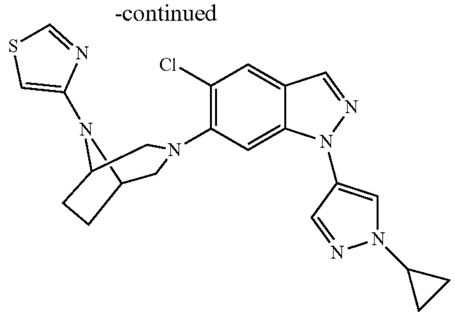

Ex. 6.82

Step 1: 6-((1R,5S)-3,8-diazabicyclo[3.2.1]octan-3-yl)-5-chloro-1-(1-cyclopropyl-1H-pyrazol-4-yl)-1H-indazole I-2 (700 mg, 2.07 mmol), 8-(tert-butoxycarbonyl)-3,8-diazabicyclo[3.2.1]octan-3-ium carboxyformate (627 mg, 2.07 mmol), sodium tert-butoxide (797 mg, 8.29 mmol) and rac-BINAP-Pd-G3 (309 mg, 0.310 mmol) in THF (12 mL) was degassed with a stream of nitrogen for 1 minute and then capped and heated at 90° C. overnight. The reaction was worked up with water/EtOAc. The combined extracts were dried over $Na_2SO_4$, filtered and evaporated in vacuo. The resulting residue was taken up by $CH_2Cl_2$ (12 mL). To the dark solution at rt was added TFA (5 mL, 64.9 mmol) and stirred at rt for 2 h. Volatiles were removed under reduced pressure. The crude was worked up with aqueous sodium bicarbonate/ethyl acetate. The combined extracts were dried over $Na_2SO_4$, filtered and evaporated in vacuo. The resulting residue was purified by flash chromatography on silica (80 g, eluting with MeOH in DCM, 0%-5%). Related fractions were pooled and evaporated in vacuo to afford 6-((1R,5S)-3,8-diazabicyclo[3.2.1]octan-3-yl)-5-chloro-1-(1-cyclopropyl-1H-pyrazol-4-yl)-1H-indazole. MS (EI) m/z: 369 $[M+H]^+$.

Step 2: 4-((1R,5S)-3-(5-chloro-1-(1-cyclopropyl-1H-pyrazol-4-yl)-1H-indazol-6-yl)-3,8-diazabicyclo[3.2.1]octan-8-yl)thiazole (Ex. 6.82)

6-((1R,5S)-3,8-diazabicyclo[3.2.1]octan-3-yl)-5-chloro-1-(1-cyclopropyl-1H-pyrazol-4-yl)-1H-indazole (50 mg, 0.14 mmol), 4-bromothiazole (22.2 mg, 0.14 mmol), sodium tert-butoxide (52.1 mg, 0.54 mmol) and rac-BINAP-Pd-G3 (20.18 mg, 0.020 mmol) in THF (2 mL) was degassed with a stream of nitrogen for 1 minute and then capped and heated at 90° C. overnight. The crude was worked up with water/EtOAc. The combined extracts were dried over $Na_2SO_4$, filtered and evaporated in vacuo. The resulting residue was purified by flash chromatography ($SiO_2$, 40 g, eluting with MeOH in DCM, 0%-20%). Related fractions were pooled and evaporated in vacuo to afford the title compound (Ex. 6.82). $^1$H NMR (400 MHz, Chloroform-d) δ 8.62 (d, J=2.1 Hz, 1H), 7.96 (d, J=0.8 Hz, 1H), 7.79 (s, 1H), 7.75 (d, J=1.3 Hz, 2H), 7.04 (s, 1H), 5.97 (d, J=2.1 Hz, 1H), 4.37 (s, 2H), 3.68 (tt, J=7.3, 3.8 Hz, 1H), 3.26 (dd, J=11.2, 2.4 Hz, 2H), 3.18 (d, J=10.7 Hz, 2H), 2.31 (q, J=6.1 Hz, 2H), 2.06-1.96 (m, 2H), 1.29-1.17 (m, 2H), 1.13-1.04 (m, 2H). MS (EI) m/z: 452 $[M+H]^+$.

Ex. 6.83 in Table 21 was prepared from common intermediate I-2 according to Scheme 79 by using the corresponding starting materials.

TABLE 21

| Ex | Structure | Name | Exact Mass [M + H]+ |
|---|---|---|---|
| Ex. 6.83 | 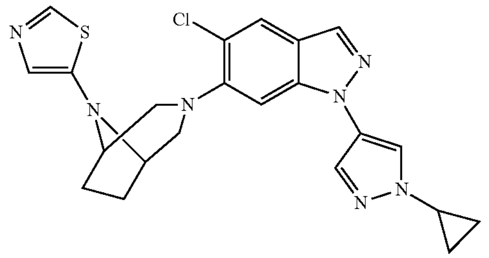 [SMILES: Clc1cc2cnn(-c3cnn(C4CC4)c3)c2cc1N1CC2CCC(C1)N2c1cncs1] | 5-chloro-1-(1-cyclopropyl-1H-pyrazol-4-yl)-6-[8-(1,3-thiazol-5-yl)-3,8-diazabicyclo[3.2.1]octan-3-yl]-1H-indazole | Calc'd 452, found 452 |

Preparation of Example 7.1: 5-chloro-1-(1-(3-(fluoromethyl)bicyclo[1.1.1]pentan-1-yl)-1H-pyrazol-4-yl)-6-(4-(3-methyloxetan-3-yl)piperazin-1-yl)-1H-indazole (Ex. 7.1) and (3-(4-(5-chloro-6-(4-(3-methyloxetan-3-yl)piperazin-1-yl)-1H-indazol-1-yl)-1H-pyrazol-1-yl)bicyclo[1.1.1]pentan-1-yl)methanol (Ex. 7.2)

Scheme 80

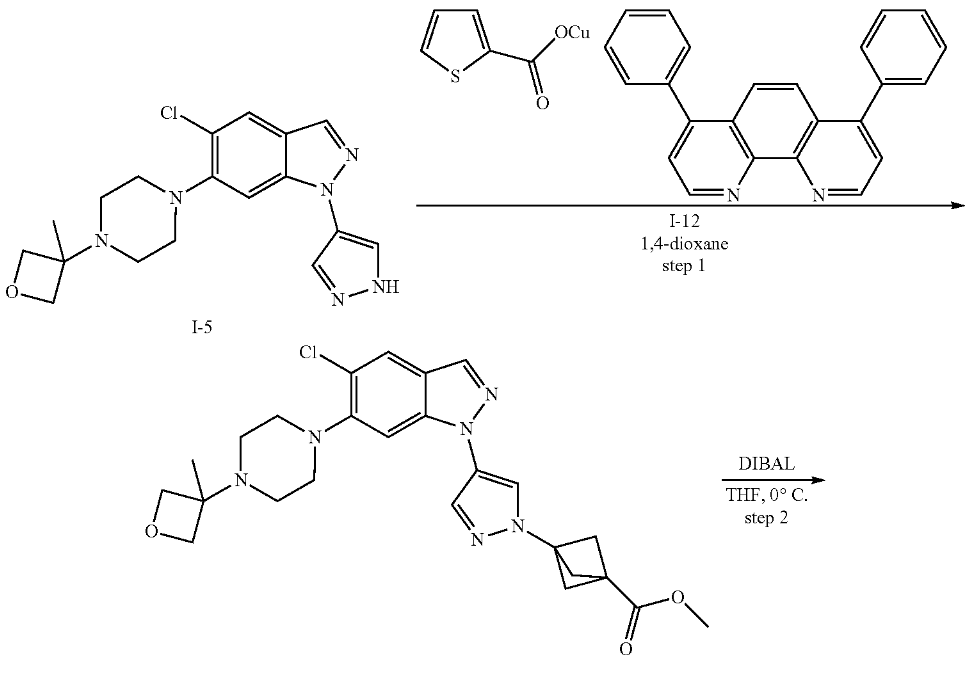

-continued

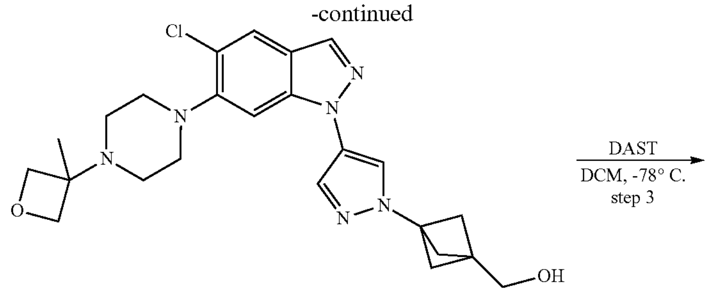

Ex. 7.2

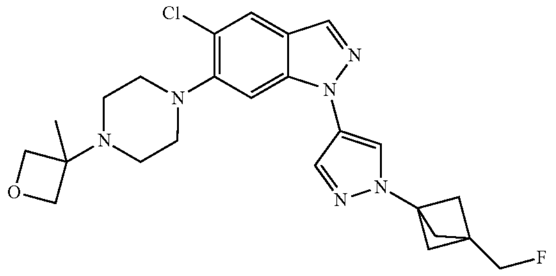

Ex. 7.1

Step 1: methyl 3-(4-(5-chloro-6-(4-(3-methyloxetan-3-yl)piperazin-1-yl)-1H-indazol-1-yl)-1H-pyrazol-1-yl)bicyclo[1.1.1]pentane-1-carboxylate To a solution of I-5 (200 mg, 0.54 mmol), 4,7-diphenyl-1,10-phenanthroline (161 mg, 0.48 mmol), and I-12 (594 mg, 1.07 mmol) in anhydrous 1,4-dioxane (5 mL) was added CuTC (61.5 mg, 0.32 mmol). The reaction mixture was then stirred at room temperature for 2 h. The material was concentrated in vacuo and then the residue was taken up with DCM (3 mL) and purified by column chromatography on silica gel (1:3 ethanol/ethyl acetate in hexane: 5-100% gradient) to afford methyl 3-(4-(5-chloro-6-(4-(3-methyloxetan-3-yl)piperazin-1-yl)-1H-indazol-1-yl)-1H-pyrazol-1-yl)bicyclo[1.1.1]pentane-1-carboxylate. MS (EI) m/z: 497 $[M+H]^+$.

Step 2: (3-(4-(5-chloro-6-(4-(3-methyloxetan-3-yl)piperazin-1-yl)-1H-indazol-1-yl)-1H-pyrazol-1-yl)bicyclo[1.1.1]pentan-1-yl)methanol (Ex. 7.2)

To a solution of methyl 3-(4-(5-chloro-6-(4-(3-methyloxetan-3-yl)piperazin-1-yl)-1H-indazol-1-yl)-1H-pyrazol-1-yl)bicyclo[1.1.1]pentane-1-carboxylate (52 mg, 0.10 mmol) in anhydrous THF (0.25 mL) at 0° C. was added DIBAL in hexane (1M, 0.3 mL, 0.3 mmol) dropwise, and the resulting solution was stirred at 0° C. for 2 h. The reaction was quenched with aqueous $NH_4Cl$ solution and allowed to warm to room temperature. The organic layer was separated and dried over sodium sulfate, filtered, and concentrated in vacuo to afford a residue which was then purified by column chromatography on silica gel (1:3 ethanol/ethyl acetate in hexane: 5-100% gradient) to afford (3-(4-(5-chloro-6-(4-(3-methyloxetan-3-yl)piperazin-1-yl)-1H-indazol-1-yl)-1H-pyrazol-1-yl)bicyclo[1.1.1]pentan-1-yl)methanol (Ex. 7.2). MS (EI) m/z: 469 $[M+H]^+$.

Step 3: 5-chloro-1-(1-(3-(fluoromethyl)bicyclo[1.1.1]pentan-1-yl)-1H-pyrazol-4-yl)-6-(4-(3-methyloxetan-3-yl)piperazin-1-yl)-1H-indazole (Ex. 7.1)

(3-(4-(5-chloro-6-(4-(3-methyloxetan-3-yl)piperazin-1-yl)-1H-indazol-1-yl)-1H-pyrazol-1-yl)bicyclo[1.1.1]pentan-1-yl)methanol (25 mg, 0.05 mmol) in DCM (0.5 ml) was cooled to −78° C., and to this mixture was added DAST (0.028 ml, 0.21 mmol) dropwise via syringe. The mixture was stirred at −78° C. for 1 h and then allowed to warm to room temperature. The solution was diluted with DCM and water, treated with 4M sodium hydroxide to adjust the pH to ~10. The organic layer was dried over $MgSO_4$, filtered and concentrated in vacuo to afford a residue which was then purified by column chromatography on silica gel (1:3 ethanol/ethyl acetate in hexane: 5-100% gradient) to afford the title compound (Ex. 7.1). $^1$HNMR (500 MHz, $CD_3OD$) δ: 8.36 (s, 1H); 8.03 (s, 1H); 7.92 (s, 1H); 7.85 (s, 1H); 7.51 (s, 1H); 4.69-4.59 (m, 2H); 4.48 (d, J=7 Hz, 2H); 4.15 (d, J=7 Hz, 2H); 3.31-3.18 (m, 3H); 3.15-3.01 (m, 2H); 2.80-2.60 (m, 2H); 2.45-2.30 (m, 6H); 1.42 (s, 4H). MS (EI) m/z: 471 $[M+H]^+$.

Ex 7.2 in Table 22 below were prepared from common intermediate I-5 and I-12 according to Scheme 80 (step 1 and 2).

Ex 7.3 and 7.4 in Table 21 were prepared from intermediate I-5 according to Scheme 80 (step 1) by using the corresponding intermediates, which were prepared from commercial acids according to Scheme 12.

TABLE 22

| Ex | Structure | Name | Exact Mass [M + H]+ |
|---|---|---|---|
| Ex 7.2 | 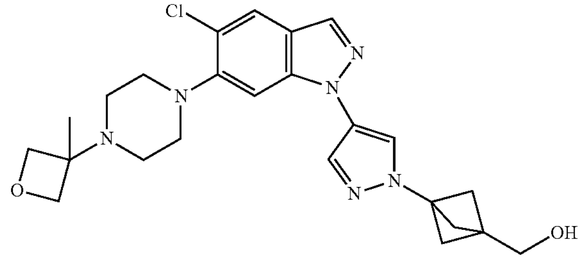 [SMILES: CC1(N2CCN(c3cc4c(cnn4-c4cnn(C56CC(CO)(C5)C6)c4)cc3Cl)CC2)COC1] | [3-(4-{5-chloro-6-[4-(3-methyloxetan-3-yl)piperazin-1-yl]-1H-indazol-1-yl}-1H-pyrazol-1-yl)bicyclo[1.1.1]pentan-1-yl]methanol | Calc'd 469, found 469 |
| Ex 7.3 | 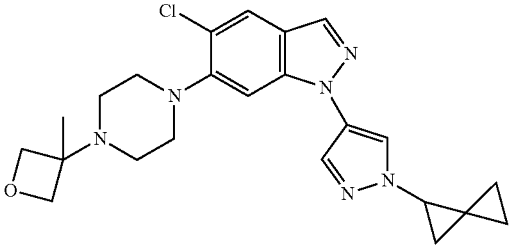 [SMILES: CC1(N2CCN(c3cc4c(cnn4-c4cnn(C5CC56CC6)c4)cc3Cl)CC2)COC1] | 5-chloro-6-[4-(3-methyloxetan-3-yl)piperazin-1-yl]-1-[1-(spiro[2.2]pentan-1-yl)-1H-pyrazol-4-yl]-1H-indazole | Calc'd 439, found 439 |
| Ex 7.4 | 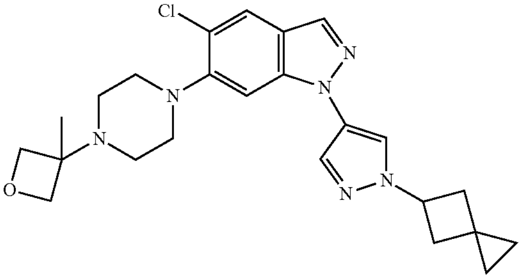 [SMILES: CC1(N2CCN(c3cc4c(cnn4-c4cnn(C5CC6(CC6)C5)c4)cc3Cl)CC2)COC1] | 5-chloro-6-[4-(3-methyloxetan-3-yl)piperazin-1-yl]-1-[1-(spiro[2.3]hexan-5-yl)-1H-pyrazol-4-yl]-1H-indazole | Calc'd 453, found 453 |

Preparation of Example 7.5: 5-chloro-1-(1-(4-(methoxymethyl)bicyclo[2.1.1]hexan-1-yl)-1H-pyrazol-4-yl)-6-(4-(3-methyloxetan-3-yl)piperazin-1-yl)-1H-indazole Scheme 81

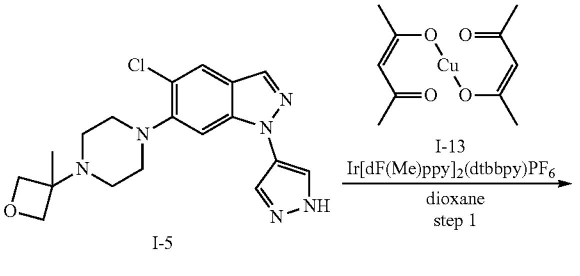

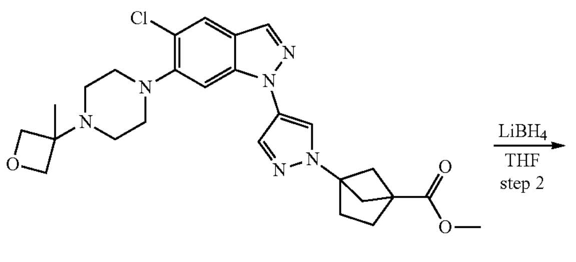

-continued

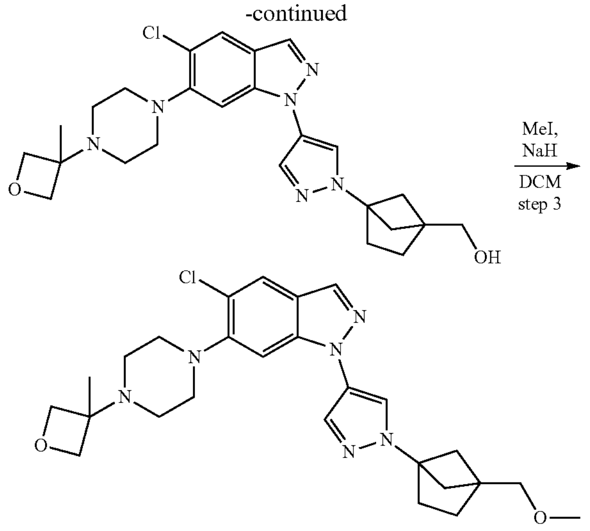

Ex. 7.5

Step 1: methyl 4-(4-(5-chloro-6-(4-(3-methyloxetan-3-yl)piperazin-1-yl)-1H-indazol-1-yl)-1H-pyrazol-1-yl)bicyclo[2.1.1]hexane-1-carboxylate A 40-mL vial was charged with I-5 (150 mg, 0.402 mmol), I-13 (349 mg, 0.570 mmol), $Ir[dF(Me)ppy]_2$ (dtbbpy)$PF_6$ (8.16 mg, 8.05 μmol), copper(II) acetylacetonate (63.2 mg, 0.241 mmol) at rt and headspace purged with $N_2$ for 10 min. Dioxane (12 ml) was added. The mixture was sparged with $N_2$ for 5 min, sealed with parafilm, then sonicated for 1 min to provide a homogenous blue mixture. The reaction was irradiated in the photoreactor (450 nm; Fan:2600 rpm; stir: 800 rpm; 100% LED) for 1.5 h. Water and EtOAc were added. The aqueous layer was extracted with EtOAc three times. The combined organic layers was washed with brine, dried over $MgSO_4$, filtered and concentrated in vacuo to afford residue, which was purified by column chromatography on silica (12 g, EtOAc in hexane, 0-100% gradient) to afford methyl 4-(4-(5-chloro-6-(4-(3-methyloxetan-3-yl)piperazin-1-yl)-1H-indazol-1-yl)-1H-pyrazol-1-yl)bicyclo[2.1.1]hexane-1-carboxylate. MS (EI) m/z: 511 $[M+H]^+$.

Step 2: (4-(4-(5-chloro-6-(4-(3-methyloxetan-3-yl)piperazin-1-yl)-1H-indazol-1-yl)-1H-pyrazol-1-yl)bicyclo[2.1.1]hexan-1-yl)methanol To the solution of methyl 4-(4-(5-chloro-6-(4-(3-methyloxetan-3-yl)piperazin-1-yl)-1H-indazol-1-yl)-1H-pyrazol-1-yl)bicyclo[2.1.1]hexane-1-carboxylate (100 mg, 0.196 mmol) in THF (1500 μl) at 0° C., was added $LiBH_4$ (250 μl, 0.500 mmol) dropwise. The reaction was warmed to rt and stirred for 18 h. The reaction was cooled to 0° C. and carefully quenched with saturated aqueous $NH_4Cl$. The mixture was extracted with EtOAc three times. The combined organic lays were washed with brine, dried over $Na_2SO_4$, filtered, and concentrated to get (4-(4-(5-chloro-6-(4-(3-methyloxetan-3-yl)piperazin-1-yl)-1H-indazol-1-yl)-1H-pyrazol-1-yl)bicyclo[2.1.1]hexan-1-yl)methanol, which was used in next step directly. MS (EI) m/z: 483 $[M+H]^+$.

Step 3: 5-chloro-1-(1-(4-(methoxymethyl)bicyclo[2.1.1]hexan-1-yl)-1H-pyrazol-4-yl)-6-(4-(3-methyloxetan-3-yl)piperazin-1-yl)-1H-indazole (Ex. 7.5)

To a solution of (4-(4-(5-chloro-6-(4-(3-methyloxetan-3-yl)piperazin-1-yl)-1H-indazol-1-yl)-1H-pyrazol-1-yl)bicyclo[2.1.1]hexan-1-yl)methanol (84.5 mg, 0.175 mmol) in DCM (1.0 ml) at 0° C. was added NaH (25 mg, 0.62 mmol). The mixture was stirred at 0° C. for 30 min. Then MeI (20 μl, 0.32 mmol) was added. The mixture was stirred at rt for 18 h. Then the reaction was quenched with $NH_4Cl$ (sat.), extracted with DCM three times. The combined organic layers was washed with brine, dried over $MgSO_4$, filtered and concentrated in vacuo to afford residue, which was purified by column chromatography on silica (12 g, EtOH/EtOAc=1/3 in hexane, 5-50% gradient) to afford the title compound (Ex. 7.5)$^1$H NMR (600 MHz, DMSO-$d_6$) δ 8.40 (s, 1H), 8.16 (s, 1H), 7.99 (s, 1H), 7.93 (s, 1H), 7.27 (s, 1H), 4.46 (d, J=5.6 Hz, 2H), 4.17 (d, J=5.6 Hz, 2H), 3.53 (s, 2H), 3.39-3.29 (m, 4H), 3.31 (s, 3H), 3.21-3.02 (m, 4H), 2.31-2.16 (m, 2H), 2.13-2.02 (m, 2H), 1.83-1.67 (m, 4H), 1.34 (s, 3H); MS (EI) m/z: 497 $[M+H]^+$.

Preparation of Example 7.6: (4-(4-(5-chloro-6-(4-(3-methyloxetan-3-yl)piperazin-1-yl)-1H-indazol-1-yl)-1H-pyrazol-1-yl)bicyclo[2.2.2]octan-1-yl)methanol Scheme 82

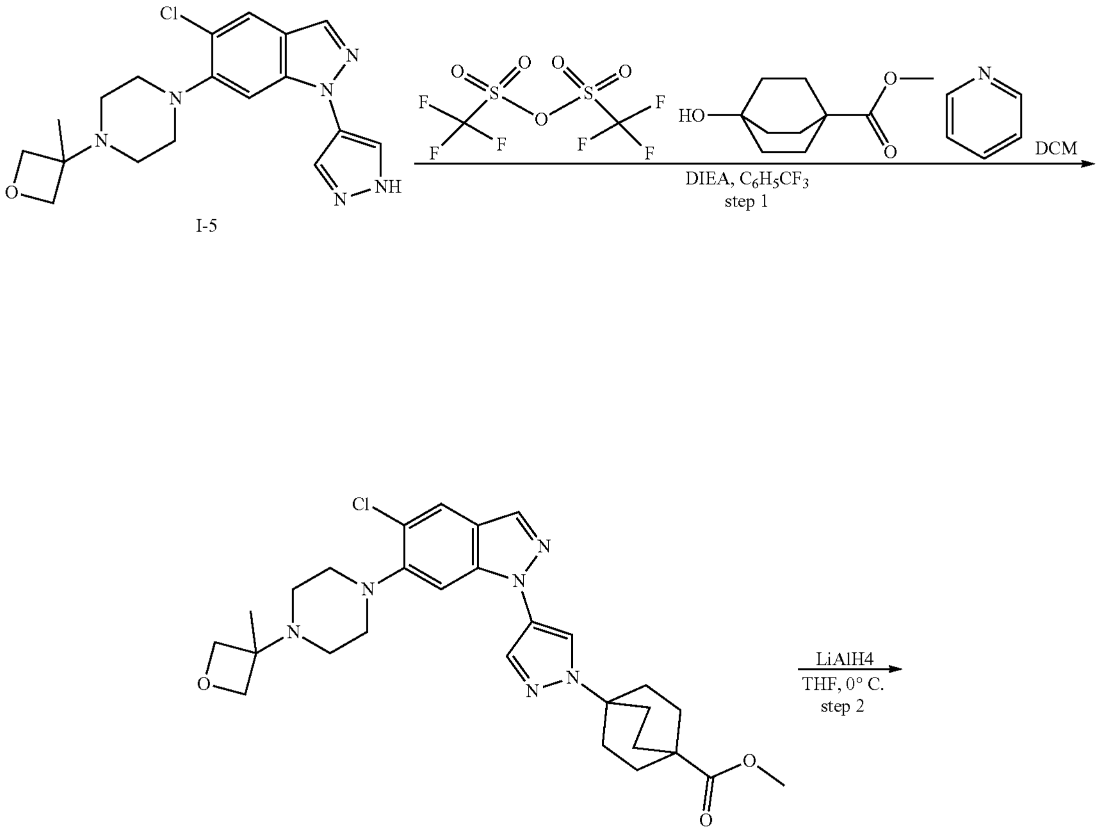

I-5

-continued

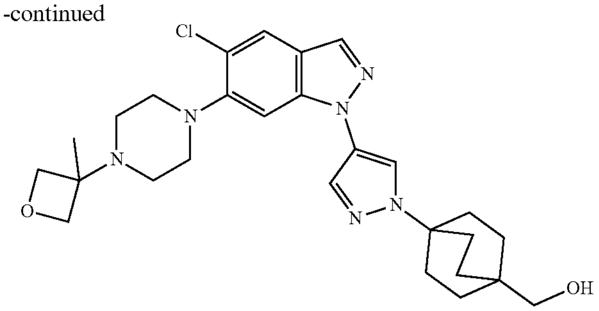

Ex. 7.6

Step 1: methyl 4-(4-(5-chloro-6-(4-(3-methyloxetan-3-yl)piperazin-1-yl)-1H-indazol-1-yl)-1H-pyrazol-1-yl)bicyclo[2.2.2]octane-1l-carboxylate To a solution of methyl 4-hydroxybicyclo[2.2.2]octane-1l-carboxylate (19.9 mg, 0.107 mmol) and pyridine (8.68 µl, 0.107 mmol) in DCM (1.0 ml) was added trifluoromethanesulfonic anhydride (0.018 ml, 0.107 mmol) slowly at 0° C. and stirred for 3 hours. The reaction mixture was diluted with dichloromethane (5 mL). The dichloromethane solution was washed sequentially with cold HCl (1 M), followed with 10% $NaHCO_3$, and then brine. The organic layer was dried over $MgSO_4$ and concentrated to give afford a yellow solid. This yellow solid was dissolved in benzotrifluoride (1 mL). To this solution were added Hunig's base (0.019 ml, 0.107 mmol) and I-5 (40 mg, 0.11 mmol). The mixture was heated to 100° C. for 48 h. The reaction crude was cooled down to room temperature and diluted with DCM. The mixture was then washed sequentially with water and brine, dried over $MgSO_4$, and concentrated under reduced pressure. The residue was purified by flash chromatography on silica gel (40 g, MeOH in DCM, 0-15% gradient) to afford methyl 4-(4-(5-chloro-6-(4-(3-methyloxetan-3-yl)piperazin-1-yl)-1H-indazol-1-yl)-1H-pyrazol-1-yl)bicyclo[2.2.2]octane-1-carboxylate. MS (EI) m/z: 539 [M+H$^+$].

Step 2: (4-(4-(5-chloro-6-(4-(3-methyloxetan-3-yl)piperazin-1-yl)-1H-indazol-1-yl)-1H-pyrazol-1-yl)bicyclo[2.2.2]octan-1-yl)methanol (Ex. 7.6)

Lithium aluminum hydride (0.093 ml, 0.093 mmol) was added into a cold (ice bath) solution of methyl 4-(4-(5-chloro-6-(4-(3-methyloxetan-3-yl)piperazin-1-yl)-1H-indazol-1-yl)-1H-pyrazol-1-yl)bicyclo[2.2.2]octane-1-carboxylate (25 mg, 0.046 mmol) in THF (2 ml). The reaction was stirred color for 10 min and quenched by adding saturated potassium sodium tartrate tetrahydrate solution. The reaction mixture was filtered and worked up with EtOAc/water. The combined extracts were dried over $MgSO_4$, and concentrated. The residue was purified by flash chromatography ($SiO_2$, 25 g, 0-15% MeOH in DCM gradient) to afford the titled compound (Ex. 7.6)$^1$H NMR (400 MHz, Chloroform-d) 7.98 (s, 1H), 7.83 (d, J=5.7 Hz, 2H), 7.76 (s, 1H), 7.11 (s, 1H), 4.64 (d, J=4.9 Hz, 2H), 4.28 (d, J=5.6 Hz, 2H), 3.38 (s, 2H), 3.18 (br, 4H), 2.59 (s, 4H), 2.23-2.12 (m, 6H), 1.76-1.66 (m, 6H), 1.45 (s, 3H). MS (EI) m/z: 511 [M+H$^+$].

Preparation of Example 7.7 5-chloro-1-(1-(3-(methoxymethyl)bicyclo[1.1.1]pentan-1-yl)-1H-pyrazol-4-yl)-6-(4-(3-methyloxetan-3-yl)piperazin-1-yl)-1H-indazole Scheme 83

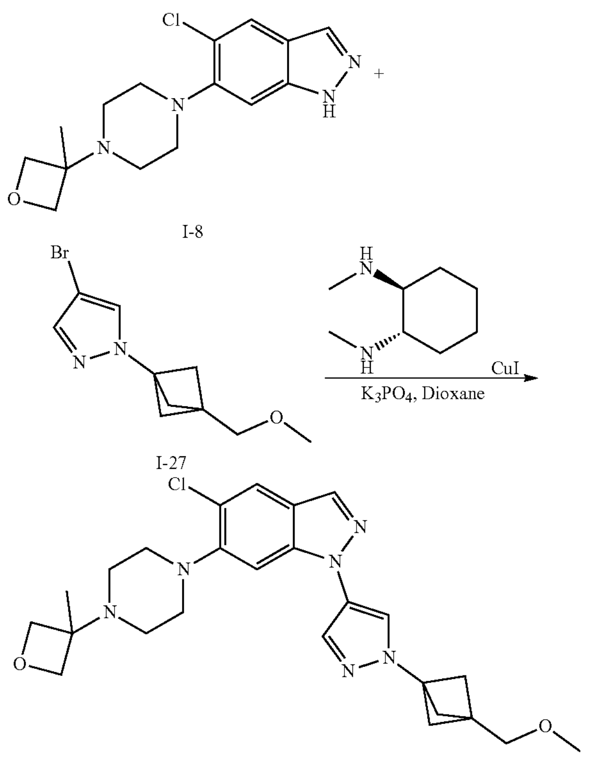

I-8

I-27

Ex. 7.7

A 2-5 mL microwave vial with small magnetic stirrer was charged with (in order) 5-chloro-6-(4-(3-methyloxetan-3-yl)piperazin-1-yl)-1H-indazole (Intermediate I-8, 100 mg, 0.326 mmol), CuI (19 mg, 0.098 mmol), potassium phosphate tri-basic (208 mg, 0.978 mmol) and (1R, 2R)—$N_1$, $N_2$-dimethylcyclohexane-1,2-diamine (27.8 mg, 0.196 mmol) and then was capped. The material was set under nitrogen (3× vacuum follow by $N_2$) and then I-27 (101 mg, 0.391 mmol) in 2.5 mL of anhydrous dioxane was added via syringe to the dry solids. The reaction was purged again (2× vacuum followed by $N_2$) and then heated to 110° C. and stirred overnight. The reaction was cooled to room temperature and filtered through a fritted funnel. The solids were washed with ethyl acetate (20 mL) and the collected filtrate concentrated to dryness under reduced pressure. The residue was taken up in DCM (5 mL) and purified by column chromatography on silica gel (12 g, eluting with 0-80% 3:1 ethyl acetate:ethanol in hexane) to afford the desired product. The product residue was taken up into 2 mL of 3:1 acetonitrile:water and filtered through a Gilmen syringe filter to which the filtrate was collected in a 20 mL scintillation vial. The material was frozen via dry ice/acetone bath and placed onto the lyophilizer to afford the title compound (Ex. 7.7). $^{1}$HNMR (500 MHz, DMSO-$d_6$) δ: 8.36 (s, 1H); 8.22 (s, 1H); 7.99 (s, 1H); 7.88 (s, 1H); 7.25 (s, 1H); 4.48 (d, J=7 Hz, 2H); 4.15 (d, J=7 Hz, 2H); 3.66 (s, 2H); 3.30 (s, 6H); 3.20-3.05 (m, 5H); 2.28-2.10 (m, 6H); 1.36 (s, 3H); MS (EI) m/z: 483 $[M+H]^+$.

Ex. 7.8 to Ex. 7.14 in Table 23 below were prepared from common intermediate I-8 according to Scheme 83 coupled with I-30, I-32, I-33, I-34, I-35, I-36, I-40 respectively.

Ex. 7.15 to Ex. 7.18 in Table 23 below were prepared from common intermediate I-48 and I-49 according to Scheme 83 coupled with I-36.

Ex. 7.15 and Ex. 7.16 were separated by chiral SFC (Column & dimensions: OJ-H, 250 mm×21 mm; Mobile phase A: $CO_2$; Mobile phase B: 1:1 ACN:MeOH with 0.1% $NH_4OH$). Ex. 7.15 retention time: 3.1 min and Ex. 7.16 retention time: 4.1 min.

Ex. 7.17 and Ex. 7.18 were separated by chiral SFC (Column & dimensions: OJ-H, 250 mm×21 mm; Mobile phase A: $CO_2$; Mobile phase B: 1:1 ACN:MeOH with 0.1% $NH_4OH$).

Ex. 7.17 retention time: 5.5 min and Ex. 7.18 retention time: 7.1 min.

Ex. 7.19 to Ex. 7.22 in Table 23 below were prepared from common intermediate I-50 according to Scheme 83 coupled with I-36, then purified by reversed phase HPLC, eluting with water (0.10% TFA)-ACN. The products as TFA salt after reverse phase HPLC were adjusted to PH=8 by adding $NaHCO_3$ solution, extracted with EtOAc. After concentration, the mixture was isolated by TLC (EtOAc) to give Ex. 7.21 and Ex. 7.22 mixture (first peak), Ex. 7.19 (second peak) and Ex. 7.20 (third peak). Ex. 7.21 and Ex. 7.22 mixture then further separated by SFC (Column & dimensions: Chiralpak AD-3 150×4.6 mm; Mobile phase A: $CO_2$; Mobile phase B: ethanol with 0.05% DEA) Ex. 7.21 retention time: 4.96 min; Ex. 7.22 retention time: 6.72 min;

TABLE 23

| Ex | Structure | Name | Exact Mass [M + H]+ |
|---|---|---|---|
| Ex. 7.8 | 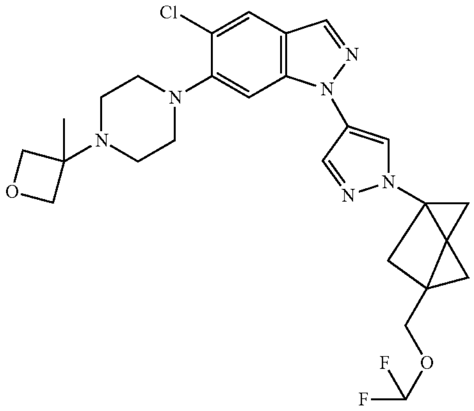 [SMILES: CC1(N2CCN(c3cc4c(cnn4-c4cnn(C56CC7(COC(F)F)CC75C6)c4)cc3Cl)CC2)COC1] | 5-chloro-1-(1-{3-[(difluoromethoxy)methyl]bicyclo[1.1.1]pentan-1-yl}-1H-pyrazol-4-yl)-6-[4-(3-methyloxetan-3-yl)piperazin-1-yl]-1H-indazole | Calc'd 519, found 519 |
| Ex. 7.9 | 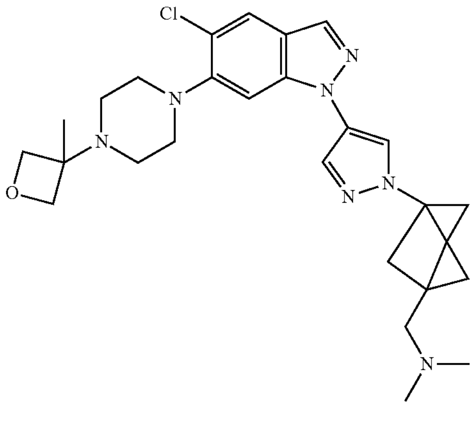 [SMILES: CN(C)CC12CC3(n4cc(-n5ncc6cc(Cl)c(N7CCN(C8(C)COC8)CC7)cc65)cn4)CC13C2] | 1-[3-(4-{5-chloro-6-[4-(3-methyloxetan-3-yl)piperazin-1-yl]-1H-indazol-1-yl}-1H-pyrazol-1-yl)bicyclo[1.1.1]pentan-1-yl]-N,N-dimethylmethanamine | Calc'd 496, found 496 |

TABLE 23-continued

| Ex | Structure | Name | Exact Mass [M + H]+ |
|---|---|---|---|
| Ex. 7.10 | 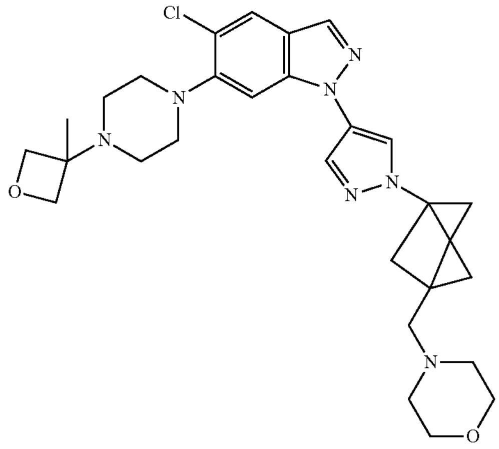 [SMILES: CC1(N2CCN(c3cc4c(cnn4-c4cnn(C56CC7(CN8CCOCC8)CC75C6)c4)cc3Cl)CC2)COC1] | 5-chloro-6-[4-(3-methyloxetan-3-yl)piperazin-1-yl]-1-(1-{3-[(morpholin-4-yl)methyl]bicyclo[1.1.1]pentan-1-yl}-1H-pyrazol-4-yl)-1H-indazole | Calc'd 538, found 538 |
| Ex. 7.11 | 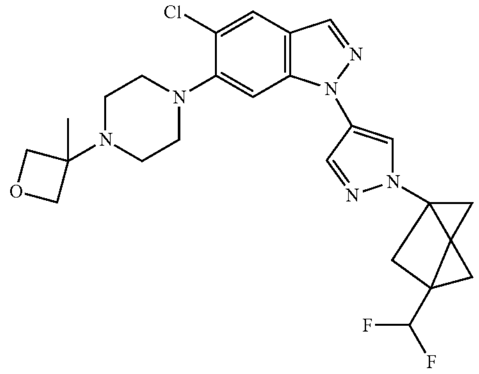 [SMILES: CC1(N2CCN(c3cc4c(cnn4-c4cnn(C56CC7(C(F)F)CC75C6)c4)cc3Cl)CC2)COC1] | 5-chloro-1-{1-[3-(difluoromethyl)bicyclo[1.1.1]pentan-1-yl]-1H-pyrazol-4-yl}-6-[4-(3-methyloxetan-3-yl)piperazin-1-yl]-1H-indazole | Calc'd 489, found 489 |
| Ex. 7.12 | 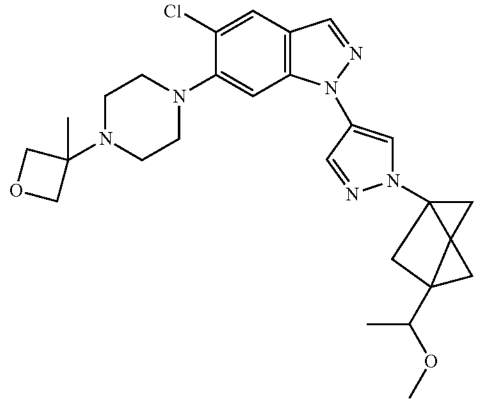 [SMILES: COC(C)C12CC3(n4cc(-n5ncc6cc(Cl)c(N7CCN(C8(C)COC8)CC7)cc65)cn4)CC13C2] | 5-chloro-1-{1-[3-(1-methoxyethyl)bicyclo[1.1.1]pentan-1-yl]-1H-pyrazol-4-yl}-6-[4-(3-methyloxetan-3-yl)piperazin-1-yl]-1H-indazole | Calc'd 497, found 497 |
| Ex. 7.13 | 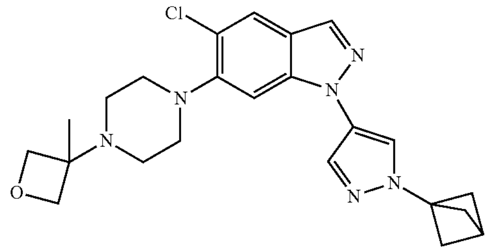 [SMILES: CC1(N2CCN(c3cc4c(cnn4-c4cnn(C56CC(C5)C6)c4)cc3Cl)CC2)COC1] | 1-(1-(bicyclo[1.1.1]pentan-1-yl)-1H-pyrazol-4-yl)-5-chloro-6-(4-(3-methyloxetan-3-yl)piperazin-1-yl)-1H-indazole | Calc'd 439, found 439 |

TABLE 23-continued

| Ex | Structure | Name | Exact Mass [M + H]+ |
|---|---|---|---|
| Ex. 7.14 | 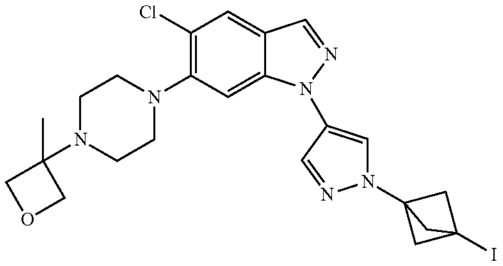 [SMILES: CC1(N2CCN(c3cc4c(cnn4-c4cnn(C56CC(I)(C5)C6)c4)cc3Cl)CC2)COC1] | 5-chloro-1-[1-(3-iodobicyclo[1.1.1]pentan-1-yl)-1H-pyrazol-4-yl]-6-[4-(3-methyloxetan-3-yl)piperazin-1-yl]-1H-indazole | Calc'd 565, found 565 |
| Ex. 7.15 | 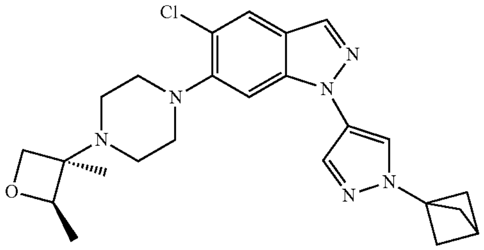 [SMILES: C[C@H]1OC[C@@]1(C)N1CCN(c2cc3c(cnn3-c3cnn(C45CC(C4)C5)c3)cc2Cl)CC1] | 1-[1-(bicyclo[1.1.1]pentan-1-yl)-1H-pyrazol-4-yl]-5-chloro-6-{4-[(2R,3R or 2S,3S)-2,3-dimethyloxetan-3-yl]piperazin-1-yl}-1H-indazole | Calc'd 453, found 453 |
| Ex. 7.16 | 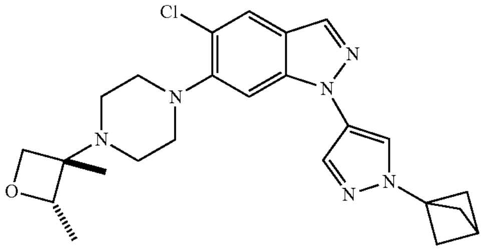 [SMILES: C[C@@H]1OC[C@]1(C)N1CCN(c2cc3c(cnn3-c3cnn(C45CC(C4)C5)c3)cc2Cl)CC1] | 1-(1-(bicyclo[1.1.1]pentan-1-yl)-1H-pyrazol-4-yl)-5-chloro-6-(4-((2S,3S or 2R,3R)-2,3-dimethyloxetan-3-yl)piperazin-1-yl)-1H-indazole | Calc'd 453, found 453 |
| Ex. 7.17 | 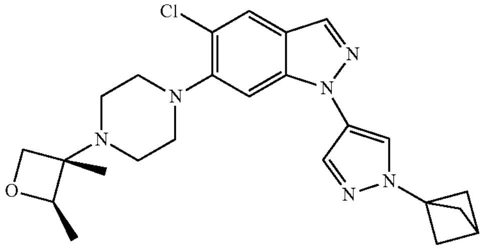 [SMILES: C[C@H]1OC[C@]1(C)N1CCN(c2cc3c(cnn3-c3cnn(C45CC(C4)C5)c3)cc2Cl)CC1] | 1-[1-(bicyclo[1.1.1]pentan-1-yl)-1H-pyrazol-4-yl]-5-chloro-6-{4-[(2R,3S or 2S,3R)-2,3-dimethyloxetan-3-yl]piperazin-1-yl}-1H-indazole | Calc'd 453, found 453 |
| Ex. 7.18 | 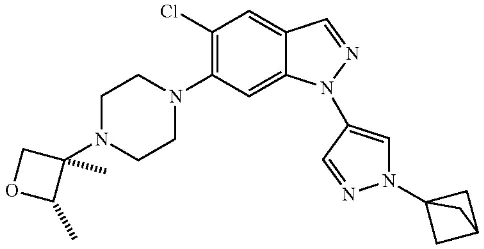 [SMILES: C[C@@H]1OC[C@@]1(C)N1CCN(c2cc3c(cnn3-c3cnn(C45CC(C4)C5)c3)cc2Cl)CC1] | 1-(1-(bicyclo[1.1.1]pentan-1-yl)-1H-pyrazol-4-yl)-5-chloro-6-(4-((2S,3R or 2R,3S)-2,3-dimethyloxetan-3-yl)piperazin-1-yl)-1H-indazole | Calc'd 453, found 453 |
| Ex. 7.19 | 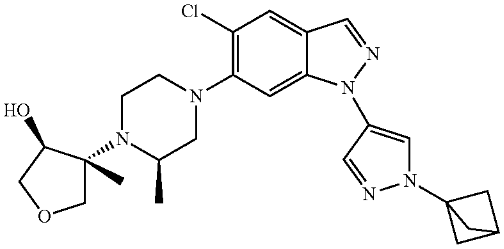 [SMILES: C[C@@H]1CN(c2cc3c(cnn3-c3cnn(C45CC(C4)C5)c3)cc2Cl)CCN1[C@]1(C)COC[C@H]1O] | (3S,4R or 3R,4S)-4-((R)-4-(1-(1-(bicyclo[1.1.1]pentan-1-yl)-1H-pyrazol-4-yl)-5-chloro-1H-indazol-6-yl)-2-melhylpiperazin-1-yl)-4-methyltetrahvdrofuran-3-ol | Calc'd 483, found 483 |

TABLE 23-continued

| Ex | Structure | Name | Exact Mass [M + H]+ |
|---|---|---|---|
| Ex. 7.20 | 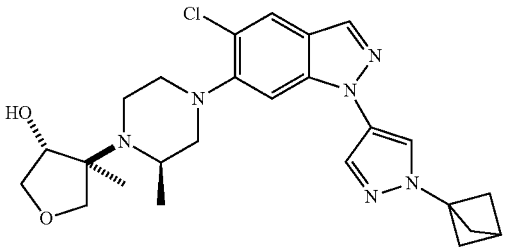 | ((3R,4S or 3S,4R)-4-((R)-4-(1-(1-(bicyclo[1.1.1]pentan-1-yl)-1H-pyrazol-4-yl)-5-chloro-1H-indazol-6-yl)-2-methylpiperazin-1-yl)-4-methyltetrahydrofuran-3-ol | Calc'd 483, found 483 |
| Ex. 7.21 | 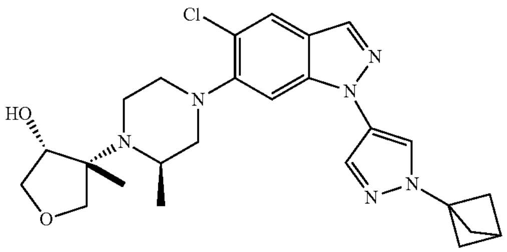 [SMILES: C[C@@H]1CN(c2cc3c(cnn3-c3cnn(C45CC(C4)C5)c3)cc2Cl)CCN1[C@]1(C)COC[C@@H]1O] | (3R.4R or 3S,4S)-4-((R)-4-(1-(1-(bicyclo[1.1.1]pentan-1-yl)-1H-pyrazol-4-yl)-5-chloro-1H-indazol-6-yl)-2-methylpiperazin-1-yl)-4-methyltetrahydrofuran-3-ol | Calc'd 483, found 483 |
| Ex. 7.22 | 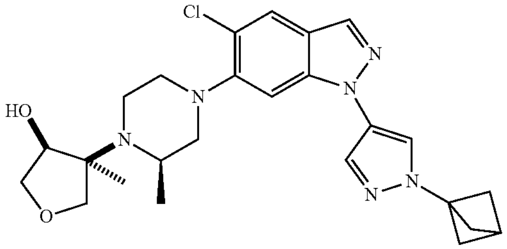 | (3S,4S or 3R,4R)-4-((R)-4-(1-(1-(bicyclo[1.1.1]pentan-1-yl)-1H-pyrazol-4-yl)-5-chloro-1H-indazol-6-yl)-2-methylpiperazin-1-yl)-4-methyltetrahydrofuran-3-ol | Calc'd 483, found 483 |

Preparation of Example 8.1: (3R,4R or 3S, 4S)-4-(4-(1-(1-(bicyclo[1.1.1]pentan-1-yl)-1H-pyrazol-4-yl)-5-chloro-1H-indazol-6-yl)piperazin-1-yl)tetrahydrofuran-3-ol Scheme 84

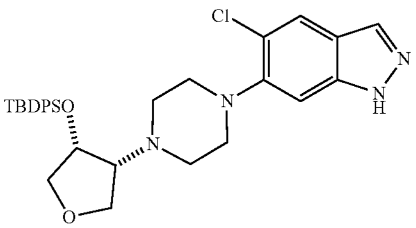

I-52

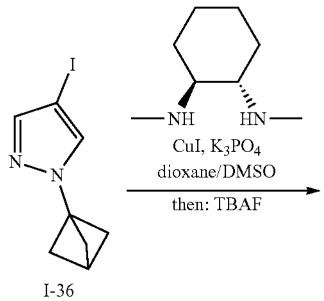

I-36

-continued

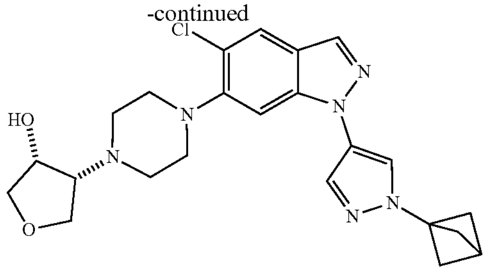

Ex. 8.1

I-52 (0.10 g, 0.18 mmol), I-36 (0.060 g, 0.22 mmol), copper iodide (10 mg, 0.053 mmol), and potassium phosphate (0.113 g, 0.535 mmol) were weighed into vial and placed under $N_2$. Degassed dioxane (1.5 ml), DMSO (0.15 ml) and N,N'-dimethyl-1,2-cyclohexanediamine (9.8 µl, 0.062 mmol) were added via syringes. The reaction heated to 90° C. and allowed to stir for 16 h. The reaction was cooled to room temperature then TBAF (1.0 ml, 1.0 mmol, 1M in THF) was added via syringe and the reaction was allowed to stir for an additional 6 h. The reaction was cooled, diluted with water (5 mL) and sat. $NaHCO_3$(10 mL) then extracted with 3:1 $CHCl_3$:IPA (4×10 mL). The combined organic extract was dried over $Na_2SO_4$, filtered and concentrated in vacuo. The residue was purified by column chromatography on silica gel (100% hexanes for 3 column volumes then switch to 20% MeOH in DCM, 0-100% gradient). The compound was further purified by reversed phase HPLC, eluting with water (0.1% TFA)-ACN, then free based with sat. $NaHCO_3$ to give the title compound (Ex. 8.1). $^1$H NMR (500 MHz, DMSO-$d_6$) δ 8.37 (s, 1H), 8.16 (s, 1H), 7.98 (s, 1H), 7.93 (s, 1H), 7.24 (s, 1H), 4.41-4.24 (m, 1H), 4.30-4.15 (m, 1H), 3.94-3.78 (m, 2H), 3.69 (d, J=9.5 Hz, 1H), 3.62 (dd, J=10.1, 7.4 Hz, 1H), 3.18-3.03 (m, 4H), 2.92-2.74 (m, 2H), 2.74-2.68 (m, 1H), 2.66 (s, 1H), 2.58-2.47 (m, 1H) 2.31 (s, 6H). MS (EI) m/z 455 $[M+H]^+$.

Ex. 8.2 in Table 24 was prepared from common intermediate I-52 according to Scheme 84 by using the corresponding starting materials

TABLE 24

| Ex | Structure | Name | Exact Mass [M + H]+ |
|---|---|---|---|
| Ex. 8.2 | 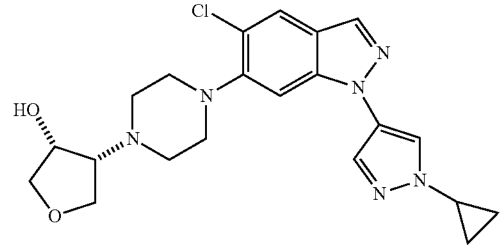 | (3S,4S or 3R,4R)-4-{4-[5-chloro-1-(1-cyclopropyl-1H-pyrazol-4-yl)-1H-indazol-6-yl]piperazin-1-yl}oxolan-3-ol | Calc'd 429, found 429 |

Preparation of Example 9.1: (3R,4R or 3S, 4S)-4-(4-(1-(1-(bicyclo[1.1.1]pentan-1-yl)-1H-pyrazol-4-yl)-5-chloro-1H-indazol-6-yl)piperazin-1-yl)-4-methyltetrahydrofuran-3-ol Scheme 85

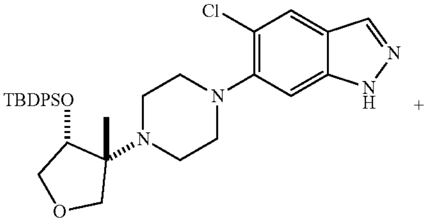

I-57

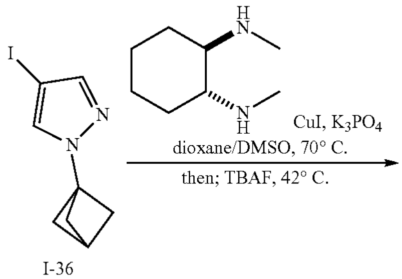

I-36

-continued

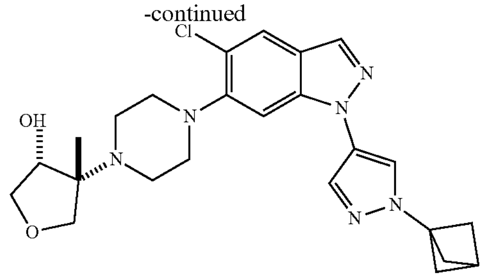

Ex. 9.1

Intermediate I-57 (150 mg, 0.261 mmol), intermediate I-36 (88 mg, 0.34 mmol), copper(I) iodide (29.8 mg, 0.156 mmol), (1R,2R)—N1,N2-dimethylcyclohexane-1,2-diamine (29.7 mg, 0.209 mmol), and potassium phosphate tribasic (194 mg, 0.913 mmol) were combined in a dry microwave vial with a stir bar, purged with nitrogen gas, and solvated in 3.5 mL of dioxane and 0.4 mL of DMSO. The vial was sealed and the mixture was heated to 70° C. and stirred overnight. The next day, the reaction was cooled to 42° C. and TBAF (0.782 mmol, 0.782 mL of 1.0 M solution in THF) was added via syringe. The reaction was stirred for another 6 hours. Upon completion, the reaction was diluted with DCM (20 mL) and the organic layer was washed two times with brine (20 mL). The resulting organic layer was dried over $Na_2SO_4$, filtered, concentrated, and directly purified via silica gel column chromatography using a gradient of 5-20% of 3:1 (EtOAc:EtOH) in hexanes to afford the title compound (Ex. 9.1). $^1$H NMR (499 MHz, DMSO-$d_6$) δ 8.35 (s, 1H), 8.16 (s, 1H), 7.98 (s, 1H), 7.93 (s, 1H), 7.24 (s, 1H), 4.32 (s, 1H), 4.00-3.92 (m, 1H), 3.80 (s, 1H), 3.70 (d, J=9.7 Hz, 1H), 3.63 (d, J=7.3 Hz, 1H), 3.54 (d, J=7.3 Hz, 1H), 3.12 (s, 4H), 2.80-2.69 (m, 2H), 2.66 (s, 1H), 2.55-2.48 (m, 2H), 2.31 (s, 6H), 1.05 (s, 3H). MS (EI) m/z 469 $[M+H]^+$.

Preparation of Example 10.1: 1-(1-(bicyclo[1.1.1]pentan-1-yl)-1H-pyrazol-4-yl)-5-chloro-6-(4-((3R,4R or 3S,4S)-4-methoxytetrahydrofuran-3-yl)piperazin-1-yl)-1H-indazole Scheme 86

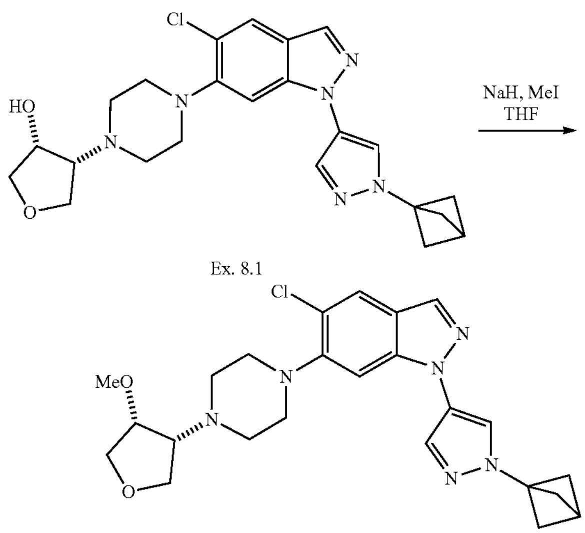

Ex. 8.1

Ex. 10.1

Ex. 8.1 (18 mg, 0.040 mmol) and sodium hydride (15.8 mg, 0.396 mmol, 60% in mineral oil) were charged into a 2-5 mL microwave vial under $N_2$ and cooled to 0° C. in an ice bath then THF (0.4 ml) was added. The reaction was stirred at 0° C. for 30 min then iodomethane (0.025 ml, 0.40 mmol) was added dropwise via syringe. The reaction was allowed to warm to room temperature and stirred for 1 h. The reaction was cooled to 0° C. and carefully quenched with MeOH (1 mL) then concentrated. The resulting oil was purified via reverse phase HPLC, eluting with water (0.1% TFA)-ACN, then free based with sat. $NaHCO_3$ to give the title compound (Ex. 10.1). $^1H$ NMR (500 MHz, DMSO-$d_6$) δ 8.36 (s, 1H), 8.15 (s, 1H), 7.99 (s, 1H), 7.92 (s, 1H), 7.27 (s, 1H), 4.01-3.79 (m, 3H), 3.79-3.68 (m, 1H), 3.67-3.44 (m, 2H), 3.27 (s, 3H), 3.15-3.00 (m, 4H), 2.89-2.67 (m, 3H), 2.66 (s, 1H), 2.59-2.50 (m, 1H), 2.30 (s, 6H). MS (EI) m/z 469 $[M+H]^+$.

Ex. 10.2 in Table 25 was prepared from Ex. 9.1 according to Scheme 86

Preparation of Example 11.1: 1-(1-(bicyclo[1.1.1]pentan-1-yl)-1H-pyrazol-4-yl)-5-chloro-6-(4-((3R4S or 3S,4R)-4-fluorotetrahydrofuran-3-yl)piperazin-1-yl)-1H-indazole Scheme 87

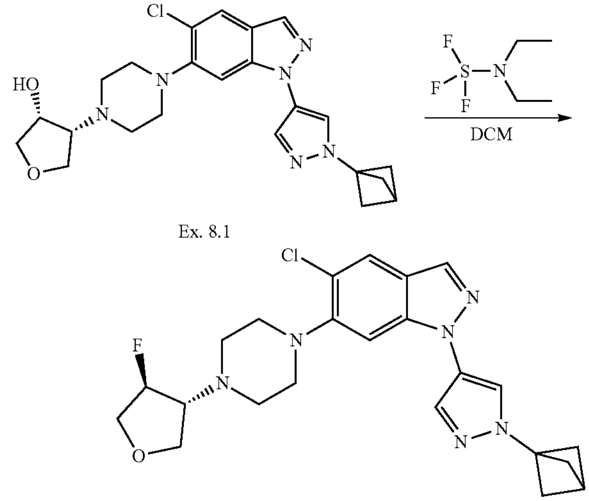

Ex. 8.1

Ex. 11.1

Ex. 8.1 (40 mg, 0.088 mmol) was dissolved in DCM (0.8 mL) in a 1 dram vial under $N_2$. The solution was cooled to −78° C. in a dry ice/acetone bath. Diethylaminosulfur trifluoride (0.023 mL, 0.18 mmol) was added via syringe. The reaction was allowed to stir at −78° C. for 1.5 hours then a second addition of diethylaminosulfur trifluoride (0.023 mL, 0.176 mmol) was added and the reaction was allowed to stir for 18 h with the dry ice bath slowly warming to room temperature. The reaction was quenched at 0° C. with sat. $NaHCO_3$(5 mL) then extracted with 3:1 $CHCl_3$:IPA (3×10 mL), dried over $Na_2SO_4$ and concentrated in vacuo. The resulting oil was purified via reverse phase HPLC, eluting with water (0.10% TFA)-ACN to afford the title compound. $^1H$ NMR (500 MHz, DMSO-$d_6$) δ 8.37 (s, 1H), 8.19 (s, 1H), 8.00 (s, 1H), 7.98 (s, 1H), 7.26 (s, 1H), 5.60 (d, J=52.1 Hz, 1H) 4.29-4.13 (m, 1H), 4.08-3.62 (m, 8H), 3.41-3.00 (m, 4H), 2.67 (s, 1H), 2.31 (s, 6H). MS (EI) m/z: 457 $[M+H]^+$.

TABLE 25

| Ex | Structure | Name | Exact Mass [M + H]+ |
|---|---|---|---|
| Ex. 10.2 | 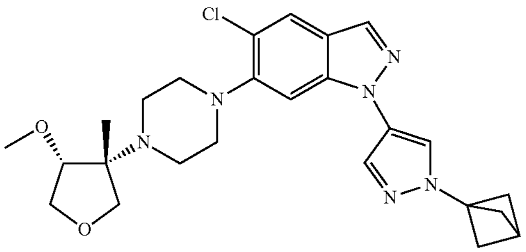 [SMILES: CO[C@H]1COC[C@@]1(C)N1CCN(c2cc3c(cnn3-c3cnn(C45CC(C4)C5)c3)cc2Cl)CC1] | 1-[1-(bicyclo[1.1.1]pentan-1-yl)-1H-pyrazol-4-yl]-5-chloro-6-{4-[(3R,4R or 3S,4S)-4-methoxy-3-methyloxolan-3-yl]piperazin-1-yl}-1H-indazole | Calc'd 483, fouind 483 |

Preparation of Example 12.1 and 12.2: (3R4R or 3S,4S)-4-(4-(5-chloro-1-(1-(3-methoxybicyclo[1.1.1]pentan-1-yl)-1H-pyrazol-4-yl)-1H-indazol-6-yl)piperazin-1-yl)-4-methyltetrahydrofuran-3-ol and (3S,4S or 3R,4R)-4-(4-(5-chloro-1-(1-(3-methoxybicyclo[1.1.1]pentan-1-yl)-1H-pyrazol-4-yl)-1H-indazol-6-yl)piperazin-1-yl)-4-methyltetrahydrofuran-3-ol Scheme 88

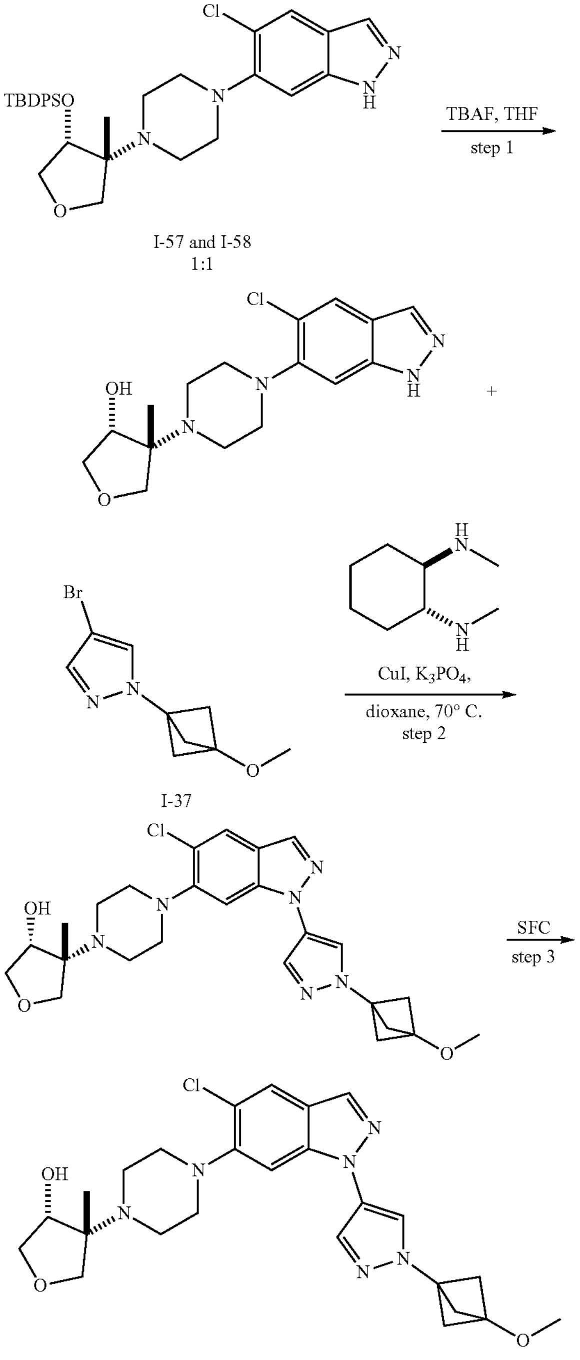

I-57 and I-58
1:1

I-37

Ex. 12.1

-continued

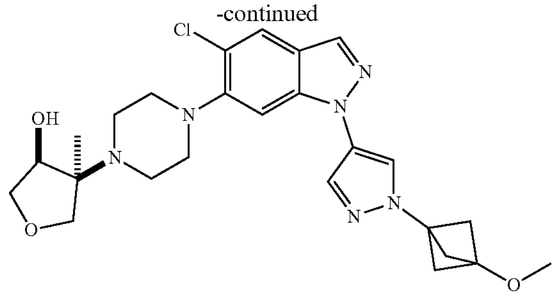

Ex. 12.2

Step 1: (3R,4R and 3S,4S)-4-(4-(5-chloro-1H-indazol-6-yl)piperazin-1-yl)-4-methyltetrahydrofuran-3-ol Racemic intermediate I-57/I-58 (2.0 g, 3.5 mmol) was solvated in THF (25 mL) in a 100 mL round bottom flask with magnetic stir bar. Then, TBAF (6.95 mmol, 6.95 mL of 1 M solution in THF) was added. The mixture was stirred at room temperature for 6 hours. Then, the reaction was diluted with DCM (50 mL) and washed four times with 1:1 brine: water (50 mL×4). The organic layer was collected, dried over $Na_2SO_4$, filtered, and concentrated. The residue was then purified by silica gel column chromotography using a gradient of 0-100% of 3:1 (EtOAc:EtOH) in hexanes to afford (3R,4R and 3S,4S)-4-(4-(5-chloro-1H-indazol-6-yl) piperazin-1-yl)-4-methyltetrahydrofuran-3-ol. MS (EI) m/z: 337 $[M+H]^+$.

Step 2: (3R4R and 3S,4S)-4-(4-(5-chloro-1-(1-(3-methoxybicyclo[1.1.1]pentan-1-yl)-1H-pyrazol-4-yl)-1H-indazol-6-yl)piperazin-1-yl)-4-methyltetrahydrofuran-3-ol (3R,4R and 3S,4S)-4-(4-(5-chloro-1H-indazol-6-yl)piperazin-1-yl)-4-methyltetrahydrofuran-3-ol (80 mg, 0.24 mmol), I-37 (48 mg, 0.20 mmol), copper(I) iodide (22.6 mg, 0.119 mmol), (1R,2R)—N1,N2-dimethylcyclohexane-1,2-diamine (27 mg, 0.19 mmol), and potassium phosphate tribasic (135 mg, 0.636 mmol) were combined in a dry microwave vial with stir bar. The vessel was purged with nitrogen gas and then 1,4-dioxane (2.5 mL) was added. The mixture was heated to 70° C. and stirred overnight. Then, the crude material was cooled and filtered through a plug of celite using EtOAc as eluent. The filtrate was then concentrated and purified using reverse phase HPLC purification, eluting with water (0.10% TFA)-ACN to afford (3R,4R and 3S,4S)-4-(4-(5-chloro-1-(1-(3-methoxybicyclo[1.1.1]pentan-1-yl)-1H-pyrazol-4-yl)-1H-indazol-6-yl)piperazin-1-yl)-4-methyltetrahydrofuran-3-ol as a TFA salt. MS (EI) m/z: 499 $[M+H]^+$.

Step 3: (3R,4R or 3S,4S)-4-(4-(5-chloro-1-(1-(3-methoxybicyclo[1.1.1]pentan-1-yl)-1H-pyrazol-4-yl)-1H-indazol-6-yl)piperazin-1-yl)-4-methyltetrahydrofuran-3-ol and (3S,4S or 3R,4R)-4-(4-(5-chloro-1-(1-(3-methoxybicyclo[1.1.1]pentan-1-yl)-1H-pyrazol-4-yl)-1H-indazol-6-yl)piperazin-1-yl)-4-methyltetrahydrofuran-3-ol (Ex. 12.1 and Ex. 12.2)

Racemic sample of (3R,4R and 3S,4S)-4-(4-(5-chloro-1-(1-(3-methoxybicyclo[1.1.1]pentan-1-yl)-1H-pyrazol-4-yl)-1H-indazol-6-yl)piperazin-1-yl)-4-methyltetrahydrofuran- 3-ol was resolved using chiral SFC conditions as follows: Column & dimensions (mm): AS-H, 21×250. Mobile phase A: $CO_2$; Mobile phase B: MeOH with 0.1% $NH_4OH$ to afford the title compounds (examples 12.1 and 12.2).

Example 12.1

$^1$H NMR (499 MHz, DMSO-$d_6$) δ 8.38 (s, 1H), 8.17 (s, 1H), 8.02 (s, 1H), 7.93 (s, 1H), 7.24 (s, 1H), 4.32 (s, 1H), 4.01-3.92 (m, 1H), 3.80 (s, 1H), 3.73-3.66 (m, 1H), 3.64 (d, J=7.3 Hz, 1H), 3.58-3.52 (m, 1H), 3.31 (s, 3H), 3.13 (s, 4H), 2.78-2.70 (m, 2H), 2.55-2.48 (m, 2H), 2.44 (s, 6H), 1.05 (s, 3H); MS (EI) m/z: 499 $[M+H]^+$. Retention time: 2.5 min Example 12.2

$^1$H NMR (499 MHz, DMSO-$d_6$) δ 8.38 (s, 1H), 8.17 (s, 1H), 8.02 (s, 1H), 7.93 (s, 1H), 7.24 (s, 1H), 4.32 (s, 1H), 4.00-3.94 (m, 1H), 3.80 (s, 1H), 3.70 (d, J=9.7 Hz, 1H), 3.64 (d, J=7.4 Hz, 1H), 3.55 (d, J=7.3 Hz, 1H), 3.31 (s, 3H), 3.19-3.06 (m, 4H), 2.79-2.69 (m, 2H), 2.55-2.48 (m, 2H), 2.44 (s, 6H), 1.05 (s, 3H); MS (EI) m/z: 499 $[M+H]^+$. Retention time: 3.2 min Preparation of Example 12.3: (3R,4R or 3S,4S)-4-(4-(5-chloro-1-(1-(3-fluorobicyclo[1.1.1]pentan-1-yl)-1H-pyrazol-4-yl)-1H-indazol-6-yl)piperazin-1-yl)-4-methyltetrahydrofuran-3-ol Scheme 89

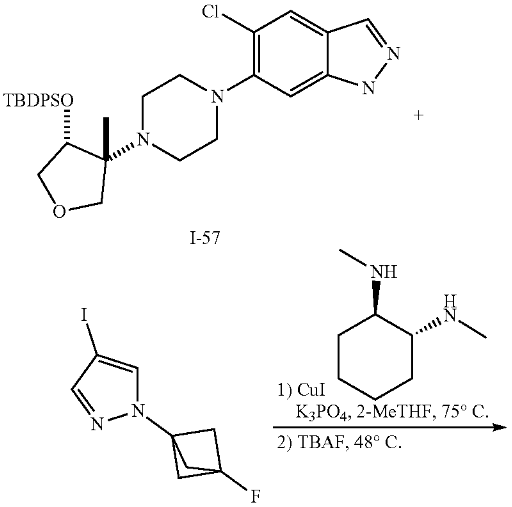

I-57

I-38

-continued

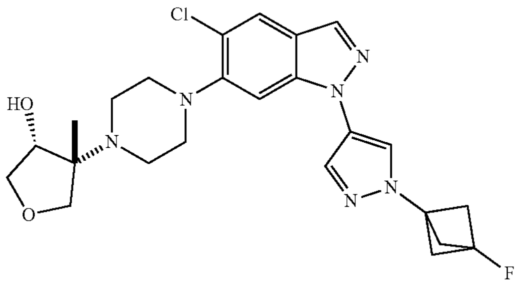

Ex. 12.3

A reaction vessel was charged with CuI (26.7 mg, 0.140 mmol), 2-MeTHF (1.3 mL) and trans-N1,N2-dimethylcyclohexane-1,2-diamine (25.9 μL, 0.164 mmol) under $N_2$ and the resulting solution was stirred for 15 min at rt. This solution was then added to a mixture of $K_3PO_4$ (255 mg, 1.2 mmol), I-57 (230 mg, 0.40 mmol) and I-38 (111 mg, 0.40 mmol). The resulting mixture was stirred at 75° C. for 18 h. The reaction was then cooled to 48° C. and TBAF (1.0 M in THF, 1.2 mL, 1.2 mmol) was added. The mixture was stirred at 48° C. for 2 h, then cooled to rt, and water/2-MeTHF were added. The layers were separated. The aqueous layer was extracted with 2-MeTHF. The combined organic layer was washed with 0.5M aqueous trisodium EDTA salt, water and brine. The resulting organic layer was dried over $Na_2SO_4$, filtered, and concentrated under reduced pressure. The residue was purified by silica gel chromatography (0 to 100% ethyl acetate in hexane) to give the title compound (Ex. 12.3). $^1$H NMR (499 MHz, Methanol-$d_4$) δ 8.22 (s, 1H), 8.08 (s, 1H), 7.98 (s, 1H), 7.85 (s, 1H), 7.20 (s, 1H), 4.10 (dd, J=9.9, 3.3 Hz, 1H), 3.96-3.85 (m, 2H), 3.81 (d, J=7.4 Hz, 1H), 3.66 (d, J=7.4 Hz, 1H), 3.18 (br s, 4H), 2.85-2.90 (m, 2H), 2.74-2.75 (m, 6H), 2.62-2.69 (m, 2H), 1.18 (s, 3H); MS (EI) m/z: 487 $[M+H]^+$.

The compound in Table 26 below were prepared from common intermediate I-57 according to Scheme 89 by using I-28, 1-29, 1-39, 1-21, 1-22 and corresponding commercial starting materials

TABLE 26

| Ex | Structure | Name | Exact Mass [M + H]+ |
|---|---|---|---|
| Ex. 12.4 | 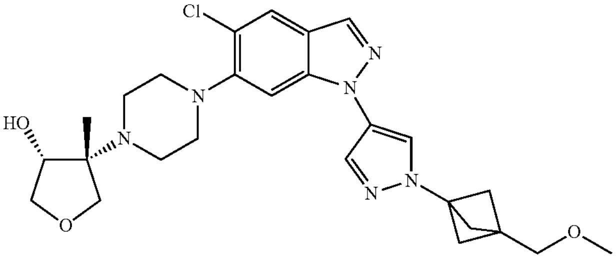 [SMILES: COCC12CC(n3cc(-n4ncc5cc(Cl)c(N6CCN([C@]7(C)COC[C@@H]7O)CC6)cc54)cn3)(C1)C2] | (3R,4R or 3S,4S)-4-[4-(5-chloro-1-{1-[3-(methoxymethyl) bicyclo[1.1.1]pentan-1-yl]-1H-pyrazol-4-yl}-1H-indazol-6-yl)piperazin-1-yl]-4-methyloxolan-3-ol | Calc'd 513, found 513 |

TABLE 26-continued

| Ex | Structure | Name | Exact Mass [M + H]+ |
| --- | --- | --- | --- |
| Ex. 12.5 | 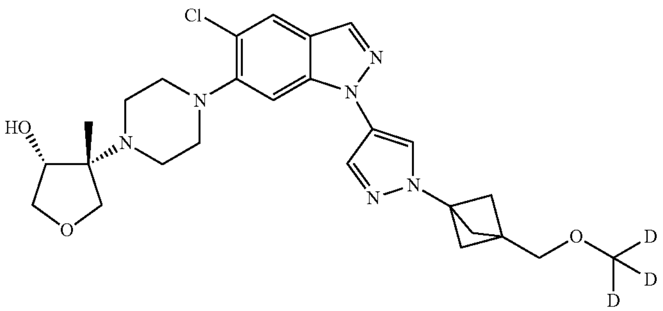 [SMILES: [2H]C([2H])([2H])OCC12CC(n3cc(-n4ncc5cc(Cl)c(N6CCN([C@]7(C)COC[C@@H]7O)CC6)cc54)cn3)(C1)C2] | (3R.4R or 3S,4S)-4-(4-{5-chloro-1-[1-(3-{[(~2~H_3_)methyl-oxy]methyl}bicyclo[1.1.1]pentan-1-yl)-1H-pyrazol-4-yl]-1H-indazol-6-yl}piperazin-1-yl)-4-methyloxolan-3-ol | Calc'd 516, found 516 |
| Ex. 12.6 | 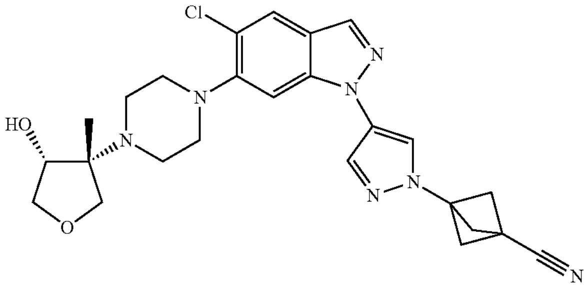 [SMILES: C[C@@]1(N2CCN(c3cc4c(cnn4-c4cnn(C56CC(C#N)(C5)C6)c4)cc3Cl)CC2)COC[C@@H]1O] | 3-[4-(5-chloro-6-{4-[(3R,4R or 3S,4S)-4-hydroxy-3-methyloxolan-3-yl]piperazin-1-yl}-1H-indazol-1-yl)-1H-pyrazol-1-yl]bicyclo[1.1.1]pentane-1-carbonitrile | Calc'd 494, found 494 |
| Ex. 12.7 | 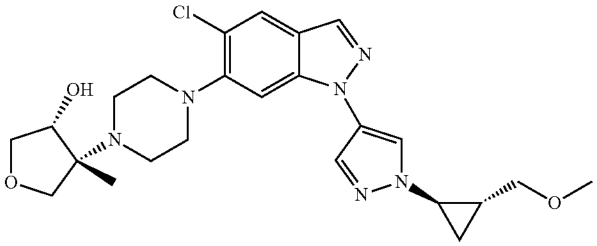 [SMILES: COC[C@@H]1C[C@H]1n1cc(-n2ncc3cc(Cl)c(N4CCN([C@]5(C)COC[C@@H]5O)CC4)cc32)cn1] | (3R,4R or 3S,4S)-4-(4-{5-chloro-1-[1-(2,2,2-trifluoroethyl)-1H-pyrazol-4-yl]-1H-indazol-6-yl}piperazin-1-yl)-4-methyloxolan-3-ol | Calc'd 487, found 487 |
| Ex. 12.8 | 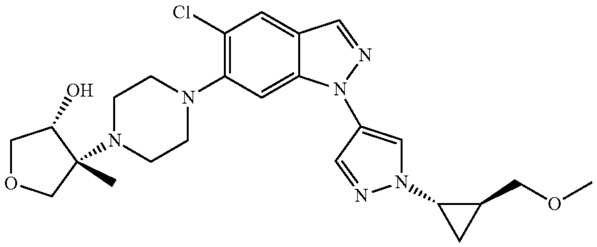 [SMILES: COC[C@H]1C[C@@H]1n1cc(-n2ncc3cc(Cl)c(N4CCN([C@]5(C)COC[C@@H]5O)CC4)cc32)cn1] | (3R.4R or 3S,4S)-4-[4-(5-chloro-1-{1-[(1S,2S)-2-(methoxymethyl)cyclopropyl]-1H-pyrazol-4-yl}-1H-indazol-6-yl)piperazin-1-yl]-4-methyloxolan-3-ol | Calc'd 487, found 487 |
| Ex. 12.9 | 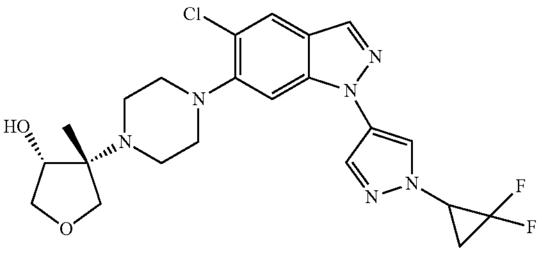 [SMILES: C[C@@]1(N2CCN(c3cc4c(cnn4-c4cnn(C5CC5(F)F)c4)cc3Cl)CC2)COC[C@@H]1O] | (3R,4R or 3S,4S)-4-(4-{5-chloro-1-[1-(2,2-difluorocyclopropyl)-1H-pyrazol-4-yl]-1H-indazol-6-yl}piperazin-1-yl)-4-methyloxolan-3-ol | Calc'd 479, found 479 |

TABLE 26-continued

| Ex | Structure | Name | Exact Mass [M + H]+ |
|---|---|---|---|
| Ex. 12.10 | 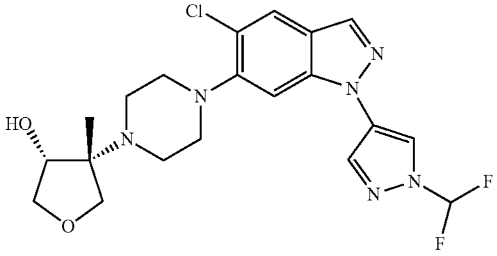 [SMILES: C[C@@]1(N2CCN(c3cc4c(cnn4-c4cnn(C(F)F)c4)cc3Cl)CC2)COC[C@@H]1O] | (3R,4R or 3S,4S)-4-(4-{5-chloro-1-[1-(difluoromethyl)-1H-pyrazol-4-yl]-1H-indazol-6-yl}piperazin-1-yl)-4-methyloxolan-3-ol | Calc'd 453, found 453 |
| Ex. 12.11 | 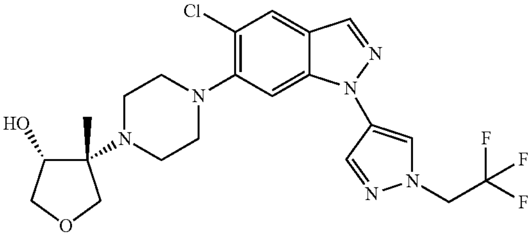 [SMILES: C[C@@]1(N2CCN(c3cc4c(cnn4-c4cnn(CC(F)(F)F)c4)cc3Cl)CC2)COC[C@@H]1O] | (3R,4R or 3S,4S)-4-(4-{5-chloro-1-[1-(2,2,2-trifluoroethyl)-1H-pyrazol-4-yl]-1H-indazol-6-yl}piperazin-1-yl)-4-methyloxolan-3-ol | Calc'd 485, found 485 |
| Ex. 12.12 | 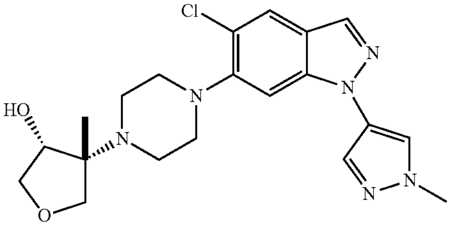 [SMILES: Cn1cc(-n2ncc3cc(Cl)c(N4CCN([C@]5(C)COC[C@@H]5O)CC4)cc32)cn1] | (3R,4R or 3S,4S)-4-{4-[5-chloro-1-(1-methyl-1H-pyrazol-4-yl)-1H-indazol-6-yl]piperazin-1-yl}-4-methyloxolan-3-ol | Calc'd 417, found 417 |

Preparation of Example 13.1 and 13.2: (3R,4R or 3S,4R or 3R,4S or 3S,4S)-4-(4-(1-(1-(bicyclo[1.1.1]pentan-1-yl)-1H-pyrazol-4-yl)-5-chloro-1H-indazol-6-yl)piperazin-1-yl)-3,4-dimethyltetrahydrofuran-3-ol and (3S,4R or 3R,4R or 3S,4S or 3R,4S)-4-(4-(1-(1-(bicyclo[1.1.1]pentan-1-yl)-1H-pyrazol-4-yl)-5-chloro-1H-indazol-6-yl)piperazin-1-yl)-3,4-dimethyltetrahydrofuran-3-ol (Ex. 13.1 and Ex. 13.2)

Scheme 90

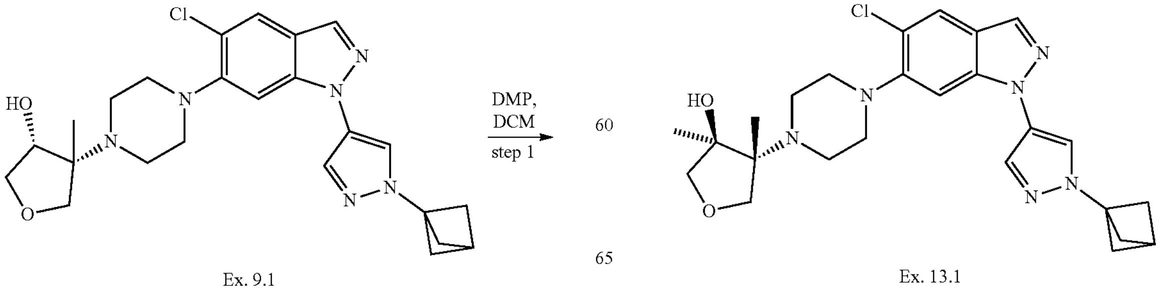

Ex. 9.1

Ex. 13.1

-continued

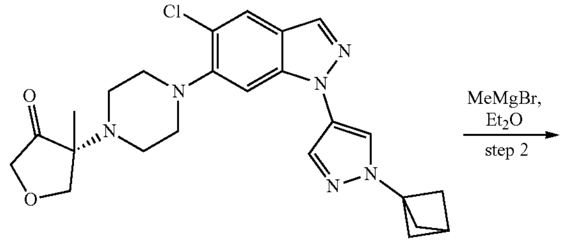

-continued

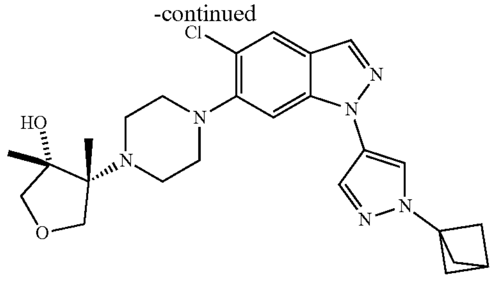

Ex. 13.2

Step 1: (R or S)-4-(4-(1-(1-(bicyclo[1.1.1]pentan-1-yl)-1H-pyrazol-4-yl)-5-chloro-1H-indazol-6-yl)piperazin-1-yl)-4-methyldihydrofuran-3(2H)-one To a solution of Ex. 9.1 (400 mg, 0.853 mmol) in DCM (8.5 mL) was added Dess Martin periodinane (362 mg, 0.853 mmol). The reaction was stirred for 3 h at rt. The reaction was diluted with DCM and quenched with saturated aqueous $NaHCO_3$ and $Na_2S_2O_3$ solution. The mixture was stirred for 30 min, then the layers were separated. The organic layer was collected, dried over $Na_2SO_4$, filtered, and concentrated under reduced pressure. The residue was purified by silica gel chromatography (0 to 100% hexane in EtOAc) to give (R or S)-4-(4-(1-(1-(bicyclo[1.1.1]pentan-1-yl)-1H-pyrazol-4-yl)-5-chloro-1H-indazol-6-yl)piperazin-1-yl)-4-methyldihydrofuran-3(2H)-one. MS (EI) m/z: 467 $[M+H]^+$.

Step 2: (3R,4R or 3S,4R or 3R,4S or 3S,4S)-4-(4-(1-(1-(bicyclo[1.1.1]pentan-1-yl)-1H-pyrazol-4-yl)-5-chloro-1H-indazol-6-yl)piperazin-1-yl)-3,4-dimethyltetrahydrofuran-3-ol and (3S,4R or 3R,4R or 3S,4S or 3R,4S)-4-(4-(1-(1-(bicyclo[1.1.1]pentan-1-yl)-1H-pyrazol-4-yl)-5-chloro-1H-indazol-6-yl)piperazin-1-yl)-3,4-dimethyltetrahydrofuran-3-ol (Ex. 13.1 and Ex. 13.2)

To a solution of (R or S)-4-(4-(1-(1-(bicyclo[1.1.1]pentan-1-yl)-1H-pyrazol-4-yl)-5-chloro-TH-indazol-6-yl)piperazin-1-yl)-4-methyldihydrofuran-3(2H)-one (90 mg, 0.19 mmol) in $Et_2O$ (6.4 mL) was added methylmagnesium bromide (3M $Et_2O$ solution, 128 μL, 0.385 mmol) dropwise at 0° C. The reaction was stirred at rt for 3 h. The mixture was diluted with EtOAc and sat. aq. $NH_4Cl$ solution. The organic layer was washed with brine, dried over $Na_2SO_4$, filtered and concentrated under reduced pressure. The residue was purified by silica gel column chromatography (0 to 100% acetone in hexanes) to give a mixture of two isomers, which was subjected to SFC chiral separation (column & dimensions: AS-H, 21×250 mm; Mobile phase A: $CO_2$; Mobile phase B: MeOH with 0.1% $NH_4OH$) to afford the title compounds (Ex. 13.1 and Ex. 13.2).

Example 13.1

$^1H$ NMR (499 MHz, Methanol-$d_4$) δ 8.18 (s, 1H), 8.09 (s, 1H), 7.94 (s, 1H), 7.87 (s, 1H), 7.20 (s, 1H), 4.00 (d, J=7.8 Hz, 1H), 3.87 (s, 2H), 3.72 (d, J=7.8 Hz, 1H), 3.19 (s, 4H), 2.98-2.92 (m, 2H), 2.73-2.64 (m, 3H), 2.41 (s, 6H), 1.36 (s, 3H), 1.28 (s, 3H); MS (EI) m/z: 483 $[M+H]^+$. Retention time: 5.6 min.

Example 13.2

$^1H$ NMR (499 MHz, Methanol-$d_4$) δ 8.19-8.15 (m, 1H), 8.10-8.06 (m, 1H), 7.93 (s, 1H), 7.85 (d, J=1.7 Hz, 1H), 7.15 (s, 1H), 3.88-3.79 (m, 3H), 3.76 (d, J=7.9 Hz, 1H), 3.68 (d, J=8.2 Hz, 1H), 3.12 (s, 5H), 2.98 (s, 2H), 2.69 (s, 1H), 2.41 (s, 6H), 1.48-1.44 (m, 3H), 1.29 (s, 3H); MS (EI) m/z: 483 $[M+H]^+$. Retention time: 7.6 min.

Preparation of examples 14.1 and 14.2: (3R,4R or 3S,4S)-4-(4-(1-(1-(bicyclo[1.1.1]pentan-1-yl)-1H-pyrazol-4-yl)-5-chloro-1H-indazol-6-yl)piperazin-1-yl)-4-methyltetrahydrofuran-3-carbonitrile (Ex. 14.1) and (3S,4R or 3R,4S)-4-(4-(1-(1-(bicyclo[1.1.1]pentan-1-yl)-1H-pyrazol-4-yl)-5-chloro-1H-indazol-6-yl)piperazin-1-yl)-4-methyltetrahydrofuran-3-carbonitrile (Ex. 14.2

Scheme 91

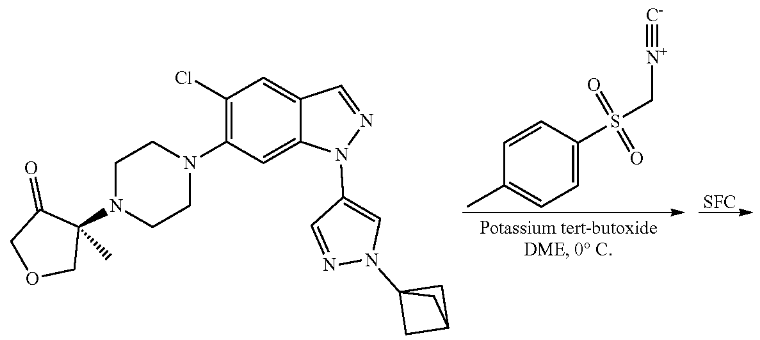

-continued

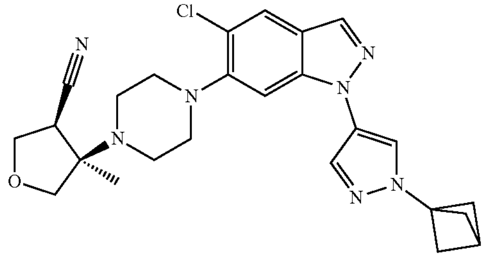

Ex. 14.1

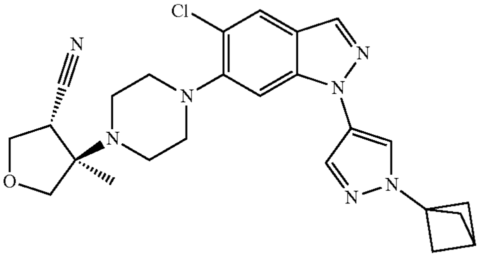

Ex. 14.2

Tosylmethyl isocyanide (53.3 mg, 0.273 mmol) was dissolved in 1,2-dimethoxyethane (600 µl) in a 4 mL vial followed by addition of potassium tert-butoxide (61.3 mg, 0.546 mmol). The solution was stirred at room temperature for 5 minutes. (S or R)-4-(4-(1-(1-(bicyclo[1.1.1]pentan-1-yl)-1H-pyrazol-4-yl)-5-chloro-1H-indazol-6-yl)piperazin-1-yl)-4-methyldihydrofuran-3(2H)-one (85 mg, 0.182 mmol, from Scheme 90, step 1) was then added and the reaction was allowed to stir at room temperature overnight. The reaction was partitioned between water and 3:1 $CHCl_3$:IPA and the organic layer was separated using a phase separator, concentrated and purified using an Isco Combiflash purification system with silica gel and a gradient of 0-10% methanol in dichloromethane. The desired fractions were pooled and concentrated to give desired product as a mixture of cis and trans isomers. The mixture was subjected to SFC chiral separation (column & dimensions: OJ-H, 250 mm×21 mm; Mobile phase A: $CO_2$; Mobile phase B: MeOH with 0.1% $NH_4OH$) to afford the title compounds (examples 14.1 and 14.2).

Example 14.1

$^1$H NMR (500 MHz, DMSO-$d_6$) δ 8.40 (s, 1H), 8.17 (s, 1H), 8.00 (s, 1H), 7.94 (s, 1H), 7.25 (s, 1H), 4.16 (dd, J=9.4, 6.8 Hz, 1H), 4.07 (d, J=9.5 Hz, 1H), 3.78 (d, J=7.9 Hz, 1H), 3.66 (d, J=7.7 Hz, 1H), 3.56 (d, J=4.7 Hz, 1H), 3.23-3.16 (m, 2H), 3.13-3.06 (m, 2H), 2.81-2.73 (m, 2H), 2.68-2.56 (m, 4H), 2.31 (s, 5H), 1.17 (s, 3H). MS (EI) m/z: 478 $[M+H]^+$. Retention time: 3.4 min.

Example 14.2

$^1$H NMR (500 MHz, DMSO-$d_6$) δ 8.38 (s, 1H), 8.17 (s, 1H), 7.99 (s, 1H), 7.94 (s, 1H), 7.24 (s, 1H), 4.20 (t, J=8.9 Hz, 1H), 3.95-3.88 (m, 1H), 3.75-3.67 (m, 2H), 3.52-3.45 (m, 1H), 3.15-3.05 (m, 4H), 2.78-2.63 (m, 5H), 2.31 (s, 6H), 1.33 (s, 3H). MS (EI) m/z: 478 $[M+H]^+$. Retention time: 4.3 min.

Preparation of Example 15.1, 15.2, 15.3 and 15.4: (3S,4S or 3R,4R)-4-((S)-4-(1-(1-(bicyclo[1.1.1]pentan-1-yl)-1H-pyrazol-4-yl)-5-chloro-1H-indazol-6-yl)-3-methylpiperazin-1-yl)-4-methyltetrahydrofuran-3-ol: (3S,4S or 3R,4R)-4-((R)-4-(1-(1-(bicyclo[1.1.1]pentan-1-yl)-1H-pyrazol-4-yl)-5-chloro-1H-indazol-6-yl)-3-methylpiperazin-1-yl)-4-methyltetrahydrofuran-3-ol: (3R,4R or 3S,4S)-4-((R)-4-(1-(1-(bicyclo[1.1.1]pentan-1-yl)-1H-pyrazol-4-yl)-5-chloro-1H-indazol-6-yl)-3-methylpiperazin-1-yl)-4-methyltetrahydrofuran-3-ol; (3R4R or 3S,4S)-4-((S)-4-(1-(1-(bicyclo[1.1.1]pentan-1-yl)-1H-pyrazol-4-yl)-5-chloro-1H-indazol-6-yl)-3-methylpiperazin-1-yl)-4-methyltetrahydrofuran-3-ol Scheme 92

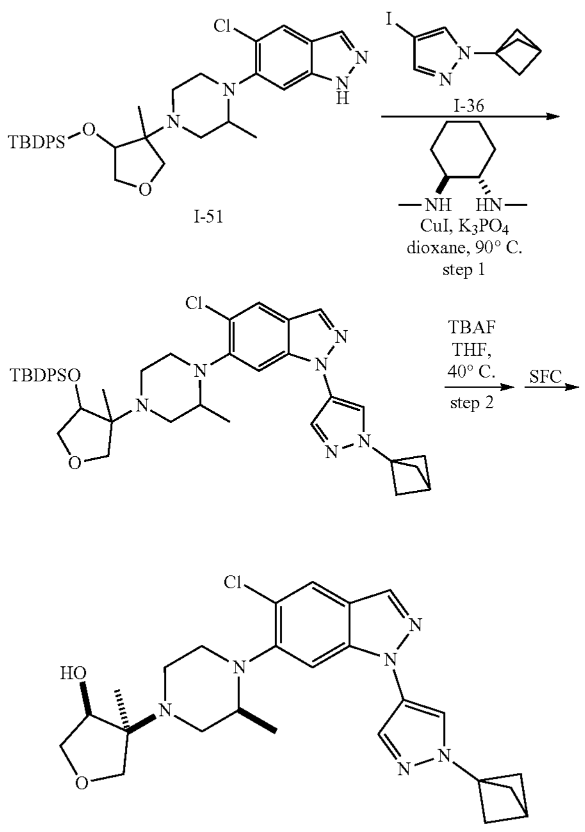

Ex. 15.1

-continued

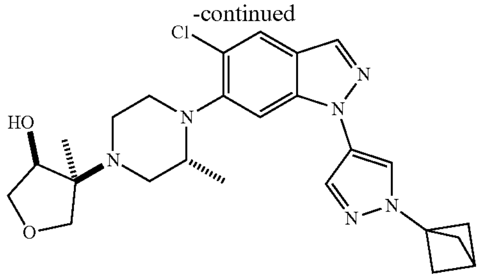

Ex. 15.2

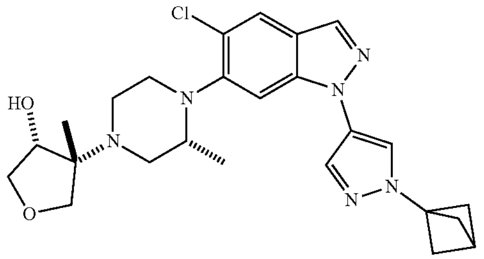

Ex. 15.3

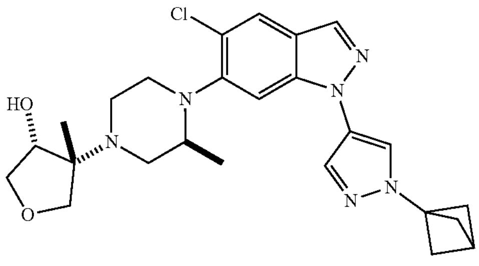

Ex. 15.4

Step 1: 1-(1-(bicyclo[1.1.1]pentan-1-yl)-1H-pyrazol-4-yl)-6-(4-(4-((tert-butyldiphenylsilyl)oxy)-3-methyltetrahydrofuran-3-yl)-2-methylpiperazin-1-yl)-5-chloro-1H-indazole To a vial were added I-51 (60 mg, 0.10 mmol), I-36 (39.7 mg, 0.153 mmol), N1,N2-dimethylcyclohexane-1,2-diamine (5.79 mg, 0.0410 mmol), copper(I) iodide (7.76 mg, 0.0410 mmol), potassium phosphate (64.8 mg, 0.305 mmol) and dioxane (1000 µl). The mixture was evacuated and back filled with $N_2$ 4 times and heated at 90° C. for 20 h. The reaction was cooled, quenched with water, extracted with EtOAc (3×). The combined organic layers were washed with brine, dried over $MgSO_4$, filtered and concentrated in vacuo to afford 1-(1-(bicyclo[1.1.1]pentan-1-yl)-1H-pyrazol-4-yl)-6-(4-(4-((tert-butyldiphenylsilyl)oxy)-3-methyltetrahydrofuran-3-yl)-2-methylpiperazin-1-yl)-5-chloro-TH-indazole, which was used in next step directly. MS (EI) m/z: 721 $[M+H]^+$.

Step 2: (3S,4S or 3R,4R)-4-((S or R)-4-(1-(1-(bicyclo[1.1.1]pentan-1-yl)-1H-pyrazol-4-yl)-5-chloro-1H-indazol-6-yl)-3-methylpiperazin-1-yl)-4-methyltetrahydrofuran-3-ol (Ex. 15.1.), (3S,4S or 3R,4R)-4-((R or S)-4-(1-(1-(bicyclo[1.1.1]pentan-1-yl)-1H-pyrazol-4-yl)-5-chloro-TH-indazol-6-yl)-3-methylpiperazin-1-yl)-4-methyltetrahydrofuran-3-ol (Ex. 15.2), (3R,4R or 3S,4S)-4-((R or S)-4-(1-(1-(bicyclo[1.1.1]pentan-1-yl)-1H-pyrazol-4-yl)-5-chloro-1H-indazol-6-yl)-3-methylpiperazin-1-yl)-4-methyltetrahydrofuran-3-ol (Ex. 15.3) and (3R,4R or 3S,4S)-4-((S or R)-4-(1-(1-(bicyclo[1.1.1]pentan-1-yl)-1H-pyrazol-4-yl)-5-chloro-TH-indazol-6-yl)-3-methylpiperazin-1-yl)-4-methyltetrahydrofuran-3-ol (Ex. 15.4)

1-(1-(bicyclo[1.1.1]pentan-1-yl)-1H-pyrazol-4-yl)-6-(4-(4-((tert-butyldiphenylsilyl)oxy)-3-methyltetrahydrofuran-3-yl)-2-methylpiperazin-1-yl)-5-chloro-1H-indazole (80.5 mg, 0.112 mmol) was dissolved in THF (1 ml) under $N_2$. TBAF in THF (0.25 ml, 0.250 mmol) was added and the reaction was allowed to stir at 40° C. for 2 h. The reaction was cooled, quenched with water, and extracted with $CHCl_3$/IPA (3:1) three times. The combined organic extracts were dried over $Na_2SO_4$, filtered and concentrated. Purified by column chromatography on silica (4 g, EtOAc/EtOH=3:1 in hexane, 0-50% gradient) to afford 4-(4-(1-(1-(bicyclo[1.1.1]pentan-1-yl)-1H-pyrazol-4-yl)-5-chloro-1H-indazol-6-yl)-3-methylpiperazin-1-yl)-4-methyltetrahydrofuran-3-ol. The product was subjected to SFC chiral separation (column & dimensions: IA, 21×250 mm; Mobile phase A: $CO_2$; Mobile phase B: MeOH with 0.1% $NH_4OH$) to afford the title compounds (examples 15.1, 15.2, 15.3 and 15.4).

Example 15.1

$^1$H NMR (600 MHz, DMSO-$d_6$) δ 8.33 (s, 1H), 8.19 (s, 1H), 7.99 (s, 1H), 7.96 (s, 1H), 7.37 (s, 1H), 4.37 (s, 1H), 4.02-3.93 (m, 1H), 3.87-3.80 (m, 1H), 3.77-3.47 (m, 5H), 2.87-2.70 (m, 3H), 2.67 (s, 1H), 2.46-2.38 (m, 1H), 2.31 (s, 6H), 2.24 (dd, J=10.9, 7.3 Hz, 1H), 1.04 (s, 3H), 0.87 (dd, J=12.3, 6.4 Hz, 3H); MS (EI) m/z 483 $[M+H]^+$. Retention time: 5.5 min.

Example 15.2

$^1$H NMR (600 MHz, DMSO-$d_6$) δ 8.33 (s, 1H), 8.19 (s, 1H), 7.99 (s, 1H), 7.96 (s, 1H), 7.36 (s, 1H), 4.30 (s, 1H), 3.97 (dd, J=9.8, 3.5 Hz, 1H), 3.84-3.52 (m, 6H), 2.91-2.79 (m, 1H), 2.77-2.65 (m, 2H), 2.67 (s, 1H), 2.50-2.42 (m, 2H), 2.31 (s, 6H), 1.05 (s, 3H), 0.87 (d, J=5.3 Hz, 3H); MS (EI) m/z 483 $[M+H]^+$. Retention time: 6.4 min.

Example 15.3

$^1$H NMR (600 MHz, DMSO-$d_6$) δ 8.33 (s, 1H), 8.19 (s, 1H), 7.99 (s, 1H), 7.96 (s, 1H), 7.37 (s, 1H), 4.37 (s, 1H), 4.02-3.93 (m, 1H), 3.87-3.80 (m, 1H), 3.77-3.47 (m, 5H), 2.87-2.70 (m, 3H), 2.67 (s, 1H), 2.46-2.38 (m, 1H), 2.31 (s, 6H), 2.24 (dd, J=10.9, 7.3 Hz, 1H), 1.04 (s, 3H), 0.87 (dd, J=12.3, 6.4 Hz, 3H); MS (EI) m/z 483 $[M+H]^+$. Retention time: 7.5 min.

Example 15.4

$^1$H NMR (600 MHz, DMSO-$d_6$) δ 8.33 (s, 1H), 8.19 (s, 1H), 7.99 (s, 1H), 7.96 (s, 1H), 7.36 (s, 1H), 4.30 (s, 1H), 3.97 (dd, J=9.8, 3.5 Hz, 1H), 3.84-3.52 (m, 6H), 2.91-2.79 (m, 1H), 2.77-2.65 (m, 2H), 2.67 (s, 1H), 2.50-2.42 (m, 2H), 2.31 (s, 6H), 1.05 (s, 3H), 0.87 (d, J=5.3 Hz, 3H); MS (EI) m/z 483 $[M+H]^+$. Retention time: 8.7 min.

Preparation of Example 16.1: (3R,4R or 3S, 4S)-4-(4-(1-(1-(bicyclo[1.1.1]pentan-1-yl)-1H-pyrazol-4-yl)-5-methyl-1H-indazol-6-yl)piperazin-1-yl)-4-methyltetrahydrofuran-3-ol Scheme 93

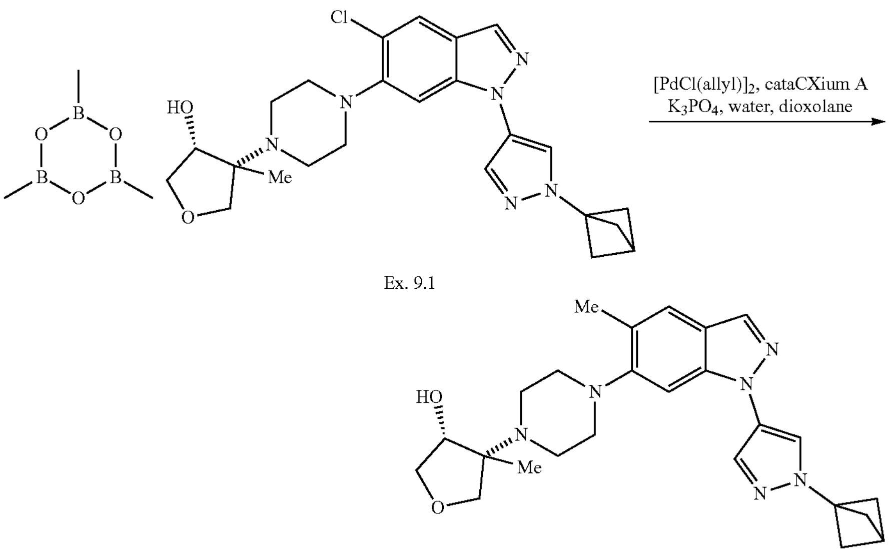

Ex. 9.1

Ex. 16.1

A 1 dram vial was charged with butlydi-1-adamanylphosphine (6.1 mg, 0.017 mmol) and allylpalladium (II) chloride dimer (3.12 mg, 8.53 μmol) and placed under $N_2$. 1,3-dioxolane (0.25 mL) was added and this mixture was stirred for 15 minutes. In a separate 2-5 mL vial, potassium phosphate (72.4 mg, 0.341 mmol) and Ex. 9.1 (40 mg, 0.085 mmol) were dissolved in 0.75 mL of 1,3-dioxolane under $N_2$. The catalyst solution, degassed water (0.1 mL) and trimethylboroxine (0.048 mL, 0.34 mmol) were added via syringes. The reaction was heated to 75° C. and allowed to stir for 18 h. The reaction was cooled, diluted with sat. $NH_4Cl$ (2 mL and extracted with 3:1 $CHCl_3$:IPA (3×3 mL). The organic extract was filtered though a phase separator and concentrated in vacuo. The resulting oil was purified via reverse-phase HPLC with water elution 0.1% TFA in ACN then free based with sat. $NaHCO_3$ to give the title compound (Ex. 16.1). $^1$H NMR (500 MHz, DMSO-$d_6$) δ 8.29 (s, 2H), 8.07 (s, 1H), 7.94 (s, 1H), 7.59 (s, 1H), 7.15 (s, 1H), 4.02-3.89 (m, 1H), 3.80 (s, 1H), 3.75-3.67 (m, 1H), 3.67-3.55 (m, 1H), 3.55-3.46 (m, 1H), 3.09-2.89 (m, 4H), 2.82-2.68 (m, 3H), 2.68-2.56 (m, 2H), 2.35 (s, 3H), 2.30 (s, 6H), 1.06 (s, 3H). MS (EI) m/z 449 $[M+H]^+$.

The compounds in Table 27 below were prepared from Ex. 8.1 and Ex. 6.58 according to Scheme 93.

TABLE 27

| Ex | Structure | Name | Exact Mass [M + H]+ |
|---|---|---|---|
| Ex. 16.2 | 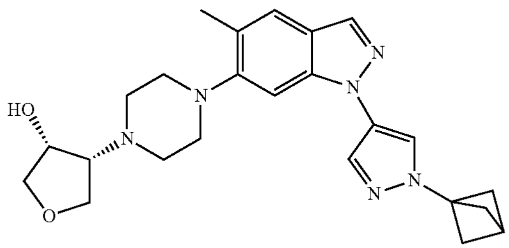 [SMILES: Cc1cc2cnn(-c3cnn(C45CC(C4)C5)c3)c2cc1N1CCN([C@@H]2COC[C@@H]2O)CC1] | (3R,4R or 3S,4S)-4-(4-{1-[1-(bicyclo[1.1.1]pentan-1-yl)-1H-pyrazol-4-yl]-5-methyl-1H-indazol-6-yl}piperazin-1-yl)oxolan-3-ol | Calc'd 435, found 435 |

TABLE 27-continued

| Ex | Structure | Name | Exact Mass [M + H]+ |
|---|---|---|---|
| Ex. 16.3 | 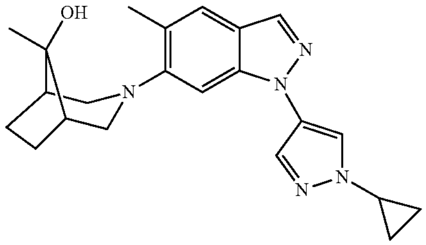 [SMILES: Cc1cc2cnn(-c3cnn(C4CC4)c3)c2cc1N1CC2CCC(C1)C2(C)O] | 3-[1-(1-cyclopropyl-1H-pyrazol-4-yl)-5-methyl-1H-indazol-6-yl]-8-methyl-3-azabicyclo[3.2.1]octan-8-ol | Calc'd 378, found 378 |

Preparation of Example 17.1: 1-(1-(bicyclo[1.1.1]pentan-1-yl)-1H-pyrazol-4-yl)-6-(4-(3-methyl-oxetan-3-yl)piperazin-1-yl)-1H-indazole-5-carbonitrile Scheme 94

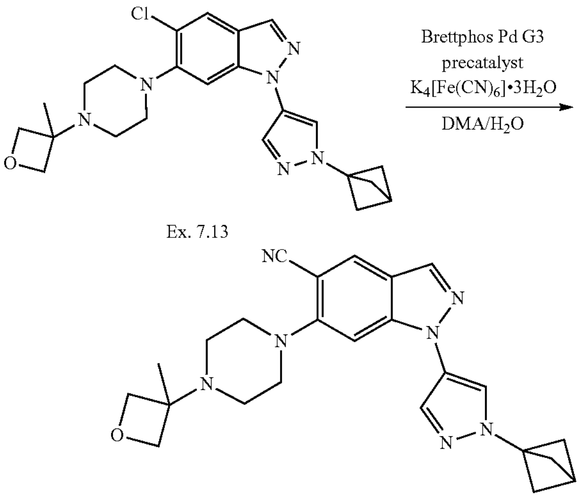

Ex. 17.1

Brettphos Pd G3 precatalyst (7.23 mg, 7.97 μmol), potassium hexacyanoferrate (II) trihydrate (50.5 mg, 0.120 mmol), and Ex. 7.13 (35 mg, 0.080 mmol) were combined in a 2-5 mL microwave vial which was flushed with $N_2$. Water (125 μl) and N,N-Dimethylacetamide (375 μl) were added, and the reaction was stirred in at 110° C. for 18 h. The reaction was cooled, diluted with water (3 mL) and extracted with 3:1 $CHCl_3$:IPA (3×5 mL). The organic extracts were filtered through a phase separator and concentrated in vacuo. The residue was purified by reverse-phase HPLC, eluting with water (0.10% TFA)-ACN to afford the title compound (Ex. 17.1). $^1$H NMR (500 MHz, DMSO-$d_6$) δ 8.41 (s, 1H), 8.36 (s, 1H), 8.31 (s, 1H), 8.01 (s, 1H), 7.18 (s, 1H), 4.45 (d, J=5.7 Hz, 2H), 4.17 (d, J=5.7 Hz, 2H), 3.22 (s, 4H), 2.67 (s, 1H), 2.55-2.51 (m, 4H), 2.31 (s, 6H), 1.34 (s, 3H). MS (EI) m/z 430 [M+H]$^+$.

Ex. 17.2 and Ex. 17.3 in Table 28 below was prepared from Ex. 4.1 and Ex. 6.58 according to Scheme 94

TABLE 28

| Ex | Structure | Name | Exact Mass [M + H]+ |
|---|---|---|---|
| Ex. 17.2 | 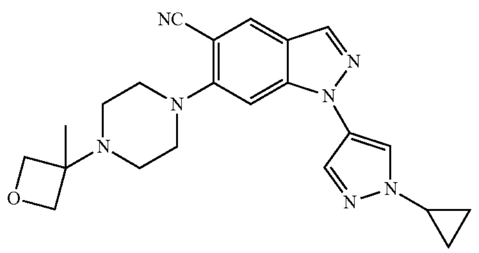 [SMILES: CC1(N2CCN(c3cc4c(cnn4-c4cnn(C5CC5)c4)cc3C#N)CC2)COC1] | 1-(1-cyclopropyl-1H-pyrazol-4-yl)-6-[4-(3-methyloxetan-3-yl)piperazin-1-yl]-1H-indazole-5-carbonitrile | Calc'd 404, found 404 |

TABLE 28-continued

| Ex | Structure | Name | Exact Mass [M + H]+ |
|---|---|---|---|
| Ex. 17.3 | 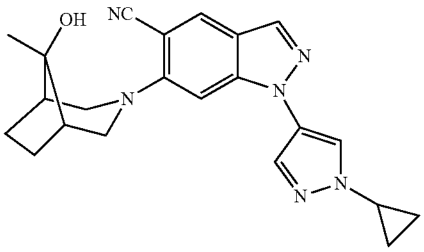 [SMILES: CC1(O)C2CCC1CN(c1cc3c(cnn3-c3cnn(C4CC4)c3)cc1C#N)C2] | 1-(1-cyclopropyl-1H-pyrazol-4-yl)-6-[(1R,5S,8r)-8-hydroxy-8-methyl-3-azabicyclo[3.2.1]octan-3-yl]-1H-indazole-5-carbonitrile | Calc'd 389, found 389 |

Preparation of Example 18.1: 1-(1-cyclopropyl-1H-pyrazol-4-yl)-5-(difluoromethyl)-6-(4-(3-methyloxetan-3-yl)piperazin-1-yl)-1H-indazole Scheme 95

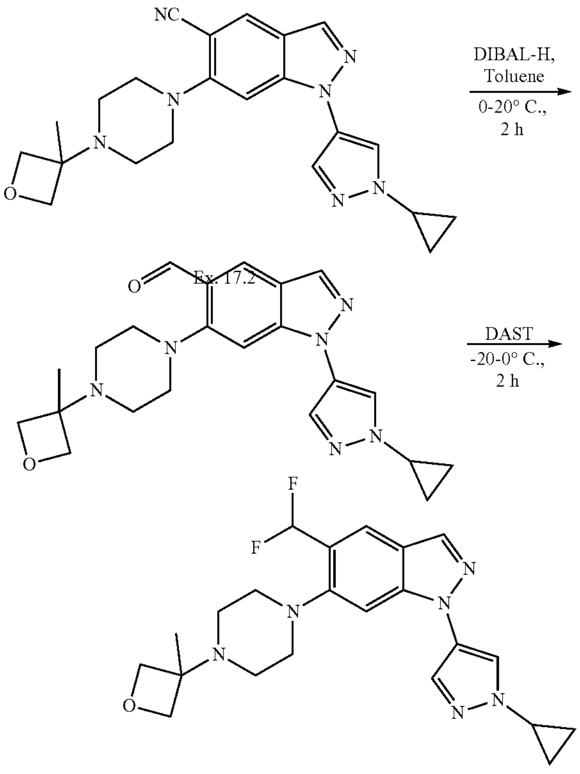

Ex. 18.1

Step 1: 1-(1-cyclopropyl-1H-pyrazol-4-yl)-6-(4-(3-methyloxetan-3-yl)piperazin-1-yl)-1H-indazole-5-carbaldehyde To a solution of 1-(1-cyclopropyl-1H-pyrazol-4-yl)-6-(4-(3-methyloxetan-3-yl)piperazin-1-yl)-1H-indazole-5-carbonitrile (20.0 mg, 0.050 mmol) in Toluene (2 mL) was added DIBAL-H (0.500 ml, 0.099 mmol) at 0° C. The resulting mixture was stirred at 20° C. for 12 hours. The reaction was diluted with methanol (5 mL) and then concentrated to give the crude product, 1-(1-cyclopropyl-1H-pyrazol-4-yl)-6-(4-(3-methyloxetan-3-yl)piperazin-1-yl)-1H-indazole-5-carbaldehyde, which was used for the next step without purification. MS (ESI) m/z: 407 $[M+H]^+$ Step 2: 1-(1-cyclopropyl-1H-pyrazol-4-yl)-5-(difluoromethyl)-6-(4-(3-methyloxetan-3-yl)piperazin-1-yl)-1H-indazole (Ex. 18.1)

To a solution of 1-(1-cyclopropyl-1H-pyrazol-4-yl)-6-(4-(3-methyloxetan-3-yl)piperazin-1-yl)-1H-indazole-5-carbaldehyde (40 mg, 0.098 mmol) in anhydrous DCM (2 mL) was added DAST (0.0370 ml, 0.295 mmol) at −78° C., and the resulting mixture was stirred for 2 hours at 20° C. under $N_2$ protection. The reaction was poured into saturated $NaHCO_3$ solvent (10 mL) and then extracted with EtOAc (15 mL×3). The combined organic layer was washed with brine (30 mL×3) and then dried by $Na_2SO_4$. After filtration and concentration, the crude product was purified by reversed phase HPLC, eluting with water (10 mM $NH_4HCO_3$)—CAN to afford the title compound (Ex. 18.1). $^1$H NMR (400 MHz, $CDCl_3$) δ 8.14 (s, 1H), 8.08 (s, 1H), 7.84 (s, 1H), 7.80 (s, 1H), 7.29 (s, 1H), 6.93-7.25 (m, 1H), 4.62 (d, J=5.48 Hz, 2H), 4.28 (d, J=5.48 Hz, 2H), 3.71 (m, 1H), 3.01-3.10 (m, 4H), 2.51-2.62 (m, 4H), 1.45 (s, 3H), 1.20-1.27 (m, 2H), 1.08-1.14 (m, 2H); MS (ESI) m/z: 429 $[M+H]^+$ Preparation of Example 19.1 and 19.2: (1S,2S or 1R,2R)-2-(4-(1-(1-(bicyclo[1.1.1]pentan-1-yl)-1H-pyrazol-4-yl)-5-chloro-1H-indazol-6-yl)piperazin-1-yl)-2-methylcyclobutan-1-ol (Ex. 19.1) and (1R,2R or 1S,2S)-2-(4-(1-(1-(bicyclo[1.1.1]pentan-1-yl)-1H-pyrazol-4-yl)-5-chloro-1H-indazol-6-yl)piperazin-1-yl)-2-methylcyclobutan-1-ol (Ex. 19.2)

Scheme 96

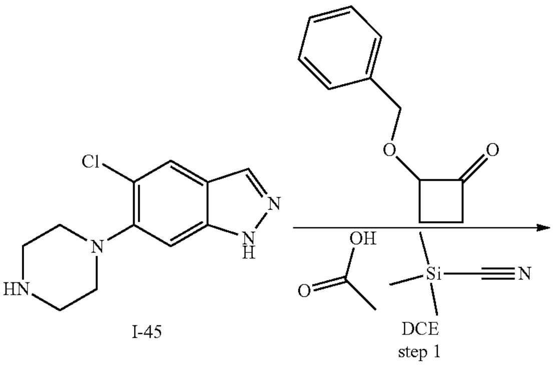

-continued

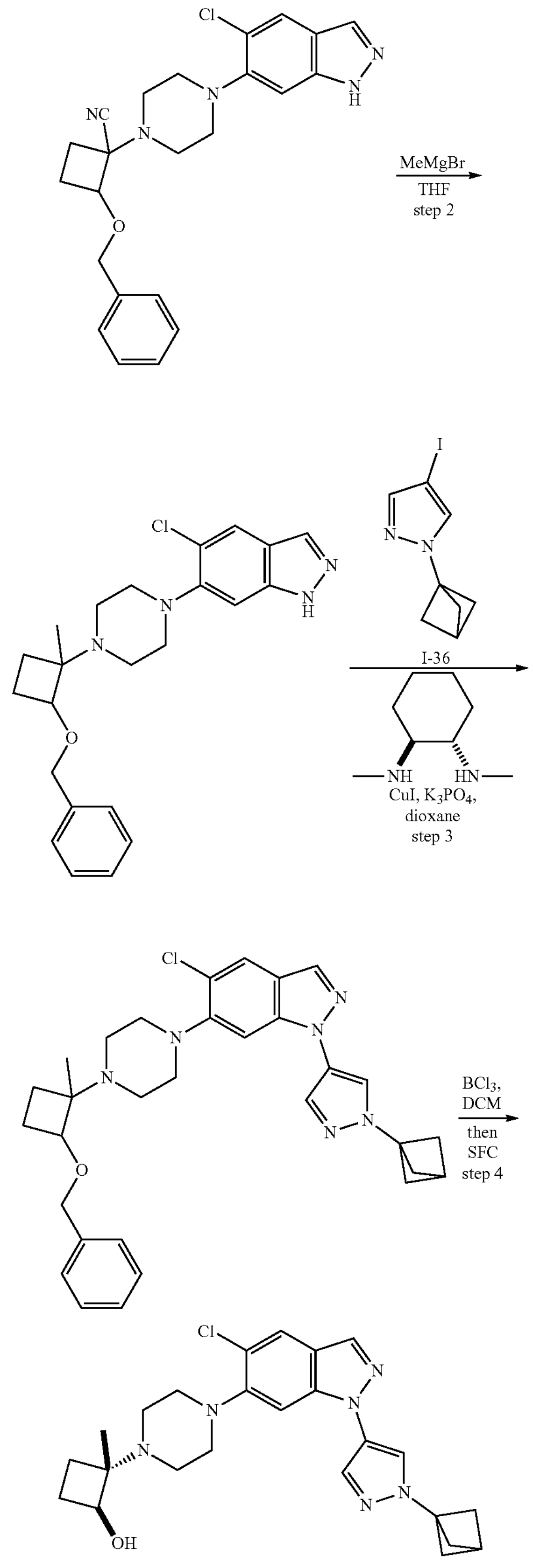

Ex. 19.1

-continued

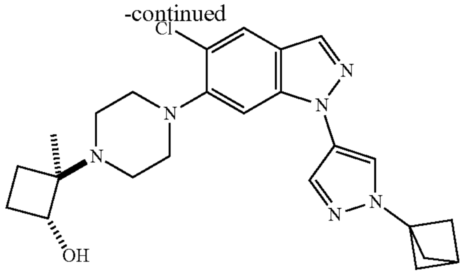

Ex. 19.2

Step 1: 2-(benzyloxy)-1-(4-(5-chloro-1H-indazol-6-yl)piperazin-1-yl)cyclobutane-1-carbonitrile To a flask were added 2-(benzyloxy)cyclobutan-1-one (2.90 g, 16.5 mmol), I-45 (3.0 g, 12 mmol) and DCE (100 ml). To this slurry was added acetic acid (1.5 ml, 26 mmol). The mixture was then heated at 65° C. for 30 min. Then trimethylsilanecarbonitrile (3.0 ml, 24 mmol) was added. The reaction was then heated to 65° C. for 2.5 h. The mixture was quenched with $NaHCO_3$ (sat.) and extracted with EtOAc three times. The combined organic layers were washed with brine, dried over $MgSO_4$, filtered and concentrated in vacuo to afford a residue, which was purified by column chromatography on silica (120 g, 0-100% EtOAc in hexane gradient) to afford 2-(benzyloxy)-1-(4-(5-chloro-1H-indazol-6-yl)piperazin-1-yl)cyclobutane-1-carbonitrile. MS (EI) m/z 422 $[M+H]^+$.

Step 2: 6-(4-(2-(benzyloxy)-1-methylcyclobutyl) piperazin-1-yl)-5-chloro-1H-indazole To a flask containing 2-(benzyloxy)-1-(4-(5-chloro-1H-indazol-6-yl)piperazin-1-yl)cyclobutane-1-carbonitrile (4.92 g, 11.6 mmol) was added THF (100 ml). To this solution was added methylmagnesium bromide (10.0 ml, 34.0 mmol, 3.4 M in THF) at 0° C. The mixture was stirred at 65° C. for 20 h. The reaction was cooled down to rt. Evaporated some solvent and set for overnight. Some solid precipitated out. After filtration, the filtrate was diluted with water, and extracted with EtOAc three times. The combined organic layers were washed with brine, dried over $MgSO_4$, filtered, and concentrated in vacuo to afford 6-(4-(2-(benzyloxy)-1-methylcyclobutyl)piperazin-1-yl)-5-chloro-1H-indazole, which was used in next step directly. MS (EI) m/z 411 $[M+H]^+$.

Step 3: 6-(4-(2-(benzyloxy)-1-methylcyclobutyl) piperazin-1-yl)-1-(1-(bicyclo[1.1.1]pentan-1-yl)-1H-pyrazol-4-yl)-5-chloro-1H-indazole To a vial were added 6-(4-(2-(benzyloxy)-1-methylcyclobutyl)piperazin-1-yl)-5-chloro-1H-indazole (2.0 g, 4.9 mmol), I-36 (1.40 g, 5.38 mmol), (1S,2S)—N1,N2-dimethylcyclohexane-1,2-diamine (0.208 g, 1.46 mmol), copper(I) iodide (0.278 g, 1.46 mmol), potassium phosphate (3.10 g, 14.6 mmol) and dioxane (20 ml). The mixture was evacuated and backfilled with $N_2$ 3 times and heated at 90° C. for 20 h. The reaction was cooled, quenched with water, then extracted with EtOAc three times. The combined organic layers were washed with brine, dried over $MgSO_4$, filtered, and concentrated in vacuo to afford a residue, which was purified by column chromatography on silica (80 g, EtOAc in hexane, 0-50% gradient) to afford 6-(4-(2-(benzyloxy)1-methylcyclobutyl)piperazin-1-yl)-1-(1-(bicyclo[1.1.1]pentan-1-yl)-1H-pyrazol-4-yl)-5-chloro-1H-indazole. MS (EI) m/z 543 $[M+H]^+$.

Step 4: (1S,2S or 1R,2R)-2-(4-(1-(1-(bicyclo[1.1.1]pentan-1-yl)-1H-pyrazol-4-yl)-5-chloro-1H-indazol-6-yl)piperazin-1-yl)-2-methylcyclobutan-1-ol (Ex. 19.1) and (1R,2R or 1S,2S)-2-(4-(1-(1-(bicyclo[1.1.1]pentan-1-yl)-1H-pyrazol-4-yl)-5-chloro-1H-indazol-6-yl)piperazin-1-yl)-2-methylcyclobutan-1-ol (Ex. 19.2)

To a flask containing 6-(4-(2-(benzyloxy)-1-methylcyclobutyl)piperazin-1-yl)-1-(1-(bicyclo[1.1.1]pentan-1-yl)-1H-pyrazol-4-yl)-5-chloro-1H-indazole (1.66 g, 3.05 mmol) was added DCM (20 ml). To this solution at −78° C. was added $BCl_3$ in DCM (8 ml, 8 mmol). The resulting mixture was allowed to warm to rt and stirred at rt for 3 h. The reaction was quenched with $NaHCO_3$ (sat.) and extracted with DCM three times. The combined organic layers were washed with brine, dried over $MgSO_4$, filtered and concentrated in vacuo. During the concentration process, the product precipitated out. After filtration, the product was subjected to SFC chiral separation (column & dimensions: IA, 21×250 mm; Mobile phase A: $CO_2$; Mobile phase B: MeOH with 0.1% $NH_4OH$) to afford the title compounds (Ex. 19.1 and Ex. 19.2).

Example 19.1

$^1$H NMR (600 MHz, DMSO-$d_6$) δ 8.38 (s, 1H), 8.16 (s, 1H), 7.98 (s, 1H), 7.92 (s, 1H), 7.25 (s, 1H), 4.95 (d, J=6.5 Hz, 1H), 3.88-3.77 (m, 1H), 3.17-2.94 (m, 4H), 2.67 (s, 1H), 2.71-2.58 (m, 2H), 2.56-2.46 (m, 2H), 2.31 (s, 6H), 2.07-1.87 (m, 1H), 1.61-1.41 (m, 2H), 1.37-1.26 (m, 1H), 1.01 (s, 3H); MS (EI) m/z 453 $[M+H]^+$. Retention time: 3.5 min.

Example 19.2

$^1$H NMR (600 MHz, DMSO-$d_6$) δ 8.38 (s, 1H), 8.16 (s, 1H), 7.98 (s, 1H), 7.92 (s, 1H), 7.25 (s, 1H), 4.95 (d, J=6.5 Hz, 1H), 3.88-3.77 (m, 1H), 3.17-2.94 (m, 4H), 2.67 (s, 1H), 2.71-2.58 (m, 2H), 2.56-2.46 (m, 2H), 2.31 (s, 6H), 2.07-1.87 (m, 1H), 1.61-1.41 (m, 2H), 1.37-1.26 (m, 1H), 1.01 (s, 3H); MS (EI) m/z 453 $[M+H]^+$. Retention time: 4.9 min.

Preparation of Example 20.1: 1-(1-(1-(bicyclo[1.1.1]pentan-1-yl)-1H-pyrazol-4-yl)-5-chloro-1H-pyrazolo[3,4-b]pyridin-6-yl)-4-methylpiperidin-4-ol Scheme 97

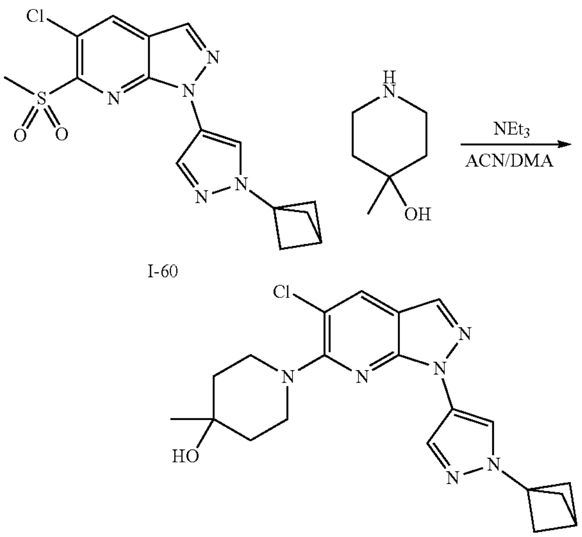

I-60

Ex. 20.1

I-60 (150 mg, 0.412 mmol) and 4-methylpiperidin-4-ol, HCl (250 mg, 1.65 mmol) were suspended in acetonitrile (3.0 ml) in a vial under $N_2$. DMA (0.3 ml) and triethylamine (0.345 ml, 2.47 mmol) were added and the reaction was heated to 100° C. and stirred for 18 h. The reaction was cooled, concentrated in vacuo, and purified by reversed phase HPLC, eluting with water (0.1% TFA)-CAN to obtain the title compound (Ex. 20.1). $^1$H NMR (500 MHz, DMSO-$d_6$) δ 8.31 (s, 1H), 8.26 (s, 1H), 8.11 (s, 2H), 4.39 (s, 1H), 3.71-3.47 (m, 2H), 3.42-3.32 (m, 2H), 2.66 (s, 1H), 2.29 (s, 6H), 1.77-1.55 (m, 4H), 1.20 (s, 3H). MS (EI) m/z 399 $[M+H]^+$.

Ex. 20.2 to Ex. 20.4 in Table 29 below were prepared from common intermediate I-59 according to Scheme 97 by using the corresponding starting materials.

Ex. 20.5 and Ex. 20.6 were prepared from common intermediate I-60 according to Scheme 97 by using the corresponding starting materials.

Ex. 20.7 was prepared from I-60 and I-55 according to Scheme 97, then de-TBDPS protection.

Ex. 20.8 was prepared from I-60 and I-61 according to Scheme 97, then de-TBDPS protection.

TABLE 29

| Ex | Structure | Name | Exact Mass [M + H]+ |
|---|---|---|---|
| Ex. 20.2 | 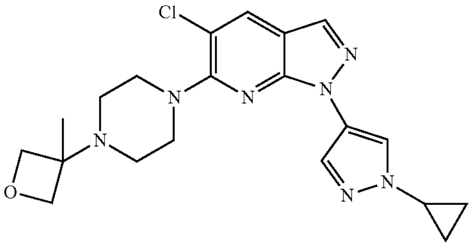 [SMILES: CC1(N2CCN(c3nc4c(cnn4-c4cnn(C5CC5)c4)cc3Cl)CC2)COC1] | 5-chloro-1-(1-cyclopropyl-1H-pyrazol-4-yl)-6-[4-(3-methyloxetan-3-yl)piperazin-1-yl]-1H-pyrazolo[3,4-b]pyridine | Calc'd 414 found 414 |

TABLE 29-continued

| Ex | Structure | Name | Exact Mass [M + H]+ |
| --- | --- | --- | --- |
| Ex. 20.3 | 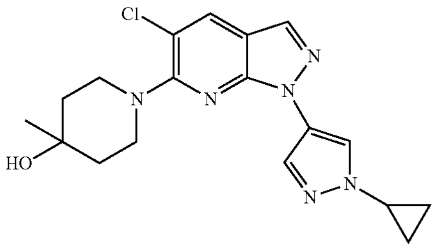 [SMILES: CC1(O)CCN(c2nc3c(cnn3-c3cnn(C4CC4)c3)cc2Cl)CC1] | 1-[5-chloro-1-(1-cyclopropyl-1H-pyrazol-4-yl)-1H-pyrazolo[3,4-b]pyridin-6-yl]-4-methylpiperidin-4-ol | Calc'd 373, found 373 |
| Ex. 20.4 | 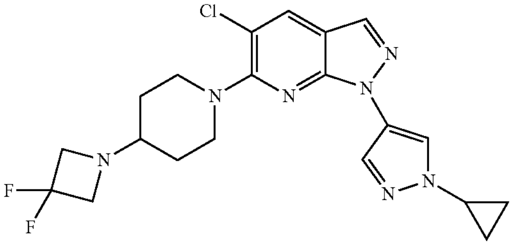 [SMILES: FC1(F)CN(C2CCN(c3nc4c(cnn4-c4cnn(C5CC5)c4)cc3Cl)CC2)C1] | 5-chloro-1-(1-cyclopropyl-1H-pyrazol-4-yl)-6-[4-(3,3-difluoroazetidin-1-yl)piperidin-1-yl]-1H-pyrazolo[3,4-b]pyridine | Calc'd 434, found 434 |
| Ex. 20.5 | 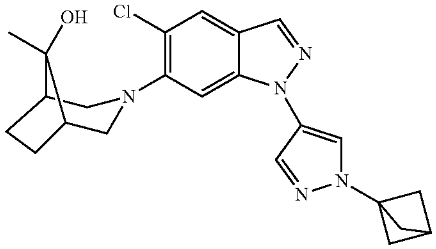 [SMILES: CC1(O)C2CCC1CN(c1cc3c(cnn3-c3cnn(C45CC(C4)C5)c3)cc1Cl)C2] | (1R,5S,8r)-3-{1-[1-(bicyclo[1.1.1]pentan-1-yl)-1H-pyrazol-4-yl]-5-chloro-1H-pyrazolo[3,4-b]pyridin-6-yl}-8-methyl-3-azabicyclo[3.2.1]octan-8-ol | Calc'd 425, found 425 |
| Ex. 20.6 | 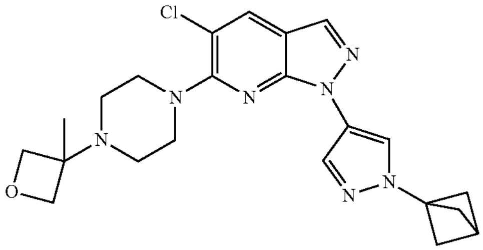 [SMILES: CC1(N2CCN(c3nc4c(cnn4-c4cnn(C56CC(C5)C6)c4)cc3Cl)CC2)COC1] | 1-[1-(bicyclo[1.1.1]pentan-1-yl)-1H-pyrazol-4-yl]-5-chloro-6-[4-(3-methyloxetan-3-yl)piperazin-1-yl]-1H-pyrazolo[3,4-b]pyridine | Calc'd 440, found 440 |
| Ex. 20.7 | 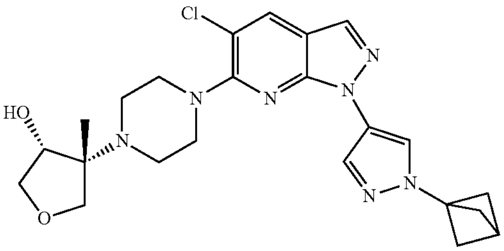 [SMILES: C[C@@]1(N2CCN(c3nc4c(cnn4-c4cnn(C56CC(C5)C6)c4)cc3Cl)CC2)COC[C@@H]1O] | (3R,4R or 3S,4S)-4-(4-{1-[1-(bicyclo[1.1.1]pentan-1-yl)-1H-pyrazol-4-yl]-5-chloro-1H-pyrazolo[3,4-b]pyridin-6-yl}piperazin-1-yl)-4-methyloxolan-3-ol | Calc'd 470, found 470 |
| Ex. 20.8 | 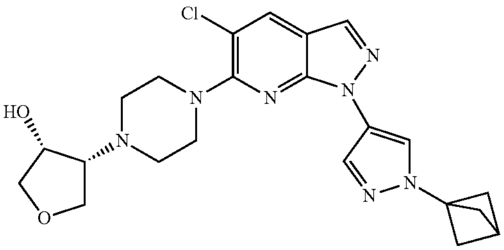 [SMILES: O[C@H]1COC[C@H]1N1CCN(c2nc3c(cnn3-c3cnn(C45CC(C4)C5)c3)cc2Cl)CC1] | (3S,4S or 3R,4R)-4-(4-{1-[1-(bicyclo[1.1.1]pentan-1-yl)-1H-pyrazol-4-yl]-5-chloro-1H-pyrazolo[3,4-b]pyridin-6-yl}piperazin-1-yl)oxolan-3-ol | Calc'd 456, found 456 |

The compounds of the invention, surprisingly and advantageously, exhibit good potency as inhibitors of LRRK2 kinase. The $IC_{50}$ values reported herein were measured as follows.

Biological Assay: LRRK2 Km ATP LanthaScreen™ Assay

The LRRK2 kinase activity reported herein as $IC_{50}$ values was determined with LanthaScreen™ technology from Life Technologies Corporation (Carlsbad, CA) using a GST-tagged truncated human mutant G2019S LRRK2 in the presence of the fluorescein-labeled peptide substrate LRRKtide, also from Life Technologies. The data presented for the Km ATP LanthaScreen™ Assay represents mean $IC_{50}$ values based on several test results and may have reasonable deviations depending on the specific conditions and reagents used. Assays were performed in the presence of 134 μM ATP (Km ATP). Upon completion, the assay was stopped, and phosphorylated substrate detected with a terbium (Tb)-labeled anti-pERM antibody (cat. no. PV4898). The compound dose response was prepared by diluting a 10 mM stock of compound to a maximum concentration of 9.99 μM in 100% dimethylsulfoxide, followed by custom fold serial dilution in dimethylsulfoxide nine times. 20 nL of each dilution was spotted via a Labcyte Echo onto a 384-well black-sided plate (Corning 3575) followed by 15 μl of a 1.25 nM enzyme solution in 1× assay buffer (50 mM Tris pH 8.5, 10 mM MgCl2, 0.01% Brij-35, 1 mM EGTA, 2 mM dithiothreitol, 0.05 mM sodium orthovanadate). Following a 15-minute incubation period at room temperature, the kinase reaction was started with the addition of 5 μl of 400 nM fluorescein-labeled LRRKtide peptide substrate and 134 μM ATP solution in 1× assay buffer. The reaction was allowed to progress at ambient temperature for 90 minutes. The reaction was then stopped by the addition of 20 μl of TR-FRET Dilution Buffer (Life Technologies, Carlsbad, CA) containing 2 nM Tb-labeled anti-phospho LRRKtide antibody and 10 mM EDTA (Life Technologies, Carlsbad, CA). After an incubation period of 1 h at room temperature, the plate was read on an EnVision® multimode plate reader (Perkin Elmer, Waltham, MA) with an excitation wavelength of 337 nm (Laser) and a reading emission at both 520 and 495 nm. Compound $IC_{50}$ values were interpolated from nonlinear regression best-fits of the log of the final compound concentration, plotted as a function of the 520/495-nm emission ratio using activity base ("Abase"). Abase uses a 4 parameter (4P) logistic fit based on the Levenberg-Marquardt algorithm. LRRK2 $IC_{50}$ values for each of the example compounds of the invention measured using this assay are set forth in the table below, where "Ex. Number" corresponds to the example number of the compounds in the tables above.

| Ex. Number | LRRK2 $IC_{50}$ |
|---|---|
| 1.1 | 2.479 |
| 1.2 | 3.32 |
| 1.3 | 7.658 |
| 1.4 | 1.765 |
| 1.5 | 7.383 |
| 1.6 | 45.46 |
| 1.7 | 6.211 |
| 1.8 | 4.819 |
| 1.9 | 1.785 |
| 2.1 | 0.625 |
| 3.1 | 0.8775 |
| 4.1 | 2.293 |
| 4.2 | 1.401 |
| 4.3 | 2.663 |
| 4.4 | 0.6717 |
| 4.4 | <0.625 |

-continued

| Ex. Number | LRRK2 $IC_{50}$ |
|---|---|
| 4.5 | 1.429 |
| 4.6 | 0.625 |
| 4.7 | 0.625 |
| 4.8 | <0.625 |
| 4.9 | 2.909 |
| 4.10 | 195.4 |
| 4.11 | 7.931 |
| 4.12 | 1.115 |
| 4.13 | 0.6506 |
| 4.14 | <0.625 |
| 4.15 | 9.721 |
| 5.1 | 1.573 |
| 5.2 | 1.259 |
| 5.3 | 1.018 |
| 5.4 | 3.661 |
| 5.5 | 0.625 |
| 5.6 | 3.471 |
| 5.7 | 8.96 |
| 5.8 | 2.828 |
| 5.9 | 2.038 |
| 5.10 | 2.885 |
| 5.11 | 1.285 |
| 5.12 | 0.8913 |
| 5.13 | 0.8502 |
| 5.14 | 1.271 |
| 5.15 | 1.103 |
| 5.16 | <0.625 |
| 5.17 | 1.002 |
| 5.18 | <0.625 |
| 5.19 | 6.154 |
| 5.20 | 2.668 |
| 5.21 | <0.625 |
| 5.22 | <0.625 |
| 5.23 | 0.7057 |
| 5.24 | <0.625 |
| 5.25 | 1.759 |
| 6.1 | 3.012 |
| 6.2 | 32.35 |
| 6.3 | 17.23 |
| 6.4 | 1.213 |
| 6.5 | 39.03 |
| 6.6 | 2.84 |
| 6.7 | 52.03 |
| 6.8 | 0.625 |
| 6.9 | 1.783 |
| 6.10 | 15.41 |
| 6.11 | 15.11 |
| 6.12 | 8.314 |
| 6.13 | 23.07 |
| 6.14 | 18.45 |
| 6.15 | 70.3 |
| 6.16 | 11.51 |
| 6.17 | 6.64 |
| 6.18 | 10.6 |
| 6.19 | 16.84 |
| 6.20 | 3.639 |
| 6.21 | 6.43 |
| 6.22 | 2.303 |
| 6.23 | 3.145 |
| 6.24 | 33.42 |
| 6.25 | 14.2 |
| 6.26 | 16.21 |
| 6.27 | 0.8635 |
| 6.28 | 0.8734 |
| 6.29 | 10.47 |
| 6.30 | 34.03 |
| 6.31 | 8.283 |
| 6.32 | 23.89 |
| 6.33 | 1.95 |
| 6.34 | 3.396 |
| 6.35 | 3.503 |
| 6.36 | 7.21 |
| 6.37 | 6.1 |
| 6.38 | 5.721 |
| 6.39 | 5.885 |
| 6.40 | 104.9 |
| 6.41 | 1.543 |

-continued

| Ex. Number | LRRK2 $IC_{50}$ |
|---|---|
| 6.42 | 14.62 |
| 6.43 | 19.71 |
| 6.44 | 21.54 |
| 6.45 | 1.058 |
| 6.46 | 0.8697 |
| 6.47 | 16.7 |
| 6.48 | 0.6889 |
| 6.49 | 1.274 |
| 6.50 | 4.71 |
| 6.51 | 0.7805 |
| 6.52 | <0.625 |
| 6.53 | 76.27 |
| 6.54 | 0.09751 |
| 6.55 | 4.276 |
| 6.56 | 2.927 |
| 6.57 | 3.037 |
| 6.58 | 1.553 |
| 6.59 | 2.58 |
| 6.60 | 0.4422 |
| 6.61 | 2.12 |
| 6.62 | 1.238 |
| 6.63 | <0.625 |
| 6.64 | 1.731 |
| 6.65 | 1.235 |
| 6.66 | 3.799 |
| 6.67 | 0.3905 |
| 6.68 | 0.5225 |
| 6.69 | 12.9 |
| 6.70 | <0.625 |
| 6.71 | 0.4107 |
| 6.72 | 0.96 |
| 6.73 | 0.2484 |
| 6.74 | <0.625 |
| 6.75 | 0.7862 |
| 6.76 | <0.625 |
| 6.77 | 1.079 |
| 6.78 | 0.9998 |
| 6.79 | 0.9803 |
| 6.80 | <0.625 |
| 6.81 | <0.625 |
| 6.82 | 8.459 |
| 6.83 | 11.07 |
| 7.1 | <0.625 |
| 7.2 | <0.625 |
| 7.3 | 2.153 |
| 7.4 | 1.909 |
| 7.5 | <0.625 |
| 7.6 | 1.167 |
| 7.7 | <0.625 |
| 7.8 | 0.7515 |
| 7.9 | 0.7583 |
| 7.10 | 0.5418 |
| 7.11 | 0.8992 |
| 7.12 | <0.625 |
| 7.13 | <0.625 |
| 7.14 | 1.236 |
| 7.15 | 1.847 |
| 7.16 | 3.548 |
| 7.17 | 0.9979 |
| 7.18 | <0.625 |
| 7.19 | 4.893 |
| 7.20 | 0.7015 |
| 7.21 | 1.905 |
| 7.22 | 1.015 |
| 8.1 | 0.3642 |
| 8.2 | 1.341 |
| 9.1 | 0.3962 |
| 10.1 | 0.1043 |
| 10.2 | 0.5639 |
| 11.1 | 0.7325 |
| 12.1 | <0.625 |
| 12.2 | 3.938 |
| 12.3 | 0.7077 |
| 12.4 | <0.0804 |
| 12.5 | 0.157 |
| 12.6 | 0.8006 |
| 12.7 | 1.327 |

-continued

| Ex. Number | LRRK2 $IC_{50}$ |
|---|---|
| 12.8 | 1.037 |
| 12.9 | 0.9668 |
| 12.10 | 1.556 |
| 12.11 | 12.11 |
| 12.12 | 12.12 |
| 13.1 | 2.722 |
| 13.2 | 4.606 |
| 14.1 | 0.394 |
| 14.2 | 0.2779 |
| 15.1 | 12.7 |
| 15.2 | 0.7085 |
| 15.3 | 0.6605 |
| 15.4 | 20.48 |
| 16.1 | 0.4667 |
| 16.2 | 0.2592 |
| 16.3 | 6.399 |
| 17.1 | <0.625 |
| 17.2 | 1.848 |
| 17.3 | 1.038 |
| 18.1 | 0.7442 |
| 19.1 | 0.5549 |
| 19.2 | 0.154 |
| 20.1 | 1.246 |
| 20.2 | 0.8034 |
| 20.3 | 1.283 |
| 20.4 | 22.48 |
| 20.5 | <0.625 |
| 20.6 | <0.625 |
| 20.7 | 2.169 |
| 20.8 | 0.9158 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound having a structural Formula (I):

(I)

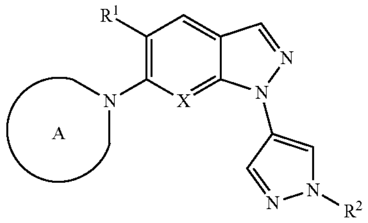

or a pharmaceutically acceptable salt thereof, wherein:

X is CH or N;

$R^1$ is selected from Cl, Br, F, $CH_3$, CN, and $CHF_2$;

$R^2$ is selected from:

optionally substituted cycloalkyl, optionally mono, di, or tri-substituted heteroaryl, mono, di, or tri-substituted heterocycloalkyl, wherein each said optional substituent is independently selected from halogen, oxo, CN, $-(O)_{0-1}(C_1-C_3)$alkyl, $-(C_3-C_6)$cycloalkyl, $-(O)_{0-1}(C_1-C_3)$haloalkyl, $NR^{2A}R^{2B}$, $CH_2NHC(O)(C_1-C_3)$alkyl, $-C(O)OH$, $-C(O)O(C_1-C_3)$alkyl, wherein the alkyl in $-(O)_{0-1}(C_1-C_3)$alkyl is optionally substituted with 1, 2, or 3 substituents independently selected from halogen, OH, $(CH_2)_nO(C_1-C_3)$alkyl, $-(O)_{0-1}(C_1-C_3)$haloalkyl, $NR^{2A}R^{2B}$, and heterocycloalkyl, wherein n is 0-2, and $C(O)NR^{2A}R^{2B}$, $R^{2A}$ is selected from H and $-(C_1-C_3)$alkyl, $R^{2B}$ is selected from H and $-(C_1-C_3)$alkyl;

the moiety

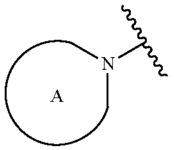

is selected from:

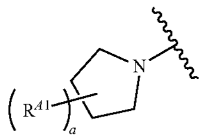 , 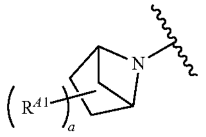 , and

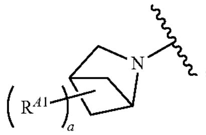 , or, alternatively, the moiety

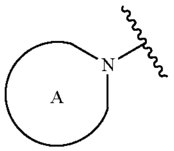

is selected from:

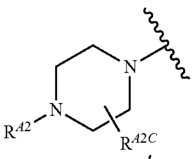 , 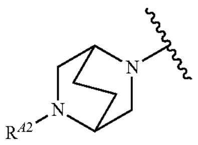 ,

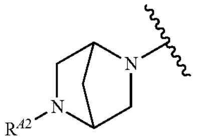 , 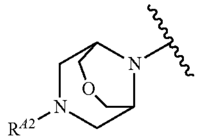

-continued

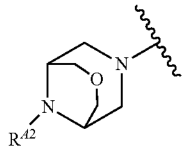 , and 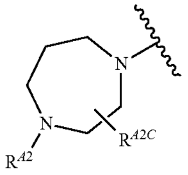 , or, alternatively, the moiety

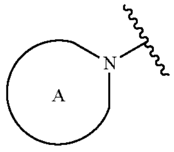

is selected from:

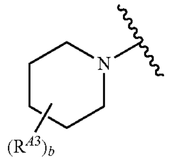 , 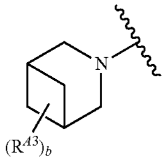 , 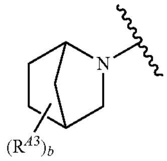 ,

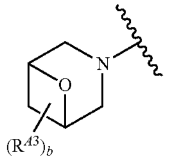 , 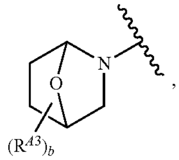 ,

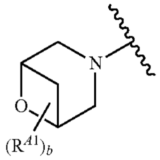 , and 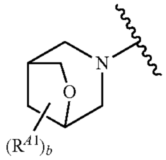

or, alternatively, the moiety

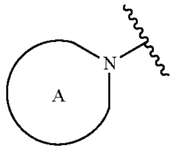

is a fused bicyclic moiety selected from:

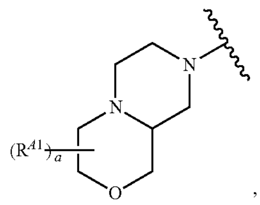 , 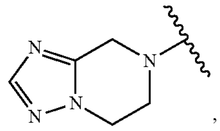 ,

-continued

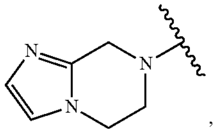, 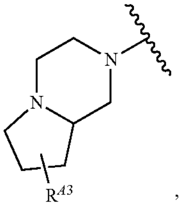,

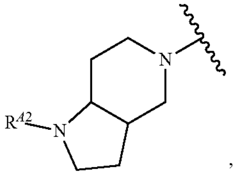, 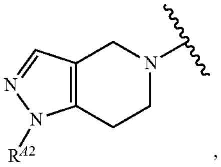,

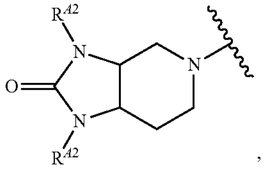, and 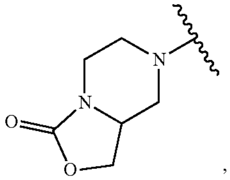,

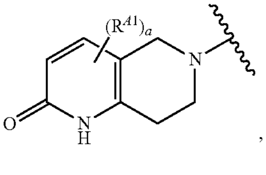, 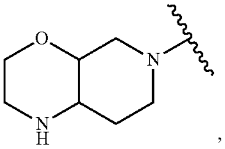,

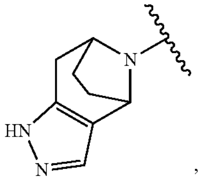, 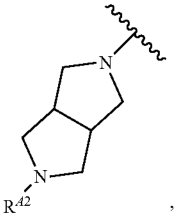, 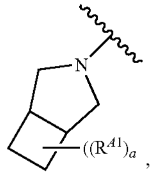,

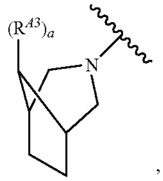, 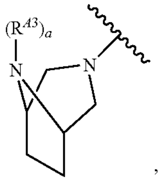, 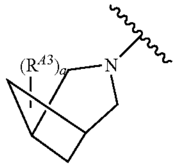, or, alternatively, the moiety

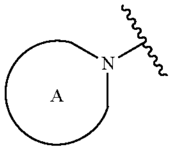

is a moiety selected from:

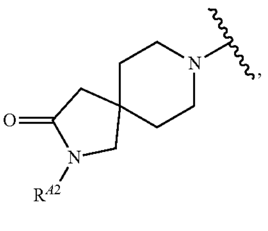, 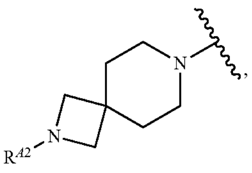,

-continued

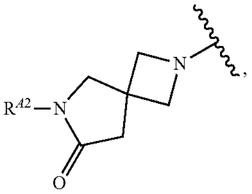, 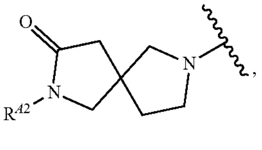,

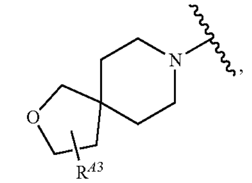, 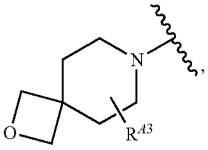,

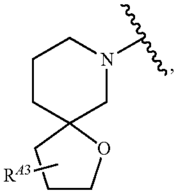, 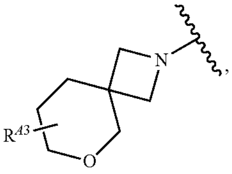,

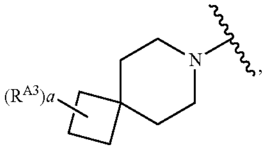, 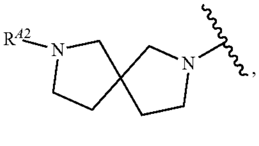,

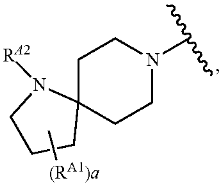, and 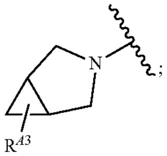;

a is 0, 1, or 2;

each $R^{A1}$ is independently selected from halogen, OH, —$(C_1$-$C_6)$alkyl, —$(C_1$-$C_6)$alkyl-OH, and —$(C_1$-$C_6)$alkyl-CN;

$R^{A2}$ is selected from H, —$(C_1$-$C_6)$alkyl, —$(C_1$-$C_6)$alkyl-OH, —$(C_1$-$C_6)$alkyl-CN, $S(O)_2(C_1$-$C_3)$alkyl, optionally mono-, di- or tri-substituted cyclopropyl, optionally mono-, di- or tri-substituted cyclobutyl, optionally mono-, di- or tri-substituted cyclopentyl, optionally mono-, di- or tri-substituted oxetanyl, optionally mono-, di- or tri-substituted tetrahydrofuranyl, optionally mono-, di- or tri-substituted thietanyl dioxide, optionally mono-, di- or tri-substituted tetrahydrothiophenyl dioxide, wherein each said optional substituent is independently selected from halogen, oxo, CN, OH, —$O(C_1$-$C_3)$alkyl, —$(C_1$-$C_3)$alkyl, and —$(C_1$-$C_3)$haloalkyl;

$R^{A2C}$ is selected from H and, —$(C_1$-$C_6)$alkyl;

b is 0, 1, 2, or 3; and each $R^{A3}$ is independently selected from H, halogen, CN, $NH_2$, OH, oxo, —$(C_1$-$C_3)$alkyl, —$(C_1$-$C_3)$alkyl-OH, —$(C_1$-$C_3)$alkyl-CN, —$(C_1$-$C_3)$haloalkyl, $O(C_1$-$C_3)$alkyl, $(C_1$-$C_3)$alkylNHS$(O)_2(C_1$-$C_3)$alkyl, $S(O)_2(C_1$-$C_3)$ alkyl, $S(O)_2(C_1$-$C_3)$ cyclopropyl, said cyclopropyl optionally mono-, di- or tri-substituted, optionally mono-, di- or tri-substituted cyclopropyl, optionally mono-, di- or tri-substituted cyclobutyl, optionally mono-, di- or tri-substituted cyclopentyl, optionally mono-, di- or tri-substituted azetidinyl, optionally mono-, di- or tri-substituted oxetanyl, optionally mono-, di- or tri-substituted tetrahydrofuranyl, optionally mono-, di- or tri-substituted thietanyl dioxide, optionally mono-, di- or tri-substituted tetrahydrothiophenyl dioxide, and optionally mono-, di- or tri-substituted heteroaryl, wherein each said optional substituent independently selected from halogen, oxo, OH, —$(C_1-C_3)$alkyl, and —$(C_1-C_3)$haloalkyl.

2. The compound of claim 1, or a pharmaceutically acceptable salt thereof, wherein $R^2$ is selected from cyclopropyl, mono-, di- or tri-substituted cyclopropyl, cyclobutyl, mono-, di- or tri-substituted cyclobutyl, bicyclopentanyl, and mono-, di- or tri-substituted bicyclopentanyl, wherein each said optional substituent is 1, 2, or 3 substituents independently selected from halogen, —$(C_1-C_3)$alkyl, —$(C_1-C_3)$haloalkyl, OH, $O(C_1-C_3)$alkyl, CN, and —C(O)O$(C_1-C_3)$alkyl.

3. The compound of claim 1, or a pharmaceutically acceptable salt thereof, wherein:

$R^2$ is selected from optionally mono, di, or tri-substituted heteroaryl and optionally mono, di, or tri-substituted heterocycloalkyl, wherein each said optional substituent on said heteroaryl is 1, 2, or 3 substituents independently selected from halogen, —$(C_1-C_3)$alkyl, and —$(C_1-C_3)$haloalkyl, and wherein each said optional substituent on said heterocycloalkyl is 1, 2, or 3 substituents independently selected from halogen, oxo, —$(C_1-C_3)$alkyl, OH, $O(C_1-C_3)$alkyl, CN, and —$(C_1-C_3)$haloalkyl.

4. The compound of claim 1, or a pharmaceutically acceptable salt thereof, wherein:

$R^2$ is selected from heterocycloalkyl and mono, di, or tri-substituted heterocycloalkyl, wherein each said substituent is 1, 2 or 3 groups independently selected from halogen, oxo, —$(C_1-C_3)$alkyl, OH, $O(C_1-C_3)$alkyl, CN, and —$(C_1-C_3)$haloalkyl.

5. The compound of claim 1, or a pharmaceutically acceptable salt thereof, wherein:

$R^2$ is selected from $CH_3$, cyclopropyl, cyclopropyl substituted with fluoro, cyclobutyl, cyclobutyl substituted with fluoro, C(O)NH$(C_1-C_3$alkyl), $(C_1-C_3$alkyl), $(C_1-C_3$haloalkyl),

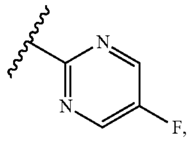

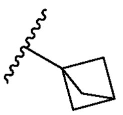

,

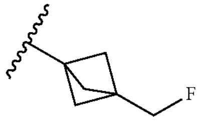

,

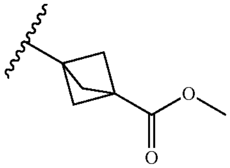

,

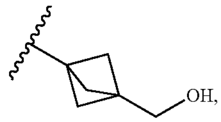

and

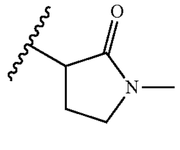

.

6. The compound according to claim 1, or a pharmaceutically acceptable salt thereof, wherein:

the moiety

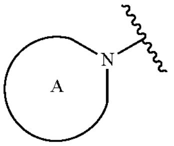

is selected from:

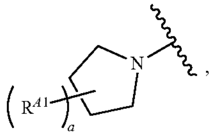

,

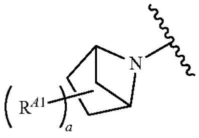

, and

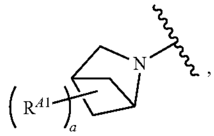

, wherein a is 0, 1, or 2; and each $R^{A1}$ is independently selected from halogen, OH, —$(C_1-C_6)$alkyl, —$(C_1-C_6)$alkyl-OH, and —$(C_1-C_6)$alkyl-CN.

7. The compound according to claim 1, or a pharmaceutically acceptable salt thereof, wherein:

the moiety

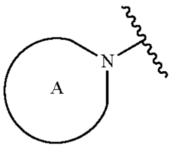

is selected from:

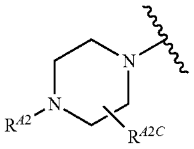

,

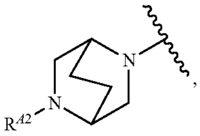

,

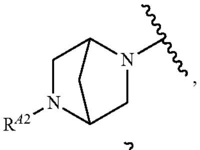

,

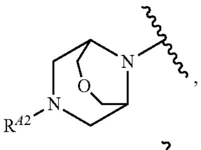

,

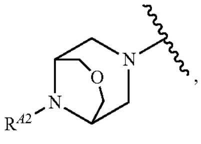

, and

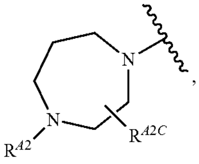

, wherein $R^{A2}$ is selected from H, —$(C_1-C_6)$alkyl, —$(C_1-C_6)$alkyl-OH, —$(C_1-C_6)$alkyl-CN, $S(O)_2(C_1-C_3)$alkyl, optionally mono-, di- or tri-substituted cyclopropyl, optionally mono-, di- or tri-substituted cyclobutyl, optionally mono-, di- or tri-substituted cyclopentyl, optionally substituted optionally mono-, di- or tri-substituted oxetanyl, optionally mono-, di- or tri-substituted tetrahydrofuranyl, optionally mono-, di- or tri-substituted thietanyl dioxide, optionally mono-, di- or tri-substituted tetrahydrothiophenyl dioxide, wherein each said optional substituent is 1, 2, or 3 substituents independently selected from halogen, oxo, —$(C_1\text{-}C_3)$alkyl, and —$(C_1\text{-}C_3)$haloalkyl; and $R^{A2C}$ is selected from H and —$(C_1\text{-}C_6)$alkyl.

8. The compound according to claim 1, or a pharmaceutically acceptable salt thereof, wherein:

the moiety

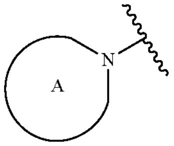

is selected from:

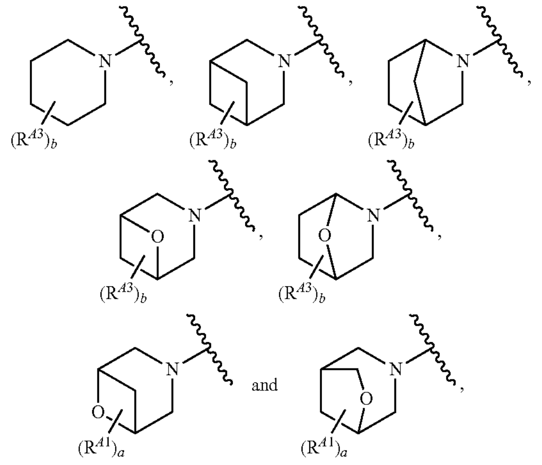

, , , , and , wherein:

b is 0, 1, 2, or 3; and each $R^{A3}$ is independently selected from halogen, $NH_2$, OH, oxo, CN—$(C_1\text{-}C_3)$alkyl, —$(C_1\text{-}C_3)$alkyl-OH, —$(C_1\text{-}C_3)$alkyl-CN, —$(C_1\text{-}C_3)$haloalkyl, $O(C_1\text{-}C_3)$alkyl, $S(O)_2(C_1\text{-}C_3)$alkyl, optionally substituted cyclopropyl, optionally substituted cyclobutyl, optionally substituted cyclopentyl, optionally substituted oxetanyl, optionally substituted tetrahydrofuranyl, optionally substituted thietanyl dioxide, optionally substituted tetrahydrothiophenyl dioxide, and optionally substituted heteroaryl, wherein each said optional substituent is 1, 2, or 3 substituents independently selected from halogen, oxo, —$(C_1\text{-}C_3)$alkyl, and —$(C_1\text{-}C_3)$haloalkyl.

9. The compound according to claim 1, or a pharmaceutically acceptable salt thereof, wherein:

the moiety

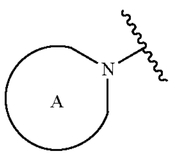

is a fused bicyclic moiety selected from:

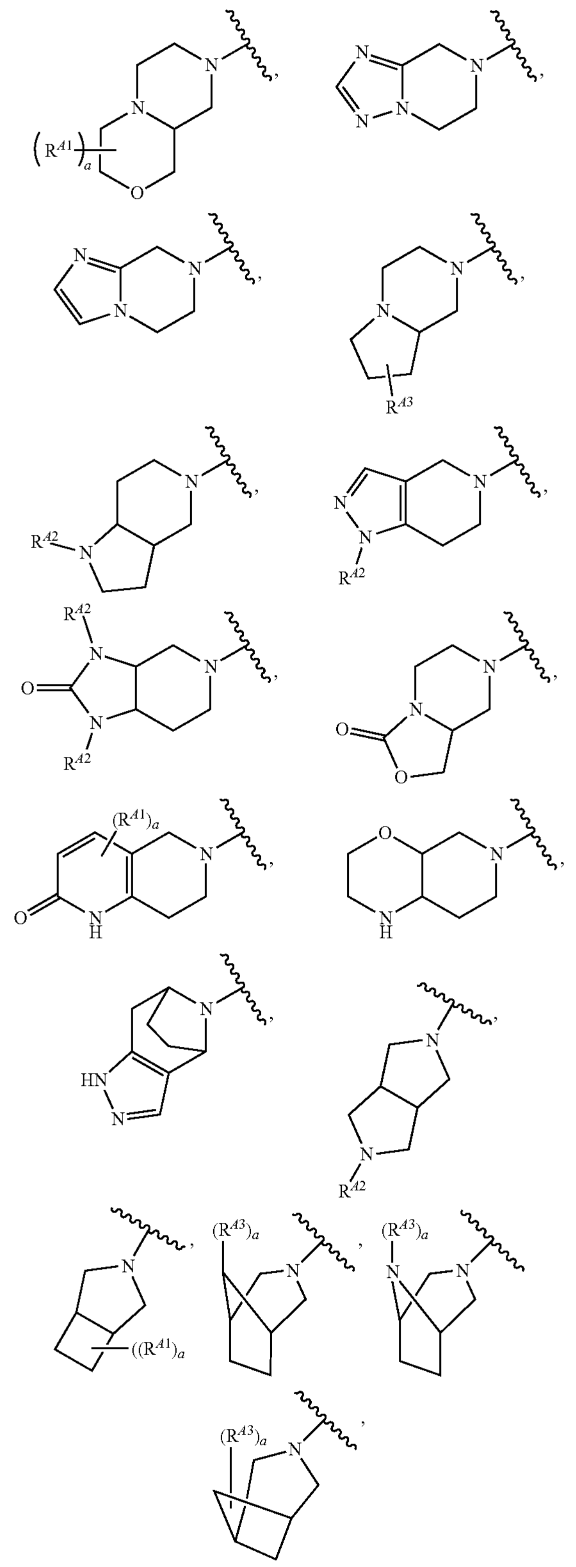

wherein a, $R^{A1}$, $R^{A2}$, and $R^{A3}$ are as defined in claim 1.

10. The compound according to claim 1, or a pharmaceutically acceptable salt thereof, wherein:

the moiety
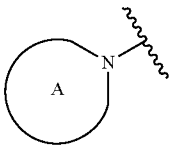
is a moiety selected from:
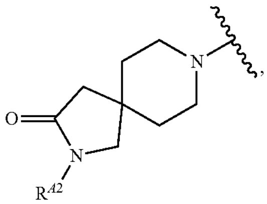,
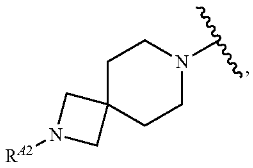,
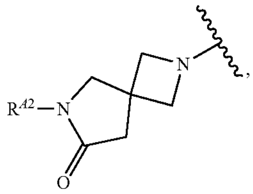,
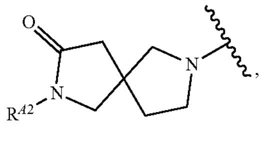,
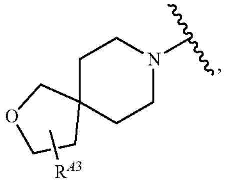,
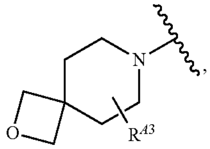,
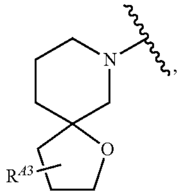,
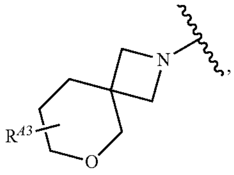,
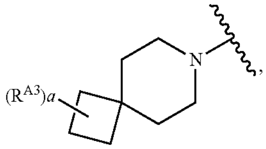,
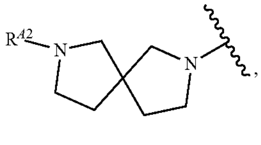,
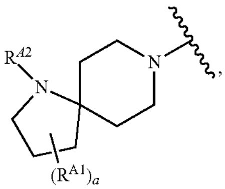, and
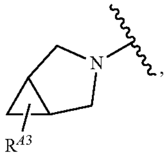,
wherein $R^{A2}$ and $R^{A3}$ are as defined in claim 1.
11. The compound of claim 1, or a pharmaceutically acceptable salt thereof, wherein said compound is selected from:
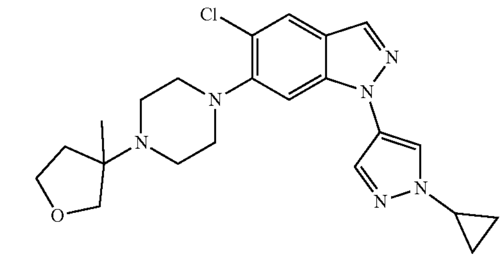
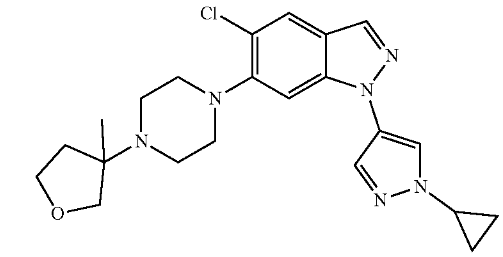
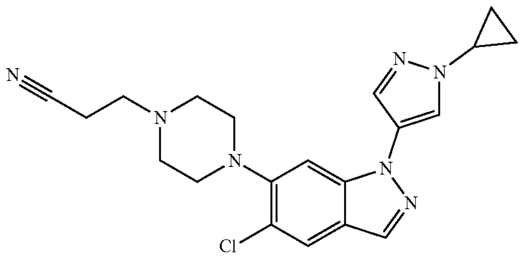
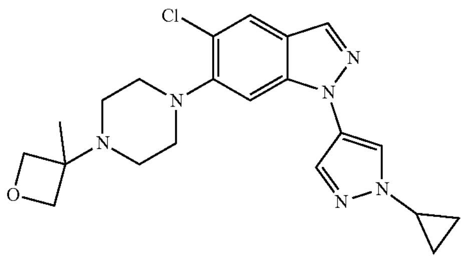
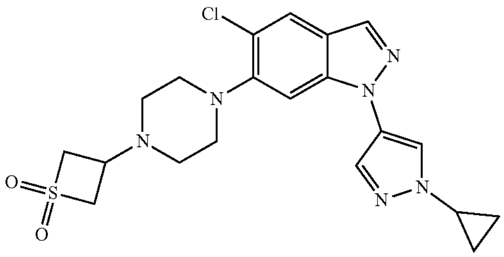
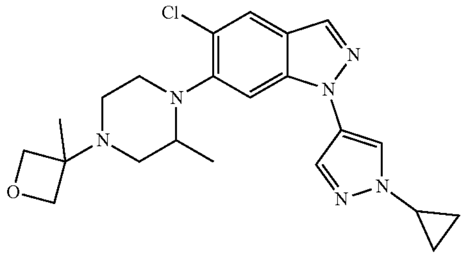

-continued
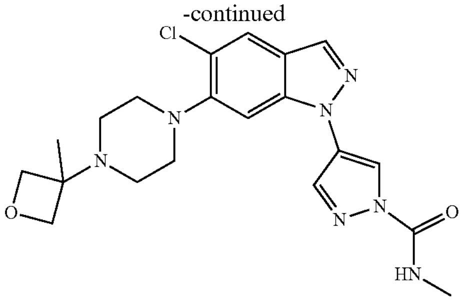
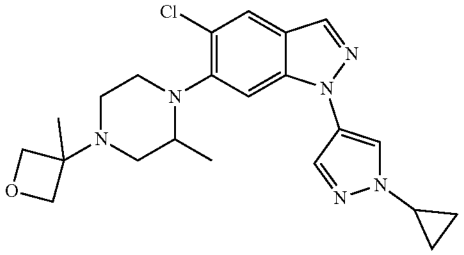
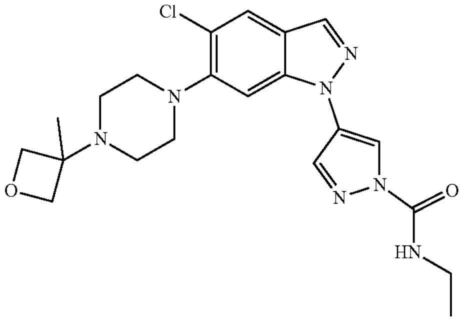
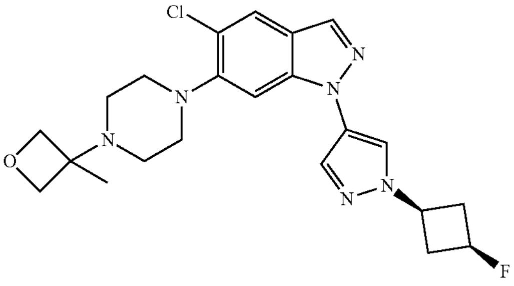
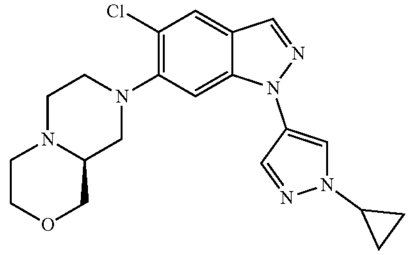
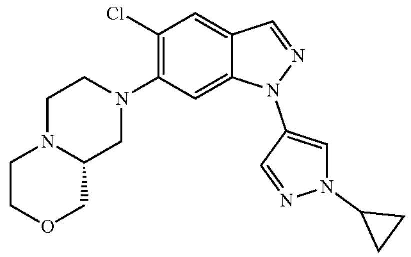
-continued
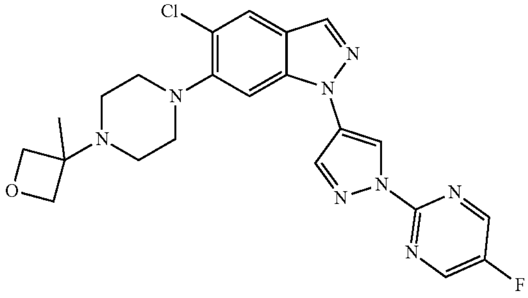
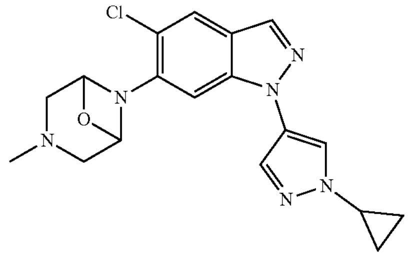
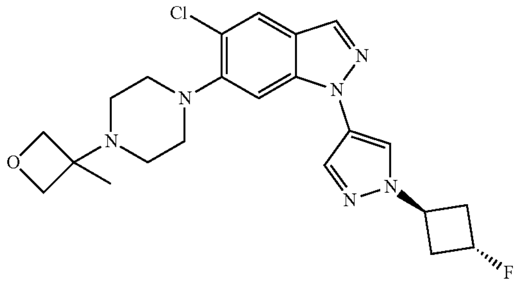
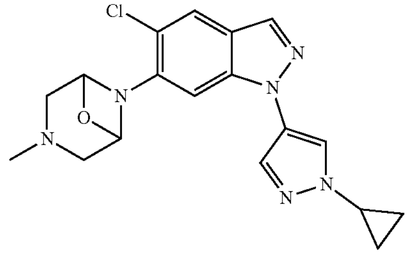
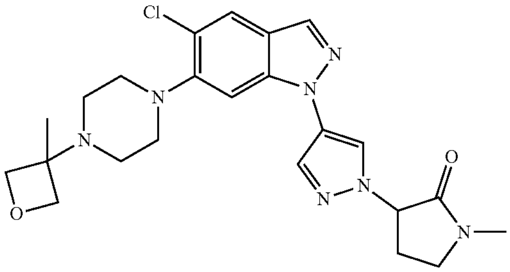
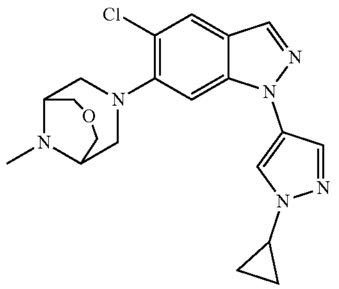

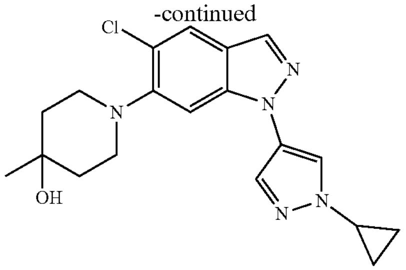
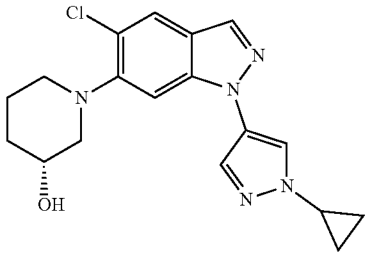
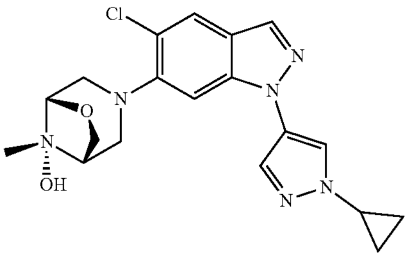
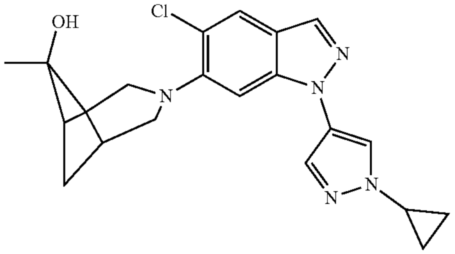
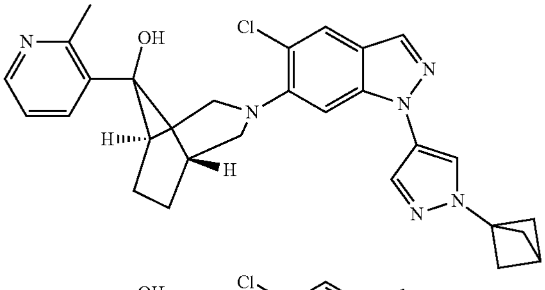
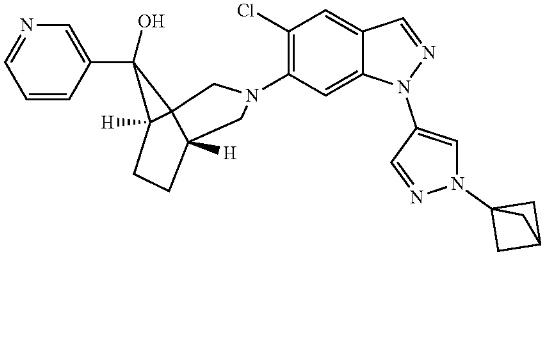
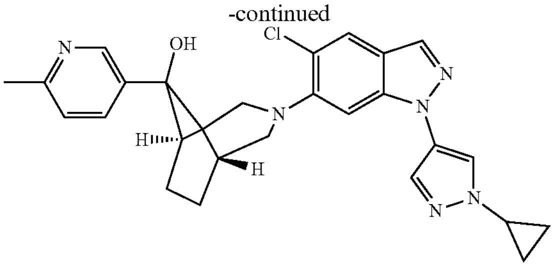
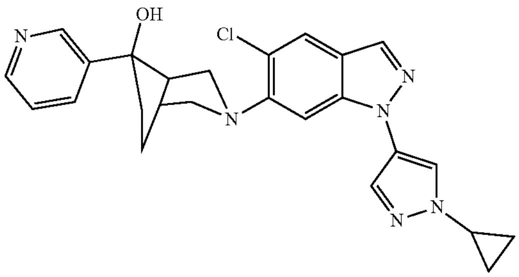
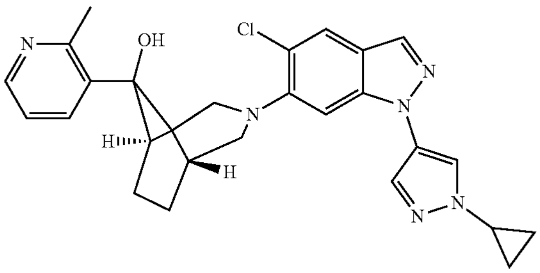
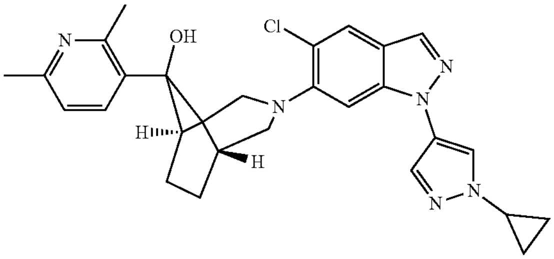
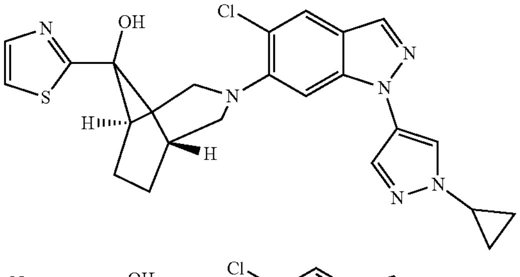
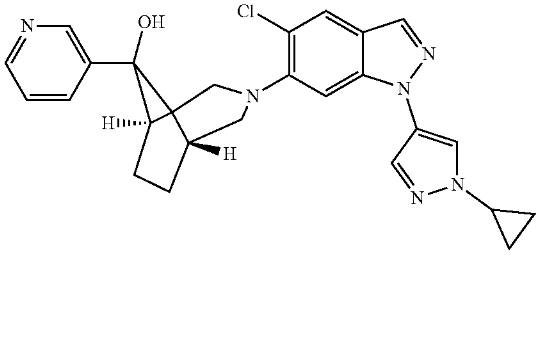

-continued

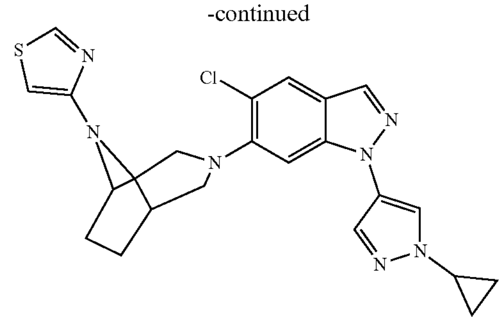

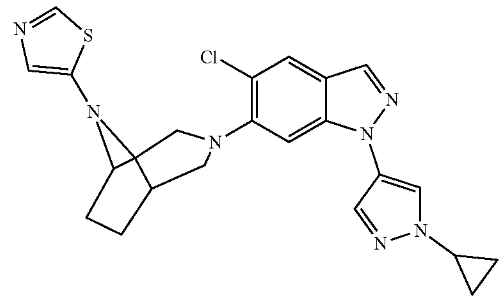

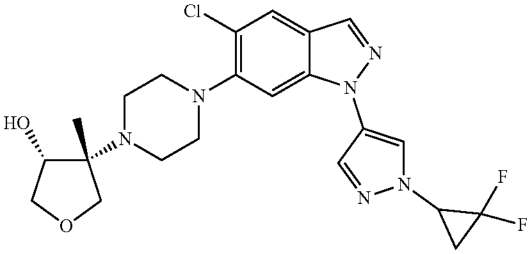

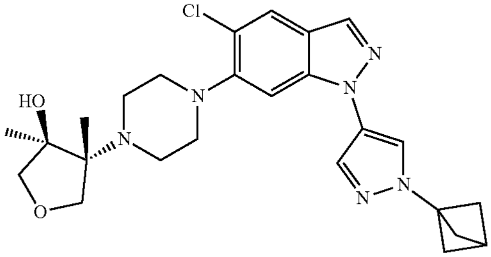

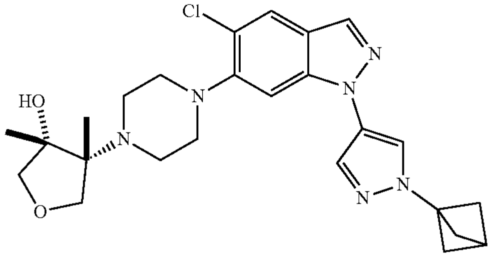

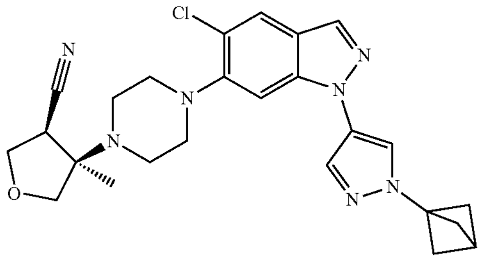

-continued

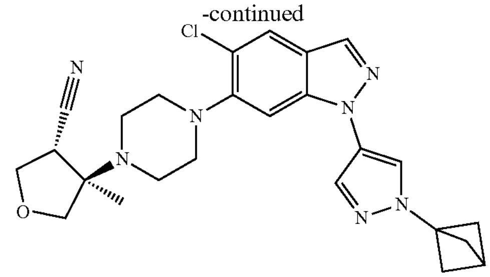

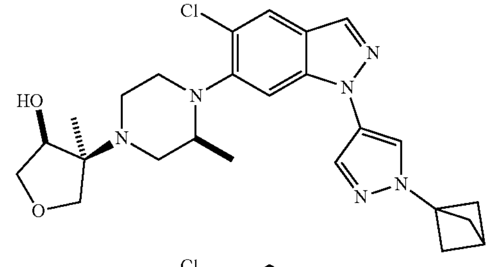

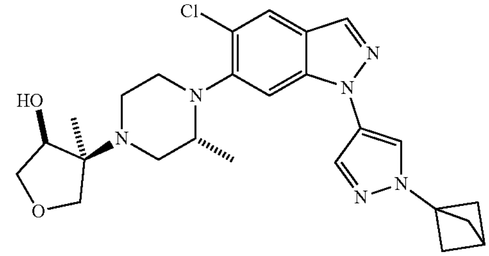

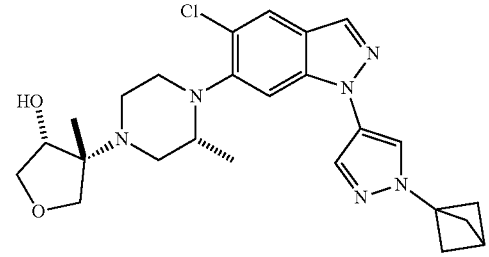

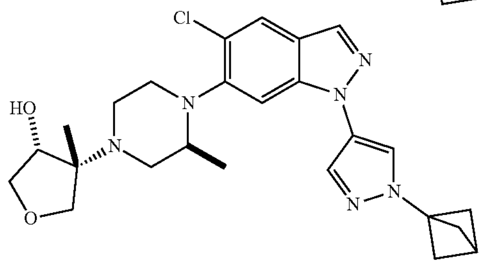

.

12. A pharmaceutical composition comprising a compound of claim 1, or a pharmaceutically acceptable salt thereof, and a pharmaceutically acceptable carrier.

13. A method of treating Parkinson's Disease comprising administering a therapeutically effective amount of a compound of claim 1, or a pharmaceutically acceptable salt thereof, to a person in need thereof.

14. A method for the treatment or prophylaxis of an indication in which LRRK2 kinase is involved, said indication selected from Parkinson's disease, comprising administering to a subject in need thereof a therapeutically effective amount of a compound according to claim 1, or a pharmaceutically acceptable salt thereof.

15. A method of treating Parkinson's Disease comprising administering an a therapeutically effective amount of a pharmaceutically acceptable composition according to claim 12 to a person in need thereof.

16. A method for the treatment or prophylaxis of an indication in which LRRK2 kinase is involved, said indication selected from Parkinson's disease, comprising administering to a subject in need thereof a therapeutically effective amount of a pharmaceutically acceptable composition according to claim 12.

* * * * *